United States Patent
Thompson et al.

(10) Patent No.: US 8,541,461 B2
(45) Date of Patent: *Sep. 24, 2013

(54) PHARMACEUTICAL COMBINATIONS COMPRISING PYRAZOLE DERIVATIVES AS PROTEIN KINASE MODULATORS

(75) Inventors: Neil Thomas Thompson, Cambridge (GB); Robert George Boyle, Cambridge (GB); Ian Collins, Redhill (GB); Michelle Dawn Garrett, Walton-on-Thames (GB); John Francis Lyons, Cambridge (GB); Kyla Merriom Thompson, Cambridge (GB)

(73) Assignees: Astex Therapeutics Limited, Cambridge (GB); The Institute of Cancer Research Royal Cancer Hospital, London (GB); Cancer Research Technology Limited, London (GB)

( * ) Notice: Subject to any disclaimer, the term of this patent is extended or adjusted under 35 U.S.C. 154(b) by 934 days.

This patent is subject to a terminal disclaimer.

(21) Appl. No.: 11/993,823

(22) PCT Filed: Jun. 21, 2006

(86) PCT No.: PCT/GB2006/002297
§ 371 (c)(1),
(2), (4) Date: Mar. 9, 2010

(87) PCT Pub. No.: WO2006/136837
PCT Pub. Date: Dec. 28, 2006

(65) Prior Publication Data
US 2010/0166699 A1 Jul. 1, 2010

Related U.S. Application Data

(60) Provisional application No. 60/693,315, filed on Jun. 23, 2005, provisional application No. 60/693,367, filed on Jun. 23, 2005, provisional application No. 60/693,314, filed on Jun. 23, 2005, provisional application No. 60/693,492, filed on Jun. 23, 2005, provisional application No. 60/693,309, filed on Jun. 23, 2005.

(51) Int. Cl.
*A61K 31/415* (2006.01)

(52) U.S. Cl.
USPC .................................................... 514/407

(58) Field of Classification Search
USPC ............................................................ 514/407
See application file for complete search history.

(56) References Cited

U.S. PATENT DOCUMENTS

| | | | |
|---|---|---|---|
| 5,532,356 A | 7/1996 | Smyser et al. | |
| 5,922,744 A | 7/1999 | Harrison et al. | |
| 6,010,837 A | 1/2000 | Clark et al. | |
| 6,015,825 A | 1/2000 | Bell et al. | |

(Continued)

FOREIGN PATENT DOCUMENTS

| | | |
|---|---|---|
| EP | 1024138 A1 | 8/2000 |
| GB | 2427406 A | 12/2006 |

(Continued)

OTHER PUBLICATIONS

Schrijvers et al 'Docetaxel, cisplatin and 5-fluorouracil in patients with locally advanced unresectable head and neck cancer: a phase I-II feasibility study' Annals of Oncology, vol. 15, p. 638-645, 2004.*

(Continued)

*Primary Examiner* — Brandon Fetterolf
*Assistant Examiner* — Christopher R Stone
(74) *Attorney, Agent, or Firm* — Heslin Rothenberg Farley & Mesiti P.C.

(57) ABSTRACT

The invention provides a combination comprising an ancillary compound (e.g. one, two or more ancillary compounds) and a compound of the formula (I) having protein kinase B inhibiting activity: wherein A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$, wherein one of the carbon atoms in the linker group may optionally be replaced by an oxygen or nitrogen atom; and wherein the carbon atoms of the linker group A may optionally bear one or more substituents selected from oxo, fluorine and hydroxy, provided that the hydroxy group when present is not located at a carbon atom α with respect to the $NR^2R^3$ group and provided that the oxo group when present is located at a carbon atom α with respect to the $NR^2R^3$ group; E is a monocyclic or bicyclic carbocyclic or heterocyclic group; $R^1$ is an aryl or heteroaryl group; and $R^2$, $R^3$, $R^4$ and $R^5$ are as defined in the claims. Also provided are patient packs, pharmaceutical kits and packs and compositions containing the combinations, methods for preparing the combinations and their use in combination therapy as anticancer agents.

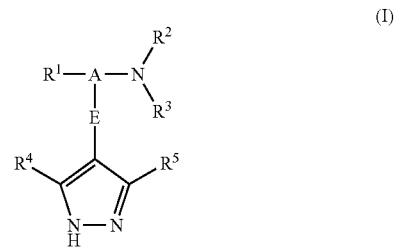

26 Claims, 1 Drawing Sheet

(56) References Cited

U.S. PATENT DOCUMENTS

| | | | |
|---|---|---|---|
| 6,020,357 A | 2/2000 | Pinto et al. | |
| 6,200,978 B1 | 3/2001 | Maw et al. | |
| 7,393,842 B2 | 7/2008 | Makriyannis et al. | |
| 7,799,782 B2 | 9/2010 | Munson et al. | |
| 2002/0091116 A1 | 7/2002 | Zhu et al. | |
| 2004/0122230 A1* | 6/2004 | Welsh et al. | 546/35 |
| 2005/0261315 A1 | 11/2005 | Mehta et al. | |
| 2011/0144080 A1 | 6/2011 | Berdini et al. | |
| 2011/0269808 A1* | 11/2011 | Woodhead et al. | 514/406 |
| 2013/0005702 A1* | 1/2013 | Berdini et al. | 514/210.2 |

FOREIGN PATENT DOCUMENTS

| | | |
|---|---|---|
| JP | 2000-16984 A | 1/2000 |
| WO | 90/09381 A1 | 8/1990 |
| WO | 91/11445 A1 | 8/1991 |
| WO | 94/29300 A1 | 12/1994 |
| WO | 95/10513 A1 | 4/1995 |
| WO | 97/01552 A1 | 1/1997 |
| WO | 97/36886 A1 | 10/1997 |
| WO | 98/04528 A2 | 2/1998 |
| WO | 98/25617 A1 | 6/1998 |
| WO | 99/38508 A1 | 8/1999 |
| WO | 00/07996 A2 | 2/2000 |
| WO | 00/14066 A1 | 3/2000 |
| WO | 00/31063 A1 | 6/2000 |
| WO | 00/39091 A1 | 7/2000 |
| WO | 00/66562 A1 | 11/2000 |
| WO | 00/69859 A1 | 11/2000 |
| WO | 01/19788 A2 | 3/2001 |
| WO | 01/19798 A2 | 3/2001 |
| WO | 01/32653 A1 | 5/2001 |
| WO | 01/64642 A2 | 9/2001 |
| WO | 01/91754 A1 | 12/2001 |
| WO | 02/088090 A2 | 11/2002 |
| WO | 03/011855 A2 | 2/2003 |
| WO | 03/028686 A1 | 4/2003 |
| WO | 03/030898 A1 | 4/2003 |
| WO | 03/048081 A2 | 6/2003 |
| WO | 03/048158 A1 | 6/2003 |
| WO | 03/059884 A1 | 7/2003 |
| WO | 03/068230 A1 | 8/2003 |
| WO | 03/080545 A2 | 10/2003 |
| WO | 03/086247 A1 | 10/2003 |
| WO | 03/090680 A2 | 11/2003 |
| WO | 2004/011460 A2 | 2/2004 |
| WO | 2004/110350 A2 | 12/2004 |
| WO | 2005/003101 A2 | 1/2005 |
| WO | 2005/012256 A1 | 2/2005 |
| WO | 2005/035506 A1 | 4/2005 |
| WO | 2005/061463 A1 | 7/2005 |
| WO | 2005/117909 A2 | 12/2005 |
| WO | 2006/046023 A1 | 5/2006 |
| WO | 2006/071819 A1 | 7/2006 |
| WO | 2006/091450 A1 | 8/2006 |
| WO | 2006/136821 A1 | 12/2006 |
| WO | 2006/136823 A1 | 12/2006 |
| WO | 2006/136829 A2 | 12/2006 |
| WO | 2006/136830 A1 | 12/2006 |
| WO | 2006/136837 A2 | 12/2006 |
| WO | 2008/110846 A2 | 9/2008 |

OTHER PUBLICATIONS

Taylor, S.S. et al., PKA: a portrait of protein kinase dynamics, Biochemica et Biophysica, 1697, 2004, pp. 259-269.

Hill, Michelle M. et al., Inhibition of protein kinase B/Akt: implications for cancer therapy, Pharmacology & Therapeutics, 93, 2002, pp. 243-251.

Barnett, Stanley F. et al., The Akt/PKB Family of Protein Kinases: a Review of Small Molecule Inhibitors and Progress Towards Target Validation, Current Topics in Medicinal Chemistry, 5, 2005, pp. 109-125.

Nagarajan, K. et al., Mechanism of Formation of p-Substituted Products in Displacement Reactions on Chlorodiphenylacetamides, Tetrahedron Letters, No. 22, 1968, pp. 2717-2720.

Simig, Gyula et al., Single Electron Transfer Inititated Thermal Reactions of Arylmethyl Halides, X, Acta Chimica Hungarica, 118(4), 1985, pp. 309-314.

Ajmani Subhash et al., A Comprehensive structure-activity analysis of protein kinase B-alpha (Aktl) inhibitors, Journal of Molecular Graphics and Modelling, 28(7), 2010, pp. 683-694.

Murray Andrew J., Pharmacological PKA Inhibition: All May Not Be What It Seems, Science Signaling, Jun. 3, 2008, pp. 1-6.

Dorwald, Florencio Zaragoza, Side Reactions in Organic Synthesis, Wiley-VCH, 2005, p. 1 and preface.

Drewry et al. CAS 143 229871 (2005).

* cited by examiner

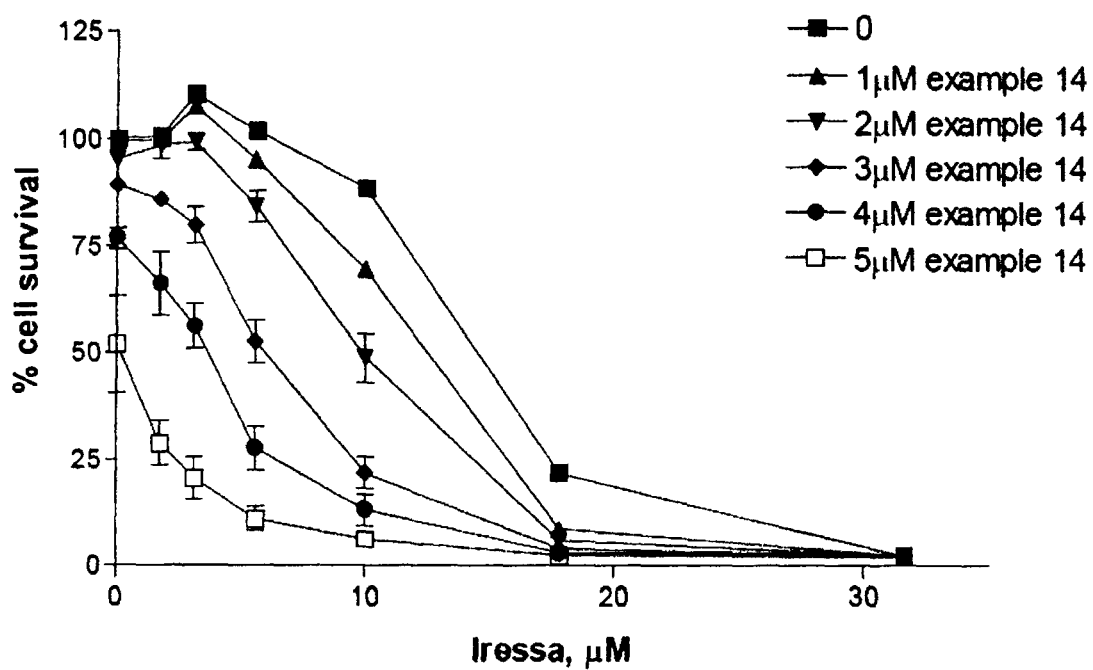

PHARMACEUTICAL COMBINATIONS COMPRISING PYRAZOLE DERIVATIVES AS PROTEIN KINASE MODULATORS

CROSS REFERENCE TO RELATED APPLICATIONS

This application is a national phase filing under 35 U.S.C. §371 of PCT International Application PCT/GB2006/002297, filed Jun. 21, 2006, and published under PCT Article 21(2) in English as WO 2006/136837 on Dec. 28, 2006. PCT/GB2006/002297 claimed priority from U.S. Provisional Applications 60/693,315, filed Jun. 23, 2005, 60/693,367, filed Jun. 23, 2005, 60/693,314, filed Jun. 23, 2005, 60/693,492, filed Jun. 23, 2005 and 60/693,309, filed Jun. 23, 2005. The entire contents of each of the prior applications are incorporated herein by reference.

This invention relates to combinations of pyrazole-containing aryl- and heteroaryl-alkylamine compounds that inhibit or modulate the activity of protein kinase B (PKB) and protein kinase A (PKA) with one or more (e.g. two or more) ancillary compounds, to the use of the combinations in the treatment or prophylaxis of disease states or conditions mediated by PKB and PKA, and to combinations comprising novel compounds having PKB and PKA inhibitory or modulating activity. Also provided are pharmaceutical compositions containing the combinations.

BACKGROUND OF THE INVENTION

Protein Kinases

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Apoptosis or programmed cell death is an important physiological process which removes cells no longer required by an organism. The process is important in early embryonic growth and development allowing the non-necrotic controlled breakdown, removal and recovery of cellular components. The removal of cells by apoptosis is also important in the maintenance of chromosomal and genomic integrity of growing cell populations. There are several known checkpoints in the cell growth cycle at which DNA damage and genomic integrity are carefully monitored. The response to the detection of anomalies at such checkpoints is to arrest the growth of such cells and initiate repair processes. If the damage or anomalies cannot be repaired then apoptosis is initiated by the damaged cell in order to prevent the propagation of faults and errors. Cancerous cells consistently contain numerous mutations, errors or rearrangements in their chromosomal DNA. It is widely believed that this occurs in part because the majority of tumours have a defect in one or more of the processes responsible for initiation of the apoptotic process. Normal control mechanisms cannot kill the cancerous cells and the chromosomal or DNA coding errors continue to be propagated. As a consequence restoring these pro-apoptotic signals or suppressing unregulated survival signals is an attractive means of treating cancer.

The signal transduction pathway containing the enzymes phosphatidylinositol 3-kinase (PI3K), PDK1 and PKB amongst others, has long been known to mediate increased resistance to apoptosis or survival responses in many cells. There is a substantial amount of data to indicate that this pathway is an important survival pathway used by many growth factors to suppress apoptosis. The enzyme PI3K is activated by a range of growth and survival factors e.g. EGF, PDGF and through the generation of polyphosphatidylinositols, initiates the activation of the downstream signalling events including the activity of the kinases PDK1 and protein kinase B (PKB) also known as Akt. This is also true in host tissues, e.g. vascular endothelial cells as well as neoplasias. PKB is a protein ser/thr kinase consisting of a kinase domain together with an N-terminal PH domain and C-terminal regulatory domain. The enzyme PKB itself is phosphorylated on Thr 308 by PDK1 and on Ser 473 by an as yet unidentified kinase. Full activation requires phosphorylation at both sites whilst association between PIP3 and the PH domain is required for anchoring of the enzyme to the cytoplasmic face of the lipid membrane providing optimal access to substrates.

Activated PKB in turn phosphorylates a range of substrates contributing to the overall survival response. Whilst we cannot be certain that we understand all of the factors responsible for mediating the PKB dependent survival response, some important actions are believed to be phosphorylation and inactivation of the pro-apoptotic factor BAD and caspase 9, phosphorylation of Forkhead transcription factors e.g. FKHR leading to their exclusion from the nucleus, and activation of the NfkappaB pathway by phosphorylation of upstream kinases in the cascade.

In addition to the anti-apoptotic and pro-survival actions of the PKB pathway, the enzyme also plays an important role in promoting cell proliferation. This action is again likely to be mediated via several actions, some of which are thought to be phosphorylation and inactivation of the cyclin dependent kinase inhibitor of $p21^{CiP1/WAF1}$, and phosphorylation and activation of mTOR, a kinase controlling several aspects of cell growth.

The phosphatase PTEN which dephosphorylates and inactivates polyphosphatidyl-inositols is a key tumour suppressor protein which normally acts to regulate the PI3K/PKB survival pathway. The significance of the PI3K/PKB pathway in tumourigenesis can be judged from the observation that PTEN is one of the most common targets of mutation in human tumours, with mutations in this phosphatase having been found in ~50% or more of melanomas (Guldberg et al 1997, Cancer Research 57, 3660-3663) and advanced prostate cancers (Cairns et al 1997 Cancer Research 57, 4997). These observations and others suggest that a wide range of tumour types are dependent on the enhanced PKB activity for growth and survival and would respond therapeutically to appropriate inhibitors of PKB.

There are 3 closely related isoforms of PKB called alpha, beta and gamma, which genetic studies suggest have distinct but overlapping functions. Evidence suggests that they can all independently play a role in cancer. For example PKB beta has been found to be over-expressed or activated in 10-40% of ovarian and pancreatic cancers (Bellacosa et al 1995, Int. J. Cancer 64, 280-285; Cheng et al 1996, PNAS 93, 3636-3641; Yuan et 2000, Oncogene 19, 2324-2330), PKB alpha is amplified in human gastric, prostate and breast cancer (Steal 1987, PNAS 84, 5034-5037; Sun et at 2001, Am. J. Pathol. 159, 431-437) and increased PKB gamma activity has been observed in steroid independent breast and prostate cell lines (Nakatani et at 1999, J. Biol. Chem. 274, 21528-21532).

The PKB pathway also functions in the growth and survival of normal tissues and may be regulated during normal physiology to control cell and tissue function. Thus disorders associated with undesirable proliferation and survival of normal cells and tissues may also benefit therapeutically from treatment with a PKB inhibitor. Examples of such disorders are disorders of immune cells associated with prolonged expansion and survival of cell population leading to a prolonged or up regulated immune response. For example, T and B lymphocyte response to cognate antigens or growth factors such as interleukin-2 activates the PI3K/PKB pathway and is responsible for maintaining the survival of the antigen specific lymphocyte clones during the immune response. Under conditions in which lymphocytes and other immune cells are responding to inappropriate self or foreign antigens, or in which other abnormalities lead to prolonged activation, the PKB pathway contributes an important survival signal preventing the normal mechanisms by which the immune response is terminated via apoptosis of the activated cell population. There is a considerable amount of evidence demonstrating the expansion of lymphocyte populations responding to self antigens in autoimmune conditions such as multiple sclerosis and arthritis. Expansion of lymphocyte populations responding inappropriately to foreign antigens is a feature of another set of conditions such as allergic responses and asthma. In summary inhibition of PKB could provide a beneficial treatment for immune disorders.

Other examples of inappropriate expansion, growth, proliferation, hyperplasia and survival of normal cells in which PKB may play a role include but are not limited to atherosclerosis, cardiac myopathy and glomerulonephritis.

In addition to the role in cell growth and survival, the PKB pathway functions in the control of glucose metabolism by insulin. Available evidence from mice deficient in the alpha and beta isoforms of PKB suggests that this action is mediated by the beta isoform. As a consequence, modulators of PKB activity may also find utility in diseases in which there is a dysfunction of glucose metabolism and energy storage such as diabetes, metabolic disease and obesity.

Cyclic AMP-dependent protein kinase (PKA) is a serine/threonine protein kinase that phosphorylates a wide range of substrates and is involved in the regulation of many cellular processes including cell growth, cell differentiation, ion-channel conductivity, gene transcription and synaptic release of neurotransmitters. In its inactive form, the PKA holoenzyme is a tetramer comprising two regulatory subunits and two catalytic subunits.

PKA acts as a link between G-protein mediated signal transduction events and the cellular processes that they regulate. Binding of a hormone ligand such as glucagon to a transmembrane receptor activates a receptor-coupled G-protein (GTP-binding and hydrolyzing protein). Upon activation, the alpha subunit of the G protein dissociates and binds to and activates adenylate cyclase, which in turn converts ATP to cyclic-AMP (cAMP).

The cAMP thus produced then binds to the regulatory subunits of PKA leading to dissociation of the associated catalytic subunits. The catalytic subunits of PKA, which are inactive when associated with the regulatory sub-units, become active upon dissociation and take part in the phosphorylation of other regulatory proteins.

For example, the catalytic sub-unit of PKA phosphorylates the kinase Phosphorylase Kinase which is involved in the phosphorylation of Phosphorylase, the enzyme responsible for breaking down glycogen to release glucose. PKA is also involved in the regulation of glucose levels by phosphorylating and deactivating glycogen synthase. Thus, modulators of PKA activity (which modulators may increase or decrease PKA activity) may be useful in the treatment or management of diseases in which there is a dysfunction of glucose metabolism and energy storage such as diabetes, metabolic disease and obesity.

PKA has also been established as an acute inhibitor of T cell activation. Anndahl at al, have investigated the possible role of PKA type I in HIV-induced T cell dysfunction on the basis that T cells from HIV-infected patients have increased levels of cAMP and are more sensitive to inhibition by cAMP analogues than are normal T cells. From their studies, they concluded that increased activation of PKA type I may contribute to progressive T cell dysfunction in HIV infection and that PKA type I may therefore be a potential target for immunomodulating therapy.-Aandahl, E. M., Aukrust, P., Skålhegg, B. S., Müller, F., Frøland, S. S., Hansson, V., Taskén, K. *Protein kinase A type I antagonist restores immune responses of T cells from HIV-infected patients.* FASEB J. 12, 855-862 (1998).

It has also been recognised that mutations in the regulatory sub-unit of PKA can lead to hyperactivation in endocrine tissue.

Because of the diversity and importance of PKA as a messenger in cell regulation, abnormal responses of cAMP can lead to a variety of human diseases such as irregular cell growth and proliferation (Stratakis, C. A.; Cho-Chung, Y. S.; Protein Kinase A and human diseases. *Trends Endrocri. Metab.* 2002, 13, 50-52). Over-expression of PKA has been observed in a variety of human cancer cells including those from ovarian, breast and colon patients. Inhibition of PKA would therefore be an approach to treatment of cancer (Li, Q.; Zhu, G-D.; *Current Topics in Medicinal Chemistry,* 2002, 2, 939-971).

For a review of the role of PKA in human disease, see for example, *Protein Kinase A and Human Disease*, Edited by Constantine A. Stratakis, Annals of the New York Academy of Sciences, Volume 968, 2002, ISBN 1-57331-412-9.

Several classes of compounds have been disclosed as having PKA and PKB inhibitory activity.

For example, a class of isoquinolinyl-sulphonamido-diamines having PKB inhibitory activity is disclosed in WO 01/91754 (Yissum).

WO00/07996 (Chiron) discloses substituted pyrazoles having estrogen receptor agonist activity. The compounds are described as being useful in treating or preventing inter alia estrogen-receptor mediated breast cancer. PKB inhibitory activity is not disclosed.

WO 00/31063 (Searle) discloses substituted pyrazole compounds as p38 kinase inhibitors.

WO 01/32653 (Cephalon) discloses a class of pyrazolone kinase inhibitors. WO 03/059884 (X-Ceptor Therapeutics) discloses N-substituted pyridine compounds as modulators of nuclear receptors.

WO 03/068230 (Pharmacia) discloses substituted pyridones as p38 MAP kinase modulators.

WO 00/66562 (Dr Reddy's Research Foundation) discloses a class of 1-phenyl-substituted pyrazoles for use as anti-inflammatory agents. The 1-phenyl group is substituted by a sulphur-containing substituent as a sulphonamide or sulphonyl group.

Ancillary Compounds

A wide variety of ancillary compounds find application in the combinations of the invention, as described in detail below.

It is an object of the invention to provide therapeutic combinations comprising an ancillary compound (e.g. one, two or more ancillary compounds) and a compound that has protein kinase B (PKB) and/or protein kinase A (PKA) inhibiting or modulating activity and which have an advantageous efficacious effect in comparison with the respective effects shown by the individual components of the combination.

SUMMARY OF THE INVENTION

The invention provides combinations of an ancillary compound (e.g. one, two or more ancillary compounds) with compounds that have protein kinase B (PKB) and/or protein kinase A (PKA) inhibiting or modulating activity, and which it is envisaged will be useful in preventing or treating disease states or conditions mediated by PKB and/or PKA.

In a first aspect, the invention provides a combination of an ancillary compound (e.g. one, two or more ancillary compounds) and a compound of the formula (I):

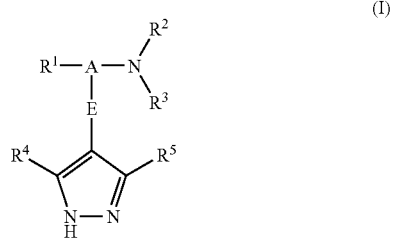

or a salt, solvate, tautomer or N-oxide thereof;

wherein A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$, wherein one of the carbon atoms in the linker group may optionally be replaced by an oxygen or nitrogen atom; and wherein the carbon atoms of the linker group A may optionally bear one or more substituents selected from oxo, fluorine and hydroxy, provided that the hydroxy group when present is not located at a carbon atom a with respect to the $NR^2R^3$ group and provided that the oxo group when present is located at a carbon atom a with respect to the $NR^2R^3$ group;

E is a monocyclic or bicyclic carbocyclic or heterocyclic group;

$R^1$ is an aryl or heteroaryl group;

$R^2$ and $R^3$ are independently selected from hydrogen, $C_{1-4}$ hydrocarbyl and $C_{1-4}$ acyl wherein the hydrocarbyl and acyl moieties are optionally substituted by one or more substituents selected from fluorine, hydroxy, amino, methylamino, dimethylamino and methoxy;

or $R^2$ and $R^3$ together with the nitrogen atom to which they are attached form a cyclic group selected from an imidazole group and a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the linker group A form a saturated monocyclic heterocyclic group having 4-7 ring members and optionally containing a second heteroatom ring member selected from O and N;

or $NR^2R^3$ and the carbon atom of linker group A to which it is attached together form a cyano group;

$R^4$ is selected from hydrogen, halogen, $C_{1-5}$ saturated hydrocarbyl, $C_{1-5}$ saturated hydrocarbyloxy, cyano, and $CF_3$; and $R^5$ is selected from selected from hydrogen, halogen, $C_{1-5}$ saturated hydrocarbyl, $C_{1-5}$ saturated hydrocarbyloxy, cyano, $CONH_2$, $CONHR^9$, $CF_3$, $NH_2$, $NHCOR^9$ or $NHCONHR^9$;

$R^9$ is a group $R^{9a}$ or $(CH_2)R^{9a}$, wherein $R^{9a}$ is a monocyclic or bicyclic group which may be carbocyclic or heterocyclic;

the carbocyclic group or heterocyclic group $R^{9a}$ being optionally substituted by one or more substituents selected from halogen, hydroxy, trifluoromethyl, cyano, nitro, carboxy, amino, mono- or di-$C_{1-4}$ hydrocarbylamino; a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$.

The combinations of the invention may comprise (or consist essentially of) an ancillary compound (e.g. one, two or more ancillary compounds) and a compound of the formula (I) as defined herein. Thus, in one embodiment, the combinations of the invention comprise (or consist essentially of) one ancillary compound and a compound of the formula (I) as defined herein. In another embodiment, the combinations of the invention comprise (or consist essentially of) two or more ancillary compounds and a compound of the formula (I) as defined herein.

The invention also provides a combination of an ancillary compound (e.g. one, two or more ancillary compounds) and a compound of the formula (Ia):

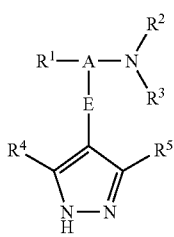

(Ia)

or a salt, solvate, tautomer or N-oxide thereof;

wherein A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$, wherein one of the carbon atoms in the linker group may optionally be replaced by an oxygen or nitrogen atom; and wherein the carbon atoms of the linker group A may optionally bear one or more substituents selected from oxo, fluorine and hydroxy, provided that the hydroxy group when present is not located at a carbon atom a with respect to the $NR^2R^3$ group and provided that the oxo group when present is located at a carbon atom a with respect to the $NR^2R^3$ group;

E is a monocyclic or bicyclic carbocyclic or heterocyclic group;

$R^1$ is an aryl or heteroaryl group;

$R^2$ and $R^3$ are independently selected from hydrogen, $C_{1-4}$ hydrocarbyl and $C_{1-4}$ acyl;

or $R^2$ and $R^3$ together with the nitrogen atom to which they are attached form a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the linker group A form a saturated monocyclic heterocyclic group having 4-7 ring members and optionally containing a second heteroatom ring member selected from O and N;

or $NR^2R^3$ and the carbon atom of linker group A to which it is attached together form a cyano group;

$R^4$ is selected from hydrogen, halogen, $C_{1-5}$ saturated hydrocarbyl, cyano and $CF_3$; and $R^5$ is selected from hydrogen, halogen, $C_{1-5}$ saturated hydrocarbyl, cyano, $CONH_2$, $CONHR^9$, $CF_3$, $NH_2$, $NHCOR^9$ or $NHCONHR^9$;

$R^9$ is phenyl or benzyl each optionally substituted by one or more substituents selected from halogen, hydroxy, trifluoromethyl, cyano, nitro, carboxy, amino, mono- or di-$C_{1-4}$ hydrocarbylamino; a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$.

Also provided are combinations of an ancillary compound (e.g. one, two or more ancillary compounds) and compounds of the general formula (Ib):

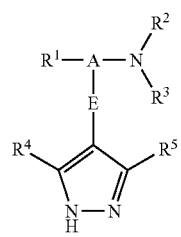

(Ib)

or salts, solvates, tautomers or N-oxides thereof;

wherein A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$, wherein one of the carbon atoms in the linker group may optionally be replaced by an oxygen or nitrogen atom; and wherein the carbon atoms of the linker group A may optionally bear one or more substituents selected from fluorine and hydroxy, provided that the hydroxy group is not located at a carbon atom a with respect to the $NR^2R^3$ group;

E is a monocyclic or bicyclic carbocyclic or heterocyclic group;

$R^1$ is an aryl or heteroaryl group;

$R^2$ and $R^3$ are independently selected from hydrogen, $C_{1-4}$ hydrocarbyl and $C_{1-4}$ acyl;

or $R^2$ and $R^3$ together with the nitrogen atom to which they are attached form a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the linker group A form a saturated monocyclic heterocyclic group having 4-7 ring members and optionally containing a second heteroatom ring member selected from O and N;

or $NR^2R^3$ and the carbon atom of linker group A to which it is attached together form a cyano group;

$R^4$ is selected from hydrogen, halogen, $C_{1-5}$ saturated hydrocarbyl, cyano, and $CF_3$; and $R^5$ is selected from selected from hydrogen, halogen, $C_{1-5}$ saturated hydrocarbyl, cyano, $CONH_2$, $CF_3$, $NH_2$, $NHCOR^9$ or $NHCONHR^9$;

$R^9$ is phenyl or benzyl each optionally substituted by one or substituents selected from halogen, hydroxy, trifluoromethyl, cyano, nitro, carboxy, amino, mono- or di-$C_{14}$ hydrocarbylamino; a group $R^a$—$R^b$ wherein $R^a$ is a bond, O, CO, $X^1C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-5}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$, is =O, =S or =$NR^c$.

The invention further provides:

A combination of an ancillary compound (e.g. one, two or more ancillary compounds) and a compound per se of the formula (II), (III), (IV), (V) or any other sub-group or embodiment of the formula (I) as defined herein.

A combination of an ancillary compound (e.g. one, two or more ancillary compounds) and a compound of the formula (I), (Ia), (Ib), (II), (III), (IV), (V) or any sub-group thereof as defined herein for use in the prophylaxis or treatment of a disease state or condition mediated by protein kinase B.

The use of a combination of an ancillary compound (e.g. one, two or more ancillary compounds) and a compound of formula (I), (Ia), (Ib), (II), (III), (IV), (V) or any sub-group thereof as defined herein for the manufacture of a medicament for the prophylaxis or treatment of a disease state or condition mediated by protein kinase B.

A method for the prophylaxis or treatment of a disease state or condition mediated by protein kinase B, which method comprises administering to a subject in need thereof a combination of an ancillary compound (e.g. one, two or more ancillary compounds) and a compound of the formula (I), (Ia), (Ib), (II), (III), (IV), (V) or any sub-group thereof as defined herein.

A method for treating a disease or condition comprising or arising from abnormal cell growth or abnormally arrested cell death in a mammal, the method comprising administering to the mammal a combination of an ancillary compound (e.g. one, two or more ancillary compounds) and a compound of the formula (I), (Ia), (Ib), (II), (III), (IV), (V) or any sub-group thereof as defined herein in an amount effective to inhibit protein kinase B activity.

A method of inhibiting protein kinase B, which method comprises contacting the kinase with a combination of an ancillary compound (e.g. one, two or more ancillary compounds) and a kinase-inhibiting compound of the formula (I), (Ia), (Ib), (II), (III), (IV), (V) or any sub-group thereof as defined herein.

A method of modulating a cellular process (for example cell division) by inhibiting the activity of a protein kinase B using a combination of an ancillary compound (e.g. one, two or more ancillary compounds) and a compound of the formula (I), (Ia), (Ib), (II), (III), (IV), (V) or any sub-group or embodiment thereof as defined herein.

A combination of an ancillary compound (e.g. one, two or more ancillary compounds) and a compound of the formula (I), (Ia), (Ib), (II), (III), (IV), (V) or any sub-group or embodiment thereof as defined herein for use in the prophylaxis or treatment of a disease state or condition mediated by protein kinase A.

The use of a combination of an ancillary compound (e.g. one, two or more ancillary compounds) and a compound of formula (I), (Ia), (Ib), (II), (III), (IV), (V) or any sub-group or embodiment thereof as defined herein for the manufacture of a medicament for the prophylaxis or treatment of a disease state or condition mediated by protein kinase A.

A method for the prophylaxis or treatment of a disease state or condition mediated by protein kinase A, which method comprises administering to a subject in need thereof a combination of an ancillary compound (e.g. one, two or more ancillary compounds) and a compound of the formula (I), (Ia), (Ib), (II), (III), (IV), (V) or any sub-group or embodiment thereof as defined herein.

A method for treating a disease or condition comprising or arising from abnormal cell growth or abnormally arrested cell death in a mammal, the method comprising administering to the mammal a combination of an ancillary compound (e.g. one, two or more ancillary compounds) and a compound of the formula (I), (Ia), (Ib), (II), (III), (IV), (V) or any sub-group or embodiment thereof as defined herein in an amount effective to inhibit protein kinase A activity.

A method of inhibiting protein kinase A, which method comprises contacting the kinase with a combination of an ancillary compound (e.g. one, two or more ancillary compounds) and a kinase-inhibiting compound of the formula (I), (Ia), (Ib), (II), (III), (IV), (V) or any sub-group or embodiment thereof as defined herein.

A method of modulating a cellular process (for example cell division) by inhibiting the activity of a protein kinase A using a combination of an ancillary compound (e.g. one, two or more ancillary compounds) and a compound of the formula (I), (Ia), (Ib), (II), (III), (IV), (V) or any sub-group or embodiment thereof as defined herein.

The use of a combination of an ancillary compound (e.g. one, two or more ancillary compounds) and a compound of the formula (I), (Ia), (Ib), (II), (III), (IV), (V) or any sub-group thereof as defined herein for the manufacture of a medicament for the prophylaxis or treatment of a disease state or condition arising from abnormal cell growth or abnormally arrested cell death.

A method for treating a disease or condition comprising or arising from abnormal cell growth in a mammal, which method comprises administering to the mammal a combination of an ancillary compound (e.g. one, two or more ancillary compounds) and a compound of the formula (I), (Ia), (Ib), (II), (III), (IV), (V) or any sub-group thereof as defined herein in an amount effective in inhibiting abnormal cell growth or abnormally arrested cell death.

A method for alleviating or reducing the incidence of a disease or condition comprising or arising from abnormal cell growth or abnormally arrested cell death in a mammal, which method comprises administering to the mammal a combination of an ancillary compound (e.g. one, two or more ancillary compounds) and a compound of the formula (I), (Ia), (Ib), (II), (III), (IV), (V) or any sub-group thereof as defined herein in an amount effective in inhibiting abnormal cell growth.

A pharmaceutical composition comprising a combination of an ancillary compound (e.g. one, two or more ancillary compounds) and a novel compound of the formula (I), (Ia), (Ib), (II), (III), (IV), (V) or any sub-group thereof as defined herein and a pharmaceutically acceptable carrier.

A combination of an ancillary compound (e.g. one, two or more ancillary compounds) and a compound of the formula (I), (Ia), (Ib), (II), (III), (IV), (V) or any sub-group thereof as defined herein for use in medicine.

The use of a combination of an ancillary compound (e.g. one, two or more ancillary compounds) and a compound of the formula (I), (Ia), (Ib), (II), (III), (IV), (V) or any sub-group thereof as defined herein for the manufacture of a medicament for the prophylaxis or treatment of any one of the disease states or conditions disclosed herein.

A method for the treatment or prophylaxis of any one of the disease states or conditions disclosed herein, which method comprises administering to a patient (e.g. a patient in need thereof) a combination of an ancillary compound (e.g. one, two or more ancillary compounds)

and a compound (e.g. a therapeutically effective amount) of the formula (I), (Ia), (Ib), (II), (III), (IV), (V) or any sub-group thereof as defined herein.

A method for alleviating or reducing the incidence of a disease state or condition disclosed herein, which method comprises administering to a patient (e.g. a patient in need thereof) a combination of an ancillary compound (e.g. one, two or more ancillary compounds) and a compound (e.g. a therapeutically effective amount) of the formula (I), (Ia), (Ib), (II), (III), (IV), (V) or any sub-group thereof as defined herein.

A method for the diagnosis and treatment of a disease state or condition mediated by protein kinase B, which method comprises (i) screening a patient to determine whether a disease or condition from which the patient is or may be suffering is one which would be susceptible to treatment with a compound having activity against protein kinase B; and (ii) where it is indicated that the disease or condition from which the patient is thus susceptible, thereafter administering to the patient a combination of an ancillary compound (e.g. one, two or more ancillary compounds) and a compound of the formula (I), (Ia), (Ib), (II), (III), (IV), (V) or any sub-group thereof as defined herein.

The use of a combination of an ancillary compound (e.g. one, two or more ancillary compounds) and a compound of the formula (I), (Ia), (Ib), (II), (III), (IV), (V) or any sub-group thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against protein kinase B.

A method for the diagnosis and treatment of a disease state or condition mediated by protein kinase A, which method comprises (i) screening a patient to determine whether a disease or condition from which the patient is or may be suffering is one which would be susceptible to treatment with a compound having activity against protein kinase A; and (ii) where it is indicated that the disease or condition from which the patient is thus susceptible, thereafter administering to the patient a combination of an ancillary compound (e.g. one, two or more ancillary compounds) and a compound of the formula (I), (Ia), (Ib), (II), (III), (IV), (V) or any sub-group or embodiment thereof as defined herein.

The use of a combination of an ancillary compound (e.g. one, two or more ancillary compounds) and a compound of the formula (I), (Ia), (Ib), (II), (III), (IV), (V) or any sub-group or embodiment thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against protein kinase A.

The invention also provides the further combinations, uses, methods, compounds and processes as set out in the claims below, including:

A combination comprising (or consisting essentially of) an ancillary compound and a compound of the formula (I) as defined herein wherein the ancillary compound and compound of formula (I) are physically associated.

A combination comprising (or consisting essentially of) an ancillary compound and a compound of the formula (I) as defined herein wherein the ancillary compound and compound of formula (I) are non-physically associated.

A combination comprising (or consisting essentially of) an ancillary compound and a compound of the formula (I) as defined herein in the form of a pharmaceutical pack, kit or patient pack.

A compound of the formula (I) as defined herein for use in the prophylaxis or treatment of a disease state or condition mediated by protein kinase B in a subject undergoing treatment with an ancillary compound.

The use of a compound of the formula (I) as defined herein for the manufacture of a medicament for the prophylaxis or treatment of a disease state or condition mediated by protein kinase B in a subject undergoing treatment with an ancillary compound.

A method for the prophylaxis or treatment of a disease state or condition mediated by protein kinase B, which method comprises administering to a subject in need thereof a compound of the formula (I) as defined herein, wherein the subject is undergoing treatment with an ancillary compound.

A method for treating a disease or condition comprising or arising from abnormal cell growth in a mammalian subject, which subject is undergoing treatment with an ancillary compound, the method comprising administering a compound of the formula (I) as defined herein in an amount effective to inhibit abnormal cell growth.

A method for treating a disease or condition comprising or arising from abnormal cell growth in a mammalian subject, which subject is undergoing treatment with an ancillary compound, the method comprising administering to the mammal a compound of the formula (I) as defined herein in an amount effective to inhibit PKB activity.

A method for treating an immune disorder in a mammalian subject, which subject is undergoing treatment with an ancillary compound, the method comprising administering to the mammal a compound of the formula (I) as defined herein in an amount effective to inhibit PKB activity.

A compound of the formula (I) defined herein for use in the prophylaxis or treatment of a disease state or condition mediated by protein kinase A in a subject undergoing treatment with an ancillary compound.

The use of a compound of the formula (I) as defined herein for the manufacture of a medicament for the prophylaxis or treatment of a disease state or condition mediated by protein kinase A in a subject undergoing treatment with an ancillary compound.

The use of a compound of the formula (I) as defined herein for the manufacture of a medicament for the prophylaxis or treatment of a disease state or condition arising from abnormal cell growth in a subject undergoing treatment with an ancillary compound.

The use of a compound of the formula (I) as defined herein for the manufacture of a medicament for the prophylaxis or treatment of a disease in which there is a disorder of proliferation, apoptosis or differentiation in a subject undergoing treatment with an ancillary compound.

A method for the prophylaxis or treatment of a disease state or condition mediated by protein kinase A in a subject undergoing treatment with an ancillary compound, which method comprises administering to the subject a compound of the formula (I) as defined herein.

A method for treating a disease or condition comprising or arising from abnormal cell growth in a mammalian subject undergoing treatment with an ancillary compound, the method comprising administering to the subject a compound of the formula (I) as defined herein in an amount effective to inhibit PKA.

A method of inhibiting a protein kinase A in a subject undergoing treatment with an ancillary compound, which method comprises contacting the kinase with a kinase-inhibiting compound of the formula (I) as defined herein.

A method of modulating a cellular process in a subject undergoing treatment with an ancillary compound by inhibiting the activity of a protein kinase A using a compound of the formula (I) as defined herein.

A method for treating an immune disorder in a mammalian subject undergoing treatment with an ancillary compound, the method comprising administering to the mammal a compound of the formula (I) as defined herein in an amount effective to inhibit PKA activity.

A method of inducing apoptosis in a cancer cell in a subject undergoing treatment with an ancillary compound, which method comprises contacting the cancer cell with a compound of the formula (I) as defined herein.

An ancillary compound (e.g. an ancillary compound selected from any of the ancillary compounds disclosed herein) for use in combination therapy with a compound of the formula (I) as defined herein.

A compound of the formula (I) as defined herein for use in combination therapy with an ancillary compound (e.g. an ancillary compound selected from any of the ancillary compounds disclosed herein).

Use of an ancillary compound (e.g. an ancillary compound selected from any of the ancillary compounds disclosed herein) for the manufacture of a medicament for use in the treatment or prophylaxis of a patient undergoing treatment with a compound of the formula (I) as defined herein.

Use of a compound of the formula (I) as defined herein for the manufacture of a medicament for use in the treatment or prophylaxis of a patient undergoing treatment with an ancillary compound (e.g. an ancillary compound selected from any of the ancillary compounds disclosed herein).

A method for the treatment of a cancer in a warm-blooded animal such as a human, which comprises administering to said animal an effective amount of an ancillary compound (e.g. an ancillary compound selected from any of the ancillary compounds disclosed herein) sequentially e.g. before or after, or simultaneously with an effective amount of a compound of the formula (I) as defined herein.

A method of combination cancer therapy in a mammal comprising administering a therapeutically effective amount of an ancillary compound (e.g. an ancillary compound selected from any of the ancillary compounds disclosed herein) and a therapeutically effective amount of a compound of the formula (I) as defined herein.

A compound of the formula (I) as defined herein for use in combination therapy with an ancillary compound (e.g. an ancillary compound selected from any of the ancillary compounds disclosed herein) to alleviate or reduce the incidence of a disease or condition comprising or arising from abnormal cell growth in a mammal.

A compound of the formula (I) as defined herein for use in combination therapy with an ancillary compound (e.g. an ancillary compound selected from any of the ancillary compounds disclosed herein) to inhibit tumour growth in a mammal.

A compound of the formula (I) as defined herein for use in combination therapy with an ancillary compound (e.g. an ancillary compound selected from any of the ancillary compounds disclosed herein) to prevent, treat or manage cancer in a patient in need thereof.

A compound of the formula (I) as defined herein for use in enhancing or potentiating the response rate in a patient suffering from a cancer where the patient is being treated with an ancillary compound (e.g. an ancillary compound selected from any of the ancillary compounds disclosed herein).

A method of enhancing or potentiating the response rate in a patient suffering from a cancer where the patient is being treated with an ancillary compound (e.g. an ancillary compound selected from any of the ancillary compounds disclosed herein), which method comprises administering to the patient, in combination with the ancillary compound, a compound of the formula (I) as defined herein.

A process for the production of a combination comprising (or consisting essentially of) an ancillary compound and a compound of the formula (I) as defined herein, which process comprises combining a compound of formula I with an ancillary compound.

BRIEF DESCRIPTION OF THE DRAWING

FIG. 1. depicts results from an $IC_{50}$ shift assay run using 4-(4-Chloro-phenyl)-4-[4-(1H-pyrazol-4-yl)-phenyl]-piperidine as compound I and gefitinib (Iressa) as compound II.

GENERAL PREFERENCES AND DEFINITIONS

As used herein, the term "modulation", as applied to PKB and/or PKA activity, is intended to define a change in the level of biological activity of the PKB and/or PKA enzyme(s). Thus, modulation encompasses physiological changes which effect an increase or decrease in PKA and/or PKB activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of PKA and/or PKB activity, or at the level of enzyme (e.g. PKB and/or PKA) activity (for example by allosteric mechanisms, competitive inhibition, active-site inactivation, perturbation of feedback inhibitory pathways etc.). Thus, modulation may imply elevated/suppressed expression or over- or under-expression of the PKA and/or PKB, including gene amplification (i.e. multiple gene copies) and/or increased or decreased expression by a transcriptional effect, as well as hyper- (or hypo-)activity and (de)activation of the PKA and/or PKB (including (de)activation) by mutation(s). The terms "modulated" and "modulate" are to be interpreted accordingly.

As used herein, the term "mediated", as used e.g. in conjunction with the PKB and/or PKAs as described herein (and applied for example to various physiological processes, diseases, states, conditions, therapies, treatments or interventions) is intended to operate limitatively so that the various processes, diseases, states, conditions, treatments and interventions to which the term is applied are those in which PKA and/or PKB plays a biological role. In cases where the term is applied to a disease, state or condition, the role played by PKA and/or PKB may be direct or indirect and may be necessary and/or sufficient for the manifestation of the symptoms of the disease, state or condition (or its aetiology or progression). Thus, PKA and/or PKB activity (and in particular aberrant levels of PKA and/or PKB activity, e.g. PKA and/or PKB over-expression) need not necessarily be the proximal cause of the disease, state or condition: rather, it is contemplated that PKA- and/or PKB-mediated diseases, states or conditions include those having multifactorial aetiologies and complex progressions in which PKA and/or PKB is only partially involved. In cases where the term is applied to treatment, prophylaxis or intervention (e.g. in the "PKB-mediated treatments" and "PKB-mediated prophylaxis" of the invention), the role played by PKA and/or PKB may be direct or indirect and may be necessary and/or sufficient for the operation of the treatment, prophylaxis or outcome of the intervention.

The term "intervention" is a term of art used herein to define any agency which effects a physiological change at any level. Thus, the intervention may comprises the induction or repression of any physiological process, event, biochemical pathway or cellular/biochemical event. The interventions of the invention typically effect (or contribute to) the therapy, treatment or prophylaxis of a disease or condition.

The following general preferences and definitions shall apply to each of the moieties A, E and $R^1$ to $R^5$ and $R^9$ and any sub-definition, sub-group or embodiment thereof, unless the context indicates otherwise.

Any references to Formula (I) herein shall be taken also to refer to formulae (Ia), (Ib), (II), (III), (IV), (V) and any other sub-group of compounds within formula (I) unless the context requires otherwise.

References to "carbocyclic" and "heterocyclic" groups as used herein shall, unless the context indicates otherwise, include both aromatic and non-aromatic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups $R^{10}$ as defined herein.

The term non-aromatic group embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings. Each ring may contain up to about four heteroatoms typically selected from nitrogen, sulphur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a a 5- or 6-membered ring containing 1, 2 or 3 ring heteroatoms;
e) a pyrazole ring fused to a a 5- or 6-membered ring containing 1 or 2 ring heteroatoms;
f) an imidazole ring fused to a 5- or 6-membered ring containing 1 or 2 ring heteroatoms;
g) an oxazole ring fused to a 5- or 6-membered ring containing 1 or 2 ring heteroatoms;
h) an isoxazole ring fused to a 5- or 6-membered ring containing 1 or 2 ring heteroatoms;
i) a thiazole ring fused to a 5- or 6-membered ring containing 1 or 2 ring heteroatoms;
j) an isothiazole ring fused to a 5- or 6-membered ring containing 1 or 2 ring heteroatoms;
k) a thiophene ring fused to a 5- or 6-membered ring containing 1, 2 or 3 ring heteroatoms;
l) a furan ring fused to a 5- or 6-membered ring containing 1, 2 or 3 ring heteroatoms;
m) an oxazole ring fused to a 5- or 6-membered ring containing 1 or 2 ring heteroatoms;
n) an isoxazole ring fused to a 5- or 6-membered ring containing 1 or 2 ring heteroatoms;
o) a cyclohexyl ring fused to a 5- or 6-membered ring containing 1, 2 or 3 ring heteroatoms; and
p) a cyclopentyl ring fused to a 5- or 6-membered ring containing 1, 2 or 3 ring heteroatoms.

Examples of bicyclic heteroaryl groups containing a six membered ring fused to a five membered ring include but are not limited to benzfuran, benzthiophene, benzimidazole, benzoxazole, benzisoxazole, benzthiazole, benzisothiazole, isobenzofuran, indole, isoindole, indolizine, indoline, isoindoline, purine (e.g., adenine, guanine), indazole, benzodioxole and pyrazolopyridine groups.

Examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur.

The heterocyclic groups can contain, for example, cyclic ether moieties (e.g as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulfolane and sulfolene), cyclic sulphoxides, cyclic sulphonamides and combinations thereof (e.g. thiomorpholine). Other examples of non-aromatic heterocyclic groups include cyclic amide moieties (e.g. as in pyrrolidone) and cyclic ester moieties (e.g. as in butyrolactone).

Examples of monocyclic non-aromatic heterocyclic groups include 5-, 6- and 7-membered monocyclic heterocyclic groups. Particular examples include morpholine, thiomorpholine and its S-oxide and S,S-dioxide (particularly thiomorpholine), piperidine (e.g. 1-piperidinyl, 2-piperidinyl 3-piperidinyl and 4-piperidinyl piperidines such as N-methyl piperidine, piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine, N-ethyl piperazine and N-isopropylpiperazine.

One sub-group of monocyclic non-aromatic heterocyclic groups includes morpholine, piperidine (e.g. 1-piperidinyl, 2-piperidinyl 3-piperidinyl and 4-piperidinyl), piperidone, pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclic groups include piperidine, pyrrolidine, azetidine, morpholine, piperazine and N-alkyl piperazines. A further particular example of a non-aromatic heterocyclic group, which also forms part of the above group of preferred non-aromatic heterocyclic groups, is azetidine.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Each of the definitions of carbocyclic and heterocyclic groups in this specification may optionally exclude any one or any combination of two or more of the following moieties:
  substituted or unsubstituted pyridone rings;
  substituted or unsubstituted pyrrolo[1,2-a]pyrimid-4-ones;
  substituted or unsubstituted pyrazolones.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a—R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is $=O$, $=S$ or $=NR^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 10, or 9, or 8, or 7, or 6, or 5 non-hydrogen atoms.

Where the carbocyclic and heterocyclic groups have a pair of substituents on adjacent ring atoms, the two substituents may be linked so as to form a cyclic group. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group. Examples of such linked substituent groups include:

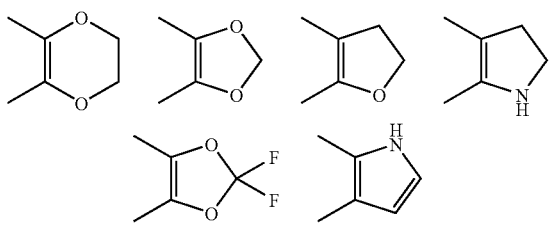

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone, except where otherwise stated. In certain cases, as defined herein, one or more of the carbon atoms making up the carbon backbone may be replaced by a specified atom or group of atoms. Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, can be substituted by one or more substituents as defined herein. The examples and preferences expressed below apply to each of the hydrocarbyl substituent groups or hydrocarbyl-containing substituent groups referred to in the various definitions of substituents for compounds of the formula (I) unless the context indicates otherwise.

Generally by way of example, the hydrocarbyl groups can have up to eight carbon atoms, unless the context requires otherwise. Within the sub-set of hydrocarbyl groups having 1 to 8 carbon atoms, particular examples are $C_{1-6}$ hydrocarbyl groups, such as $C_{1-4}$ hydrocarbyl groups (e.g. $C_{1-3}$ hydrocarbyl groups or $C_{1-2}$ hydrocarbyl groups), specific examples being any individual value or combination of values selected from $C_1$, $C_2$, $C_3$, $C_4$, $C_5$, $C_6$, $C_7$ and $C_8$ hydrocarbyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-6}$ cycloalkyl groups.

Examples of alkenyl groups include, but are not limited to, ethenyl (vinyl), 1-propenyl, 2-propenyl(allyl), isopropenyl, butenyl, buta-1,4-dienyl, pentenyl, and hexenyl. Within the sub-set of alkenyl groups the alkenyl group will have 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

Examples of alkynyl groups include, but are not limited to, ethynyl and 2-propynyl (propargyl) groups. Within the sub-set of alkynyl groups having 2 to 8 carbon atoms, particular examples are $C_{2-6}$ alkynyl groups, such as $C_{2-4}$ alkynyl groups.

Examples of carbocyclic aryl groups include substituted and unsubstituted phenyl, naphthyl, indane and indene groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members.

The definition "$R^a$—$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, $OC(NR^c)$, $SC(NR^c)$, $NR^cC(NR^c)$, C(O)O, C(O)S, $C(O)NR^c$, C(S)O, C(S)S, $C(S)NR^c$, $C(NR^c)O$, $C(NR^c)S$, $C(NR^c)NR^c$, OC(O)O, SC(O)O, $NR^cC(O)O$, OC(S)O, SC(S)O, $NR^cC(S)$ O, $OC(NR^c)O$, $SC(NR^c)O$, $NR^cC(NR^c)O$, OC(O)S, SC(O)S, $NR^cC(O)S$, OC(S)S, SC(S)S, $NR^cC(S)S$, $OC(NR^c)S$, $SC(NR^c)S$, $NR^cC(NR^c)S$, $OC(O)NR^c$, $SC(O)NR^c$, $NR^cC(O)NR^c$, $OC(S)NR^c$, $SC(S)NR^c$, $NR^cC(S)NR^c$, $OC(NR^c)NR^c$, $SC(NR^c)NR^c$, $NR^cC(NR^cNR^c$, S, SO, $SO_2$, $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-8}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups may be substituted by, for example, a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-8}$ hydrocarbyl group, examples of hydrocarbyl groups $R^a$—$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl, difluoromethyl, 2,2,2-trifluoroethyl and perfluoroalkyl groups such as trifluoromethyl), or hydroxy (e.g. hydroxymethyl and hydroxyethyl), $C_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl, phenethyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$—$R^b$ where $R^a$ is $SO_2NR^c$ include aminosulphonyl, $C_{1-4}$ alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$—$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-8}$ hydrocarbyl group, or a carbocyclic or heterocyclic group. Examples of $R^a$—$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Specific Embodiments of and Preferences for A, E, $R^1$ to $R^5$ and $R^9$

The Group "A"

In formula (I), A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$. Within these constraints, the moieties E and $R^1$ can each be attached at any location on the group A.

The term "maximum chain length" as used herein refers to the number of atoms lying directly between the two moieties in question, and does not take into account any branching in the chain or any hydrogen atoms that may be present. For example, in the structure A shown below:

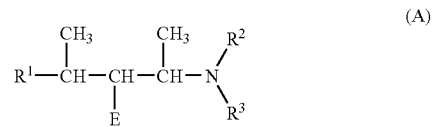

the chain length between $R^1$ and $NR^2R^3$ is 3 atoms whereas the chain length between E and $NR^2R^3$ is 2 atoms.

In general it is presently preferred that the linker group has a maximum chain length of 3 atoms (for example 1 or 2 atoms).

In one embodiment, the linker group has a chain length of 1 atom extending between $R^1$ and $NR^2R^3$.

In another embodiment, the linker group has a chain length of 2 atoms extending between $R^1$ and $NR^2R^3$.

In a further embodiment, the linker group has a chain length of 3 atoms extending between $R^1$ and $NR^2R^3$.

It is preferred that the linker group has a maximum chain length of 3 atoms extending between E and $NR^2R^3$.

In one particularly preferred group of compounds, the linker group has a chain length of 2 or 3 atoms extending between $R^1$ and $NR^2R^3$ and a chain length of 2 or 3 atoms extending between E and $NR^2R^3$.

One of the carbon atoms in the linker group may optionally be replaced by an oxygen or nitrogen atom.

When present, the nitrogen atom may be linked directly to the group E.

In one embodiment, the carbon atom to which the group $R^1$ is attached is replaced by an oxygen atom.

In another embodiment, $R^1$ and E are attached to the same carbon atom of the linker group, and a carbon atom in the chain extending between E and $NR^2R^3$ is replaced by an oxygen atom.

When a nitrogen atom or oxygen atom are present, it is preferred that the nitrogen or oxygen atom and the $NR^2R^3$ group are spaced apart by at least two intervening carbon atoms.

In one particular group of compounds within formula (I), the linker atom linked directly to the group E is a carbon atom and the linker group A has an all-carbon skeleton.

The carbon atoms of the linker group A may optionally bear one or more substituents selected from oxo, fluorine and hydroxy, provided that the hydroxy group is not located at a carbon atom with respect to the $NR^2R^3$ group, and provided also that the oxo group is located at a carbon atom with respect to the $NR^2R^3$ group. Typically, the hydroxy group, if present, is located at a position β with respect to the $NR^2R^3$ group. In general, no more than one hydroxy group will be present. Where fluorine is present, it may be present as a single fluorine substituent or may be present in a difluoromethylene or trifluoromethyl group, for example. In one embodiment, a fluorine atom is located at a position β with respect to the $NR^2R^3$ group.

It will be appreciated that that when an oxo group is present at the carbon atom adjacent the $NR^2R^3$ group, the compound of the formula (I) will be an amide.

In one embodiment of the invention, no fluorine atoms are present in the linker group A.

In another embodiment of the invention, no hydroxy groups are present in the linker group A.

In a further embodiment, no oxo group is present in the linker group A.

In one group of compounds of the formula (I) neither hydroxy groups nor fluorine atoms are present in the linker group A, e.g. the linker group A is unsubstituted.

Preferably, when a carbon atom in the linker group A is replaced by a nitrogen atom, the group A bears no more than one hydroxy substituent and more preferably bears no hydroxy substituents.

When there is a chain length of four atoms between E and $NR^2R^3$, it is preferred that the linker group A contains no nitrogen atoms and more preferably has an all carbon skeleton.

In order to modify the susceptibility of the compounds to metabolic degradation in vivo, the linker group A can have a branched configuration at the carbon atom attached to the $NR^2R^3$ group. For example, the carbon atom attached to the $NR^2R^3$ group can be attached to a pair of gem-dimethyl groups.

In one particular group of compounds of the formula (I), the portion $R^1$-A-$NR^2R^3$ of the compound is represented by the formula $R^1$-$(G)_k$-$(CH_2)_m$—W—$O_b$—$(CH_2)_n$—$(CR^6R^7)_p$—$NR^2R^3$ wherein G is NH, NMe or O; W is attached to the group E and is selected from $(CH_2)_j$—$CR^{20}$, $(CH_2)_j$—N and $(NH)_j$—CH; b is 0 or 1, j is 0 or 1, k is 0 or 1, m is 0 or 1, n is 0, 1, 2, or 3 and p is 0 or 1; the sum of b and k is 0 or 1; the sum of j, k, m, n and p does not exceed 4; $R^6$ and $R^7$ are the same or different and are selected from methyl and ethyl, or $CR^6R^7$ forms a cyclopropyl group; and $R^{20}$ is selected from hydrogen, methyl, hydroxy and fluorine;

In another sub-group of compounds of the formula (I), the portion $R^1$-A-$NR^2R^3$ of the compound is represented by the formula $R^1$-$(G)_k$-$(CH_2)_m$—X—$(CH_2)_n$—$(CR^8R^7)_p$—$NR^2R^3$ wherein G is NH, NMe or O; X is attached to the group E and is selected from $(CH_2)_j$—CH, $(CH_2)_j$—N and $(NH)_j$—CH; j is 0 or 1, k is 0 or 1, m is 0 or 1, n is 0, 1, 2, or 3 and p is 0 or 1, and the sum of j, k, m, n and p does not exceed 4; and $R^6$ and $R^7$ are the same or different and are selected from methyl and ethyl, or $CR^6R^7$ forms a cyclopropyl group.

A particular group $CR^6R^7$ is $C(CH_3)_2$.

Preferably X is $(CH_2)_j$—CH.

Particular configurations where the portion $R^1$-A-$NR^2R^3$ of the compound is represented by the formula $R^1$-$(G)_k$-$(CH_2)_m$—X—$(CH_2)_n$—$(CR^6R^7)_p$—$NR^2R^3$ are those wherein:

k is 0, m is 0 or 1, n is 0, 1, 2 or 3 and p is 0.
k is 0, m is 0 or 1, n is 0, 1 or 2 and p is 1.
X is $(CH_2)_j$—CH, k is 1, m is 0, n is 0, 1, 2 or 3 and p is 0.
X is $(CH_2)_j$—CH, k is 1, m is 0, n is 0, 1 or 2 and p is 1.
X is $(CH_2)_j$—CH, G is O, k is 1, m is 0, n is 0, 1, 2 or 3 and p is 0.

Particular configurations wherein the portion $R^1$-A-$NR^2R^3$ of the compound is represented by the formula $R^1$-$(G)_k$-$(CH_2)_m$—W—$O_b$—$(CH_2)_n$—$(CR^6R^7)_p$—$NR^2R^3$ are those wherein:

k is 0, m is 0, W is $(CH_2)_j$—$CR^{20}$, j is 0, $R^{20}$ is hydrogen, b is 1, n is 2 and p is 0.
k is 0, m is 0, W is $(CH_2)_j$—$CR^{20}$, j is 0, $R^{20}$ is hydroxy, b is 0, n is 1 and p is 0.
k is 0, m is 0, W is $(CH_2)_j$—$CR^{20}$, j is 0, $R^{20}$ is methyl, b is 0, n is 1 and p is 0.
k is 0, m is 0, W is $(CH_2)_j$—$CR^{20}$, j is 0, $R^{20}$ is fluorine, b is 0, n is 1 and p is 0.

In one preferred configuration, the portion $R^1$-A-$NR^2R^3$ of the compound is represented by the formula $R^1$—X—$(CH_2)_n$—$NR^2R^3$ wherein X is attached to the group E and is a group CH, and n is 2.

Particular examples of the linker group A, together with their points of attachment to the groups $R^1$, E and $NR^2R^3$, are shown in Table 1 below.

TABLE 1

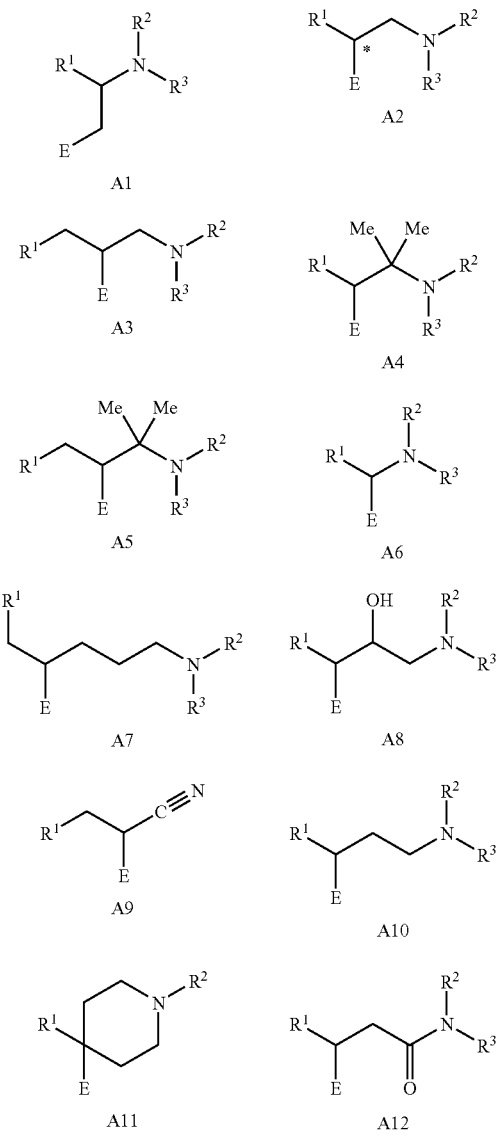

TABLE 1-continued

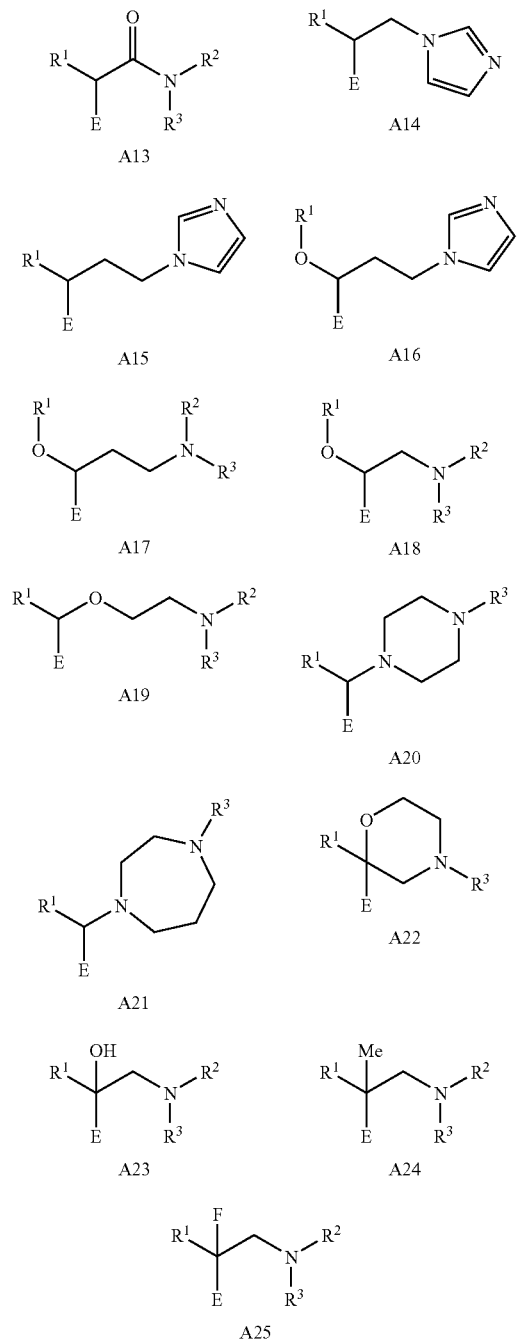

Currently preferred groups include A1, A2, A3, A6, A10, A11, A22 and A23.

One particular set of groups includes A1, A2, A3, A10 and A11.

A further particular set of groups includes A2 and A11.

Another particular set of groups includes A6, A22 and A23.

A further set of groups includes A1, A2 and A3.

In group A2, the asterisk designates a chiral centre. Compounds having the R configuration at this chiral centre represent one preferred sub-group of compounds of the invention.

$R^1$

The group $R^1$ is an aryl or heteroaryl group and may be selected from the list of such groups set out in the section headed General Preferences and Definitions.

$R^1$ can be monocyclic or bicyclic and, in one preferred embodiment, is monocyclic. Particular examples of monocyclic aryl and heteroaryl groups are six membered aryl and heteroaryl groups containing up to 2 nitrogen ring members, and five membered heteroaryl groups containing up to 3 heteroatom ring members selected from O, S and N.

Examples of such groups include phenyl, naphthyl, thienyl, furan, pyrimidine and pyridine, with phenyl being presently preferred.

The group $R^1$ can be unsubstituted or substituted by up to 5 substituents, and examples of substituents are those listed in group $R^{10}$ above.

Particular substituents include hydroxy; $C_{1-4}$ acyloxy; fluorine; chlorine; bromine; trifluoromethyl; cyano; $CONH_2$; nitro; $C_{1-4}$ hydrocarbyloxy and $C_{1-4}$ hydrocarbyl each optionally substituted by $C_{1-2}$ alkoxy, carboxy or hydroxy; $C_{1-4}$ acylamino; benzoylamino; pyrrolidinocarbonyl; piperidinocarbonyl; morpholinocarbonyl; piperazinocarbonyl; five and six membered heteroaryl and heteroaryloxy groups containing one or two heteroatoms selected from N, O and S; phenyl; phenyl-$C_{1-4}$ alkyl; phenyl-$C_{1-4}$ alkoxy; heteroaryl-$C_{1-4}$ alkyl; heteroaryl-$C_{1-4}$ alkoxy and phenoxy, wherein the heteroaryl, heteroaryloxy, phenyl, phenyl-$C_{1-4}$ alkyl, phenyl-$C_{1-4}$ alkoxy, heteroaryl-$C_{1-4}$ alkyl, heteroaryl-$C_{1-4}$ alkoxy and phenoxy groups are each optionally substituted with 1, 2 or 3 substituents selected from $C_{1-2}$ acyloxy, fluorine, chlorine, bromine, trifluoromethyl, cyano, $CONH_2$, $C_{1-2}$ hydrocarbyloxy and $C_{1-2}$ hydrocarbyl each optionally substituted by methoxy or hydroxy.

Preferred substituents include hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy; $C_{1-4}$ acylamino; benzoylamino; pyrrolidinocarbonyl; piperidinocarbonyl; morpholinocarbonyl; piperazinocarbonyl; five and six membered heteroaryl groups containing one or two heteroatoms selected from N, O and S, the heteroaryl groups being optionally substituted by one or more $C_{1-4}$ alkyl substituents; phenyl; pyridyl; and phenoxy wherein the phenyl, pyridyl and phenoxy groups are each optionally substituted with 1, 2 or 3 substituents selected from $C_{1-2}$ acyloxy, fluorine, chlorine, bromine, trifluoromethyl, cyano, $C_{1-2}$ hydrocarbyloxy and $C_{1-2}$ hydrocarbyl each optionally substituted by methoxy or hydroxy.

In one sub-group of compounds, the substituents for $R^1$ are chosen from hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy.

Although up to 5 substituents may be present, more typically there are 0, 1, 2, 3 or 4 substituents, preferably 0, 1, 2 or 3, and more preferably 0, 1 or 2.

In one embodiment, the group $R^1$ is unsubstituted or substituted by up to 5 substituents selected from hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy.

In a further embodiment, the group $R^1$ can have one or two substituents selected from hydroxy, fluorine, chlorine, cyano, phenyloxy, pyrazinyloxy, benzyloxy, methyl and methoxy.

In another embodiment, the group $R^1$ can have one or two substituents selected from fluorine, chlorine, trifluoromethyl, methyl and methoxy.

When $R^1$ is a phenyl group, particular examples of substituent combinations include mono-chlorophenyl and dichlorophenyl.

Further examples of substituent combinations include those wherein $R^1$ is hydroxyphenyl, fluorochlorophenyl, cyanophenyl, methoxyphenyl, methoxy-chlorophenyl, fluorophenyl, difluorophenyl, phenoxyphenyl, pyrazinyloxyphenyl or benzyloxyphenyl.

When $R^1$ is a six membered aryl or heteroaryl group, a substituent may advantageously be present at the para position on the six-membered ring. Where a substituent is present at the pare position, it is preferably larger in size than a fluorine atom.

$R^2$ and $R^3$

In one group of compounds of the formula (I), $R^2$ and $R^3$ are independently selected from hydrogen, $C_{1-4}$ hydrocarbyl and $C_{1-4}$ acyl wherein the hydrocarbyl and acyl moieties are optionally substituted by one or more substituents selected from fluorine, hydroxy, amino, methylamino, dimethylamino and methoxy.

When the hydrocarbyl moiety is substituted by a hydroxy, amino, methylamino, dimethylamino or methoxy group, typically there are at least two carbon atoms between the substituent and the nitrogen atom of the group $NR^2R^3$. Particular examples of substituted hydrocarbyl groups are hydroxyethyl and hydroxypropyl.

In another group of compounds of the invention, $R^2$ and $R^3$ are independently selected from hydrogen, $C_{1-4}$ hydrocarbyl and $C_{1-4}$ acyl.

Typically the hydrocarbyl group, whether substituted or unsubstituted, is an alkyl group, more usually a $C_1$, $C_2$ or $C_3$ alkyl group, and preferably a methyl group. In one particular sub-group of compounds, $R^2$ and $R^3$ are independently selected from hydrogen and methyl and hence $NR^2R^3$ can be an amino, methylamino or dimethylamino group. In one particular embodiment, $NR^2R^3$ can be an amino group. In another particular embodiment, $NR^2R^3$ can be a methylamino group.

In an alternative embodiment, the $C_{1-4}$ hydrocarbyl group can be a cyclopropyl, cyclopropylmethyl or cyclobutyl group.

In another group of compounds, $R^2$ and $R^3$ together with the nitrogen atom to which they are attached form a cyclic group selected from an imidazole group and a saturated monocyclic heterocyclic group having 4-7 ring members and optionally containing a second heteroatom ring member selected from 0 and N.

In a further group of compounds, $R^2$ and $R^3$ together with the nitrogen atom to which they are attached form a saturated monocyclic heterocyclic group having 4-7 ring members and optionally containing a second heteroatom ring member selected from O and N.

The saturated monocyclic heterocyclic group can be unsubstituted or substituted by one or more substituents $R^{10}$ as defined above in the General Preferences and Definitions section of this application. Typically, however, any substituents on the heterocyclic group will be relatively small substituents such as $C_{1-4}$ hydrocarbyl (e.g. methyl, ethyl, n-propyl, i-propyl, cyclopropyl, n-butyl, sec-butyl and test-butyl), fluorine, chlorine, hydroxy, amino, methylamino, ethylamino and dimethylamino. Particular substituents are methyl groups.

The saturated monocyclic ring can be an azacycloalkyl group such as an azetidine, pyrrolidine, piperidine or azepane ring, and such rings are typically unsubstituted.

Alternatively, the saturated monocyclic ring can contain an additional heteroatom selected from O and N, and examples of such groups include morpholine and piperazine. Where an additional N atom is present in the ring, this can form part of an NH group or an $N-C_{1-4}$alkyl group such as an N-methyl, N-ethyl, N-propyl or N-isopropyl group.

Where $NR^2R^3$ forms an imidazole group, the imidazole group can be unsubstituted or substituted, for example by one or more relatively small substituents such as $C_{1-4}$ hydrocarbyl (e.g. methyl, ethyl, propyl, cyclopropyl and butyl), fluorine, chlorine, hydroxy, amino, methylamino, ethylamino and dimethylamino. Particular substituents are methyl groups.

In a further group of compounds, one of $R^2$ and $R^3$ together with the nitrogen atom to which they are attached and one or more atoms from the linker group A form a saturated monocyclic heterocyclic group having 4-7 ring members and optionally containing a second heteroatom ring member selected from O and N.

Examples of such compounds include compounds wherein $NR^2R^3$ and A form a unit of the formula:

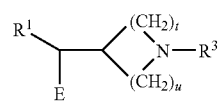

where t and u are each 0, 1, 2 or 3 provided that the sum of t and u falls within the range of 2 to 4.

Further examples of such compounds include compounds wherein $NR^2R^3$ and A form a cyclic group of the formula:

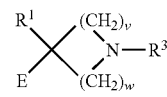

where v and w are each 0, 1, 2 or 3 provided that the sum of v and w falls within the range of 2 to 5. Particular examples of cyclic compounds are those in which v and w are both 2.

Further examples of such compounds include compounds wherein $NR^2R^3$ and A form a cyclic group of the formula:

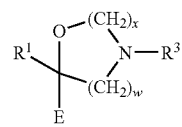

where x and w are each 0, 1, 2 or 3 provided that the sum of x and w falls within the range of 2 to 4. Particular examples of cyclic compounds are those in which x is 2 and w is 1.

$R^4$

In formula (I), $R^4$ is selected from hydrogen, halogen, $C_{1-5}$ saturated hydrocarbyl, $C_{1-5}$ saturated hydrocarbyloxy, cyano, and $CF_3$.

More typically, $R^4$ is selected from hydrogen, halogen, $C_{1-5}$ saturated hydrocarbyl, cyano and $CF_3$. Preferred values for $R^4$ include hydrogen and methyl. In a particular embodiment, $R^4$ is hydrogen.

$R^5$

In formula (I), $R^5$ is selected from hydrogen, halogen, $C_{1-5}$ saturated hydrocarbyl, $C_{1-5}$ saturated hydrocarbyloxy, cyano, $CONH_2$, $CONHR^9$, $CF_3$, $NH_2$, $NHCOR^9$ and $NHCONHR^9$; $NHCONHR^9$ where $R^9$ is a group $R^{9a}$ or $(CH_2)R^{9a}$, wherein $R^{9a}$ is an optionally substituted monocyclic or bicyclic group which may be carbocyclic or heterocyclic.

Examples of carbocyclic and heterocyclic groups are set out above in the General Preferences and Definitions section.

Typically the carbocyclic and heterocyclic groups are monocyclic.

Preferably the carbocyclic and heterocyclic groups are aromatic.

Particular examples of the group $R^9$ are optionally substituted phenyl or benzyl.

Preferably, $R^5$ is selected from selected from hydrogen, halogen, $C_{1-5}$ saturated hydrocarbyl, cyano, $CONH_2$, $CONHR^9$, $CF_3$, $NH_2$, $NHCOR^9$ and $NHCONHR^9$ where $R^9$ is optionally substituted phenyl or benzyl.

More preferably, $R^5$ is selected from selected from hydrogen, halogen, $C_{1-5}$ saturated hydrocarbyl, cyano, $CF_3$, $NH_2$, $NHCOR^9$ and $NHCONHR^9$ where $R^9$ is optionally substituted phenyl or benzyl.

The group $R^9$ is typically unsubstituted phenyl or benzyl, or phenyl or benzyl substituted by 1, 2 or 3 substituents selected from halogen; hydroxy; trifluoromethyl; cyano; carboxy; $C_{1-4}$alkoxycarbonyl; $C_{1-4}$ acyloxy; amino; mono- or di-$C_{1-4}$alkylamino; $C_{1-4}$ alkyl optionally substituted by halogen, hydroxy or $C_{1-2}$ alkoxy; $C_{1-4}$ alkoxy optionally substituted by halogen, hydroxy or $C_{1-2}$ alkoxy; phenyl, five and six membered heteroaryl groups containing up to 3 heteroatoms selected from O, N and S; and saturated carbocyclic and heterocyclic groups containing up to 2 heteroatoms selected from O, S and N.

Particular examples of the moiety $R^5$ include hydrogen, fluorine, chlorine, bromine, methyl, ethyl, hydroxyethyl, methoxymethyl, cyano, $CF_3$, $NH_2$, $NHCOR^{9b}$ and $NHCONHR^{9b}$ where $R^{9b}$ is phenyl or benzyl optionally substituted by hydroxy, $C_{1-4}$ acyloxy, fluorine, chlorine, bromine, trifluoromethyl, cyano, $C_{1-4}$ hydrocarbyloxy (e.g. alkoxy) and $C_{1-4}$ hydrocarbyl (e.g. alkyl) optionally substituted by $C_{1-2}$ alkoxy or hydroxy.

Preferred examples of $R^5$ include hydrogen, methyl and cyano. Preferably $R^5$ is hydrogen or methyl.

The Group "E"

In formula (I), E is a monocyclic or bicyclic carbocyclic or heterocyclic group and can be selected from the groups set out above in the section headed General Preferences and Definitions.

Preferred groups E are monocyclic and bicyclic aryl and heteroaryl groups and, in particular, groups containing a six membered aromatic or heteroaromatic ring such as a phenyl, pyridine, pyrazine, pyridazine or pyrimidine ring, more particularly a phenyl, pyridine, pyrazine or pyrimidine ring, and more preferably a pyridine or phenyl ring.

Examples of bicyclic groups include benzo-fused and pyrido-fused groups wherein the group A and the pyrazole ring are both attached to the benzo- or pyrido-moiety.

In one embodiment, E is a monocyclic group.

Particular examples of monocyclic groups include monocyclic aryl and heteroaryl groups such as phenyl, thiophene, furan, pyrimidine, pyrazine and pyridine, phenyl being presently preferred.

One subset of monocyclic aryl and heteroaryl groups comprises phenyl, thiophene, furan, pyrimidine and pyridine.

Examples of non-aromatic monocyclic groups include cycloalkanes such as cyclohexane and cyclopentane, and nitrogen-containing rings such as piperazine and piperazone.

It is preferred that the group A and the pyrazole group are not attached to adjacent ring members of the group E. For example, the pyrazole group can be attached to the group E in a meta or para relative orientation.

Examples of such groups E include 1,4-phenylene, 1,3-phenylene, 2,5-pyridylene and 2,4-pyridylene, 1,4-piperazinyl, and 1,4-piperazonyl. Further examples include 1,3-disubstituted five membered rings.

The groups E can be unsubstituted or can have up to 4 substituents $R^8$ which may be selected from the group $R^{10}$ as hereinbefore defined. More typically however, the substituents $R^8$ are selected from hydroxy; oxo (when E is non-aromatic); halogen (e.g. chlorine and bromine); trifluoromethyl; cyano; $C_{1-4}$ hydrocarbyloxy optionally substituted by $C_{1-2}$ alkoxy or hydroxy; and $C_{1-4}$ hydrocarbyl optionally substituted by $C_{1-2}$ alkoxy or hydroxy.

Preferably there are 0-3 substituents, more preferably 0-2 substituents, for example 0 or 1 substituent. In one embodiment, the group E is unsubstituted.

E may be other than:
a substituted pyridone group;
a substituted thiazole group;
a substituted or unsubstituted pyrazole or pyrazolone group;
a substituted or unsubstituted bicyclic fused pyrazole group;
a phenyl ring fused to a thiophene ring or a six membered nitrogen-containing heteroaryl ring fused to a thiophene ring;
a substituted or unsubstituted piperazine group;

The group E can be an aryl or heteroaryl group having five or six members and containing up to three heteroatoms selected from O, N and S, the group E being represented by the formula:

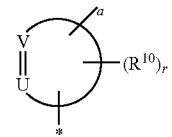

where * denotes the point of attachment to the pyrazole group, and "a" denotes the attachment of the group A;
r is 0, 1 or 2;
U is selected from N and $CR^{12a}$; and
V is selected from N and $CR^{12b}$; where $R^{12a}$ and $R^{12b}$ are the same or different and each is hydrogen or a substituent containing up to ten atoms selected from C, N, O, F, Cl and S provided that the total number of non-hydrogen atoms present in $R^{12a}$ and $R^{12b}$ together does not exceed ten;
or $R^{12a}$ and $R^{12b}$ together with the carbon atoms to which they are attached form an unsubstituted five or six membered saturated or unsaturated ring containing up to two heteroatoms selected from O and N; and
$R^{10}$ is as hereinbefore defined.

In one preferred group of compounds, E is a group:

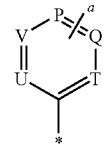

where * denotes the point of attachment to the pyrazole group, and "a" denotes the attachment of the group A; P, Q and T are the same or different and are selected from N, CH and $NCR^{10}$, provided that the group A is attached to a carbon atom; and U, V and $R^{10}$ are as hereinbefore defined.

Examples of $R^{12a}$ and $R^{12b}$ include hydrogen and substituent groups $R^{10}$ as hereinbefore defined having no more than ten non-hydrogen atoms. Particular examples of $R^{12a}$ and $R^{12b}$ include methyl, ethyl, propyl, isopropyl, cyclopropyl, cyclobutyl, cyclopentyl, fluorine, chlorine, methoxy, trifluoromethyl, hydroxymethyl, hydroxyethyl, methoxymethyl, difluoromethoxy, trifluoromethoxy, 2,2,2-trifluoroethyl, cyano, amino, methylamino, dimethylamino, $CONH_2$, $CO_2Et$, $CO_2H$, acetamido, azetidinyl, pyrrolidino, piperidine, piperazino, morpholino, methylsulphonyl, aminosulphonyl, mesylamino and trifluoroacetamido.

Preferably, when U is $CR^{12a}$ and/or V is $CR^{12b}$ the atoms or groups in $R^{12a}$ and $R^{12b}$ that are directly attached to the carbon atom ring members C are selected from H, O (e.g. as in methoxy), NH (e.g. as in amino and methylamino) and $CH_2$ (e.g. as in methyl and ethyl).

Particular examples of the linker group E, together with their points of attachment to the group A ($^a$) and the pyrazole ring (*) are shown in Table 2 below.

TABLE 2

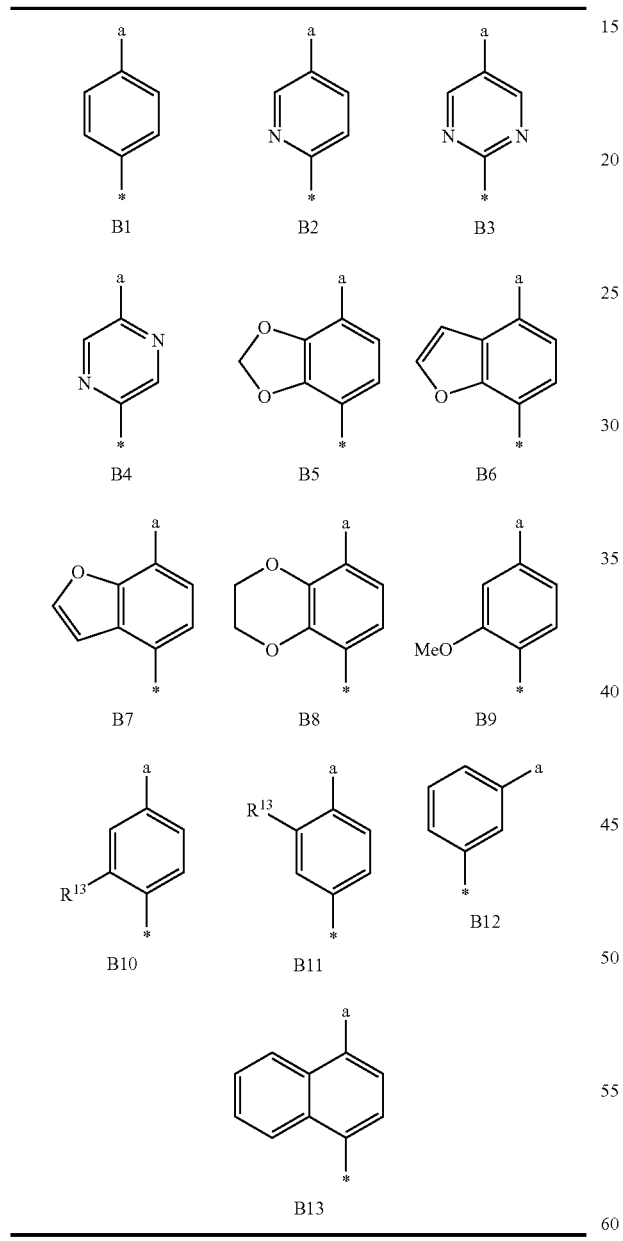

In the table, the substituent group $R^{13}$ is selected from methyl, chlorine, fluorine and trifluoromethyl.

The following optional exclusions may apply to the definition of E in any of formulae (I), (Ia), (Ib), (II), (III), (IV) and (V) and any sub-groups or sub-definitions thereof as defined herein:

E may be other than a phenyl group having a sulphur atom attached to the position para with respect to the pyrazole group.

E may be other than a substituted or unsubstituted benzimidazole, benzoxazole or benzthiazole group.

One sub-group of compounds of the formula (I) has the general formula (II):

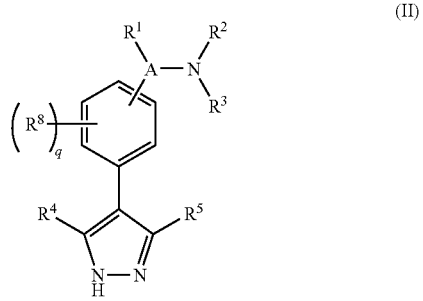

(II)

wherein the group A is attached to the meta or para position of the benzene ring, q is 0-4; $R^1$, $R^2$, $R^3$, $R^4$ and $R^5$ are as defined herein in respect of formula (I) and sub-groups, examples and preferences thereof; and $R^8$ is a substituent group as hereinbefore defined. In formula (II), q is preferably 0, 1 or 2, more preferably 0 or 1 and most preferably 0. Preferably the group A is attached to the para position of the benzene ring.

Within formula (II), one particular sub-group of compounds of the invention is represented by the formula (III):

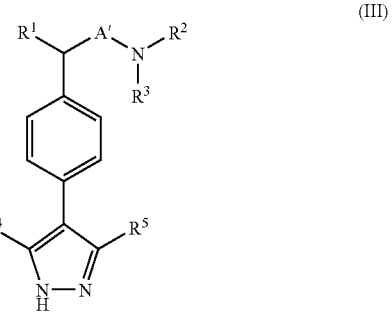

(III)

where A' is the residue of the group A and $R^1$ to $R^5$ are as defined herein.

Within formula (III), one preferred group of compounds is presented by the formula (IV):

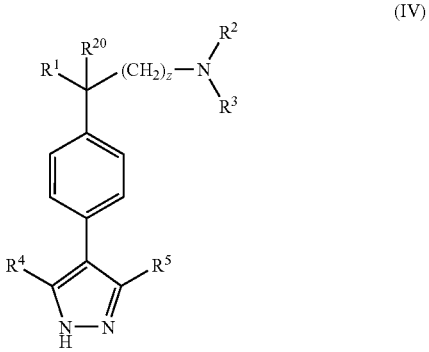

(IV)

wherein z is 0, 1 or 2, $R^{20}$ is selected from hydrogen, methyl, hydroxy and fluorine and $R^1$ to $R^5$ are as defined herein, provided that when z is 0, $R^{20}$ is other than hydroxy.

Another group of compounds within formula (III) is represented by formula (V):

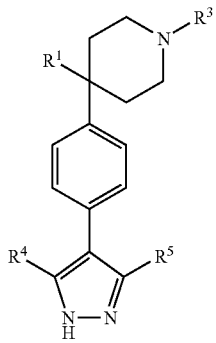

wherein and $R^1$ and $R^3$ to $R^5$ are as defined herein.

In formula (V), $R^3$ is preferably selected from hydrogen and $C_{1-4}$ hydrocarbyl, for example $C_{1-4}$ alkyl such as methyl, ethyl and isopropyl. More preferably $R^3$ is hydrogen.

In each of formulae (II) to (V), $R^1$ is preferably an optionally substituted phenyl group as defined herein.

In another sub-group of compounds of the invention, A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$, wherein one of the carbon atoms in the linker group may optionally be replaced by an oxygen or nitrogen atom; and wherein the carbon atoms of the linker group A may optionally bear one or more substituents selected from fluorine and hydroxy, provided that the hydroxy group when present is not located at a carbon atom α with respect to the $NR^2R^3$ group; and $R^5$ is selected from hydrogen, $C_{1-5}$ saturated hydrocarbyl, cyano, $CONH_2$, $CF_3$, $NH_2$, $NHCOR^9$ and $NHCONHR^9$.

For the avoidance of doubt, it is to be understood that each general and specific preference, embodiment and example of the groups $R^1$ may be combined with each general and specific preference, embodiment and example of the groups $R^2$ and/or $R^3$ and/or $R^4$ and/or $R^5$ and/or $R^9$ and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular compounds of the invention are as illustrated in the examples below and are selected from:

2-phenyl-2-[4-(1H-pyrazol-4-yl)-phenyl]-ethylamine;
3-phenyl-2-[3-(1H-pyrazol-4-yl)-phenyl]-propionitrile;
2-[4-(3,5-dimethyl-1H-pyrazol-4-yl)-phenyl]-2-phenyl-ethylamine;
2-(4-chloro-phenyl)-2-[4-(1H-pyrazol-4-yl)-phenyl]-ethylamine;
2-[3-(3,5-dimethyl-1H-pyrazol-4-yl)-phenyl]-1-phenyl-ethylamine;
3-phenyl-2-[3-(1H-pyrazol-4-yl)-phenyl]-propylamine;
3-phenyl-2-[4-(1H-pyrazol-4-yl)-phenyl]-propylamine;
{3-(4-chloro-phenyl)-3-[4-(1H-pyrazol-4-yl)-phenyl]-propyl}-methyl-amine;
{3-(3,4-difluoro-phenyl)-3-[4-(1H-pyrazol-4-yl)-phenyl]-propyl}-methyl-amine;
{3-(3-chloro-phenyl)-3-[4-(1H-pyrazol-4-yl)-phenyl]-propyl}-methyl-amine;
3-(4-chloro-phenyl)-3-[4-(1H-pyrazol-4-yl)-phenyl]-propionamide;
3-(4-chloro-phenyl)-3-[4-(1H-pyrazol-4-yl)-phenyl]-propylamine;
3-(3,4-dichloro-phenyl)-3-[4-(1H-pyrazol-4-yl)-phenyl]-propylamine;
4-(4-chloro-phenyl)-4-[4-(1H-pyrazol-4-yl)-phenyl]-piperidine;
4-(4-methoxy-phenyl)-4-[4-(1H-pyrazol-4-yl)-phenyl]-piperidine;
4-(4-chloro-phenyl)-1-methyl-4-[4-(1H-pyrazol-4-yl)-phenyl]-piperidine;
4-phenyl-4-[4-(1H-pyrazol-4-yl)-phenyl]-piperidine;
4-[4-(3,5-dimethyl-1H-pyrazol-4-yl)-phenyl]-4-phenyl-piperidine;
dimethyl-{3-[4-(1H-pyrazol-4-yl)-phenyl]-3-pyridin-2-yl-propyl}-amine;
{2-(4-chloro-phenyl)-2-[4-(1H-pyrazol-4-yl)-phenyl]-ethyl}-dimethyl-amine;
{2-(4-chloro-phenyl)-2-[4-(1H-pyrazol-4-yl)-phenyl]-ethyl}-methyl-amine;
{2-(4-chloro-phenyl)-2-[4-(1H-pyrazol-4-yl)-phenyl]-ethyl}-methyl-amine (R);
{2-(4-chloro-phenyl)-2-[4-(1H-pyrazol-4-yl)-phenyl]-ethyl}-methyl-amine (S);
4-{2-(4-chloro-phenyl)-2-[4-(1H-pyrazol-4-yl)-phenyl]-ethyl}-morpholine;
4-{4-[1-(4-chloro-phenyl)-2-pyrrolidin-1-yl-ethyl]-phenyl}-1H-pyrazole;
{2-(4-chloro-phenyl)-2-[4-(1H-pyrazol-4-yl)-phenyl]-ethyl}-isopropyl-amine;
dimethyl-{2-phenyl-2-[4-(1H-pyrazol-4-yl)-phenyl]ethyl}-amine;
{2,2-bis-[4-(1H-pyrazol-4-yl)-phenyl]-ethyl}-dimethyl-amine;
{2,2-bis-[4-(1H-pyrazol-4-yl)-phenyl]-ethyl}-methyl-amine;
2-(4-chloro-phenyl)-2-[4-(1H-pyrazol-4-yl)-phenyl]-ethylamine (R);
2-(4-chloro-phenyl)-2-[4-(1H-pyrazol-4-yl)-phenyl]-ethylamine (S);
2-(4-chloro-phenyl)-2-[4-(1H-pyrazol-4-yl)-phenyl]-acetamide;
1-{2-(4-chloro-phenyl)-2-[4-(1H-pyrazol-4-yl)-phenyl]-ethyl}-piperazine;
1-{2-(4-chloro-phenyl)-2-[4-(1H-pyrazol-4-yl)-phenyl]-ethyl}-piperidine;
4-{4-[2-azetidin-1-yl-1-(4-chloro-phenyl)-ethyl]-phenyl}-1H-pyrazole;
1-phenyl-2-[4-(1H-pyrazol-4-yl)-phenyl]-ethylamine;
2-(4-chloro-phenyl)-N-methyl-2-[4-(1H-pyrazol-4-yl)-phenyl]-acetamide;
N-methyl-2,2-bis-[4-(1H-pyrazol-4-yl)-phenyl]-acetamide;
{2-(4-chloro-phenyl)-2-[4-(1H-pyrazol-4-yl)-phenyl]-ethyl}methyl-amine;   {2-(4-chloro-phenyl)-2-[4-(1H-pyrazol-4-yl)-phenyl]-ethyl}-ethyl-amine;
4-{4-[1-(4-chloro-phenyl)-2-imidazol-1-yl-ethyl]-phenyl}-1H-pyrazole;
methyl-{2-(4-phenoxy-phenyl)-2-[4-(1H-pyrazol-4-yl)-phenyl]-ethyl}-amine;

{2-(4-methoxy-phenyl)-2-[4-(1H-pyrazol-4-yl)-phenyl]-ethyl}-methyl-amine;
methyl-{2-[4-(pyrazin-2-yloxy)-phenyl]-2-[4-(1H-pyrazol-4-yl)-phenyl]-ethyl}-amine;
methyl-{2-phenoxy-2-[4-(1H-pyrazol-4-yl)-phenyl]-ethyl}-amine;
2-{(4-chloro-phenyl)-[4-(1H-pyrazol-4-yl)-phenyl]-methoxy}-ethylamine;
4-{4-[1-(4-chloro-phenyl)-3-pyrrolidin-1-yl-propyl]-phenyl}-1H-pyrazole;
4-{4-[3-azetidin-1-yl-1-(4-chloro-phenyl)-propyl]-phenyl}-1H-pyrazole;
methyl-{3-naphthalen-2-yl-3-[4-(1H-pyrazol-4-yl)-phenyl]-propyl}-amine;
dimethyl-(4-(3-methylamino-1-[4-(1H-pyrazol-4-yl)-phenyl]-propyl)-phenyl)-amine;
{3-(4-fluoro-phenyl)-3-[4-(1H-pyrazol-4-yl)-phenyl]-propyl}-methyl-amine;
4-{4-[4-(4-chloro-phenyl)-piperidin-4-yl]-phenyl}-1H-pyrazole-3-carbonitrile;
3-(4-phenoxy-phenyl)-3-[4-(1H-pyrazol-4-yl)-phenyl]-propylamine;
1-{(4-chloro-phenyl)-[4-(1H-pyrazol-4-yl)-phenyl]-methyl}-piperazine;
1-methyl-4-{phenyl-[4-(1H-pyrazol-4-yl)-phenyl]-methyl}-[1,4]diazepane;
{3-(3-chloro-phenoxy)-3-[4-(1H-pyrazol-4-yl)-phenyl]-propyl}-methyl-amine;
methyl-{2-phenyl-2-[6-(1H-pyrazol-4-yl)-pyridin-3-yl]-ethyl}-amine;
4-{4-[1-(4-chloro-phenyl)-3-imidazol-1-yl-propyl]-phenyl}-1H-pyrazole;
4-[4-(3-imidazol-1-yl-1-phenoxy-propyl)-phenyl]-1H-pyrazole;
4-{4-[4-(1H-pyrazol-4-yl)-phenyl]-piperidin-4-yl}-phenol;
1-{(4-chloro-phenyl)-[4-(1H-pyrazol-4-yl)-phenyl]-methyl}-piperazine;
{2-(4-fluoro-phenyl)-2-[4-(1H-pyrazol-4-yl)-phenyl]-ethyl}-methyl-amine;
{2-(3-chloro-phenyl)-2-[4-(1H-pyrazol-4-yl)-phenyl]-ethyl}-methyl-amine;
4-[4-(2-methoxy-ethoxy)-phenyl]-4-[4-(1H-pyrazol-4-yl)-phenyl]-piperidine;
4-[4-(3-methoxy-propoxy)-phenyl]-4-[4-(1H-pyrazol-4-yl)-phenyl]-piperidine;
3-(3,4-dichloro-phenyl)-3-[4-(1H-pyrazol-4-yl)-phenyl]-propionamide;
2-(4-{2-methylamino-1-[4-(1H-pyrazol-4-yl)-phenyl]-ethyl}-phenoxy)-isonicotinamide;
{2-(3-chloro-phenoxy)-2-[4-(1H-pyrazol-4-yl)-phenyl]-ethyl}-methyl-amine;
3-{2-(4-chloro-phenyl)-2-[4-(1H-pyrazol-4-yl)-phenyl]-ethylamino}-propan-1-ol;
2-{2-(4-chloro-phenyl)-2-[4-(1H-pyrazol-4-yl)-phenyl]-ethylamino}-ethanol;
3-{2-(4-chloro-phenyl)-2-[4-(1H-pyrazol-4-yl)-phenyl]-ethylamino}-propan-1-ol;
2-{2-(4-chloro-phenyl)-2-[4-(1H-pyrazol-4-yl)-phenyl]-ethylamino}-ethanol;
{2-(4-Chloro-phenyl)-2-[4-(1H-pyrazol-4-yl)-phenyl]-ethyl}-cyclopropylmethyl-amine;
methyl-[2-[4-(1H-pyrazol-4-yl)-phenyl]-2-(4-pyridin-3-yl-phenyl)-ethyl]-amine;
4-{3-methylamino-1-[4-(1H-pyrazol-4-yl)-phenyl]-propyl}-phenol;
3-(4-methoxy-phenyl)-3-[4-(1H-pyrazol-4-yl)-phenyl]-propylamine;
4-(4-chloro-phenyl)-4-[4-(3-methyl-1H-pyrazol-4-yl)-phenyl]-piperidine;
2-(4-chloro-phenyl)-2-[4-(1H-pyrazol-4-yl)-phenyl]-morpholine;
(4-{4-[4-(1H-pyrazol-4-yl)-phenyl]-piperidin-4-yl}-phenoxy)-acetic acid;
(4-{4-[4-(1H-pyrazol-4-yl)-phenyl]-piperidin-4-yl}-phenoxy)-acetic acid, methyl ester;
4-{4-[4-(1H-pyrazol-4-yl)-phenyl]-piperidin-4-yl}-benzonitrile;
{2-(4-chloro-phenyl)-2-[4-(1H-pyrazol-4-yl)-phenyl]-propyl}-methyl-amine;
1-(4-chloro-phenyl)-2-methylamino-1-[4-(1H-pyrazol-4-yl)-phenyl]-ethanol;
2-amino-1-(4-chloro-phenyl)-1-[4-(1H-pyrazol-4-yl)-phenyl]-ethanol;
4-(3,4-dichloro-phenyl)-4-[4-(1H-pyrazol-4-yl)-phenyl]-piperidine;
4-(3-chloro-4-methoxy-phenyl)-4-[4-(1H-pyrazol-4-yl)-phenyl]-piperidine;
4-(4-chloro-3-fluoro-phenyl)-4-[4-(1H-pyrazol-4-yl)-phenyl]-piperidine;
4-{4-[4-(1H-pyrazol-4-yl)-phenyl]-piperidin-4-yl}-benzoic acid;
4-[4-(1H-pyrazol-4-yl)-phenyl]-1,2,3,4,5,6-hexahydro-[4,4']bipyridinyl;
3-(3-chloro-phenyl)-3-[4-(1H-pyrazol-4-yl)-phenyl]-propylamine;
2-methylamino-1-(4-nitro-phenyl)-1-[4-(1H-pyrazol-4-yl)-phenyl]-ethanol;
2-(3-chloro-4-methoxy-phenyl)-2-[4-(1H-pyrazol-4-yl)-phenyl]-ethylamine;
2-(4-chloro-phenyl)-2-fluoro-2-[4-(1H-pyrazol-4-yl)-phenyl]-ethylamine;
3-(3,4-dichloro-phenyl)-3-[6-(1H-pyrazol-4-yl)-pyridin-3-yl]-propylamine;
2-(4-chloro-3-fluoro-phenyl)-2-[4-(1H-pyrazol-4-yl)-phenyl]-ethylamine;
4-(2-chloro-3-fluoro-phenyl)-4-[4-(1H-pyrazol-4-yl)-phenyl]-piperidine;
1-{(3,4-dichloro-phenyl)-[4-(1H-pyrazol-4-yl)-phenyl]-methyl}-piperazine;
2-(3,4-dichloro-phenyl)-2-[4-(1H-pyrazol-4-yl)-phenyl]-ethylamine;
{2-(3-chloro-4-methoxy-phenyl)-2-[4-(1H-pyrazol-4-yl)-phenyl]-ethyl}-methyl-amine;
4-{4-[2-azetidin-1-yl-1-(4-chloro-phenoxy)-ethyl]-phenyl}-1H-pyrazole;
3-(3-chloro-4-methoxy-phenyl)-3-[4-(1H-pyrazol-4-yl)-phenyl]-propylamine;
{3-(3-chloro-4-methoxy-phenyl)-3-[4-(1H-pyrazol-4-yl)-phenyl]-propyl}-methyl-amine;
1-{(3,4-dichloro-phenyl)-[4-(1H-pyrazol-4-yl)-phenyl]-methyl}-piperazine; and
C-(4-chloro-phenyl)-C-[4-(1H-pyrazol-4-yl)-phenyl]-methylamine;
and salts, solvates, tautomers and N-oxides thereof.

In one embodiment, the compound of the formula (I) is selected from the group consisting of:
{2-(4-chloro-phenyl)-2-[4-(1H-pyrazol-4-yl)-phenyl]-ethyl}-methyl-amine (R);
4-(4-chloro-phenyl)-4-[4-(1H-pyrazol-4-yl)-phenyl]-piperidine;
3-(4-chloro-phenyl)-3-[4-(1H-pyrazol-4-yl)-phenyl]-propylamine;
3-(3,4-dichloro-phenyl)-3-[4-(1H-pyrazol-4-yl)-phenyl]-propylamine;

{3-(4-chloro-phenyl)-3-[4-(1H-pyrazol-4-yl)-phenyl]-propyl}-methyl-amine;
{2-(4-chloro-phenyl)-2-[4-(1H-pyrazol-4-yl)-phenyl]-ethyl}-dimethyl-amine; and
2-(4-chloro-phenyl)-2-[4-(1H-pyrazol-4-yl)-phenyl]-ethylamine.

A further subset of compounds of the formula (I) consists of
4-(3-chloro-4-methoxy-phenyl)-4-[4-(1H-pyrazol-4-yl)-phenyl]-piperidine;
2-(4-chloro-phenyl)-2-[4-(1H-pyrazol-4-yl)-phenyl]-ethylamine (R isomer);
and salts, solvates, tautomers and N-oxides thereof.

Salts, Solvates, Tautomers, Isomers, N-Oxides, Esters, Prodrugs and Isotopes

In this section, as in all other sections of this application, unless the context indicates otherwise, references to formula (I) included references to formulae (Ia), (Ib), (II), (III), (IV) and (V) and all other sub-groups, preferences and examples thereof as defined herein.

Unless otherwise specified, a reference to a particular compound (including inter alia any of the compounds of formula (I) or the ancillary compounds described herein) also includes ionic, salt, solvate, and protected forms thereof, for example, as discussed below.

Many compounds (including those of the formula (I) and many of the ancillary compounds described herein) can exist in the form of salts, for example acid addition salts or, in certain cases salts of organic and inorganic bases such as carboxylate, sulphonate and phosphate salts. All such salts are within the scope of this invention, and references to compounds (e.g. compounds of the formula (I) or ancillary compounds) include the salt forms of the compounds. As in the preceding sections of this application, all references to formula (I) should be taken to refer also to formula (II) and sub-groups thereof unless the context indicates otherwise.

Salt forms may be selected and prepared according to methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. For example, acid addition salts may be prepared by dissolving the free base in an organic solvent in which a given salt form is insoluble or poorly soluble and then adding the required acid in an appropriate solvent so that the salt precipitates out of solution.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of acid addition salts includes salts formed with hydrochloric, hydriodic, phosphoric, nitric, sulphuric, citric, lactic, succinic, maleic, malic, isethionic, fumaric, benzenesulphonic, toluenesulphonic, methanesulphonic, ethanesulphonic, naphthalenesulphonic, valeric, acetic, propanoic, butanoic, malonic, glucuronic and lactobionic acids.

Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

The compounds comprised in the combinations of the invention may exist as mono- or di-salts depending upon the pKa of the acid from which the salt is formed. In stronger acids, the basic pyrazole nitrogen, as well as the nitrogen atom in the group $NR^2R^3$, may take part in salt formation. For example, where the acid has a pKa of less than about 3 (e.g. an acid such as hydrochloric acid, sulphuric acid or trifluoroacetic acid), the compounds will typically form salts with 2 molar equivalents of the acid.

If the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds contain an amine function, these may form quaternary ammonium salts, for example by reaction with an alkylating agent according to methods well known to the skilled person. Such quaternary ammonium compounds are within the scope of formula (I).

Compounds containing an amine function may also form N-oxides. A reference herein to a compound (e.g. a compound of the formula (I)) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the combinations of the invention (for example, the compounds of formula (I)) may exist in a number of different geometric isomeric, and tautomeric forms and references to such compounds include all such forms. For the avoidance of doubt, where a compound can exist in one of several geometric isomeric or tautomeric forms and only one is specifically described or shown, all others are nevertheless embraced (particularly in the case of formula (I)).

For example, in compounds of the formula (I) the pyrazole group may take either of the following two tautomeric forms A and B.

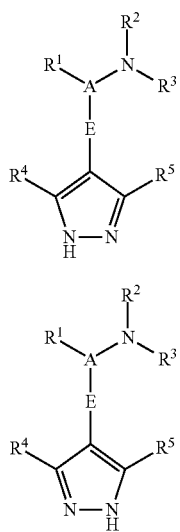

For simplicity, the general formula (I) illustrates form A but the formula is to be taken as embracing both form A and form B.

Where any constituent compound of the combination of the invention (e.g. of the formula (I)) contain one or more chiral centres, and can exist in the form of two or more optical isomers, references to the compounds include all optical isomeric forms thereof (e.g. enantiomers and diastereoisomers), either as individual optical isomers, or mixtures or two or more optical isomers, unless the context requires otherwise.

For example, the group A can include one or more chiral centres. Thus, when E and are both attached to the same carbon atom on the linker group A, the said carbon atom is typically chiral and hence the compound of the formula (I) will exist as a pair of enantiomers (or more than one pair of enantiomers where more than one chiral centre is present in the compound).

The optical isomers may be characterised and identified by their optical activity (i.e. as + and − isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluloyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where any one constituent compound of the combinations of the invention (e.g. a compound of the formula (I)) exist as two or more optical isomeric forms, one enantiomer in a pair of enantiomers may exhibit advantages over the other enantiomer, for example, in terms of biological activity. Thus, in certain circumstances, it may be desirable to use as a component in the combination of the invention only one of a pair of enantiomers, or only one of a plurality of diastereoisomers. Accordingly, the invention provides combinations containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Esters such as carboxylic acid esters and acyloxy esters of the compounds (e.g. of formula (I)) bearing a carboxylic acid group or a hydroxyl group are also contemplated (and in the case of compounds of formula (I) intended to be embraced by that formula). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Also contemplated are any polymorphic forms of the compounds, solvates (e.g. hydrates), complexes (e.g. inclusion complexes or clathrates with compounds such as cyclodextrins, or complexes with metals) of the constituent compounds of the combinations of the invention (and of Formula (I) in particular), and pro-drugs of these constituent compounds. By "prodrugs" is meant for example any compound that is converted in vivo into a biologically active compound (e.g. into an ancillary compound or into a compound of the formula (I)).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl (e.g., -Me, -Et, -nPr, -iPr, -nBu, -sBu, -iBu, -tBu);
$C_{1-7}$ aminoalkyl (e.g., aminoethyl; 2-(N,N-diethylamino) ethyl; 2-(4-morpholino)ethyl); and acyloxy-$C_{1-4}$alkyl (e.g., acyloxymethyl; acyloxyethyl; pivaloyloxymethyl; acetoxymethyl; 1-acetoxyethyl; 1-(1-methoxy-1-methyl) ethyl-carbonyloxyethyl; 1-(benzoyloxy)ethyl; isopropoxycarbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)-carbonyloxyethyl; (4-tetrahydropyranyl)carbonyloxymethyl; and 1-(4-tetrahydropyranyl)-carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT). For example, the prodrug may be a sugar derivative or other glycoside conjugate, or may be an amino acid ester derivative.

As used herein, the term "combination", as applied to two or more compounds, is intended to define material in which the two or more compounds are associated. The terms "combined" and "combining" in this context are to be interpreted accordingly.

The association of the two or more compounds in a combination may be physical or non-physical. Examples of physically associated combined compounds include:
  compositions (e.g. unitary formulations) comprising the two or more compounds in admixture (for example within the same unit dose);
  compositions comprising material in which the two or more compounds are chemically/physicochemically linked (for example by crosslinking, molecular agglomeration or binding to a common vehicle moiety);
  compositions comprising material in which the two or more compounds are chemically/physicochemically co-packaged (for example, disposed on or within lipid vesicles, particles (e.g. micro- or nanoparticles) or emulsion droplets);
  pharmaceutical kits, pharmaceutical packs or patient packs in which the two or more compounds are co-packaged or co-presented (e.g. as part of an array of unit doses);

Examples of non-physically associated combined compounds include:
  material (e.g. a non-unitary formulation) comprising at least one of the two or more compounds together with instructions for the extemporaneous association of the at least one compound to form a physical association of the two or more compounds;
  material (e.g. a non-unitary formulation) comprising at least one of the two or more compounds together with instructions for combination therapy with the two or more compounds;
  material comprising at least one of the two or more compounds together with instructions for administration to a patient population in which the other(s) of the two or more compounds have been (or are being) administered;
  material comprising at least one of the two or more compounds in an amount or in a form which is specifically adapted for use in combination with the other(s) of the two or more compounds.

As used herein, the term "combination therapy" is intended to define therapies which comprise the use of a combination of two or more compounds (as defined above). Thus, references to "combination therapy", "combinations" and the use of compounds "in combination" in this application may refer to compounds that are administered as part of the same overall treatment regimen. As such, the posology of each of the two or more compounds may differ: each may be administered at the same time or at different times. It will therefore be appreciated that the compounds of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds, the individual compounds may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds, the individual compounds may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The combinations of the invention may produce a therapeutically efficacious effect relative to the therapeutic effect of the individual compounds when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect. Efficacious combinations may be determined, for example, by the methods described herein (see Example 109, below).

A "synergistic" effect in the present context refers to a therapeutic effect produced by the combination which is larger than the sum of the therapeutic effects of the components of the combination when presented individually.

An "additive" effect in the present context refers to a therapeutic effect produced by the combination which is larger than the therapeutic effect of any of the components of the combination when presented individually.

The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

The term "ancillary compound" as used herein is intended to define any compound which yields an efficacious combination (as herein defined) when combined with a compound of the formula (I). The ancillary compound may therefore act as an adjunct to the compound of formula (I), or may otherwise contribute to the efficacy of the combination (for example, by producing a synergistic or additive effect or improving the response rate, as herein defined). In embodiments where the combinations comprise two or more ancillary compounds, each of the two ancillary compounds may be independently efficacious, or they may yield efficacious combinations when each of the two or more compounds are combined with the compound of formula I.

Methods for the Preparation of Compounds of the Formula (I)

In this section, as in all other sections of this application, unless the context indicates otherwise, references to formula (I) included references to formulae (Ia), (Ib), (II), (III), (IV) and (V) and all other sub-groups, preferences and examples thereof as defined herein.

Compounds of the formula (I) can be prepared by reaction of a compound of the formula (X) with a compound of the formula (XI) or an N-protected derivative thereof:

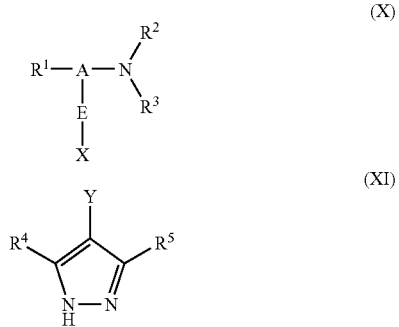

wherein A, E, and $R^1$ to $R^5$ are as hereinbefore defined, one of the groups X and Y is chlorine, bromine or iodine or a trifluoromethanesulphonate (triflate) group, and the other one of the groups X and Y is a boronate residue, for example a boronate ester or boronic acid residue.

The reaction can be carried out under typical Suzuki Coupling conditions in the presence of a palladium catalyst such as bis(tri-t-butylphosphine)palladium and a base (e.g. a carbonate such as potassium carbonate). The reaction may be carried out in an aqueous solvent system, for example aqueous ethanol, and the reaction mixture is typically subjected to heating, for example to a temperature in excess of 100° C.

An illustrative synthetic route involving a Suzuki coupling step is shown in Scheme 1. The starting material for the synthetic route shown in scheme 1 is the halo-substituted aryl- or heteroarylmethyl nitrile (XII) in which X is a chlorine, bromine or iodine atom or a triflate group. The nitrile (XII) is condensed with the aldehyde $R^1$CHO in the presence of an alkali such as sodium or potassium hydroxide in an aqueous solvent system such as aqueous ethanol. The reaction can be carried out at room temperature.

The resulting substituted acrylonitrile derivative (XIII) is then treated with a reducing agent that will selectively reduce the alkene double bond without reducing the nitrile group. A borohydride such as sodium borohydride may be used for this purpose to give the substituted acetonitrile derivative (XIV). The reduction reaction is typically carried out in a solvent such as ethanol and usually with heating, for example to a temperature up to about 65° C.

The reduced nitrile (XIV) is then coupled with the pyrazole boronate ester (XV) under the Suzuki coupling conditions described above to give a compound of the formula (I) in which $A\text{-}NR^2R^3$ is a substituted acetonitrile group.

Scheme 1

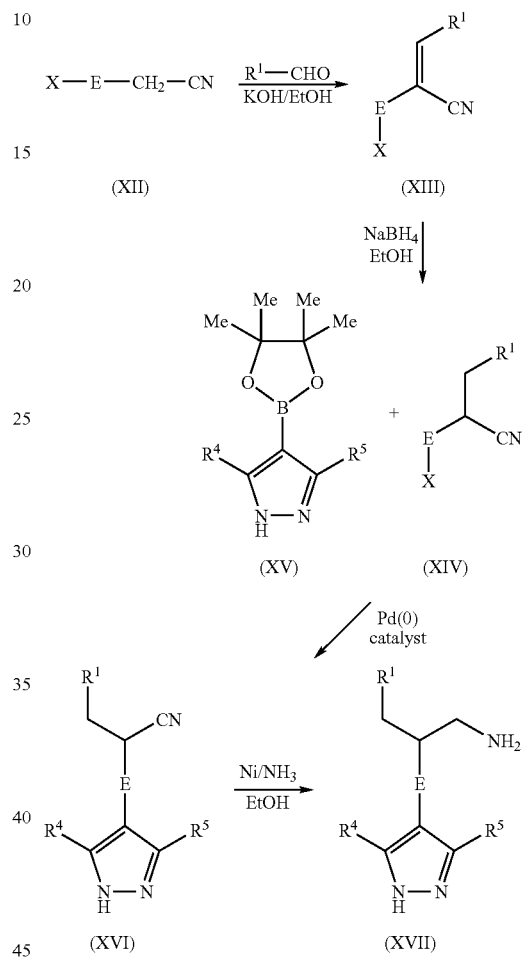

The substituted acetonitrile compound (XVI) may then be reduced to the corresponding amine (XVII) by treatment with a suitable reducing agent such as Raney nickel and ammonia in ethanol.

The synthetic route shown in Scheme 1 gives use to amino compounds of the formula (I) in which the aryl or heteroaryl group E is attached to the S-position of the group A relative to the amino group. In order to give amino compounds of the formula (I) in which $R^1$ is attached to the β-position relative to the amino group, the functional groups on the two starting materials in the condensation step can be reversed so that a compound of the formula X-E-CHO wherein X is bromine, chlorine, iodine or a triflate group is condensed with a compound of the formula $R^1$—$CH_2$—CN to give a substituted acrylonitrile derivative which is then reduced to the corresponding acetonitrile derivative before coupling with the pyrazole boronate (XV) and reducing the cyano group to an amino group.

Compounds of the formula (I) in which $R^1$ is attached to the α-position relative to the amino group can be prepared by the sequence of reactions shown in Scheme 2.

In Scheme 2, the starting material is a halo-substituted aryl- or heteroarylmethyl Grignard reagent (XVIII, X=bromine or chlorine) which is reacted with the nitrile R¹—CN in a dry ether such as diethyl ether to give an intermediate imine (not shown) which is reduced to give the amine (XIX) using a reducing agent such as lithium aluminium hydride. The amine (XIX) can be reacted with the boronate ester (XV) under the Suzuki coupling conditions described above to yield the amine (XX).

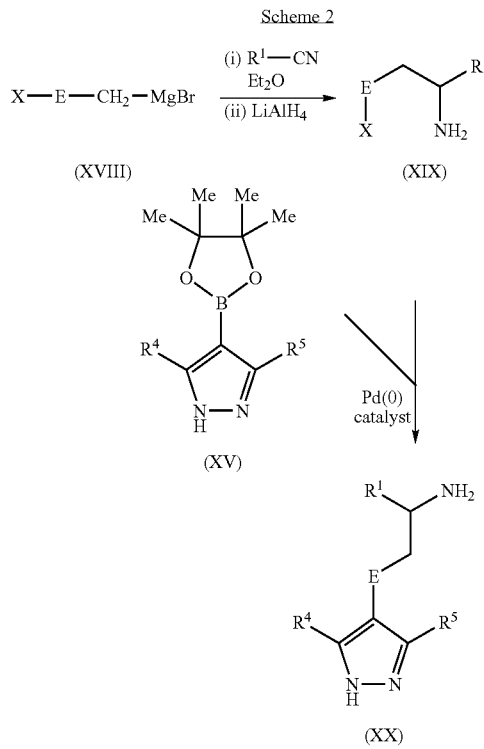

Compounds of the formula (I) can also be prepared from the substituted nitrile compound (XXI):

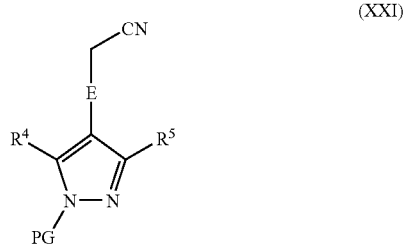

wherein PG is a protecting group such as a tetrahydropyranyl group. The nitrile (XXI) can be condensed with an aldehyde of the formula $R^1$—$(CH_2)_r$—CHO, wherein r is 0 or 1, and the resulting substituted acrylonitrile subsequently reduced to the corresponding substituted nitrile under conditions analogous to those set out in Scheme 1 above. The protecting group PG can then be removed by an appropriate method. The nitrile compound may subsequently be reduced to the corresponding amine by the use of a suitable reducing agent as described above.

The nitrile compound (XXI) may also be reacted with a Grignard reagent of the formula $R^1$—$(CH_2)_r$—MgBr under standard Grignard reaction conditions followed by deprotection to give an amino compound of the invention which has the structure shown in formula (XXII).

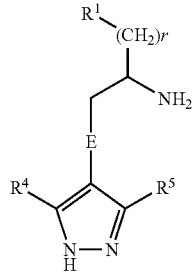

In the preparative procedures outlined above, the coupling of the aryl or heteroaryl group E to the pyrazole is accomplished by reacting a halo-pyrazole or halo-aryl or heteroaryl compound with a boronate ester or boronic acid in the presence of a palladium catalyst and base. Many boronates suitable for use in preparing compounds of the invention are commercially available, for example from Boron Molecular Limited of Noble Park, Australia, or from Combi-Blocks Inc, of San Diego, USA. Where the boronates are not commercially available, they can be prepared by methods known in the art, for example as described in the review article by N. Miyaura and A. Suzuki, *Chem. Rev.* 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

Compounds of the formula (I) in which the group A contains a nitrogen atom attached to the group E can be prepared by well known synthetic procedures from compounds of the formula (XXIII) or a protected form thereof. Compounds of the formula (XXIII) can be obtained by a Suzuki coupling reaction of a compound of the formula (XV) (see Scheme 1) with a compound of the formula Br-E-NH₂ such as 4-bromoaniline.

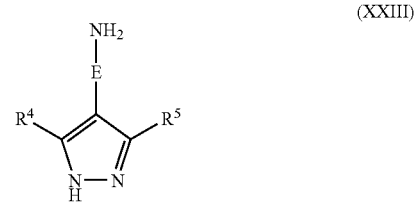

Compounds of the formula (I) in which R¹ and E are connected to the same carbon atom can be prepared as shown in Scheme 3.

Scheme 3

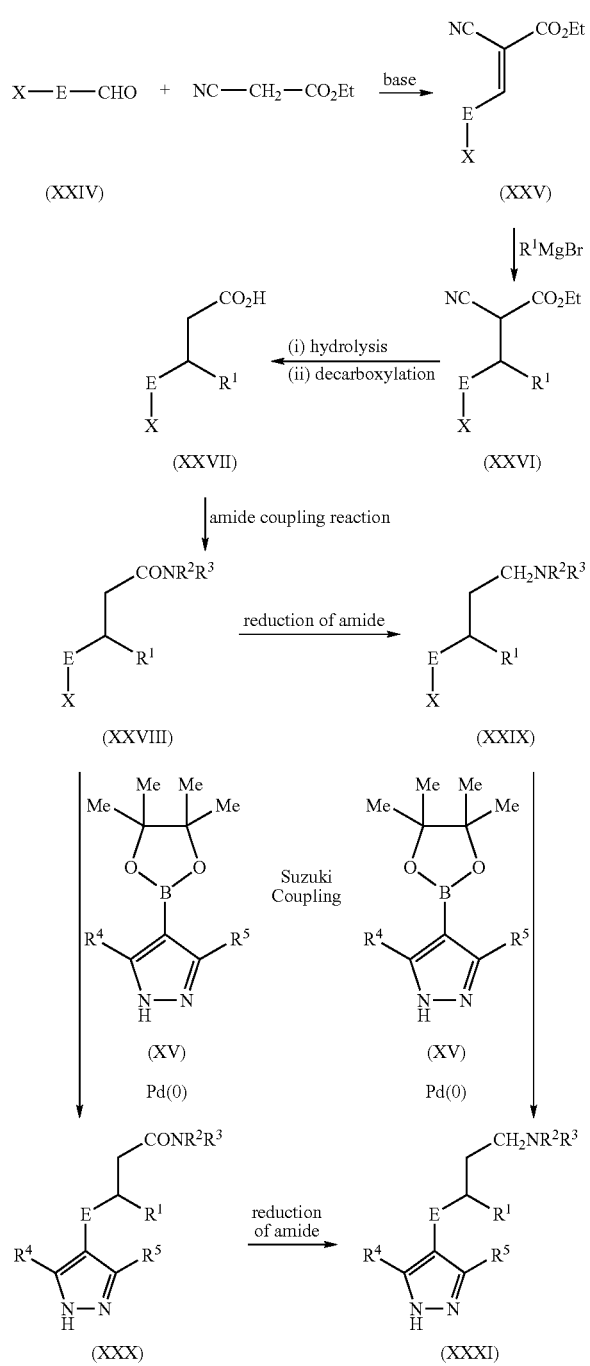

In Scheme 3, an aldehyde compound (XXIV) where X is bromine, chlorine, iodine or a triflate group is condensed with ethyl cyanoacetate in the presence of a base to give a cyanoacrylate ester intermediate (XXV). The condensation is typically carried out in the presence of a base, preferably a non-hydroxide such as piperidine, by heating under Dean Stark conditions.

The cyanoacrylate intermediate (XXV) is then reacted with a Grignard reagent $R^1MgBr$ suitable for introducing the group $R^1$ by Michael addition to the carbon-carbon double bond of the acrylate moiety. The Grignard reaction may be carried out in a polar non-protic solvent such as tetrahydrofuran at a low temperature, for example at around 0° C. The product of the Grignard reaction is the cyano propionic acid ester (XXVI) and this is subjected to hydrolysis and decarboxylation to give the propionic acid derivative (XXVII). The hydrolysis and decarboxylation steps can be effected by heating in an acidic medium, for example a mixture of sulphuric acid and acetic acid.

The propionic acid derivative (XXVII) is converted to the amide (XXVIII) by reaction with an amine $HNR^2R^3$ under conditions suitable for forming an amide bond. The coupling reaction between the propionic acid derivative (XXVII) and the amine $HNR^2R^3$ is preferably carried out in the presence of a reagent of the type commonly used in the formation of peptide linkages. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC) (Sheehan of al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Preferred coupling reagents include EDC (EDAC) and DCC in combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

Where the amine $HNR^2R^3$ is ammonia, the amide coupling reaction can be carried out using 1,1'-carbonyldiimidazole (CDI) to activate the carboxylic acid before addition of the ammonia.

As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine.

The amide (XXVIII) can be converted to a compound of the formula (XXX) (which corresponds to a compound of the formula (I) wherein A has an oxo substituent next to the $NR^2R^3$ group) by reaction with a boronate (XV) under Suzuki coupling conditions as described above. The amide (XXX) can subsequently be reduced using a hydride reducing agent such as lithium aluminium hydride in the presence of aluminium chloride to give an amine of the formula (XXXI) (which corresponds to a compound of the formula (I) wherein A is $CH-CH_2-CH_2-$). The reduction reaction is typically carried out in an ether solvent, for example diethyl ether, with heating to the reflux temperature of the solvent.

Rather than reacting the amide (XXVIII) with the boronate (XV), the amide may instead be reduced with lithium aluminium hydride/aluminium chloride, for example in an ether solvent at ambient temperature, to give the amine (XXIX)

which is then reacted with the boronate (XV) under the Suzuki coupling conditions described above to give the amine (XXX).

In order to obtain the homologue of the amine (XXIX) containing one fewer methylene group, the carboxylic acid (XXVII) can be converted to the azide by standard methods and subjected to a Curtius rearrangement in the presence of an alcohol such as benzyl alcohol to give a carbamate (see *Advanced Organic Chemistry*, 4$^{th}$ edition, by Jerry March, John Wiley & sons, 1992, pages 1091-1092). The benzylcarbamate can function as a protecting group for the amine during the subsequent Suzuki coupling step, and the benzyloxycarbonyl moiety in the carbamate group can then be removed by standard methods after the coupling step. Alternatively, the benzylcarbamate group can be treated with a hydride reducing agent such as lithium aluminium hydride to give a compound in which $NR^2R^3$ is a methylamino group instead of an amino group.

Intermediate compounds of the formula (X) where the moiety X is a chlorine, bromine or iodine atom and A is a group $CH-CH_2-$ can be prepared by the reductive amination of an aldehyde compound of the formula (XXXII):

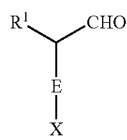
(XXXII)

with an amine of the formula $HNR^2R^3$ under standard reductive amination conditions, for example in the presence of sodium cyanoborohydride in an alcohol solvent such as methanol or ethanol.

The aldehyde compound (XXXII) can be obtained by oxidation of the corresponding alcohol (XXXIII) using, for example, the Dess-Martin periodinane (see Dess, D. B.; Martin, J. C. *J. Org. Soc.*, 1983, 48, 4155 and *Organic Syntheses*, Vol. 77, 141).

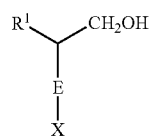
(XXXIII)

Compounds of the formula (I) where A, N and $R^2$ together form a cyclic group can be formed by the Suzuki coupling of a boronate compound of the formula (XV) with a cyclic intermediate of the formula (XXXIV) or an N-protected derivative thereof.

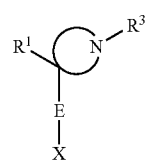
(XXXIV)

Cyclic intermediates of the formula (XXXIV), where $R^1$ is an aryl group such as an optionally substituted phenyl group, can be formed by Friedel Crafts alkylation of an aryl compound $R^1-H$ with a compound of the formula (XXXV):

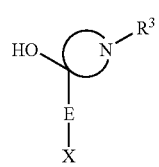
(XXXV)

The alkylation is typically carried out in the presence of a Lewis acid such as aluminium chloride at a reduced temperature, for example less than 5° C.

The Friedel Crafts reaction has been found to be of general applicability to the preparation of a range of intermediates of the formula (X). Accordingly, in a general method of making compounds of the formula (X), a compound of the formula (LXX):

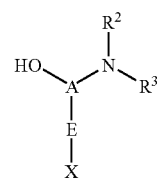
(LXX)

is reacted with a compound of the formula $R^1-H$ under Friedel Crafts alkylation conditions, for example in the presence of an aluminium, halide (e.g. $AlCl_3$).

In a further method for the preparation of a compound of the formula (I) wherein the moiety $NR^2R^3$ is attached to a $CH_2$ group of the moiety A, an aldehyde of the formula (XXXVI) can be coupled with an amine of the formula $HNR^2R^3$ under reductive amination conditions as described above. In the formulae (XXXVI) and (XXXVII), A' is the residue of the group A—i.e. the moieties A' and $CH_2$ together form the group A. The aldehyde (XXXVII) can be formed by oxidation of the corresponding alcohol using, for example, Dess-Martin periodinane.

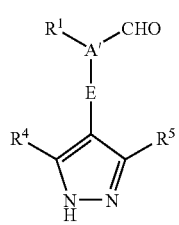
(XXXVI)

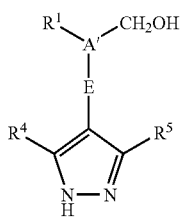
(XXXVII)

A Friedel Crafts alkylation procedure of the type described above for the synthesis of intermediates of the formula (XXXIV) can also be used to prepare intermediates of the formula (X) wherein X is bromine. An example of such a procedure is shown in Scheme 4.

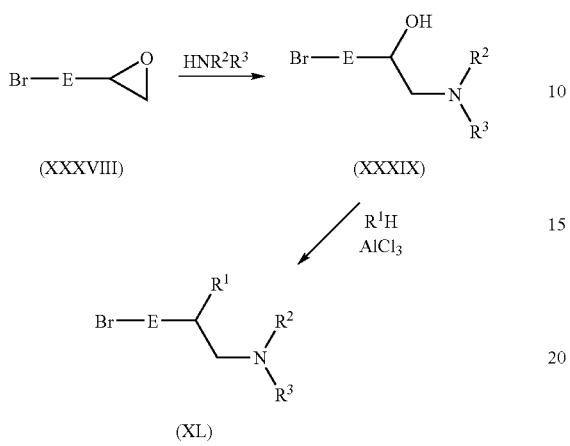

The starting material for the synthetic route shown in Scheme 4 is the epoxide (XXXVIII) which can either be obtained commercially or can be made by methods well known to the skilled person, for example by reaction of the aldehyde Br-E-CHO with trimethylsulphonium iodide. The epoxide (XXXVIII) is reacted with an amine $HNR^2R^3$ under conditions suitable for a ring-opening reaction with the epoxide to give a compound of the formula (XXXIX). The ring opening reaction can be carried out in a polar solvent such as ethanol at room temperature or optionally with mild heating, and typically with a large excess of the amine.

The amine (XXXIX) is then reacted with an aryl compound $R^1H$, typically a phenyl compound, capable of taking part in a Friedel Crafts alkylation (see for example *Advanced Organic Chemistry*, by Jerry March, pages 534-542). Thus, the amine of formula (XXXIX) is typically reacted with the aryl compound $R^1H$ in the presence of an aluminium chloride catalyst at or around room temperature. Where the aryl compound $R^1H$ is a liquid, e.g. as in the case of a methoxybenzene (e.g. anisole) or a halobenzene such as chlorobenzene, the aryl compound may serve as the solvent. Otherwise, a less reactive solvent such as nitrobenzene may be used. The Friedel Crafts alkylation of the compound $R^1H$ with the amine (XXXIX) gives a compound of the formula (XL) which corresponds to a compound of the formula (X) wherein X is bromine and A is $CHCH_2$.

The hydroxy intermediate (XXXIX) in Scheme 4 can also be used to prepare compounds of the formula (X) in which the carbon atom of the hydrocarbon linker group A adjacent the group $R^1$ is replaced by an oxygen atom. Thus the compound of formula (XXXIX), or an N-protected derivative thereof (where $R^2$ or $R^3$ are hydrogen) can be reacted with a phenolic compound of the formula $R^1$—OH under Mitsunobu alkylation conditions, e.g. in the presence of diethyl azodicarboxylate and triphenylphosphine. The reaction is typically carried out in a polar non-protic solvent such as tetrahydrofuran at a moderate temperature such as ambient temperature.

A further use of the hydroxy-intermediate (XXXIX) is for the preparation of the corresponding fluoro-compound. Thus, the hydroxy group can be replaced by fluorine by reaction with pyridine:hydrogen fluoride complex (Olah's reagent). The fluorinated intermediate can then be subjected to a Suzuki coupling reaction to give a compound of the formula (I) with a fluorinated hydrocarbon group A. A fluorinated compound of the formula (I) could alternatively be prepared by first coupling the hydroxy intermediate (XXXIX), or a protected form thereof, with a pyrazole boronic acid or boronate under Suzuki conditions and then replacing the hydroxy group in the resulting compound of formula (I) with fluorine using pyridine:hydrogen fluoride complex.

Compounds of the formula (I) in which the moiety:

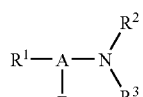

is a group:

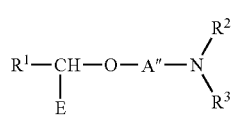

where A" is the hydrocarbon residue of the group A, can be prepared by the sequence of reactions shown in Scheme 5.

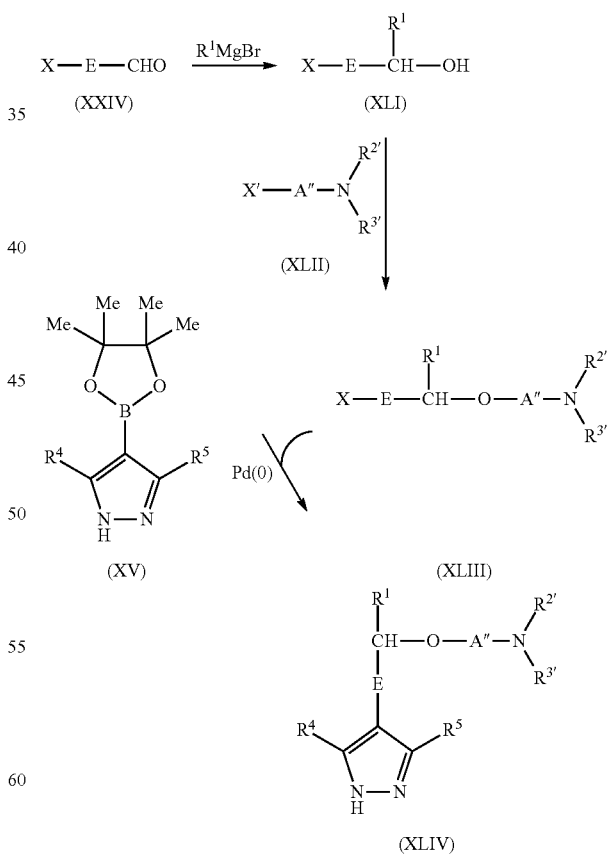

As shown in Scheme 5, the aldehyde (XXIV) is reacted with a Grignard reagent $R^1MgBr$ under standard Grignard conditions to give the secondary alcohol (XLI). The secondary alcohol can then be reacted with a compound of the formula (XLII) in which R[2'] and R[3'] represent the groups R[2] and R[3] or an amine-protecting group, A" is the residue of the group A, and X' represents a hydroxy group or a leaving group.

The amine protecting group can be, for example, a phthalolyl group in which case NR[2']R[3'] is a phthalimido group.

When X' is a hydroxy group, the reaction between compound (XLI) and (XLII) can take the form of an toluene sulphonic acid catalysed condensation reaction. Alternatively, when X' is a leaving group such as halogen, the alcohol (XLI) can first be treated with a strong base such as sodium hydride to form the alcoholate which then reacts with the compound (XLII).

The resulting compound of the formula (XLIII) is then subjected to a Suzuki coupling reaction with the pyrazole boronate reagent (XV) under typical Suzuki coupling conditions of the type described above to give a compound of the formula (XLIV). The protecting group can then be removed from the protected amine group NR[2']R[3'] to give a compound of the formula (I).

Compounds of the formula (I) in which the moiety:

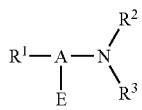

is a group:

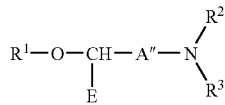

where A" is the hydrocarbon residue of the group A, can be prepared by the sequence of reactions shown in Scheme 6.

Scheme 6

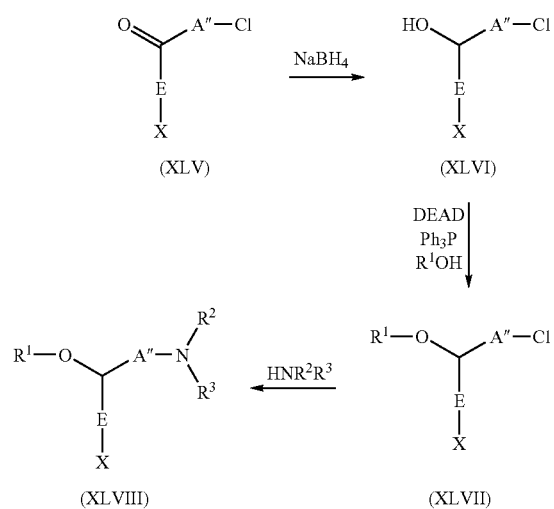

(XLV), (XLVI), (XLVII), (XLVIII)

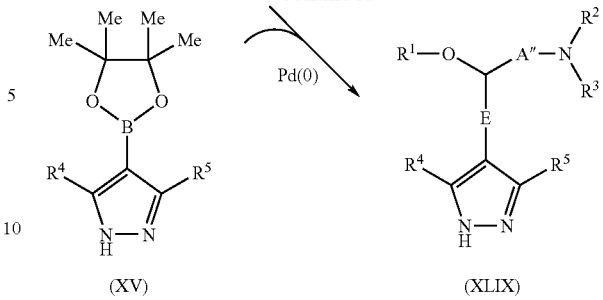

(XV), (XLIX)

The starting material in Scheme 6 is the chloroacyl compound (XLV) which can be prepared by literature methods (e.g. the method described in *J. Med. Chem.*, 2004, 47, 3924-3926) or methods analogous thereto. Compound (XLV) is converted into the secondary alcohol (XLVI) by reduction with a hydride reducing agent such as sodium borohydride in a polar solvent such as water/tetrahydrofuran.

The secondary alcohol (XLVI) can then be reacted with a phenolic compound of the formula R[1]—OH under Mitsunobu alkylation conditions, e.g. in the presence of diethyl azodicarboxylate and triphenylphosphine, as described above, to give the aryl ether compound (XLVII).

The chorine atom in the aryl ether compound (XLVII) is then displaced by reaction with an amine HNR[2]R[3] to give a compound of the formula (XLVIII). The nucleophilic displacement reaction may be carried out by heating the amine with the aryl ether in a polar solvent such as an alcohol at an elevated temperature, for example approximately 100° C. The heating may advantageously be achieved using a microwave heater. The resulting amine (XLVIII) can then be subjected to a Suzuki coupling procedure with a boronate of the formula (XV) as described above to give the compound (XLIX).

In a variation on the reaction sequence shown in Scheme 6, the secondary alcohol (XLVI) can be subjected to a nucleophilic displacement reaction with an amine HNR[2]R[3] before introducing the group R[1] by means of the Mitsunobu ether-forming reaction.

Another route to compounds of the formula (I) in which E and R[1] are attached to the same carbon atom in the group A is illustrated in Scheme 7.

Scheme 7

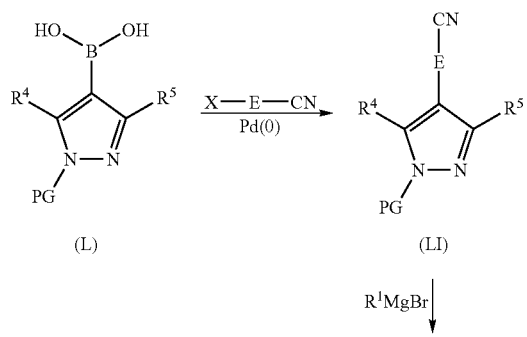

(L), (LI)

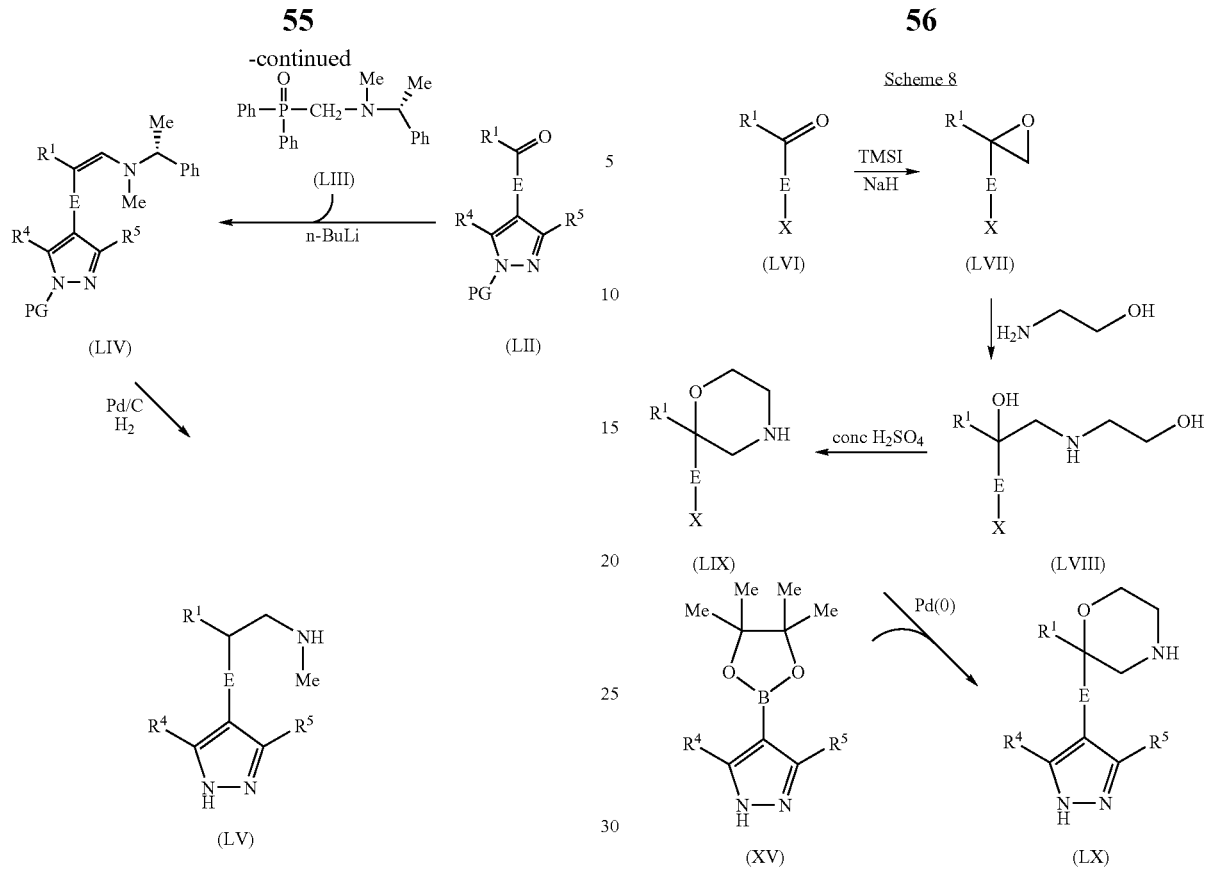

In Scheme 7, an N-protected pyrazolyl boronic acid (L) is reacted under Suzuki coupling conditions with the cyano compound X-E-CN in which X is typically a halogen such as bromine or chlorine. The protecting group PG at the 1-position of the pyrazole ring may be, for example, a triphenylmethyl (trityl) group. The boronic acid (L) can be prepared using the method described in EP 1382603 or methods analogous thereto.

The resulting nitrile (LI) may then be reacted with a Grignard reagent $R^1$—MgBr to introduce the group $R^1$ and form the ketone (LII). The ketone (LII) is converted to the enamine (LIV) by reaction with the diphenylphosphinoylmethylamine (LIII) in the presence of a strong base such as an alkyl lithium, particularly butyl lithium.

The enamine (LIV) is then subjected to hydrogenation over a palladium on charcoal catalyst to reduce the double bond of the enamine and remove the 1-phenethyl group. Where the protecting group PG is a trityl group, hydrogenation also removes the trityl group, thereby yielding a compound of the formula (LV).

Alternatively, the enamine (LIV) can be reduced with a hydride reducing agent under the conditions described in *Tetrahedron: Asymmetry* 14 (2003) 1309-1316 and subjected to a chiral separation. Removal of the protecting 2-phenethyl group and the protecting group PG then gives an optically active form of the compound of formula (LV).

Intermediates of the formula (X) wherein A and $R^2$ link to form a ring containing an oxygen atom can be prepared by the general method illustrated in Scheme 8.

In Scheme 8, a ketone (LVI) is reacted with trimethylsulphonium iodide to form the epoxide (LVII). The reaction is typically carried out in the presence of a hydride base such as sodium hydride in a polar solvent such as dimethylsulphoxide.

The epoxide (LVII) is subjected to a ring opening reaction with ethanolamine in the presence of a non-interfering base such as triethylamine in a polar solvent such as an alcohol (e.g. isopropanol), usually with mild heating (e.g. up to approximately 50° C. The resulting secondary alcohol is then cyclised to form the morpholine ring by treatment with concentrated sulphuric acid in a solvent such as ethanolic dichloromethane.

The morpholine intermediate (LIX) can then reacted with the boronate (XV) under Suzuki coupling conditions to give the compound of formula (LX), which corresponds to a compound of the formula (I) in which A-$NR^2R^3$ forms a morpholine group.

Instead of reacting the epoxide (LVII) with ethanolamine, it may instead be reacted with mono- or dialkylamines thereby providing a route to compounds containing the moiety:

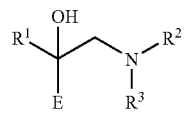

Compounds wherein $R^2$ and $R^3$ are both hydrogen can be prepared by reacting the epoxide (LVII) with potassium phthalimide in a polar solvent such as DMSO. During the Suzuki coupling step, the phthalimide group may undergo partial hydrolysis to give the corresponding phthalamic acid which can be cleaved using hydrazine to give the amino group NH$_2$. Alternatively, the phthalamic acid can be recyclised to the phthalimide using a standard amide-forming reagent and the phthaloyl group then removed using hydrazine to give the amine.

A further synthetic route to compounds of the formula (I) wherein A and NR$^2$R$^3$ combine to form a cyclic group is illustrated in Scheme 9.

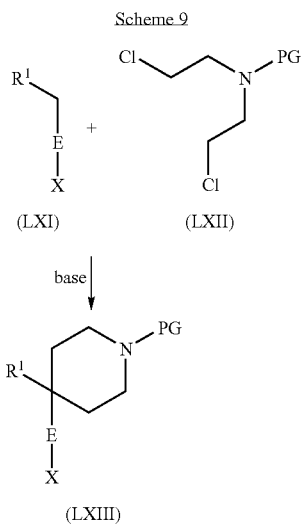

In Scheme 9, the starting material (LXI) is typically a di-aryl/heteroaryl methane in which one or both of the aryl/heteroaryl groups is capable of stabilising or facilitating formation of an anion formed on the methylene group between E and R$^1$. For example, R$^1$ may advantageously be a pyridine group. The starting material (LXI) is reacted with the N-protected bis-2-chloroethylamine (LXII) in the presence of a non-interfering strong base such as sodium hexamethyldisilazide in a polar solvent such as tetrahydrofuran at a reduced temperature (e.g. around 0° C.) to give the N-protected cyclic intermediate (LXIII). The protecting group can be any standard amine-protecting group such as a Boc group. Following cyclisation, the intermediate (LXIII) is coupled to a boronate of the formula (XV) under Suzuki coupling conditions and then deprotected to give the compound of the formula (I).

Compounds of the formula (I) in which the moiety:

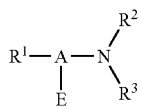

is a group:

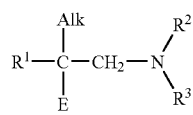

wherein "Alk" is a small alkyl group such as methyl or ethyl can be formed by the synthetic route illustrated in Scheme 10.

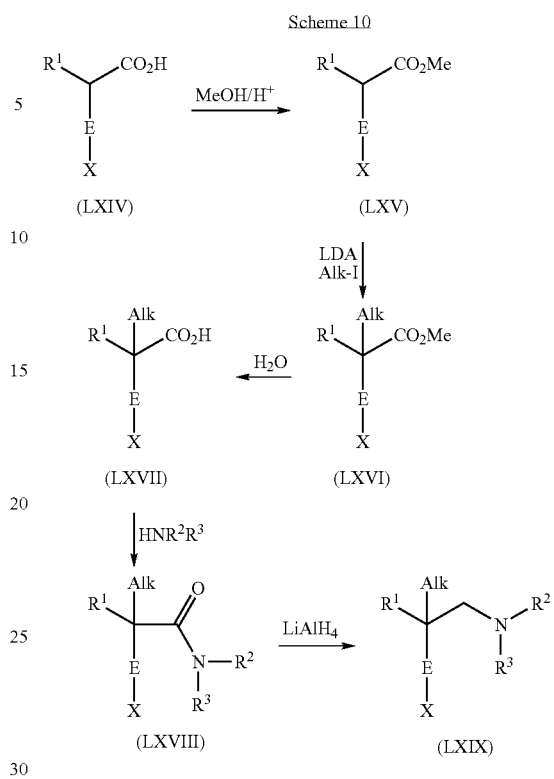

In Scheme 10, a carboxylic acid of the formula (LXIV) is esterified by treatment with methanol in the presence of an acid catalyst such as hydrochloric acid. The ester (LXV) is then reacted with a strong base such as lithium diisopropylamide (LDA) and an alkyl iodide such as methyl iodide at reduced temperature (e.g. between 0° C. and −78° C.). The branched ester (LXVI) is then hydrolysed to the acid (LXVII) and coupled with an amine HNR$^2$R$^3$ under standard amide forming conditions of the type described above. The amide (LXVIII) can then be reduced to the amine (LXIX) using lithium aluminium hydride, and the amine (LXIX) is then reacted with a pyrazole boronate or boronic acid under Suzuki coupling conditions to give a compound of the formula (I).

Once formed, many compounds of the formula (I) can be converted into other compounds of the formula (I) using standard functional group interconversions. For example, compounds of the formula (I) in which the NR$^2$R$^3$ forms part of a nitrile group can be reduced to the corresponding amine. Compounds in which NR$^2$R$^3$ is an NH$_2$ group can be converted to the corresponding alkylamine by reductive alkylation, or to a cyclic group. Compounds wherein R$^1$ contains a halogen atom such as chlorine or bromine can be used to introduce an aryl or heteroaryl group substituent into the R$^1$ group by means of a Suzuki coupling reaction. Further examples of interconversions of one compound of the formula (I) to another compound of the formula (I) can be found in the examples below. Additional examples of functional group interconversions and reagents and conditions for carrying out such conversions can be found in, for example, *Advanced Organic Chemistry*, by Jerry March, 4$^{th}$ edition, 119, Wiley Interscience, New York, *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0-471-31192-8).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(═O)R), for example, as: a t-butyl ether, a benzyl, benzhydryl (diphenylmethyl), or trityl (triphenylmethyl) ether; a trimethylsilyl or t-butyldimethylsilyl ether; or an acetyl ester (—OC(═O)CH$_3$, —OAc). An aldehyde or ketone group may be protected, for example, as an acetal (R—CH(OR)$_2$) or ketal (R$_2$C(OR)$_2$), respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2-(phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an C$_{1-7}$ alkyl ester (e.g., a methyl ester, a t-butyl ester); a C$_{1-7}$ haloalkyl ester (e.g., a C$_{1-7}$ trihaloalkyl ester); a triC$_{1-7}$alkylsilyl-C$_{1-7}$alkyl ester, or a C$_{6-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether an acetamidomethyl ether (—S—CH$_2$NHC(═O)CH$_3$).

The 1(H) position of the pyrazole group in the compounds of the formula (I) or its precursors can be protected by a variety of groups, the protecting group being selected according to the nature of the reaction conditions to which the group is exposed. Examples of protecting groups for the pyrazole N—H include tetrahydropyranyl, benzyl and 4-methoxybenzyl groups.

Ancillary Compounds for Use According to the Invention

Any of a wide variety of ancillary compounds may be used in the combinations of the invention. Particular examples are described in detail in sections 1 to 18, below.

Preferably, the ancillary compound(s) is (are) selected from Groups A to E, set out below:

Group A

In one aspect of the invention, the ancillary compound for use in combination with the compounds that have protein kinase B (PKB) and/or protein kinase A (PKA) inhibiting or modulating activity of the invention are independently selected from the following classes:

1. signalling inhibitors;
2. ancillary PKB inhibitors;
3. CDK inhibitors;
4. COX-2 inhibitors;
5. HDAC inhibitors;
6. DNA methyltransferase inhibitors;
7. proteosome inhibitors;
8. a combination of two or more of the foregoing classes.

A reference to a particular ancillary compound herein (for example, a reference to a signalling inhibitor, ancillary PKB inhibitor, CDK inhibitors, COX-2 inhibitors, HDAC inhibitor, DNA methyltransferase inhibitor or proteosome inhibitor) is intended to include ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof).

Group B: Cytotoxic Compounds

In another aspect of the invention, the ancillary compound for use with the compounds that have protein kinase B (PKB) and/or protein kinase A (PKA) inhibiting or modulating activity of the invention is a cytotoxic compound. Cytotoxicity may be assayed or determined using any of a wide variety of techniques well-known to those skilled in the art.

Preferably, the cytotoxic compound for use in combination with the compounds that have protein kinase B (PKB) and/or protein kinase A (PKA) inhibiting or modulating activity of the invention is selected from the following classes:

1. camptothecin compounds;
2. antimetabolites;
3. vinca alkaloids;
4. taxanes;
5. platinum compounds;
6. DNA binders and Topo II inhibitors (including anthracycline derivatives);
7. alkylating agents (including aziridine, nitrogen mustard and nitrosourea alkylating agents);
8. a combination of two or more of the foregoing classes.

Epothilones constitute another class of suitable cytotoxic agents for use in combination with the compounds that have protein kinase B (PKB) and/or protein kinase A (PKA) inhibiting or modulating activity of the invention. Accordingly, the cytotoxic compound for use in combination with the compounds that have protein kinase B (PKB) and/or protein kinase A (PKA) inhibiting or modulating activity of the invention may be selected from the following classes:

1. camptothecin compounds;
2. antimetabolites;
3. vinca alkaloids;
4. taxanes;
5. epothilones;
6. platinum compounds;
7. DNA binders and Topo II inhibitors (including anthracycline derivatives);
8. alkylating agents (including aziridine, nitrogen mustard and nitrosourea alkylating agents);
9. a combination of two or more of the foregoing classes.

A reference to a particular cytotoxic compound herein (for example, a reference to a camptothecin compound, antimetabolite, vinca alkaloid, taxane, platinum compound, DNA binder, Topo II inhibitor (including anthracycline derivatives), as well as alkylating agents (including the aziridine, nitrogen mustard and nitrosourea alkylating agents) is intended to include ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof).

Group C: Monoclonal Antibodies

In another aspect of the invention, the ancillary compound for use with the compounds that have protein kinase B (PKB) and/or protein kinase A (PKA) inhibiting or modulating activity of the invention is a monoclonal antibody. Any monoclonal antibody (e.g. to one or more cell surface antigen(s))

may be used in combination with the compounds that have protein kinase B (PKB) and/or protein kinase A (PKA) inhibiting or modulating activity of the invention. Antibody specificity may be assayed or determined using any of a wide variety of techniques well-known to those skilled in the art.

Group D

In another aspect of the invention, the ancillary compound for use in combination with the compounds that have protein kinase B (PKB) and/or protein kinase A (PKA) inhibiting or modulating activity of the invention is selected from the following classes:
1. hormones, hormone agonists, hormone antagonists and hormone modulating agents (including antiandrogens, antiestrogens and GNRAs);
2. cytokines and cytokine activating agents;
3. retinoids;
4. a combination of two or more of the foregoing classes.

A reference to a particular ancillary compound herein (for example, a reference to a hormone, hormone agonist, hormone antagonist, hormone modulating agent, cytokine, cytokine activating agent and retinoid) is intended to include ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof).

Group E: Multiple Combinations

In another aspect of the invention, two or more ancillary compounds are used in combination with the compounds that have protein kinase B (PKB) and/or protein kinase A (PKA) inhibiting or modulating activity of the invention, and in such embodiments the two or more ancillary compounds may be independently selected from the following classes:
1. hormones, hormone agonists, hormone antagonists and hormone modulating agents (including antiandrogens, antiestrogens and GNRAs);
2. cytokines and cytokine activating agents;
3. retinoids;
4. a combination of two or more of the foregoing classes (1) to (3);
5. monoclonal antibodies;
6. camptothecin compounds;
7. antimetabolites;
8. vinca alkaloids;
9. taxanes;
10. epothilones
11. platinum compounds;
12. DNA binders and Topo II inhibitors (including anthracycline derivatives);
13. alkylating agents (including aziridine, nitrogen mustard and nitrosourea alkylating agents);
14. a combination of two or more of the foregoing classes (6)-(12).
15. signalling inhibitors;
16. ancillary PKB inhibitors;
17. CDK inhibitors;
18. COX-2 inhibitors;
19. HDAC inhibitors;
20. DNA methylase inhibitors;
21. proteosome inhibitors;
22. a combination of two or more of the foregoing classes (14)-(20);
23. a combination of two or more of the foregoing classes (1)-(21).

A reference to a particular ancillary compound herein is intended to include ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof).

1. Hormones, Hormone Agonists, Hormone Antagonists and Hormone Modulating Agents Definition:

The terms "antiandrogen", "antiestrogen", "antiandrogen agent" and "antiestrogen agent" as used herein refers to those described herein and analogues thereof, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological Activity:

The hormones, hormone agonists, hormone antagonists and hormone modulating agents (including the antiandrogens and antiestrogen agents) working via one or more pharmacological actions as described herein have been identified as suitable anti-cancer agents.

Technical Background:

Hormonal therapy plays an important role in the treatment of certain types of cancer where tumours are formed in tissues that are sensitive to hormonal growth control such as the breast and prostate. Thus, for example, estrogen promotes growth of certain breast cancers and testosterone promotes growth of some prostate cancers. Since the growth of such tumours is dependent on specific hormones, considerable research has been carried out to investigate whether it is possible to affect tumour growth by increasing or decreasing the levels of certain hormones in the body. Hormonal therapy attempts to control tumour growth in these hormone-sensitive tissues by manipulating the activity of the hormones, With regard to breast cancer, tumour growth is stimulated by estrogen, and antiestrogen agents have therefore been proposed and widely used for the treatment of this type of cancer. One of the most widely used of such agents is tamoxifen which is a competitive inhibitor of estradiol binding to the estrogen receptor (ER). When bound to the ER, tamoxifen induces a change in the three-dimensional shape of the receptor, inhibiting its binding to the estrogen responsive element on DNA. Under normal physiological conditions, estrogen stimulation increases tumour cell production of transforming growth cell b (TGF-b), an autocrine inhibitor of tumour cell growth. By blocking these pathways, the net effect of tamoxifen treatment is to decrease the autocrine stimulation of breast cancer growth. In addition, tamoxifen decreases the local production of insulin-like growth factor (IGF-1) by surrounding tissues: IGF-I is a paracrine growth factor for the breast cancer cell (Jordan and Murphy, Endocr. Rev., 1990, 1 1; 578-610). Tamoxifen is the endocrine treatment of choice for post-menopausal women with metastatic breast cancer or at a high risk of recurrences from the disease. Tamoxifen is also used in pre-menopausal women with ER-positive tumours. There are various potential side-effects of long-term tamoxifen treatment, for example the possibility of endometrial cancer and the occurrence of thrombo-embolic events.

Other estrogen receptor antagonists or selective estrogen receptor modulators (SERMs) include fulvestrant, toremifene and raloxifene. Fulvestrant which has the chemical name 7-α-[9-(4,4,5,5,5-pentafluoropentylsulphinyl)-nonyl]estra-1,3,5-(10)-triene-3,17-beta-diol, is used as a second line treatment of advanced breast cancer but side-effects include hot flushes and endometrial stimulation. Toremifene is a non-steroidal SERM, which has the chemical name 2-(4-[(Z)-4-chloro-1,2-diphenyl-1-butenyl]-phenoxy)-N,N-dimethylethylamine, and is used for the treatment of metastatic breast cancer, side-effects including hot flushes, nausea and dizziness. Raloxifene is a benzothiophene SERM, which has the chemical name [6-hydroxy-2-(4-hydroxyphenyl)benzo[b]thien-3-yl]-[4-[2-(1-piperidinyl)ethoxy]-phenyl]-methanone hydrochloride, and is being investigated for the treatment of breast cancer, side-effects including hot flushes and leg cramps.

With regard to prostate cancer, such cancer cells have a high level of expression of androgen receptor, and antiandrogens have therefore been used to treat the disease. Antiandrogens are androgen receptor antagonists which bind to the androgen receptor and prevent dihydrotestosterone from binding. Dihydrotestosterone stimulates new growth of prostate cells, including cancerous prostate cells. An example of an antiadrogen is bicalutamide, which has the chemical name (R,S)-N-(4-cyano-3-(4-fluorophenylsulfonyl)-2-hydroxy-2-methyl-3-(trifluoromethyl)propanamide, and has been approved for use in combination with luteinizing hormone-releasing hormone (LHRH) analogs for the treatment of advanced prostate cancer, side effects including hot flushes, bone pain, hematuria and gastro-intestinal symptoms.

A further type of hormonal cancer treatment comprises the use of progestin analogs. Progestin is the synthetic form of progesterone. Progesterone is a hormone secreted by the ovaries and endometrial lining of the uterus. Acting with estrogen, progesterone promotes breast development and growth of endometrial cells during the menstrual cycle. It is believed that progestins may act by suppressing the production of estrogen from the adrenal glands (an alternate source particularly in post-menopausal women), lowering estrogen receptor levels, or altering tumour hormone metabolism.

Progestin analogs are commonly used in the management of advanced uterine cancer. They can also be used for treating advanced breast cancer, although this use is less common, due to the numerous anti-estrogen treatment options available. Occasionally, progestin analogs are used as hormonal therapy for prostate cancer. An example of a progestin analog is megestrol acetate (a.k.a. megestrel acetate), which has the chemical name 17α-acetyloxy-6-methylpregna-4,6-diene-3,20-dione, and is a putative inhibitor of pituitary gonadotrophin production with a resultant decrease in estrogen secretion, The drug is used for the palliative treatment of advanced carcinoma of the breast or endometrium (i.e., recurrent, inoperable, or metastatic disease), side-effects including oedema and thromoembolic episodes.

Preferences and Specific Embodiments:

A particularly preferred antiestrogen agent for use in accordance with the invention is tamoxifen. Tamoxifen is commercially available for example from AstraZeneca plc under the trade name Nolvadex, or may be prepared for example as described in U.K. patent specifications 1064629 and 1354939, or by processes analogous thereto.

Other preferred antiestrogen agents include fulvestrant, raloxifene and toremifene. Yet another preferred antiestrogen agent is droloxifene. Fulvestrant is commercially available for example from AstraZeneca plc under the trade name Faslodex, or may be prepared for example as described in European patent specification No. 138504, or by processes analogous thereto. Raloxifene is commercially available for example from Eli Lilly and Company under the trade name Evista, or may be prepared for example as described in U.S. Pat. No. 4,418,068, or by processes analogous thereto. Toremifene is commercially available for example from Schering Corporation under the trade name Fareston, or may be prepared for example as described in U.S. Pat. No. 4,696,949, or by processes analogous thereto. The antiestrogen agent droloxifene, which may be prepared for example as described in U.S. Pat. No. 5,047,431, or by processes analogous thereto, can also be used in accordance with the invention.

A preferred antiandrogen for use in accordance with the invention is bicalutamide which is commercially available for example from AstraZeneca plc under the trade name Casodex, or may be prepared for example as described in European patent specification No. 100172, or by processes analogous thereto. Other preferred antiandrogens for use in accordance with the invention include tamoxifen, fulvestrant, raloxifene, toremifene, droloxifene, letrazole, anastrazole, exemestane, bicalutamide, luprolide, megestrol/megestrel acetate, aminoglutethimide and bexarotene.

A preferred progestin analog is megestrol/megestrel acetate which is commercially available for example from Bristol-Myers Squibb Corporation under the trade name Megace, or may be prepared for example as described in U.S. Pat. No. 2,891,079, or by processes analogous thereto.

Thus, specific embodiments of these anti-cancer agents for use in the combinations of the invention include: tamoxifen; toremifene; raloxifene; medroxyprogesterone; megestrol/megestrel; aminoglutethimide; letrozole; anastrozole; exemestane; goserelin; leuprolide; abarelix; fluoxymestrone; diethylstilbestrol; ketoconazole; fulvestrant; flutamide; bicalutimide; nilutamide; cyproterone and buserelin.

Thus, contemplated for use in the combinations of the invention are antiandrogens and antiestrogens.

In other embodiments, the hormone, hormone agonist, hormone antagonist or hormone modulating agent is fulvestrant, raloxifene, droloxifene, toremifene, megestrol/megestrel and bexarotene.

Posology:

The antiandrogen or antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day (or 20 mg once a day), continuing the therapy for sufficient time to achieve and maintain a therapeutic effect.

With regard to the other preferred antiestrogen agents: fulvestrant is advantageously administered in the form of a 250 mg monthly injection (though doses of 250-750 mg per month may also be employed); toremifene is advantageously administered orally in a dosage of about 60 mg once a day, continuing the therapy for sufficient time to achieve and maintain a therapeutic effect; droloxifene is advantageously administered orally in a dosage of about 20-100 mg once a day; and raloxifene is advantageously administered orally in a dosage of about 60 mg once a day.

With regard to the preferred antiandrogen bicalutamide, this is generally administered in an oral dosage of 50 mg daily.

With regard to the preferred progestin analog megestrol/megestrel acetate, this is generally administered in an oral dosage of 40 mg four times daily.

The dosages noted above may generally be administered for example once, twice or more per course of treatment, which may be repeated for example every 7, 14, 21 or 28 days.

Aromatase Inhibitors

Of the hormones, hormone agonists, hormone antagonists and hormone modulating agents for use in the combinations of the invention, preferred are aromatase inhibitors.

In post-menopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some post-menopausal patients with hormone-dependent breast cancer. Examples of such hormone modulating agents include aromatase inhibitors or inactivators, such as exemestane, anastrozole, letrozole and aminoglutethimide.

Exemestane, which has the chemical name 6-methylenandrosta-1,4-diene-3,17-dione, is used for the treatment of advanced breast cancer in post-menopausal women whose disease has progressed following tamoxifen therapy, side effects including hot flashes and nausea. Anastrozole, which has the chemical name, $\alpha,\alpha,\alpha',\alpha'$-tetramethyl-5-(1H-1,2,4-triazol-1-ylmethyl)-1,3-benzenediacetonitrile, is used for adjuvant treatment of post-menopausal women with hormone receptor-positive early breast cancer, and also for the first-line treatment of post-menopausal women with hormone receptor-positive or hormone receptor-unknown locally advanced or metastatic breast cancer, and for the treatment of advanced breast cancer in post-menopausal women with disease progression following tamoxifen therapy. Administration of anastozole usually results in side-effects including gastrointestinal disturbances, rashes and headaches. Letrozole, which has the chemical name 4,4'-(1H-1,2,4-triazol-1-ylmethylene)-dibenzonitrile, is used for first-line treatment of post-menopausal women with hormone receptor-positive or hormone receptor-unknown locally advanced or metastatic breast cancer, and for the treatment of advanced breast cancer in post-menopausal women with disease progression following antiestrogen therapy, possible side-effects including occasional transient thrombocytopenia and elevation of liver transaminases. Aminoglutethimide, which has the chemical name 3-(4-aminophenyl)-3-ethyl-2,6-piperidinedione, is also used for treating breast cancer but suffers from the side-effects of skin rashes and less commonly thrombocytopenia and leukopenia.

Preferred aromatase inhibitors include letrozole, anastrozole, exemestane and aminoglutethimide. Letrozole is commercially available for example from Novartis A.G. under the trade name Femara, or may be prepared for example as described in U.S. Pat. No. 4,978,672, or by processes analogous thereto. Anastrozole is commercially available for example from AstraZeneca plc under the trade name Arimidex, or may be prepared for example as described in U.S. Pat. No. 4,935,437, or by processes analogous thereto. Exemestane is commercially available for example from Pharmacia Corporation under the trade name Aromasin, or may be prepared for example as described in U.S. Pat. No. 4,978,672, or by processes analogous thereto. Aminoglutethimide is commercially available for example from Novartis A.G. under the trade name Cytadren, or may be prepared for example as described in U.S. Pat. No. 2,848,455, or by processes analogous thereto. The aromatase inhibitor vorozole, which may be prepared for example as described in European patent specification No. 293978, or by processes analogous thereto, can also be used in accordance with the invention.

With regard to the preferred aromatase inhibitors, these are generally administered in an oral daily dosage in the range 1 to 1000 mg, for example letrozole in a dosage of about 2.5 mg once a day; anastrozole in a dosage of about 1 mg once a day; exemestane in a dosage of about 25 mg once a day; and aminoglutethimide in a dosage of 250 mg 2-4 times daily.

Particularly preferred are aromatase inhibitors selected from the agents described herein, for example, letrozole, anastrozole, exemestane and aminoglutethimide.

GNRAs

Of the hormones, hormone agonists, hormone antagonists and hormone modulating agents for use in the combinations of the invention, preferred are agents of the GNRA class.

Definition:

As used herein the term GNRA is intended to define gonadotropin-releasing hormone (GnRH) agonists and antagonists (including those described below), together with the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

When released from the hypothalamus in the brain, gonadotropin-releasing hormone (GnRH) agonists stimulate the pituitary gland to produce gonadotropins. Gonadotropins are hormones that stimulate androgen synthesis in the testes and estrogen synthesis in the ovaries. When GnRH agonists are first administered, they can cause an increase in gonadotropin release, but with continued administration, GnRH will block gonadotropin release, and therefore decrease the synthesis of androgen and estrogen. GnRH analogs are used to treat metastatic prostate cancer. They have also been approved for treatment of metastatic breast cancer in pre-menopausal women. Examples of GnRH analogs include goserelin acetate and leuprolide acetate. In contrast GnRH antagonists such as aberelix cause no initial GnRH surge since they have no agonist effects. However, due to their narrow therapeutic index, their use is currently limited to advanced prostate cancer that is refractory to other hormonal treatment such as GnRH agonists and anti-androgens.

Goserelin acetate is a synthetic decapeptide analog of LHRH or GnRH, and has the chemical structure is pyro-Glu-His-Trp-Ser-Tyr-D-Ser(Bu)-Leu-Arg-Pro-Azgly-$NH_2$ acetate, and is used for the treatment of breast and prostate cancers and also endometriosis, side effects including hot flashes, bronchitis, arrhythmias, hypertension, anxiety and headaches. Leuprolide acetate is a synthetic nonapeptide analog of GnRH or LHRH, and has the chemical name 5-oxo-L-prolyl-L-histidyl-L-tryptophyl-L-seryl-L-tyrosyl-D-leucyl-L-leucyl-L-arginyl-N-ethyl-L-prolinamide acetate. Leuprolide acetate is used for the treatment of prostate cancer, endometriosis, and also breast cancer, side effects being similar to those of goserelin acetate.

Abarelix is a synthetic decapeptide Ala-Phe-Ala-Ser-Tyr-Asn-Leu-Lys-Pro-Ala, and has the chemical name N-Acetyl-3-(2-naphthalenyl)-D-alanyl-4-chloro-D-phenylalanyl-3-(3-pyridinyl)-D-alanyl-L-seryl-N-methyl-L-tyrosyl-D-asparaginyl-L-leucyl-N6-(1-methylethyl)-L-lysyl-L-protyl-D-alaninamide. Abarelix can be prepared according to R. W. Roeske, WO9640757 (1996 to Indiana Univ. Found.).

Preferences and Specific Embodiments:

Preferred GnRH agonists and antagonists for use in accordance with the invention include any of the GNRAs described herein, including in particular goserelin, leuprolide/leuporelin, triptorelin, buserelin, abarelix, goserelin acetate and leuprolide acetate. Particularly preferred are goserelin and leuprolide. Goserelin acetate is commercially available for example from AstraZeneca plc under the trade name Zoladex, or may be prepared for example as described in U.S. Pat. No. 5,510,460, or by processes analogous thereto. Leuprolide acetate is commercially available for example from TAP Pharmaceuticals Inc. under the trade name Lupron, or may be prepared for example as described in U.S. Pat. No. 3,914,412, or by processes analogous thereto. Goserelin is commercially available from AstraZeneca under the trade name Zoladex may be prepared for example as described in ICI patent publication US4100274 or Hoechst patent publication EP475184 or by processes analagous thereto. Leuprolide is commercially available in the USA from TAP Pharmaceuticals Inc. under the trade name Lupron and in Europe from Wyeth under the trade name Prostap and may be prepared for example as described in Abbott patent publication US4005063 or by processes analogous thereto. Triptorelin is commercially available from Watson Pharma under the trade name Trelstar and may be prepared for example as described in Tulane patent publication US5003011 or by processes analagous thereto. Buserelin is commercially available under the trade name Suprefact and may be prepared for example as described in Hoechst patent publication U.S. Pat. No. 4,024,248 or by processes analogous thereto. Abarelix is commercially available from Praecis Pharmaceuticals under the trade name Plenaxis and may be prepared for example as described by Jiang at al., J Med Chem (2001), 44(3), 453-467 or Polypeptide Laboratories patent publication WO2003055900 or by processes analogous thereto.

Other GnRH agonists and antagonists for use in accordance with the invention include, but are not limited to, Histrelin from Ortho Pharmaceutical Corp, Nafarelin acetate from Roche, and Deslorelin from Shire Pharmaceuticals.

Posology:

The GnRH agonists and antagonists are advantageously administered in dosages of 1.8 mg to 100 mg, for example 3.6 mg monthly or 10.8 mg every three months for goserelin or 7.5 mg monthly, 22.5 mg every three months or 30 mg every four months for leuprolide.

With regard to the preferred GnRH analogs, these are generally administered in the following dosages, namely goserelin acetate as a 3.6 mg subcutaneous implant every 4 weeks, and leuprolide as a 7.5 mg intramuscular depot every month.

2. Cytokines and Cytokine-Activating Agents

Definition:

The term "cytokine" is a term of art, and references to cytokines herein is intended to cover the cytokine per se together with the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. The term "cytokine-activating agent" is intended to cover any agent which (directly or indirectly) induces, potentiates, stimulates, activates or promotes endogenous cytokine production or the activity thereof in vivo, together with the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

Cytokines are a class of proteins or polypeptides predominantly produced by cells of the immune system which have the capacity to control the function of a second cell. In relation to anticancer therapy cytokines are used to control the growth or kill the cancer cells directly and to modulate the immune system more effectively to control the growth of tumours.

Cytokines, such interferon (IFN) alpha and IL-6, have been shown to interact directly with tumor cells, inducing growth arrest or apoptotic cell death. IFN-alpha is used the treatment of malignant melanoma, chronic myelogenous leukemia (CML), hairy cell leukemia, and Kaposi's sarcoma.

Cytokines also have antitumour actions by stimulating immune cells to fight tumors through a variety of different pathways. For example, the T cell growth factor, IL-2 promotes T-cell and natural killer (NK) cell growth. Other cytokines such as the interferons and granulocyte-macrophage colony-stimulating factor (GM-CSF) act on antigen presenting cells to facilitate the activation of the key immune effector B cells and T cells.

IL-2 is used in both metastatic melanoma and renal cell carcinoma either alone or in combination with IFN-alpha. In particular in late stage kidney cancer IL-2 is the treatment of choice.

Preferences and Specific Embodiments:

Any of the cytokines and cytokine-modulating agents described herein may find application in the invention, including in particular interferons (such as interferon-γ and interferon α) and interleukins (e.g. interleukin 2). Interferon α-2b (recombinant) is available commercially under the trade name of INTRON® A from Schering Plough.

Other preferred interferons include Interferon α-2a which is available under the trade name of ROFERON from Roche.

A particularly preferred interleukin is PROLEUKIN® IL-2 (aldesleukin) which is available from Chiron Corp.

Posology:

The interferons are administered by injection in a schedule which is dependent on tha particular indication. For IntronA treatment of malignant melanoma preferably in a schedule that includes induction treatment 5 consecutive days per week for 4 weeks as an intravenous (IV) infusion at a dose of 20 million IU/m2, followed by maintenance treatment three times per week for 48 weeks as a subcutaneous (SC) injection, at a dose of 10 million IU/m2. For intron A treatment of non-Hodgkin's Lymphoma preferably in a schedule of 5 million IU subcutaneously three times per week for up to 18 months in conjunction with an anthracycline-containing chemotherapy regimen.

The recommended initial dose of Roferon-A for CML is 9 MIU daily administered as a subcutaneous or intramuscular injection. Based on clinical experience short-term tolerance may be improved by gradually increasing the dose of Roferon-A over the first week of administration from 3 MIU daily for 3 days to 6 MIU daily for 3 days to the target dose of 9 MIU daily for the duration of the treatment period. The induction dose of Roferon-A for Hairy cell leukaemia is 3 MIU daily for 16 to 24 weeks, administered as a subcutaneous or intramuscular injection. Subcutaneous administration is particularly suggested for, but not limited to, thrombocytopenic patients (platelet count <50,000) or for patients at risk for bleeding. The recommended maintenance dose is 3 MIU, three times a week (tiw).

For PROLEUKIN the following schedule has been used to treat adult patients with metastatic renal cell carcinoma (metastatic RCC) or metastatic melanoma (each course of treatment consists of two 5-day treatment cycles separated by a rest period): 600,000 IU/kg (0.037 mg/kg) dose administered every 8 hours by a 15-minute IV infusion for a maximum of 14 doses. Following 9 days of rest, the schedule is repeated for another 14 doses, for a maximum of 28 doses per course, as tolerated.

Cytokine-Activating Agents:

Preferred cytokine-activating agents include: (a) Picibanil from Chugai Pharmaceuticals, an IFN-gamma-inducing molecule for carcinoma treatment; (b) Romurtide from Daiichi which activates the cytokine network by stimulation of colony stimulating factor release; (c) Sizofiran from Kaken Pharmaceutical, a beta1-3, beta1-6 D-glucan isolated from suehirotake mushroom, which stimulates production of IFN-gamma and IL-2 by mitogen-stimulated peripheral blood mononuclear cells, and is useful in uterine cervix tumour and lung tumour treatment; (d) Virulizin from Lorus Therapeutics Inc, a NK agonist and cytokine release modulator which stimulates IL-17 synthesis and IL-12 release for the treatment of sarcoma, melanoma, pancreas tumours, breast tumours, lung tumours, and Kaposis sarcoma Phase III pancreatic; and (e) Thymosin alpha 1, a synthetic 28-amino acid peptide with multiple biological activities primarily directed towards immune response enhancement for increased production of Th1 cytokines, which is useful in the treatment of non-small-cell lung cancer, hepatocellular carcinoma, melanoma, carcinoma, and lung brain and renal tumours.

3. Retinoids

Definition:

The term "retinoid" is a term of art used herein in a broad sense to include not only the specific retinoids disclosed herein, but also the ionic, salt, solvate, isomers, tautomers, N-oxides, ester, prodrugs, isotopes and protected forms thereof (preferably the salts or tautomers or Isomers or N-oxides or solvates thereof, and more preferably, the salts or tautomers or N-oxides or solvates thereof), as described above.

Technical Background:

Tretinoin is an endogenous metabolite of retinol. It induces terminal differentiation in several hemopoietic precursor cell lines, including human myeloid lines. Acute Promyelocytic Leukemia (APL) is associated with a specific translocation between chromosomes 15 and 17; the retinoic acid receptor—α is located on chromosome 17. The translocation appears in inhibit differentiation and lead to carcinogenesis; tretinoin may overcome this when used in high doses. Tretinoin induces remissions in 64-100% of APL patients, with time to remission usually between 8 and 119 days of therapy. Acquired resistance during therapy is common especially with prolonged dosing (4-6 months). Alitretinoin is a 9-cis-retinoic acid derivative which appears to be selective for the RXR subfamily of retinoid receptors. This selectivity may preserve therapeutic antineoplastic effects while reducing significant side effects of retinoid therapy including birth defects at fetal exposure, irritation of skin and mucosal surfaces or skeletal abnormalities. Topical alitretinoin is approved in the US for the treatment of Kaposi's Sarcoma. Oral and gel (topical) formulations of bexarotene (Targretin; LGD-1069), a retinoid X receptor (RXR)-selective antitumor retinoid, are available for the treatment of cutaneous T-cell lymphoma (CTCL).

U.S. Pat. No. 6,127,382, WO 01/70668, WO 00/68191, WO 97/48672, WO 97/19052 and WO 97/19062 (all to Allergan) each describe compounds having retinoid-like activity for use in the treatment of various hyperproliferative diseases including cancers.

Preferences and Specific Embodiments:

Preferred retinoids for use in accordance with the invention Include any of the retinoids disclosed herein, including in particular tretinoin (all-trans retinoic acid), alitretinoin and bexarotene. Tretinoin (Retacnyl, Aknoten, Tretin M) is commercially available from Roche under the trade name Vesanoid and may be prepared for example as described in D. A. van Dorp, J. R. Arens, Rec. Trav. Chim. 65, 338 (1946); C. D. Robeson et al., J. Am. Chem. Soc. 77, 4111 (1955); R. Marbet, DE 2061507; U.S. Pat. No. 3,746,730 (1971, 1973 both to Hoffmann-La Roche), or by processes analogous thereto. Alitretinoin (9-cis-Tretinoln, Panrexin) is commercially available from Ligand Pharmaceuticals under the trade name Panretin and may be prepared for example as described in C. D. Robeson et al., J. Am. Chem. Soc. 77, 4111 (1955); M. Matsui et al., J. Vitaminol. 4, 178 (1958); M. F. Boehm et al., J. Med. Chem. 37, 408 (1994), or by processes analogous thereto. Bexarotene (Targrexin, Targret) is commercially available from Ligand Pharmaceuticals under the trade name Targretin and may be prepared for example as described in M. F. Boehm et al., WO 9321146 (1993 to Ligand Pharm.); M. L. Dawson et al., U.S. Pat. No. 5,466,861 (1995 to SRI Int.; La Jolla Cancer Res. Found.), or by processes analogous thereto.

Posology:

Tretinoin is advantageously administered in dosages of 25 $mg/m^2/day$ to 45 $mg/m^2/day$ by mouth in two divided doses for 30 days after complete remission or up to a maximum of 90 days. Alitretinoin gel 0.1% is advantageously administered initially by application two (2) times a day to cutaneous KS lesions. Bexarotene is advantageously administered initially as a single daily oral dose of 300 $mg/m^2/day$. The dose may be adjusted to 200 $mg/m^2/day$ then to 100 $mg/m^2/day$, or temporarily suspended, if necessitated by toxicity. If there is no tumor response after eight weeks of treatment and if the initial dose of 300 $mg/m^2/day$ is well tolerated, the dose may be escalated to 400 $mg/m^2/day$ with careful monitoring. Bexarotene gel is advantageously applied initially once every other day for the first week. The application frequency may be increased at weekly intervals to once daily, then twice daily, then three times daily and finally four times daily according to individual lesion tolerance.

4. Monoclonal Antibodies.

Any monoclonal antibody (e.g. to one or more cell surface antigen(s)) may be used in the combinations of the invention. Antibody specificity may be assayed or determined using any of a wide variety of techniques well-known to those skilled in the art.

Definition:

The term "monoclonal antibody" used herein refers to antibodies from any source, and so includes those that are fully human and also those which contain structural or specificity determining elements derived from other species (and which can be referred to as, for example, chimeric or humanized antibodies).

Technical Background:

The use of monoclonal antibodies is now widely accepted in anticancer chemotherapy as they are highly specific and can therefore bind and affect disease specific targets, thereby sparing normal cells and causing fewer side-effects than traditional chemotherapies.

One group of cells which have been investigated as targets for antibody chemotherapy for the treatment of various cancers are those bearing the cell-surface antigens comprising the cluster designation (CD) molecules which are over-expressed or aberrantly expressed in tumour cells, for example CD20, CD22, CD33 and CD52 which are over-expressed on the tumour cell surface, most notably in tumours of hematopoietic origin. Antibodies to these CD targets (anti-CD antibodies) Include the monoclonal antibodies rituximab (a.k.a. rituxamab), tositumomab and gemtuzumab ozogamicin.

Rituximab/rituxamab is a mouse/human chimeric anti-CD20 monoclonal antibody which has been used extensively for the treatment of B-cell non-Hodgkin's lymphoma including relapsed, refractory low-grade or follicular lymphoma. The product is also being developed for various other indications Including chronic lymphocytic leukaemia. Side effects of rituximab/rituxamab may include hypoxia, pulmonary infiltrates, acute respiratory distress syndrome, myocardial infarction, ventricular fibrillation or cardiogenic shock. Tositumomab is a cell-specific anti-CD20 antibody labelled with iodine-131, for the treatment of non-Hodgkin's lymphoma and lymphocytic leukaemia. Possible side-effects of tositumomab include thrombocytopenia and neutropenia. Gemtuzumab ozogamicin is a cytotoxic drug (calicheamicin) linked to a human monoclonal antibody specific for CD33. Calicheamicin is a very potent antitumour agent, over 1,000 times more potent than adriamycin. Once released inside the cell, calicheamicin binds in a sequence-specific manner to the minor groove of DNA, undergoes rearrangement, and exposes free radicals, leading to breakage of double-stranded DNA, and resulting in cell apoptosis (programmed cell death). Gemtuzumab ozogamicin is used as a second-line treatment for acute myeloid leukaemia, possible side-effects including severe hypersensitivity reactions such as anaphylaxis, and also hepatotoxicity.

Alemtuzumab (Millennium Pharmaceuticals, also known as Campath) is a humanized monoclonal antibody against CD52 useful for the treatment of chronic lymphocytic leukaemia and Non-Hodgkin lymphoma which induces the secretion of TNF-alpha, IFN-gamma and IL-6.

Preferences:

Preferred monoclonal antibodies for use according to the invention include anti-CD antibodies, including alemtuzumab, CD20, CD22 and CD33. Particularly preferred are monoclonal antibody to cell surface antigens, including anti-CD antibodies (for example, CD20, CD22, CD33) as described above.

Specific Embodiments:

In one embodiment, the monoclonal antibody is an antibody to the cluster designation CD molecules, for example, CD20, CD22, CD33 and CD52. In another embodiment, the monoclonal antibody to cell surface antigen is selected from rituximab/rituxamab, tositumomab and gemtuzumab ozogamicin. Other monoclonal antibodies that may be used according to the invention include bevacizumab.

Exemplary Formulations:

Monoclonal antibodies to cell surface antigen(s) for use according to the invention include CD52 antibodies (e.g. alemtuzumab) and other anti-CD antibodies (for example, CD20, CD22 and CD33), as described herein. Preferred are therapeutic combinations comprising a monoclonal antibody to cell surface antigen(s), for example anti-CD antibodies (e.g. CD20, CD22 and CD33) which exhibit an advantageous efficacious effect, for example, against tumour cell growth, in comparison with the respective effects shown by the individual components of the combination.

Preferred examples of monoclonal antibodies to cell surface antigens (anti-CD antibodies) include rituximab/rituxamab, tositumomab and gemtuzumab ozogamicin. Rituximab/rituxamab is commercially available from F Hoffman-La Roche Ltd under the trade name Mabthera, or may be obtained as described in PCT patent specification No. WO 94/11026. Tositumomab is commercially available from GlaxoSmithKline plc under the trade name Bexxar, or may be obtained as described in U.S. Pat. No. 5,595,721. Gemtuzumab ozogamicin is commercially available from Wyeth Research under the trade name Mylotarg, or may be obtained as described in U.S. Pat. No. 5,877,296.

Biological Activity:

Monoclonal antibodies (e.g. monoclonal antibodies to one or more cell surface antigen(s)) have been identified as suitable anti-cancer agents. Antibodies are effective through a variety of mechanisms. They can block essential cellular growth factors or receptors, directly induce apoptosis, bind to target cells or deliver cytotoxic payloads such as radioisotopes and toxins.

Posology:

The anti-CD antibodies may be administered for example in dosages of 5 to 400 mg per square meter ($mg/m^2$) of body surface; in particular gemtuzumab ozogamicin may be administered for example in a dosage of about 9 $mg/m^2$ of body surface; rituximab/rituxamab may be administered for example in a dosage of about 375 $mg/m^2$ as an IV infusion once a week for four doses; the dosage for tositumomab must be individually quantified for each patient according to the usual clinical parameters such as age, weight, sex and condition of the patient.

These dosages may be administered for example once, twice or more per course of treatment, which may be repeated for example every 7, 14, 21 or 28 days.

5. Camptothecin Compounds

Definition:

The term "camptothecin compound" as used herein refers to camptothecin per se or analogues of camptothecin as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

Camptothecin compounds are compounds related to or derived from the parent compound camptothecin which is a water-insoluble alkaloid derived from the Chinese tree *Camptothecin acuminata* and the Indian tree *Nothapodytes foetida*. Camptothecin has a potent inhibitory activity against DNA biosynthesis and has shown high activity against tumour cell growth in various experimental systems. Its clinical use in anti-cancer therapy is however, limited significantly by its high toxicity, and various analogues have been developed in attempts to reduce the toxicity of camptothecin while retaining the potency of its anti-tumour effect. Examples of such analogues include irinotecan and topotecan.

These compounds have been found to be specific inhibitors of DNA topoisomerase I. Topoisomerases are enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme having a molecular weight of approximately 100,000. The enzyme binds to DNA and introduces a transient single-strand break, unwinds the double helix (or allows it to unwind) and subsequently reseals the break before dissociating from the DNA strand.

Irinotecan, namely 7-ethyl-10-(4-(1-piperidino)-1-piperidino)carbonyloxy-(20S)-camptothecin, and its hydrochloride, also known as CPT 11, have been found to have improved potency and reduced toxicity, and superior water-solubility. Irinotecan has been found to have clinical efficacy in the treatment of various cancers especially colorectal cancer. Another important camptothecin compound is topotecan, namely (S)-9-dimethylaminomethyl-10-hydroxy-camptothecin which, in clinical trials, has shown efficacy against several solid tumours, particularly ovarian cancer and non-small cell lung carcinoma.

Exemplary Formulations:

A parenteral pharmaceutical formulation for administration by injection and containing a camptothecin compound can be prepared by dissolving 100 mg of a water soluble salt of the camptothecin compound (for example a compound as described in EP 0321122 and in particular the examples therein) in 10 ml of sterile 0.9% saline and then sterilising the solution and filling the solution into a suitable container.

Biological Activity:

The camptothecin compounds of the combinations of the invention are specific inhibitors of DNA topoisomerase I are described above and have activity against various cancers.

Prior Art References:

WO 01/64194 (Janssen) discloses combinations of famesyl transferase inhibitors and camptothecin compounds. EP 137145 (Rhone Poulenc Rorer) discloses camptothecin compounds including irinotecan. EP 321122 (SmithKline Beecham) discloses camptothecin compounds including topotecan.

Problems:

Although camptothecin compounds have widely used as chemotherapeutic agents in humans, they are not therapeutically effective in all patients or against all types of tumours. There is therefore a need to increase the inhibitory efficacy of camptothecin compounds against tumour growth and also to provide a means for the use of lower dosages of camptothecin compounds to reduce the potential for adverse toxic side effects to the patient.

Preferences:

Preferred camptothecin compounds for use in accordance with the invention include irinotecan and topotecan referred to above. Irinotecan is commercially available for example from Rhone-Poulenc Rorer under the trade name "Campto" and may be prepared for example as described in European patent specification No. 137145 or by processes analogous thereto. Topotecan is commercially available for example from SmithKline Beecham under the trade name "Hycamtin" and may be prepared for example as described in European patent number 321122 or by processes analogous thereto. Other camptothecin compounds may be prepared in conventional manner for example by processes analogous to those described above for irinotecan and topotecan.

Specific Embodiments:

In one embodiment, the camptothecin compound is irinotecan. In another embodiment, the camptothecin compound is a camptothecin compound other than irinotecan, for example a camptothecin compound such as topotecan.

Posology:

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment. These dosages may be administered for example once, twice or more per course of treatment, which may be repeated for example every 7, 14, 21 or 28 days.

6. Antimetabolites

Definition:

The terms "antimetabolic compound" and "antimetabolite" are used as synonyms and define antimetabolic compounds or analogues of antimetabolic compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. Thus, the antimetabolic compounds, otherwise known as antimetabolites, referred to herein constitute a large group of anticancer drugs that interfere with metabolic processes vital to the physiology and proliferation of cancer cells. Such compounds include nucleoside derivatives, either pyrimidine or purine nucleoside analogs, that inhibit DNA synthesis, and inhibitors of thymidylate synthase and/or dihydrofolate reductase enzymes.

Technical Background:

Antimetabolites (or antimetabolic compounds), constitute a large group of anticancer drugs that interfere with metabolic processes vital to the physiology and proliferation of cancer cells. Such compounds include nucleoside derivatives, either pyrimidine or purine nucleoside analogues, that inhibit DNA synthesis, and inhibitors of thymidylate synthase and/or dihydrofolate reductase enzymes. Anti-tumour nucleoside derivatives have been used for many years for the treatment of various cancers. Among the oldest and most widely used of these derivatives is 5-fluorouracil (5-FU) which has been used to treat a number of cancers such as colorectal, breast, hepatic and head and neck tumours.

In order to enhance the cytotoxic effect of 5-FU, leucovorin has been used with the drug to modulate levels of thymidylate synthase which are critical to ensure that malignant cells are sensitive to the effect of 5-FU. However, various factors limit the use of 5-FU, for example tumour resistance, toxicities, including gastrointestinal and haematological effects, and the need for intravenous administration. Various approaches have been taken to overcome these disadvantages including proposals to overcome the poor bioavailability of 5-FU and also to increase the therapeutic Index of 5-FU, either by reducing systemic toxicity or by increasing the amount of active drug reaching the tumour.

One such compound which provides improved therapeutic advantage over 5-FU is capecitabine, which has the chemical name [1-(5-deoxy-β-D-ribofuranosyl)-5-fluoro-1,2-dihydro-2-oxo-4-pyrimidinyl]-carbamic acid pentyl ester. Capecitabine is a pro-drug of 5-FU which is well absorbed after oral dosing and delivers pharmacologically-active concentrations of 5-FU to tumours, with little systemic exposure to the active drug. As well as offering potentially superior activity to 5-FU, it can also be used for oral therapy with prolonged administration. Another anti-tumour nucleoside derivative is gemcitabine which has the chemical name 2'-deoxy-2',2'-difluoro-cytidine, and which has been used in the treatment of various cancers including non-small cell lung cancer and pancreatic cancer. Further anti-tumour nucleosides include cytarabine and fludarabine. Cytarabine, also known as ara-C, which has the chemical name 1-β-D-arabinofuranosylcytosine, has been found useful in the treatment of acute myelocytic leukemia, chronic myelocytic leukemia (blast phase), acute lymphocytic leukemia and erythroleukemia. Fludarabine is a DNA synthesis inhibitor, which has the chemical name 9-β-D-arabinofuranosyl-2-fluoro-adenine, and is used for the treatment of refractory B-cell chronic lymphocytic leukaemia. Other antimetabolites used in anticancer chemotherapy include the enzyme inhibitors raltitrexed, pemetrexed, and methotrexate. Raltitrexed is a folate-based thymidylate synthase inhibitor, which has the chemical name N-[5-[N-[(3,4-dihydro-2-methyl-4-oxo-6-quinazolinyl)-methyl-N-methylamino]-2-thenoyl]-L-glutamic acid, and is used in the treatment of advanced colorectal cancer. Pemetrexed is a thymidylate synthase and transferase inhibitor, which has the chemical name N-[4-[2-(2-amino-4,7-dihydro-4-oxo-1H-pyrrolo[2,3-d]pyrimidin-5-yl)ethyl]benzoyl]-L-glutamic acid, disodium salt, and is used for the treatment of mesothelloma and locally advanced or metastatic non-small-cell lung cancer (SCLC) in previously treated patients. Methotrexate is an antimetabolite which interrupts cell division by inhibiting DNA replication through dihydrofolate reductase inhibition, resulting in cell death, and has the chemical name is N-[4-[[(2,4-diamino-6-pteridinyl) methyl]-ethylamino]benzoyl]-glutamic acid, and is used for the treatment of acute lymphocytic leukemia, and also in the treatment of breast cancer, epidermoid cancers of the head and neck, and lung cancer, particularly squamous cell and small cell types, and advanced stage non-Hodgkin's lymphomas.

Biological Activity:

The antimetabolic compounds of the combinations of the invention interfere with metabolic processes vital to the physiology and proliferation of cancer cells as described above and have activity against various cancers.

Problems:

These anticancer agents have a number of side-effects especially myelosuppression and in some cases nausea and diarrhoea. There is therefore a need to provide a means for the use of lower dosages to reduce the potential of adverse toxic side effects to the patient.

Preferences:

Preferred antimetabolic compounds for use in accordance with the invention include anti-tumour nucleosides such as 5-fluorouracil, gemcitabine, capecitabine, cytarabine and fludarabine and enzyme inhibitors such as railtrexed, pemetrexed and methotrexate referred to herein. Thus, preferred antimetabolic compounds for use in accordance with the invention are anti-tumour nucleoside derivatives including 5-fluorouracil, gemcitabine, capecitabine, cytarabine and fludarabine referred to herein. Other preferred antimetabolic compounds for use in accordance with the invention are enzyme inhibitors including ralitrexed, pemetrexed and methotrexate.

5-Fluorouracil is widely available commercially, or may be prepared for example as described in U.S. Pat. No. 2,802,005. Gemcitabine is commercially available for example from Eli Lilly and Company under the trade name Gemzar, or may be prepared for example as described in European patent specification No. 122707, or by processes analogous thereto. Capecitabine is commercially available for example from Hoffman-La Roche Inc under the trade name Xeloda, or may be prepared for example as described in European patent specification No. 698611, or by processes analogous thereto. Cytarabine is commercially available for example from Pharmacia and Upjohn Co under the trade name Cytosar, or may be prepared for example as described in U.S. Pat. No. 3,116,282, or by processes analogous thereto. Fludarabine is commercially available for example from Schering AG under the trade name Fludara, or may be prepared for example as described in U.S. Pat. No. 4,357,324, or by processes analogous thereto. Ralitrexed is commercially available for example from AstraZeneca plc under the trade name Tomudex, or may be prepared for example as described in European patent specification No. 239632, or by processes analogous thereto. Pemetrexed is commercially available for example from Eli Lilly and Company under the trade name Alimta, or may be prepared for example as described in European patent specification No. 432677, or by processes analogous thereto. Methotrexate is commercially available for example from Lederle Laboraories under the trade name Methotrexate-Lederle, or may be prepared for example as described In U.S. Pat. No. 2,512,572, or by processes analogous thereto. Other antimetabolites for use in the combinations of the invention include 6-mercapto purine, 6-thioguanine, cladribine, 2'-deoxycoformycin and hydroxyurea.

Specific Embodiments:

In one embodiment, the antimetabolic compound is gemcitabine. In another embodiment, the antimetabolic compound is a antimetabolic compound other than 5-fluorouracil or fludarabine, for example an antimetabolic compound such as gemcitabine, capecitabine, cytarabine, ralitrexed, pemetrexed or methotrexate.

Posology:

The antimetabolite compound will be administered in a dosage that will depend on the factors noted above. Examples of dosages for particular preferred antimetabolites are given below by way of example. With regard to anti-tumour nucleosides, these are advantageously administered in a daily dosage of 10 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of 800 to 1200 $mg/m^2$, for capecitabine in a dosage of 1000 to 1200 $mg/m^2$, for cytarabine in a dosage of 100-200 $mg/m^2$ and for fludarabine in a dosage of 10 to 50 $mg/m^2$.

For the following enzyme inhibitors, examples are given of possible doses. Thus, raltitrexed can be administered in a dosage of about 3 $mg/m^2$, pemetrexed in a dosage of 500 $mg/m^2$ and methotrexate in a dosage of 30-40 $mg/m^2$.

The dosages noted above may generally be administered for example once, twice or more per course of treatment, which may be repeated for example every 7, 14, 21 or 28 days.

7. Vinca Alkaloids

Definition:

The term "vinca alkaloid" as used herein refers to vinca alkaloid compounds or analogues of vinca alkaloid compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

The vinca alkaloids for use in the combinations of the invention are anti-tumour vinca alkaloids related to or derived from extracts of the periwinkle plant (vinca roses). Among these compounds, vinblastine and vincristine are important clinical agents for the treatment of leukaemias, lymphomas and testicular cancer, and vinorelbine has activity against lung cancer and breast cancer.

Biological Activity:

The vinca alkaloid compounds of the combinations of the invention are tubulin targeting agents and have activity against various cancers.

Problems:

Vinca alkaloids suffer from toxicological effects. For example, vinblastine causes leukopenia which reaches a nadir in 7 to 10 days following drug administration, after which recovery ensues within 7 days, while vincristine demonstrates some neurological toxicity for example numbness and trembling of the extremities, loss of deep tendon reflexes and weakness of distal limb musculature. Vinorelbine has some toxicity in the form of granulocytopenia but with only modest thrombocytopenia and less neurotoxicity than other vinca alkaloids. There is therefore a need to increase the inhibitory efficacy of anti-tumour vinca alkaloids against tumour growth and also to provide a means for the use of lower dosages of anti-tumour vinca alkaloids to reduce the potential of adverse toxic side effects to the patient.

Preferences:

Preferred anti-tumour vinca alkaloids for use in accordance with the invention include vindesine, vinvesir, vinblastine, vincristine and vinorelbine. Particularly preferred anti-tumour Arica alkaloids for use in accordance with the invention include vinblastine, vincristine and vinorelbine referred to above. Vinblastine is commercially available for example as the sulphate salt for injection from Eli Lilly and Co under the trade name Velban, and may be prepared for example as described in German patent specification No. 2124023 or by processes analogous thereto. Vincristine is commercially available for example as the sulphate salt for injection from Eli Lilly and Co under the trade name Oncovin and may be prepared for example as described in the above German patent specification No. 2124023 or by processes analogous thereto. Vincristine is also available as a liposomal formulation under the name Onco-TCS™. Vinorelbine is commercially available for example as the tartrate salt for injection from Glaxo Wellcome under the trade name Navelbine and may be prepared for example as described in U.S. Pat. No. 4,307,100, or by processes analogous thereto. Other anti-tumour vinca alkaloids may be prepared in conventional manner for example by processes analogous to those described above for vinoblastine, vincristine and vinorelbine.

Another preferred vinca alkaloid is vindesine. Vindesine is a synthetic derivative of the dimeric catharanthus alkaloid vinblastine, is available from Lilly under the tradename Eldisine and from Shionogi under the tradename Fildesin. Details of the synthesis of Vindesine are described in Lilly patent DE2415980 (1974) and by C. J. Burnett et al., J. Med. Chem. 21, 88 (1978).

Specific Embodiments:

In one embodiment, the vinca alkaloid compound is selected from vinoblastine, vincristine and vinorelbine. In another embodiment, the vinca alkaloid compound is vinoblastine.

Posology:

The anti-tumour vinca alkaloid is advantageously administered in a dosage of 2 to 30 mg or square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment. These dosages may be administered for example once, twice or more per course of treatment, which may be repeated for example every 1, 14, 21 or 28 days.

8. Taxanes

Definition:

The term "taxane compound" as used herein refers to taxane compounds or analogues of taxane compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

The taxanes are a class of compounds having the taxane ring system and related to or derived from extracts from certain species of yew (Taxus) trees. These compounds have been found to have activity against tumour cell growth and certain compounds in this class have been used in the clinic for the treatment of various cancers. Thus, for example, paclitaxel is a diterpene isolated from the bark of the yew tree, Taxus brevifolia, and can be produced by partial synthesis from 10-acetylbacctin, a precursor obtained from yew needles and twigs or by total synthesis, see Holton et al, J. Am. Chem. Soc. 116; 1597-1601 (1994) and Nicholau et al, Nature 367:630 (1994). Paclitaxel has shown anti-neoplastic activity and more recently it has been established that its antitumour activity is due to the promotion of microtubule polymerisation, Kumar N. J., Biol. Chem. 256: 1035-1041 (1981); Rowinsky et al, J. Natl. Cancer Inst. 82: 1247-1259 (1990); and Schiff et al, Nature 277: 655-667 (1979). Paclitaxel has now demonstrated efficacy in several human tumours in clinical trials, McGuire et al, Ann. Int. Med., 111:273-279 (1989); Holmes at al, J. Natl. Cancer Inst. 83: 1797-1805 (1991); Kohn et al J. Natl. Cancer Inst. 86: 18-24 (1994); and Kohn et al, American Society for Clinical Oncology, 12 (1993). Paclitaxel has for example been used for the treatment of ovarian cancer and also breast cancer.

Another taxane compound which has been used in the clinic is docetaxel which has been shown to have particular efficacy in the treatment of advanced breast cancer. Docetaxel has shown a better solubility in excipient systems than paclitaxel, therefore increasing the ease with which it can be handled and used in pharmaceutical compositions.

Biological Activity:

The taxane compounds of the combinations of the invention are tubulin targeting agents and have activity against various cancers.

Problems:

Clinical use of taxanes has demonstrated a narrow therapeutic index with many patients unable to tolerate the side effects associated with its use. There is therefore a need to increase the inhibitory efficacy of taxane compounds against tumour growth and also to provide a means for the use of lower dosages of taxane compounds to reduce the potential of adverse toxic side effects to the patient.

Preferences:

Preferred taxane compounds for use in accordance with the invention include paclitaxel or docetaxel referred to herein. Paclitaxel is available commercially for example under the trade name Taxol from Bristol Myers Squibb and docetaxel is available commercially under the trade name Taxotere from Rhone-Poulenc Rorer. Both compounds and other taxane compounds may be prepared in conventional manner for example as described in EP 253738, EP 253739 and WO 92/09589 or by processes analogous thereto.

Specific Embodiments:

In one embodiment, the taxane compound is paclitaxel. In another embodiment, the taxane compound is docetaxel.

Posology:

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment. These dosages may be administered for example once, twice or more per course of treatment, which may be repeated for example every 7, 14, 21 or 28 days.

9. Epothilones

Definition:

As used herein, the term "epothilone" is used to define a class of cytotoxic macrolides with a similar mechanism of action to paclitaxel but with the potential advantage of activity in taxane-resistant settings in preclinical models. The epothilones ixabepilone, patupilone, BMS-310705, KOS-862 and ZK-EPO are in early clinical trials for cancer treatment. Phase I studies have shown that dose-limiting toxicities of epothilones are generally neurotoxicity and neutropoenia although initial studies with patupilone indicated that diarrhoea was dose limiting. Neuropathy induced by ixabepilone may be schedule dependent. Response rates in taxane-refractory metastatic breast cancer are relatively modest, but ixabepilone and patupilone have shown promising efficacy in hormone-refractory metastatic prostate cancer and in taxane-refractory ovarian cancer.

Technical Background:

Epothilones A and B were originally isolated as anti-fungal fermentation products of the myxobacteria *Sorangium cellulosum*. Shortly thereafter these agents were demonstrated to stabilize microtubules and induce mitotic arrest. Epothilones are known to compete with Taxol for microtubule binding. Though their cytotoxic activity relies on the same mechanism as that of the taxanes, the epothilones have a couple of key advantages. Firstly they are not substrates for the multi-drug resistance pump P-gylycoprotein. Secondly they are easier both to produce (because of their bacterial origin) and to manipulate. Chemical syntheses, either total or partial, of these molecules and their analogs allows for modification to enhance their efficacy Mani et al. Anticancer Drugs 2004; 15(6):553-8). Several epothilones or epothilone-derivatives have been shown effective against cell lines and tumor xenografts and are now in clinical trials (Goodin et al. J Clin Oncol 2004; 22(10): 2015-25). An unexpected source for the identification of microtubule stabilizing agents has been marine organisms. Laulimalide and isolaulimalide are natural products of the marine sponge *Cacospongia mycofijiensis* with strong Taxol-like activity, even against P-gp expressing cell lines. Eluetherobin, similar in both respects, is a product of the *Eleutherobia* species of soft coral.

Biological Activity:

Formation of microtubules involves polymerization of heterodimeric α/β-tubulin subunits with multiple isoforms of both α- and β-tubulin present in human cells. Intact microtubule function is required for formation and functioning of the mitotic spindle, and cells treated with agents that bind either tubulin subunits or polymerized microtubules exhibit alterations in spindle formation, as well as arrest at the G2/M phase of the cell cycle, which is associated with induction of apoptosis. Compounds that target microtubules are potent cytotoxic agents, exemplified by the convergent evolution of microtubule-targeting compounds by a variety of plant and marine species. Published studies of three epothilones in current clinical development, epothilone B, aza-epothilone B, and desoxyepothilone B, indicate that these compounds exhibit broad spectrum antitumor activity in cell culture models and in xenografts. Furthermore, epothilones are generally more cytotoxic than paclitaxel in cell culture studies, with $IC_{50}$ values in the sub- or low nanomolar range in a variety of tumor cell lines (Bollag et al. Cancer Res 55:2325-2333, 1995; Lee et al. Clin Cancer Res 7:1429-1437, 2001; Chou et al. Proc Natl Acad Sci U S A 95:9642-9647, 1998; Newman et al. Cancer Chemother Pharmacol 48:319-326, 2001). Preclinical studies also demonstrated important differences with regard to drug resistance mechanisms between epothilones and taxanes. In particular, overexpression of P-glycoprotein minimally affects the cytotoxicity of epothilone B, aza-epothilone B, and desoxyepothilones in cell culture models. Comparison of the cytotoxic effects of epothilone B, aza-epothilone B, and desoxyepothilone B among P-glycoprotein-overexpressing cell lines suggests that desoxyepothilone B is least affected, whereas aza-epothilone B is most affected by P-glycoprotein expression. However, it should be noted that differences among the $IC_{50}$s of these compounds in P-glycoprotein-overexpressing cell lines are small compared with the differences between these values and $IC_{50}$s for paclitaxel in these cell lines. Although the significance of P-glycoprotein expression in clinical resistance to taxanes remains uncertain, these results suggest that epothilones may be more active than taxanes in patients with malignancies characterized by high levels of P-glycoprotein expression. In vivo studies indicate that epothilones are active in paclitaxel-sensitive and -resistant tumor models using a variety of schedules. When administered intravenously to mice using intermittent daily or weekly schedules, aza-epothilone B is highly active in ovarian, colon, and breast xenografts and induces cures in an ovarian xenograft model (Pat-7) that is resistant to paclitaxel. Notably, unlike paclitaxel, aza-epothilone B is effective when administered orally in preclinical models. This phenomenon likely relates to the expression of P-glycoprotein in intestinal mucosa, resulting in poor absorption of paclitaxel but not epothilones.

Problems:

Sensory Neuropathy has been Documented with Epothilones

Preferences:

Existing structure-activity data provide some insight into the interaction between epothilones and microtubules. Results from several groups indicate that modifications at or near the C12-13 epoxide can affect microtubule-stabilizing activity (Wartmann and Altmann, Curr Med Chem Anti-Canc Agents 2:123-148, 2002). For example, addition of a methyl group to epothilone A at position C12 yields epothilone B, which is approximately twice as potent as epothilone A or paclitaxel in inducing tubulin polymerization in vitro (Kowalski et al. J Biol Chem 272: 2534-2541, 1997; Nicolaou et al. Nature 387:268-272, 1997, abstr 428). In addition, it is clear that an epoxide at C12-13 is not required for microtubule-binding, because desoxyepothilone B (also known as epothilone D or KOS-862) lacks the C12-13 epoxide and is a more potent microtubule stabilizer in vitro than epothilone A or B. Less data are available regarding the effects of modifying other regions of epothilone. Despite attempts to improve microtubule binding by altering the C9-C12 region (on the basis of molecular modeling), alterations in this area resulted in loss of cytotoxic activity. By contrast, replacement of the lactone oxygen of epothilone B with a lactam (aza-epothilone B, also known as BMS-247550) does not impair microtubule-polymerizing activity or cytotoxicity. Although a variety of other epothilone analogs have been synthesized, it should be noted that increasing microtubule-stabilizing activity does not always result in increased cytotoxicity, presumably because of the importance of other variables such as cellular accumulation and metabolic stability (Wartmann and Altmann, Curr Med Chem Anti-Canc Agents 2:123-148, 2002). Indeed, replacement of the methyl group at C12 position of desoxyepothilone B with a propanol group results in a compound that is as effective as desoxyepothilone B against the leukemic cell line CCRF-CEM but is significantly less active against a P-glycoprotein-overexpressing subline ($IC_{50}$ of 17 nmol/L for desoxyepothilone B v 167 nmol/L for the propanol derivative) (Chou et al. Proc Natl Acad Sci U S A 95:9642-9647, 1998). Additional modifications of naturally occurring epothilones have been made in an effort to improve solubility, such as BMS-310705, which is a C-21-substituted derivative of epothilone B (Lee et al. Proc Am Assoc Cancer Res 43'a3928, 2002).

Specific Embodiments:

In one embodiment, the epothilone compound is BMS-247550. In another embodiment, the epothilone compound is Desoxyepothilone and in another embodiment the epothilone compound is BMS-310705

Posology:

BMS-247550 is dosed either 40 mg/m² over 3 hours every 21 days or 6 mg/m² administered over 1 hour daily times 5 days every 3 weeks. Because of the frequency of mucositis and neutropenia in the first 18 patients on the single-dose every-3-week schedule, the dose was reduced to 32 mg/m². EP0906 is dosed either at 2.5 mg/m² weekly for 3 weeks followed by 1 week of rest in one trial, and 6 mg/m² once every 3 weeks. KOS-862 is scheduled at either a single dose every 3 weeks, a daily dose times 3 every 3 weeks, a fixed rate dose every 3 weeks, and a weekly dose for 3 weeks with 1 week rest.

10. Platinum Compounds

Definition:

The term "platinum compounds" as used herein refers to any tumour cell growth inhibiting platinum compound including platinum coordination compounds, compounds which provide platinum in the form of an ion and analogues of platinum compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

In the chemotherapeutic treatment of cancers, cisplatin (cis-diaminodichloroplatinum (II)) has been used successfully for many years in the treatment of various human solid malignant tumours for example testicular cancer, ovarian cancer and cancers of the head and neck, bladder, oesophagus and lung.

More recently, other diamino-platinum complexes, for example carboplatin (diamino(I,1-cyclobutane-dicarboxylato)platinum (II)), have also shown efficacy as chemotherapeutic agents in the treatment of various human solid malignant tumours, carboplatin being approved for the treatment of ovarian cancer. A further antitumour platinum compound is oxaliplatin (L-OHP), a third generation diamino-cyclohexane platinum-based cytotoxic drug, which has the chemical name (1,2-diaminocyclohexane)oxalato-platinum (II). Oxaliplatin is used, for example, for the treatment of metastatic colorectal cancer, based on its lack of renal toxicity and higher efficacy in preclinical models of cancer in comparison to cisplatin.

Biological Activity:

The platinum compounds of the combinations of the invention have activity against various cancers.

Problems:

Although cisplatin and other platinum compounds have been widely used as chemotherapeutic agents in humans, they are not therapeutically effective in all patients or against all types of tumours. Moreover, such compounds need to be administered at relatively high dosage levels which can lead to toxicity problems such as kidney damage. Also, and especially with cisplatin, the compounds cause nausea and vomiting in patients to a varying extent, as well as leucopenia, anemia and thrombocytopenia. There is therefore a need to increase efficacy and also to provide a means for the use of lower dosages to reduce the potential of adverse toxic side effects to the patient.

Preferences:

Preferred platinum compounds for use in accordance with the invention include cisplatin, carboplatin and oxaliplatin. Other platinum compounds include chloro(diethylenediamino)-platinum (II) chloride; dichloro(ethylenediamine)-platinum (II); spiroplatin; iproplatin; diamino(2-ethylmalonato)platinum (II); (1,2-diaminocyclohexane) malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; and tetraplatin. Cisplatin is commercially available for example under the trade name Platinol from Bristol-Myers Squibb Corporation as a powder for constitution with water, sterile saline or other suitable vehicle. Cisplatin may also be prepared for example as described by G. B. Kauffman and D. O. Cowan, Inorg. Synth. 7, 239 (1963), or by processes analogous thereto. Carboplatin is commercially available for example from Bristol-Myers Squibb Corporation under the trade name Paraplatin, or may be prepared for example as described in U.S. Pat. No. 4,140,707, or by processes analogous thereto. Oxaliplatin is commercially available for example from Sanofi-Synthelabo Inc under the trade name Eloxatin, or may be prepared for example as described in U.S. Pat. No. 4,169,846, or by processes analogous thereto. Other platinum compounds and their pharmaceutical compositions are commercially available and/or can be prepared by conventional techniques.

Specific Embodiments:

In one embodiment, the platinum compound is selected from chloro(diethylenediamino)-platinum (II) chloride; dichloro(ethylenediamine)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; tetraplatin, cisplatin, carboplatin and oxaliplatin. In another embodiment, the platinum compound is a platinum compound other than cisplatin, for example a platinum compound such as chloro(diethylenediamino)-platinum (II) chloride; dichloro(ethylenediamine)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; tetraplatin, carboplatin or oxaliplatin, preferably selected from carboplatin and oxaliplatin.

Posology:

The platinum coordination compound is advantageously administered in a dosage of 1 to 500 mg per square meter (mg/m$^2$) of body surface area, for example 50 to 400 mg/m$^2$ particularly for cisplatin in a dosage of about 75 mg/m$^2$, for carboplatin in about 300 mg/m$^2$ and for oxaliplatin in about 50-100 mg/m$^2$. These dosages may be administered for example once, twice or more per course of treatment, which may be repeated for example every 7, 14, 21 or 28 days.

11. Topoisomerase 2 Inhibitors

Definition:

The term "topoisomerase 2 inhibitor" as used herein refers to topoisomerase 2 inhibitor or analogues of topoisomerase 2 inhibitor as described above, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

An important class of anticancer drugs are the inhibitors of the enzyme topoisomerase 2 which causes double-strand breaks to release stress build-up during DNA transcription and translation. Compounds that inhibit the function of this enzyme are therefore cytotoxic and useful as anti-cancer agents.

Among the topoisomerase 2 inhibitors which have been developed and used in cancer chemotherapy are the podophyllotoxins. These drugs act by a mechanism of action which involves the induction of DNA strand breaks by an interaction with DNA topoisomerase 2 or the formation of free radicals. Podophyllotoxin, which is extracted from the mandrake plant, is the parent compound from which two glycosides have been developed which show significant therapeutic activity in several human neoplasms, including pediatric leukemia, small cell carcinomas of the lung, testicular tumours, Hodgkin's disease, and large cell lymphomas. These derivatives are etoposide (VP-16), which has the chemical name 4'-demethylepipodophyllotoxin 9-[4,6-O-(R)-ethylidene-β-D-glucopyranoside], and teniposide (VM-26), which has the chemical name 4'-demethylepipodophyllotoxin 9-[4,6-O-(R)-2-thenylidene-β-D-glucopyranoside].

Both etoposide and teniposide, however, suffer from certain toxic side-effects especially myelosuppression. Another important class of topoisomerase 2 inhibitors are the anthracycline derivatives which are important anti-tumour agents and comprise antibiotics obtained from the fungus *Streptomyces peuticus* var. *caesius* and their derivatives, characterized by having a tetracycline ring structure with an unusual sugar, daunosamine, attached by a glycosidic linkage. Among these compounds, the most widely used include daunorubicin, which has the chemical name 7-(3-amino-2,3,6-trideoxy-L-lyxohexosyloxy)-9-acetyl-7,8,9,10-tetrahydro-6,9,11-trihydroxy-4-methoxy-5,12-naphthacenequinone, doxorubicin, which has the chemical name 10-[(3-amino-2, 3,6-trideoxy-α-L-lyxohexopyranosyl)oxy]-7,8,9,10-tetrahydro-6,8,11-trihydroxy-8-(hydroxylacetyl)-I-methoxy-5,12-naphthacenedione, and idarubicin, which has the chemical name 9-acetyl-[(3-amino-2,3,6-trideoxy-α-L-lyxohexopyranosyl)oxy]-7,8,9,10-tetrahydro-6,9,11-trihydroxy-5,12-naphthacenedione.

Daunorubicin and idarubicin have been used primarily for the treatment of acute leukaemias whereas doxorubicin displays broader activity against human neoplasms, including a variety of solid tumours particularly breast cancer. Another anthracycline derivatives which is useful in cancer chemotherapy is epirubicin. Epirubicin, which has the chemical name (8S-cis)-10-[(3-amino-2,3,6-trideoxy-α-L-arabinohexopyranosyl)oxy]-7,8,9,10-tetrahydro-6,8,11-trihydroxy-8-(hydroxyacetyl)-1-methoxy-5,12-naphthacenedione, is a doxorubicin analog having a catabolic pathway that involves glucuronidation, by uridine diphosphate-glucuronosyl transferase in the liver (unlike that for doxorubicin), which is believed to account for its shorter half-life and reduced cardiotoxicity. The compound has been used for the treatment of various cancers including cervical cancer, endometrial cancer, advanced breast cancer and carcinoma of the bladder but suffers from the side-effects of myelosuppression and cardiotoxicity. The latter side-effect is typical of anthracycline derivatives which generally display a serious cardiomyopathy at higher doses, which limits the doses at which these compounds can be administered. A further type of topoisomerase 2 inhibitor is represented by mitoxantrone, which has the chemical name 1,4-dihydroxy-5,8-bis[[2-[(2-hydroxyethyl)amino]ethyl]amino]-9,10-anthracenedione, and is used for the treatment of multiple sclerosis, non-Hodgkin's lymphoma, acute myelogenous leukaemia, and breast, prostate and liver tumours. Others include losoxantrone and actinomycin D.

Side-effects from administration of mitoxantrone include myelosuppression, nausea, vomiting, stomatitis, alopecia but less cardiotoxicity than anthracyclines.

Biological Activity:

The topoisomerase 2 inhibitors of the combinations of the invention have activity against various cancers as described above.

Problems:

This class of cytotoxic compound is associated with side effects, as mentioned above. Thus, there is a need to provide a means for the use of lower dosages to reduce the potential of adverse toxic side effects to the patient.

Preferences:

Preferred topoisomerase 2 inhibitor compounds for use in accordance with the invention include anthracycline derivatives, mitoxantrone and podophyllotoxin derivatives as defined to herein.

Preferred anti-tumour anthracycline derivatives for use in accordance with the invention include daunorubicin, doxorubicin, idarubicin and epirubicin referred to above. Daunorubicin is commercially available for example as the hydrochloride salt from Bedford Laboratories under the trade name Cerubidine, or may be prepared for example as described in U.S. Pat. No. 4,020,270, or by processes analogous thereto. Doxorubicin is commercially available for example from Pharmacia and Upjohn Co under the trade name Adriamycin, or may be prepared for example as described in U.S. Pat. No. 3,803,124, or by processes analogous thereto. Doxorubicin derivatives include pegylated doxorubicin hydrochloride and liposome-encapsulated doxorubicin citrate. Pegylated doxorubicin hydrochloride is commercially available from Schering-Plough Pharmaceuticals under the trade name Caeylx; liposome-encapsulated doxorubicin citrate is commercially available for example from Elan Corporation under the trade name Myocet. Idarubicin is commercially available for example as the hydrochloride salt from Pharmacia & Upjohn under the trade name Idamycin, or may be prepared for example as described in U.S. Pat. No. 4,046,878, or by processes analogous thereto. Epirubicin is commercially available for example from Pharmacia and Upjohn Co under the trade name Pharmorubicin, or may be prepared for example as described in U.S. Pat. No. 4,058,519, or by processes analogous thereto. Mitoxantrone is commercially available for example from OSI Pharmaceuticals, under the trade name Novantrone, or may be prepared for example as described in U.S. Pat. No. 4,197,249, or by processes analogous thereto.

Other anti-tumour anthracycline derivatives may be prepared in conventional manner for example by processes analogous to those described above for the specific anthracycline derivatives.

Preferred anti-tumour anti-tumour podophyllotoxin derivatives for use in accordance with the invention include etoposide and teniposide referred to above. Etoposide is commercially available for example from Bristol-Myers Squibb Co under the trade name VePesid, or may be prepared for example as described in European patent specification No 111058, or by processes analogous thereto. Teniposide is commercially available for example from Bristol-Myers Squibb Co under the trade name Vumon, or may be prepared for example as described in PCT patent specification No. WO 93/02094, or by processes analogous thereto. Other anti-tumour podophyllotoxin derivatives may be prepared in conventional manner for example by processes analogous to those described above for etoposide and teniposide.

Specific Embodiments:

In one embodiment, the topoisomerase 2 inhibitor is an anthracycline derivative, mitoxantrone or a podophyllotoxin derivative. In another embodiment, the topoisomerase 2 inhibitor is selected from daunorubicin, doxorubicin, idarubicin and epirubicin. In a further embodiment, the topoisomerase 2 inhibitor is selected from etoposide and teniposide. Thus, in a preferred embodiment, the topoisomerase 2 inhibitor is etoposide. In another embodiment, the topoisomerase 2 inhibitor is an anthracycline derivative other than doxorubicin, for example a topoisomerase 2 inhibitor such as daunorubicin, idarubicin and epirubicin.

Posology:

The anti-tumour anthracycline derivative is advantageously administered in a dosage of 10 to 150 mg per square meter ($mg/m^2$) of body surface area, for example 15 to 60 $mg/m^2$, particularly for doxorubicin in a dosage of about 40 to 75 $mg/m^2$, for daunorubicln in a dosage of about 25 to 45 $mg/m^2$, for idarubicin in a dosage of about 10 to 15 $mg/m^2$ and for epirubicin in a dosage of about 100-120 $mg/m^2$.

Mitoxantrone is advantageously administered in a dosage of about 12 to 14 $mg/m^2$ as a short intravenous infusion about every 21 days.

The anti-tumour podophyllotoxin derivative is advantageously administered in a dosage of 30 to 300 $mg/m^2$ of body surface area, for example 50 to 250 mg/m particularly for etoposide in a dosage of about 35 to 100 mg/m, and for teniposide in about 50 to 250 $mg/m^2$.

The dosages noted above may generally be administered for example once, twice or more per course of treatment, which may be repeated for example every 7, 14, 21 or 28 days.

12. Alkylating Agents

Definition:

The term "alkylating agent" or "alkylating agents" as used herein refers to alkylating agents or analogues of alkylating agents as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

Alkylating agents used in cancer chemotherapy encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation, in particular DNA synthesis and cell division. The capacity of alkylating agents to interfere with DNA function and integrity in rapidly proliferating tissues provides the basis for their therapeutic applications and for many of their toxic properties. Alkylating agents as a class have therefore been investigated for their anti-tumour activity and certain of these compounds have been widely used in anti-cancer therapy although they tend to have in common a propensity to cause dose-limiting toxicity to bone marrow elements and to a lesser extent the intestinal mucosa.

Among the alkylating agents, the nitrogen mustards represent an important group of anti-tumour compounds which are characterised by the presence of a bis-(2-chloroethyl) grouping and include cyclophosphamide, which has the chemical name 2-[bis(2-chloroethyl)amino]tetrahydro-2H-1,3,2-oxazaphospholine oxide, and chlorambucil, which has the chemical name 4-[bis(2-chloroethyl)amino]-benzenebutoic acid. Cyclophosphamide has a broad spectrum of clinical activity and is used as a component of many effective drug combinations for malignant lymphomas, Hodgkin's disease, Burkitt's lymphoma and in adjuvant therapy for treating breast cancer.

Ifosfamide (a.k.a. Ifosphamide) is a structural analogue of cyclophosphamide and its mechanism of action is presumed to be identical. It has the chemical name 3-(2-chloroethyl)-2-[(2-chloroethyl)amino]tetrahydro-2H-1,3,2-oxazaphosphorin-2-oxide, and is used for the treatment of cervical cancer, sarcoma, and testicular cancer but may have severe urotoxic effects. Chlorambucil has been used for treating chronic leukocytic leukaemia and malignant lymphomas including lymphosarcoma.

Another important class of alkylating agents are the nitrosoureas which are characterised by the capacity to undergo spontaneous non-enzymatic degradation with the formation of the 2-chloroethyl carbonium ion. Examples of such nitrosourea compounds include carmustine (BCNU) which has the chemical name 1,3-bis(2-chloroethyl)-I-nitrosourea, and lomustine (CCNU) which has the chemical name 1-(2-chloroethyl)cyclohexyl-I-nitrosourea. Carmustine and lomustine each have an important therapeutic role in the treatment of brain tumours and gastrointestinal neoplasms although these compounds cause profound, cumulative myelosuppression that restricts their therapeutic value.

Another class of alkylating agent is represented by the bifunctional alkylating agents having a bis-alkanesulfonate group and represented by the compound busulfan which has the chemical name 1,4-butanediol dimethanesulfonate, and is used for the treatment of chronic myelogenous (myeloid, myelocytic or granulocytic) leukaemia. However, it can induce severe bone marrow failure resulting in severe pancytopenia.

Another class of alkylating agent are the aziridine compounds containing a three-membered nitrogen-containing ring which act as anti-tumour agents by binding to DNA, leading to cross-linking and inhibition of DNA synthesis and function. An example of such an agent is mitomycin, an antibiotic isolated from *Streptomyces caespitosus*, and having the chemical name 7-amino-9α-methoxymitosane.

Mitomycin is used to treat adenocarcinoma of stomach, pancreas, colon and breast, small cell and non-small cell lung cancer, and, in combination with radiation, head and neck cancer, side-effects including myelosuppression, nephrotoxicity, interstitial pneumonitis, nausea and vomiting.

Biological Activity:

One of the most important pharmacological actions of the alkylating agent in the combinations of the invention is its ability to disturb the fundamental mechanisms concerned with cell proliferation as herein before defined. This capacity to interfere with DNA function and integrity in rapidly proliferating tissues provides the basis for their therapeutic application against various cancers.

Problems:

This class of cytotoxic compound is associated with side effects, as mentioned above. Thus, there is a need to provide a means for the use of lower dosages to reduce the potential of adverse toxic side effects to the patient.

Preferences:

Preferred alkylating agents for use in accordance with the invention include the nitrogen mustard compounds cyclophosphamide, ifosfamide/ifosphamide and chlorambucil and the nitrosourea compounds carmustine and lomustine referred to above. Preferred nitrogen mustard compounds for use in accordance with the invention include cyclophosphamide, ifosfamidenfosphamide and chlorambucil referred to above. Cyclophosphamide is commercially available for example from Bristol-Myers Squibb Corporation under the trade name Cytoxan, or may be prepared for example as described in U.K. patent specification No. 1235022, or by processes analogous thereto. Chlorambucil is commercially available for example from GlaxoSmithKline plc under the trade name Leukeran, or may be prepared for example as described in U.S. Pat. No. 3,046,301, or by processes analogous thereto. Ifosfamide/ifosphamide is commercially available for example from Baxter Oncology under the trade name Mitoxana, or may be prepared for example as described in U.S. Pat. No. 3,732,340, or by processes analogous thereto. Preferred nitrosourea compounds for use in accordance with the invention include carmustine and lomustine referred to above. Carmustine is commercially available for example from Bristol-Myers Squibb Corporation under the trade name BiCNU, or may be prepared for example as described in European patent specification No. 902015, or by processes analogous thereto. Lomustine is commercially available for example from Bristol-Myers Squibb Corporation under the trade name CeeNU, or may be prepared for example as described in U.S. Pat. No. 4,377,687, or by processes analogous thereto. Busulfan is commercially available for example from GlaxoSmithKline plc under the trade name Myleran, or may be prepared for example as described in U.S. Pat. No. 2,917,432, or by processes analogous thereto. Mitomycin is commercially available for example from Bristol-Myers Squibb Corporation under the trade name Mutamycin. Others include estramustine, mechlorethamine, melphalan, bischloroethylnitrosurea, cyclohexylchloroethylnitrosurea, methylcyclohexylchloroethylnitrosurea, nimustine, procarbazine, dacarbazine, temozoiimide and thiotepa.

Specific Embodiments:

In one embodiment, the alkylating agent is a nitrogen mustard compound selected from cyclophosphamide, ifosfamide/ifosfamide and chlorambucil. In another embodiment, the alkylating agent is a nitrosourea selected from carmustine and lomustine. The alkylating agents further include Busulfan. In one embodiment, the alkylating agents are as herein before defined other than mitomycin C or cyclophosphamide.

Posology:

The nitrogen mustard or nitrosourea alkylating agent is advantageously administered in a dosage of 100 to 2500 mg per square meter (mg/m$^2$) of body surface area, for example 120 to 500 mg/m$^2$, particularly for cyclophosphamide in a dosage of about 100 to 500 mg/m$^2$, for ifosfamide/ifosfamide in a dosage of 500-2600 mg/m$^2$, for chlorambucil in a dosage of about 0.1 to 0.2 mg/kg, for carmustine in a dosage of about 150 to 200 mg/m$^2$ and for lomustine in a dosage of about 100 to 150 mg/m$^2$. For bis-alkanesulfonate compounds such Aziridine alkylating agents such as mitomycin can be administered for example in a dosage of 15 to 25 mg/m$^2$ preferably about 20 mg/m$^2$.

The dosages noted above may be administered for example once, twice or more per course of treatment, which may be repeated for example every 7, 14, 21 or 28 days.

13. Signalling Inhibitors

Definition:

The term "signalling inhibitor" as used herein refers to signalling inhibitors or analogues of signalling inhibitors as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs.

One driver for growth is the epidermal growth factor (EGF), and the receptor for EGF (EGFR) has been implicated in the development and progression of a number of human solid tumours including those of the lung, breast, prostate, colon, ovary, head and neck. EGFR is a member of a family of four receptors, namely EGFR (HER1 or ErbB1), ErbB2 (HER2/neu), ErbB3 (HER3), and ErbB4 (HER4). These receptors are large proteins that reside in the cell membrane, each having a specific external ligand binding domain, a transmembrane domain and an internal domain which has tyrosine kinase enzyme activity. When EGF attaches to EGFR, it activates the tyrosine kinase, triggering reactions that cause the cells to grow and multiply. EGFR is found at abnormally high levels on the surface of many types of cancer cells, which may divide excessively in the presence of EGF. Inhibition of EGRF activity has therefore been a target for chemotherapeutic research in the treatment of cancer. Such inhibition can be effected by direct Interference with the target EGRF on the cell surface, for example by the use of antibodies, or by inhibiting the subsequent tyrosine kinase activity.

Examples of antibodies which target EGRF are the monoclonal antibodies trastuzumab and cetuximab. Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor. In vitro and in vivo preclinical studies have shown that administration of trastuzumab alone or in combination with paclitaxel or carboplatin significantly inhibits the growth of breast tumour-derived cell lines that over-express the HER2 gene product. In clinical studies trastuzumab has been shown to have clinical activity in the treatment of breast cancer. The most common adverse effects of trastuzumab are fever and chills, pain, asthenia, nausea, vomiting, diarrhea, headache, dyspnea, rhinitis, and insomnia. Trastuzumab has been approved for the treatment of metastatic breast cancer involving over-expression of the HER2 protein in patients who have received one or more chemotherapy regimes.

Cetuximab has been used for the treatment of irotecan-refractory colorectal cancer. It is also being evaluated both as a single agent and in combination with other agents for use in the treatment of a variety of other cancers for example head and neck cancer, metastatic pancreatic carcinoma, and non-small-cell lung cancer. The administration of cetuximab can cause serious side effects, which may include difficulty in breathing and low blood pressure.

Examples of agents which target EGRF tyrosine kinase activity include the tyrosine kinase inhibitors gefitinib and erlotinib. Gefitinib which has the chemical name 4-(3-chloro-4-fluoroanilino)-7-methoxy-6-(3-morpholinopropoxy) quinazoline, is used for the treatment of non-small-cell lung cancer, and is also under development for other solid tumours that over-express EGF receptors such as breast and colorectal cancer. It has been found that patients receiving gefitinib may develop interstitial lung disease that causes inflammation within the lung. Eye irritation has also been observed in patients receiving gefitinib. Erlotinib, which has the chemical name N-(3-ethynyl-phenyl)-6,7-bis(2-methonethoxy)-4-quinazoline, has also been used for the treatment of non-small-cell lung cancer, and is being developed for the treatment of various other solid tumours such as pancreatic cancer, the most common side effects being rash, loss of appetite and fatigue; a more serious side effect which has been reported is interstitial lung disease.

Another growth factor which has received attention as a target for anticancer research is the vascular endothelial growth factor (VEGF). VEGF is a key regulator of vasculogenesis during angiogenic processes including wound healing, retinopathy, psoriasis, inflammatory disorders, tumour growth and metastasis. Studies have shown that over-expression of VEGF is strongly associated with invasion and metastasis in human malignant disease.

An example of an antibody that targets the VEGF antigen on the surface of a cell is the monoclonal antibody bevacizumab which is a recombinant humanised monoclonal IgG1 antibody that binds to and inhibits VEGF. Bevacizumab has been used for the treatment of colorectal cancer, for example in combination with 5-fluorouracil. Bevacizumab also being developed as a potential treatment for other solid tumours such as metastatic breast cancer, metastatic non-small-cell lung cancer and renal cell carcinoma. The most serious adverse events associated with bevacizumab include gastrointestinal perforations, hypertensive crises, nephrotic syndrome and congestive heart failure. Other therapeutic agents in development which target the action of VEGF at alternate points in the signal transduction cascade initiated by this growth factor include sunitinib which is marketed under the trade name Sutent by Sugen/Pfizer and inhibits the kinase activity of the VEGF receptor. Sutent has demonstrated efficacy in Phase III trials in gastrointestinal tumours.

Another growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment on chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. The most frequently reported drug-related adverse events were edema, nausea, vomiting, cramps and musculosketetal pain.

A further growth factor target for cancer chemotherapy is inhibition of Raf which is a key enzyme in the chain reaction of the body's chemistry that triggers cell growth. Abnormal activation of this pathway is a common factor in the development of most cancers, including two-thirds of melanomas. By blocking the action of Raf kinase, it may be possible to reverse the progression of these tumours. One such inhibitor is sorafenib (BAY 43-9006) which has the chemical name 4-(4-(3-(4-chloro-3-(trifluoromethyl)phenyl)ureido)phenoxy)-N2-methylpyridine-2-carboxamide. Sorafenib targets both the Raf signalling pathway to inhibit cell proliferation and the VEGFR/PDGFR signalling cascades to inhibit tumour angiogenesis. Raf kinase is a specific enzyme in the Ras pathway. Mutations in the Ras gene occur in approximately 20 percent of all human cancers, including 90 percent of pancreatic cancers, 50 percent of colon cancers and 30 percent of non-small cell lung cancers. Sorafenib is being investigated for the treatment of a number of cancers including liver and kidney cancer. The most common side effects of sorafenib are pain, swelling, redness of the hands and/or feet, and also rash, fatigue and diarrhea.

Biological Activity:

The signalling inhibitors of the combinations of the invention are specific inhibitors of cell signalling proteins as described above and have activity against various cancers. Combinations of compounds of Formula I with signalling inhibitors may be beneficial in the treatment and diagnosis of many types of cancer. Combination with a molecularly targeted agent such as a signalling inhibitor (e.g. Iressa, Avastin, herceptin, or Gleevec™) would find particular application in relation to cancers which express or have activated the relevant molecular target such as EGF receptor, VEGF receptor, ErbB2, BCRabl, c-kit, PDGF. Diagnosis of such tumours could be performed using techniques known to a person skilled in the art and as described herein such as RTPCR and FISH.

Problems:

There is a need to increase the inhibitory efficacy of signalling inhibitors against tumour growth and also to provide a means for the use of lower dosages of signaling inhibitors to reduce the potential for adverse toxic side effects to the patient.

Preferences:

Preferred signalling inhibitors for use in accordance with the invention include antibodies targeting EGFR such as monoclonal antibodies trastuzumab and cetuximab, EGFR tyrosine kinase inhibitors such as gefitinib and erlotinib, VEGF targeting antibody is bevacizumab, PDGFR inhibitor such as imatinib mesylate and Raf inhibitor such as sorafenib referred to herein.

Preferred antibodies targeting EGFR include the monoclonal antibodies trastuzumab and cetuximab. Trastuzumab is commercially available from Genentech Inc under the trade name Herceptin, or may be obtained as described in U.S. Pat. No. 5,821,337. Cetuximab is commercially available from Bristol-Myers Squibb Corporation under the trade name Erbitux, or may be obtained as described in PCT patent specification No. WO 96/40210.

Preferred EGFR tyrosine kinase inhibitors include gefitinib and erlotinib. Gefitinib is commercially available from AstraZeneca plc under the trade name Iressa, or may be obtained as described in PCT patent specification No. WO 96/33980. Erlotinib is commercially available from Pfizer Inc under the trade name Tarceva, or may be obtained as described in PCT patent specification No. WO 96/30347.

A preferred antibody targeting VEGF is bevacizumab which is commercially available from Genentech Inc under the trade name Avastin, or may be obtained as described in PCT patent specification No. WO 94/10202.

A preferred PDGFR inhibitor is imatinib mesylate which is commercially available from Novartis AG under the trade name Gleevec™ (a.k.a. Glivece), or may be obtained as described in European patent specification No 564409.

A preferred Raf inhibitor is sorafenib which is available from Bayer AG, or may be obtained as described in PCT patent specification No. WO 00/42012.

Specific Embodiments:

In one embodiment, the signalling inhibitor is gefitinib (Iressa). In other embodiments the signalling Inhibitor is selected from trastuzumab, cetuximab, gefitinib, erlotinib, bevacizumab, imatinib mesylate and sorafenib.

Posology:

With regard to the EGFR antibodies, these are generally administered in a dosage of 1 to 500 mg per square meter (mg/m$^2$) of body surface area, trastuzumab being advantageously administered in a dosage of 1 to 5 mg/m$^2$ of body surface area, particularly 2 to 4 mg/m$^2$; cetuxumab is advantageously administered in a dosage of about 200 to 400 mg/m$^2$, preferably about 250 mg/m$^2$.

With regard to the EGFR tyrosine kinase inhibitors, these are generally administered in a daily oral dosage of 100 to 500 mg, for example gefitinib in a dosage of about 250 mg and erlotinib in a dosage of about 150 mg.

With regard to the VEGF monoclonal antibody bevacizumab, this is generally administered in a dosage of about 1 to 10 mg/kg for example about 5 mg/kg.

With regard to the PDGF inhibitor imatinib, this is generally administered in a dosage of about 400 to 800 mg per day preferably about 400 mg per day.

With regard to the Raf inhibitor sorfenib, this is still under evaluation but a possible dosage is about 800 mg daily.

These dosages may be administered for example once, twice or more per course of treatment, which may be repeated for example every 7, 14, 21 or 28 days.

PKA/B Inhibitors, PKB Pathway Inhibitors and Ancillary PKB Inhibitors

Another preferred class of signaling inhibitor for use in the combinations of the invention are PKA/B inhibitors, PKB pathway inhibitors and ancillary PKB inhibitors.

PKB pathway inhibitors are those that inhibit the activation of PKB, the activity of the kinase itself or modulate downstream targets, blocking the proliferative and cell survival effects of the pathway. Target enzymes in the pathway include phosphatidyl inositol-3 kinase (PI3K), PKB itself, mammalian target of rapamycin (MTOR), PDK-1 and p70 S6 kinase and forkhead translocation. Several components of the PI 3-kinase/PKB/PTEN pathway are implicated in oncogenesis. In addition to growth factor receptor tyrosine kinases, integrin-dependent cell adhesion and G-protein coupled receptors activate PI 3-kinase both directly and indirectly through adaptor molecules. Functional loss of PTEN (the most commonly mutated tumour-suppressor gene in cancer after p53), oncogenic mutations in PI 3-kinase, amplification of PI 3-kinase and overexpression of PKB have been established in many malignancies. In addition, persistent signaling through the PI 3-kinase/PKB pathway by stimulation of the Insulin-like growth factor receptor is a mechanism of resistance to epidermal growth factor receptor inhibitors.

The discovery of non-random, somatic mutations in the gene encoding p110α in a range of human tumours suggests an oncogenic role for the mutated PI 3-kinase enzyme (Samuels, et al., Science, 304 554, April 2004). Mutations in p110α have since been detected in the following human tumours: colon (32%), hepatocellular (36%) and endometroid and clear cell cancer (20%). p110α is now the most commonly mutated gene in breast tumours (25-40%). Forkhead family translocations often occur in acute leukemia.

The PI 3-kinase/PKB/PTEN pathway is thus an attractive target for cancer drug development since such agents would be expected to inhibit proliferation and surmount resistance to cytotoxic agents in cancer cells. Examples of PKB pathway inhibitors include PI3K Inhibitors such as Semaphore, SF1126 and MTOR inhibitors such as Rapamycin Analogues. RAD 001 (everolimus) from Novartis is an orally available derivative of the compound rapamycin. The compound is a novel macrolide, which is being developed as an antiproliferative drug with applications as an immunosuppressant and anticancer agent. RAD001 exerts its activity on growth-factor dependent proliferation of cells through its high affinity for an intracellular receptor protein, FKBP-12. The resulting FKBP-12/RAD001 complex then binds with mTOR to inhibit downstream signaling events. The compound is currently in clinical development for a wide variety of oncology indications. CCI 779 (temsirolemus) from Wyeth Pharmaceuticals and AP23573 from Ariad Pharmaceuticals are also rapamycin analogues. AP23841 and AP23573 from Ariad Pharmaceutical also target mTOR. Calmodulin inhibitors from Harvard are forkhead translocation inhibitors. (Nature Reviews drug discovery, Exploiting the PI3K/AKT Pathway for Cancer Drug Discovery; Bryan T. Hennessy, Debra L. Smith, Prahlad T. Ram, Yiling Lu and Gordon B. Mills; December 2005, Volume 4; pages 988-1004).

Preferred PKA/B inhibitors for use as ancillary agents in the combinations of the invention are compounds of formula (I) as defined herein. PKB pathway inhibitors for use in the combinations of the invention include the ancillary PKB inhibitors described in more detail below as well as compounds of formula (I) that have protein kinase B (PKB) and/or protein kinase A (PKA) inhibiting or modulating activity (described herein). Thus, the combinations of the present invention may comprise (or consist essentially of) two or more compounds of formula (I) as defined herein. Preferred ancillary PKB inhibitors are discussed in more detail below.

Definitions:

The term "PKA/B inhibitor" is used herein to define a compound of formula (I) which has protein kinase B (PKB) and/or protein kinase A (PKA) inhibiting or modulating activity, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

The term "ancillary PKB inhibitor" is used herein to define a compound which inhibits or modulates protein kinase B (PKB) and which does not conform to the structure of formula (I) as defined herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

The term "PKB pathway inhibitor" is used herein to define a compound which Inhibits the activation of PKB, the activity of the kinase itself or modulate downstream targets, blocking the proliferative and cell survival effects of the pathway (including one or more of the target enzymes in the pathway as described herein, including phosphatidyl inositol-3 kinase (PI3K), PKB itself, mammalian target of rapamycin (MTOR), PDK-1 and p70 S6 kinase and forkhead translocation).

Technical Background:

KRX-0401 (Perifosine/NSC 639966) is a synthetic substituted heterocyclic alkylphosphocholine that acts primarily at the cell membrane targeting signal transduction pathways, including inhibition of PKB phosphorylation. KRX-0401 has been evaluated in phase 1 studies as a potential oral anticancer drug. Dose limiting toxicities included nausea, vomiting and fatigue. Gastrointestinal toxicities increased at higher doses. A phase II trial in refractory sarcoma is planned.

API-2/TCN is a small molecule inhibitor of PKB signaling pathway in tumour cells. Phase I and II clinical trials of API-2/TCN have been conducted on advanced tumours. API-2/TCN exhibited some side effects, which include hepatotoxicity, hypertriglyceridemia, thrombocytopenia, and hyperglycemia. Due to its severe side effects at high doses, API-2/TCN has been limited in the clinic.

RX-0201 is being developed as an AKT protein kinase inhibitor for the treatment of solid tumours. In July 2004, a phase I trial was initiated in patients with advanced or metastasized cancers. Data from this showed RX-0201 inhibited overexpression of Akt and suppressed cancer growth in brain, breast, cervix, liver, lung, ovary, prostate and stomach tumours, and was well tolerated. By March 2005, US Orphan Drug status had been granted to RX-0201 for several solid tumour types.

Enzastaurin HCl (LY317615) suppresses angiogenesis and was advanced for clinical development based upon anti-angiogenic activity. It is described as a selective PKCβ inhibitor. It also has a direct anti-tumour effect, and suppresses GSK3β phosphorylation.

SR-13668 is claimed to be an orally active specific AKT inhibitor that significantly inhibits phospho-AKT in breast cancer cells both in vitro and in vivo. In vivo assessment in mice showed no adverse effects at doses 10 times more than were needed for antitumour activity.

PX-316 is a D-3-deoxy-phosphatidyl-myo-inositol that binds to the PH domain of PKB, trapping it in the cytoplasm and thus preventing PKB activation. Anti-tumour activity was seen in early xenografts and was well tolerated.

Allosteric, selective inhibitors of PKB based on a 2,3-diphenylquinoxaline core or a 5,6-diphenylpyrazin-2(1H)-one core have been developed (Merck).

KRX-0401: in a Phase I weekly dosing study conducted in Europe, the recommended Phase II dose was 600/mg/week. Subsequent studies conducted in the U.S. have shown that much higher doses are well tolerated when the doses are divided and administered at 4 to 6 hour intervals. In addition, it has been shown that KRX-0401 has a very long half-life in the range of 100 hours. This makes the possibility of a relative non-toxic, intermittent dosing schedule very plausible.

A phase I trial of API-2 was conducted using a 5-day continuous infusion schedule. Dose levels ranged from 10 mg/sq m/day×5 days to 40 mg/sq m/day×5 days. Initially, courses were repeated every 3 to 4 weeks. As cumulative toxicity became manifested, the interval between courses was changed to every 6 weeks. Recommended schedule for Phase II studies is 20 mg/sq m/day for 5 days every 6 weeks. A Phase II trial of TCN-P was conducted in metastatic or recurrent squamous cell carcinoma of the cervix using a 5-day continuous infusion schedule. The starting dose was 35 mg/m$^2$×5 days and courses were repeated every 6 weeks.

Further PKB inhibitors include Perifosine from Keryx Biopharmaceuticals. Perifosine is an oral Akt inhibitor which exerts a marked cytotoxic effect on human tumour cell lines, and is currently being tested in several phase II trials for treatment of major human cancers. KRX-0401 (Perifosine/NSC 639966) has the structure:

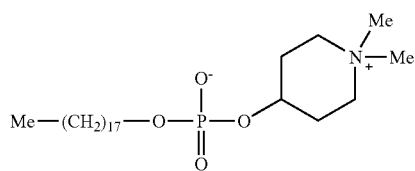

It can be prepared according to Aste Medica patent publication DE4222910 or Xenoport patent publication US2003171303.

API-2/TCN (Triciribine) has the structure:

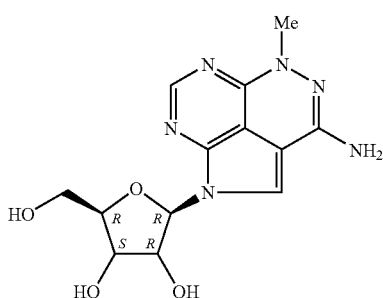

It can be prepared according to Bodor patent publication WO9200988 or Ribapharm patent publication WO2003061385.

Enzastaurin hydrochloride has the structure:

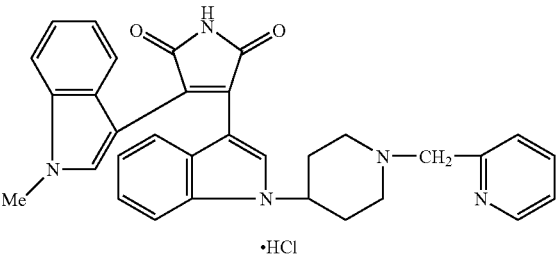 [SMILES: Cn1cc(C2=C(c3cn(C4CCN(Cc5ccccn5)CC4)c4ccccc34)C(=O)NC2=O)c2ccccc21 ; Cl]

It can be prepared according to Eli Lilly patent publication WO2004006928.

SR 13668 has the structure:

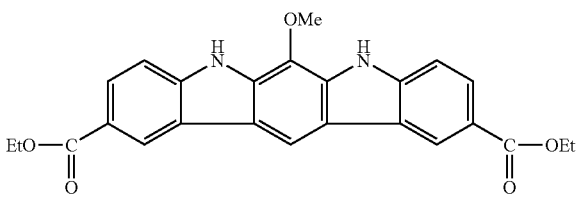 [SMILES: CCOC(=O)c1ccc2[nH]c3c(OC)c4[nH]c5ccc(C(=O)OCC)cc5c4cc3c2c1]

It can be prepared according to SRI International patent publication US2004043965.

NL-71-101 has the structure:

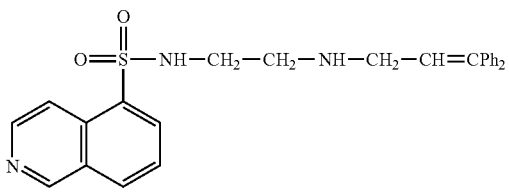

It can be prepared according to Biochemistry (2002), 41(32), 10304-10314 or Peptor patent publication WO2001091754.

DeveloGen (formerly Peptor) is investigating NL-71-101, a protein kinase B (PKB) inhibitor, for the potential treatment of cancer [466579], [539004]. At the beginning of 2003, the compound was undergoing lead optimization [495463]. By February 2004, the company was seeking to outlicense certain development rights to its protein kinase B program [523638].

In 2002, data were published showing that NL-71-101 inhibited the activity of PKB over PKA, PKG and PKC with IC50 values of 3.7, 9, 36 and 104 microM, respectively. NL-71-101 induced apoptosis in OVCAR-3 tumour cells, in which PKB is amplified at concentrations of 50 and 100 microM [466579]. This compound has the structure:

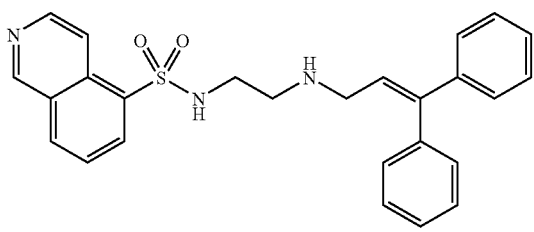 [SMILES: O=S(=O)(NCCNCC=C(c1ccccc1)c1ccccc1)c1cccc2cnccc12]

Specific Embodiments:

Embodiments contemplated include combinations in which the anti-cancer agent is a PKB inhibitor selected from one or more of the specific compounds described above.

14. CDK Inhibitors

Definition:

The term "CDK inhibitor" as used herein refers to compounds that inhibit or modulate the activity of cyclin dependent kinases (CDK), including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background:

CDKs play a role in the regulation of the cell cycle, apoptosis, transcription, differentiation and CNS function. Therefore, CDK inhibitors may find application in the treatment of diseases in which there is a disorder of proliferation, apoptosis or differentiation such as cancer. In particular RB+ve tumours may be particularly sensitive to CDK inhibitors. RB-ye tumours may also be sensitive to CDK inhibitors.

Examples of CDK inhibitors which may be used in combinations according to the invention include selicidib, alvocidib, 7-hydroxy-staurosporine, JNJ-7706621, BMS-387032, PHA533533, PD332991, ZK-304709 and AZD-5438.

Selicidib, which is the R isomer of roscovitine, and otherwise known as CYC 202, has the chemical name (2R)-2-[[9-(1-methylethyl)-6-[(phenylmethyl)-amino]-9H-purin-2-yl]amino]-1-butanol. It is being evaluated in clinical trials for the potential treatment of various cancers including lymphoid leukaemia, non-small-cell lung cancer, glomerulonephritis, mantle cell lymphoma, multiple myeloma, and breast cancer. Observed toxicities in clinical trials include nausea/vomiting and asthenia, skin rash and hypokalemia. Other toxicities included reversible renal impairment and transaminitis, and emesis.

Alvocidib, which is otherwise known as flavopiridol, HMR 1275 or L 86-8275, and which has the chemical name 5,7-dihydroxy-8-(4-N-methyl-2-hydroxypyridyl)-6'-chloroflavone, is being investigated in clinical trials for the potential treatment of various cancers including cancer of the esophagus, stomach, prostate, lung and colon, and also chronic lymphocytic leukaemia, and multiple myeloma, lymphoma; the most common toxicities observed were diarrhea, tumour pain, anemia, dyspnea and fatigue.

7-Hydroxystaurosporine, which is otherwise known as UCN-01 is being evaluated in clinical trials for the potential treatment of various cancers including chronic lymphocytic leukaemia, pancreas tumours and renal tumours; adverse events observed included nausea, headache and hyperglycemia.

JNJ-7706621, which has the chemical name N3-[4-(aminosulfonyl)-phenyl]-1-(2,6-difluorobenzoyl)-1H-1,2,4-triazole-3,5-diamine, is the subject of pre-clinical testing for the potential treatment of melanoma and prostate cancer. BMS-387032 which has the chemical name N-[5-[[[5-(1,1-dimethylethyl)-2-oxazolyl]-methyl]thio]-2-thiazolyl]-4-piperidinecarboxamide, has been evaluated in phase I studies as a potential anticancer drug for patients with metastatic solid tumours such as renal cell carcinomas, non-small-cell lung cancer, head and neck cancers and leiomyosarcoma The drug was well tolerated with transient neutropenia noted as the primary toxicity. Other side-effects included transient liver aminase elevations, gastrointestinal toxicity, nausea, vomiting, diarrhea and anorexia. PHA533533, which has the chemical name (αS)-N-(5-cyclopropyl-1H-pyrazol-3-yl)-α-methyl-4-(2-oxo-1-pyrrolidinyl)-benzene-acetamide, is the subject of pre-clinical testing for the potential treatment of various cancers such as tumours of the prostate, colon and ovary. PD332991, which has the chemical name 8-cyclohexyl-2-[[4-(4-methyl-1-piperazinyl)phenyl]amino]-pyrido[2,3-d]pyrimidin-7(8H)-one, is the subject of pre-clinical testing for the potential treatment of various cancers. Pre-clinical data suggests that it is a highly selective and potent CDK4 inhibitor, demonstrating marked tumour regression in vivo models.

ZK-304709 is an oral dual specificity CDK and VEGFR kinase inhibitor, described in PCT patent specification No. WO 02/096888, and is the subject of pre-clinical testing for the potential treatment of various cancers. AZD-5438 is a selective cyclin-dependent kinase (CDK) Inhibitor, which is in pre-clinical development for the treatment of solid cancers. Seliciclib may be prepared for example as described in PCT patent specification No. WO 97/20842, or by processes analogous thereto. Alvocidib, may be prepared for example as described in U.S. Pat. No. 4,900,727 or by processes analogous thereto. 7-Hydroxystaurosporine may be prepared for example as described in U.S. Pat. No. 4,935,415, or by processes analogous thereto. JNJ-7706621 may be prepared for example as described in PCT patent specification No. WO 02/057240, or by processes analogous thereto. BMS-387032 may be prepared for example as described in PCT patent specification No. WO 01/44242, or by processes analogous thereto. PHA533533 may be prepared for example as described in U.S. Pat. No. 6,455,559, or by processes analogous thereto. PD332991, may be prepared for example as described in PCT patent specification No. WO 98/33798, or by processes analogous thereto. ZK-304709 may be prepared for example as described in PCT patent specification No. WO 02/096888, or by processes analogous thereto.

Preferences and Specific Embodiments:

Embodiments contemplated include combinations in which the anti-cancer agent is a CDK inhibitor selected from one or more of the specific compounds described above. Thus, preferred CDK inhibitors for use in combinations according to the invention include seliciclib, alvocidib, 7-hydroxystaurosporine, JNJ-7706621, BMS-387032, PHA533533, PD332991, ZK-304709 and AZD-5438.

Posology:

The CDK inhibitor may be administered for example in a daily dosage of for example 0.5 to 2500 mg, more preferably 10 to 1000 mg, or alternatively 0.001 to 300 mg/kg, more preferably 0.01 to 100 mg/kg, particularly for seliciclib, in a dosage of 10 to 50 mg; for alvocidib, in a dosage in accordance with the above-mentioned U.S. Pat. No. 4,900,727; for 7-hydroxystaurosporine in a dosage of 0.01 to 20 mg/kg; for JNJ-7706621 in a dosage of 0.001 to 300 mg/kg; for BMS-387032 in a dosage of 0.001 to 100 mg/kg more preferably 0.01 to 50 mg/kg, and most preferably 0.01 to 20 mg/kg; for PHA533533 in a dosage of 10 to 2500 mg; for PD332991 in a dosage of 1 to 100 mg/kg; and for ZK-304709 in a dosage of 0.5 to 1000 mg preferably 50 to 200 mg.

These dosages may be administered for example once, twice or more per course of treatment, which may be repeated for example every 7, 14, 21 or 28 days.

15. COX-2 Inhibitors

Definition:

The term "COX-2 inhibitor" is used herein to define compounds which inhibit or modulate the activity of the cyclo-oxygenase-2 (COX-2) enzyme, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological Activity:

The COX-2 inhibitors working via one or more pharmacological actions as described herein have been identified as suitable anti-cancer agents.

Technical Background:

Recently, research in cancer chemotherapy has focused on the role of the cyclo-oxygenase-2 (COX-2) enzyme. Epidemiological studies have shown that people who regularly take non-steroidal anti-inflammatory drugs (NSAIDs), for example aspirin and ibuprofen to treat conditions such as arthritis, have lower rates of colorectal polyps, colorectal cancer, and death due to colorectal cancer. NSAIDs block cyclooxygenase enzymes, which are produced by the body in inflammatory processes, and which are also produced by pre-cancerous tissues. For example in colon cancers, a dramatic increase of COX-2 levels is observed. One of the key factors for tumour growth is the supply of blood to support its increased size. Many tumours can harness chemical pathways that prompt the body to create a web of new blood vessels around the cancer, a process called angiogenesis. COX-2 is believed to have a role in this process. It has therefore been concluded that inhibition of COX-2 may be effective for treating cancer, and COX-2 inhibitors have been developed for this purpose. For example celecoxib, which has the chemical name 4-[5-(4-methylphenyl)-3-(trifluoromethyl)-1H-pyrazol-1-yl]benzenesulfonamide, is a selective COX-2 inhibitor that is being investigated for the treatment of various cancers including bladder and esophageal cancer, renal cell carcinoma, cervical cancer, breast cancer, pancreatic cancer non-Hodgkin's lymphoma and non-small cell lung cancer.

Posology:

The COX-2 inhibitor (for example celecoxib) can be administered in a dosage such as 100 to 200 mg.

These dosages may be administered for example once, twice or more per course of treatment, which may be repeated for example every 7, 14, 21 or 28 days.

Problems:

The most common adverse effects are headache, abdominal pain, dyspepsia, diarrhea, nausea, flatulence and insomnia. There is a need to provide a means for the use of lower dosages of COX-2 inhibitors to reduce the potential for adverse toxic side effects to the patient.

Preferences and Specific Embodiments:

In one embodiment the COX-2 inhibitor is celecoxib. Celecoxib is commercially available for example from Pfizer Inc under the trade name Celebrex, or may be prepared for example as described in PCT patent specification No. WO 95/15316, or by processes analogous thereto.

16. HDAC Inhibitors

Definition:

The term "HDAC inhibitor" is used herein to define compounds which inhibit or modulate the activity of histone deacetylases (HDAC), including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological Activity:

The HDAC inhibitors working via one or more pharmacological actions as described herein have been identified as suitable anti-cancer agents.

Technical Background:

Reversible acetylation of histones is a major regulator of gene expression that acts by altering accessibility of transcription factors to DNA. In normal cells, histone deacetylase (HDA or HDAC) and histone acetyltrasferase (HDA) together control the level of acetylation of histones to maintain a balance. Inhibition of HDA results in the accumulation of hyperacetylated histones, which results in a variety of cellular responses. Inhibitors of HDA (HDAI) have been studied for their therapeutic effects on cancer cells. Recent developments in the field of HDAI research have provided active compounds, both highly efficacious and stable, that are suitable for treating tumours.

Accruing evidence suggests that HDAI are even more efficacious when used in combination with other chemotherapeutic agents. There are both synergistic and additive advantages, both for efficacy and safety. Therapeutic effects of combinations of chemotherapeutic agents with HDAI can result in lower safe dosage ranges of each component in the combination.

The study of inhibitors of histone deacetylases (HDAC) indicates that indeed these enzymes play an important role in cell proliferation and differentiation. The inhibitor Trichostatin A (TSA) causes cell cycle arrest at both G1 and G2 phases, reverts the transformed phenotype of different cell lines, and induces differentiation of Friend leukaemia cells and others. TSA (and suberoylanilide hydroxamic acid SAHA) have been reported to inhibit cell growth, induce terminal differentiation, and prevent the formation of tumours in mice (Finnin et al., Nature, 401:188-193, 1999).

Trichostatin A has also been reported to be useful in the treatment of fibrosis, e.g. liver fibrosis and liver chirrhosis. (Geerts et al., European Patent Application EP0 827 742, published 11 Mar. 1998).

Preferences and Specific Embodiments:

Preferred HDAC inhibitors for use in accordance with the invention are selected from TSA, SAHA, JNJ-16241199, LAQ-824, MGCD-0103 and PXD-101 (referred to above).

Thus, synthetic inhibitors of histone deacetylases (HDAC) which are suitable for use in the present invention include JNJ-16241199 from Johnson and Johnson Inc, LAQ-824 from Novartis, MGCD-0103 from MethylGene, and PXD-101 from Prolifix.

JNJ-16241199 has the following structure:

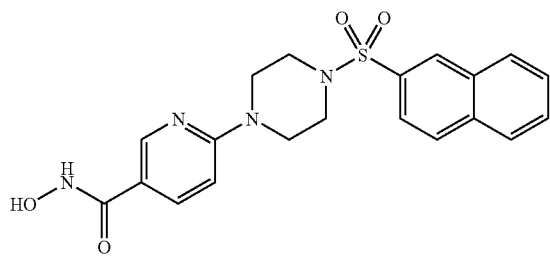 [SMILES: O=C(NO)c1ccc(N2CCN(S(=O)(=O)c3ccc4ccccc4c3)CC2)nc1]

MGCD-0103 has the structure:

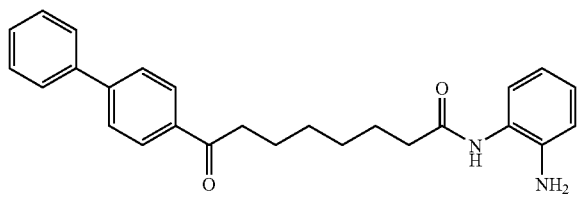 [SMILES: Nc1ccccc1NC(=O)CCCCCCC(=O)c1ccc(-c2ccccc2)cc1]

LAQ-824 has the structure:

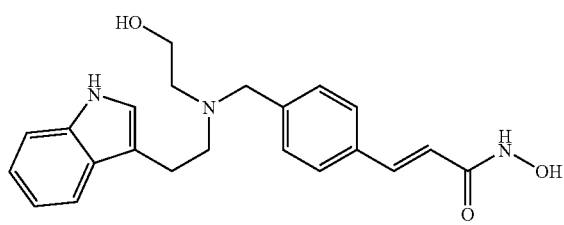 [SMILES: O=C(/C=C/c1ccc(CN(CCO)CCc2c[nH]c3ccccc23)cc1)NO]

Other inhibitors of histone deacetylases (HDAC) which are suitable for use in the present invention include, but are not limited to, the peptide chlamydocin, and A-173, also from Abbott Laboratories.

A-173 is a succinimide macrocyclic compound with the following structure:

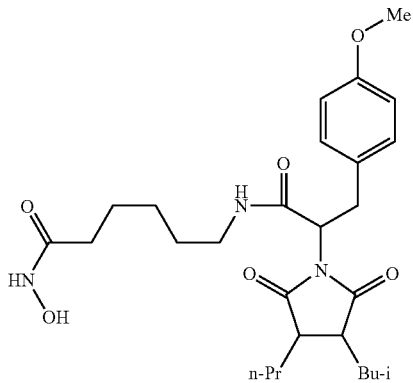

Posology:

In general, for HDAC inhibitors it is contemplated that a therapeutically effective amount would be from 0.005 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

17. DNA Methylase Inhibitors

Definition:

The term "DNA methylase inhibitor" or "DNA methyltransferase inhibitor" as used herein refers to a compound which directly or indirectly perturbs, disrupts, blocks, modulates or inhibits the methylation of DNA, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological Activity:

The DNA methylase inhibitors working via one or more pharmacological actions as described herein have been identified as suitable anti-cancer agents.

Technical Background:

One target for cancer chemotherapy is DNA synthesis, which may depend on appropriate methylation of tumour DNA. Compounds which directly or indirectly perturb, disrupt, block, modulate or inhibit the methylation of DNA may therefore be useful anticancer drugs.

The DNA methylase inhibitor temozolomide is used for the treatment of glioblastoma multiforme, and is also being investigated and used for the treatment of malignant glioma at first relapse and first-line treatment of patients with advanced metastatic malignant melanoma. This compound undergoes rapid chemical conversion at physiological pH to the active compound, monomethyl triazeno imidazole carboxamide (MTIC) which is responsible for the methylation of DNA at the $O^6$ position of guanine residues (which appears to lead to a suppression in expression of DNA methyltransferase and so produce hypomethylation).

Problems:

The most common side effects associated with temozolomide therapy are nausea, vomiting, headache, fatigue, and constipation. There is a need to increase the inhibitory efficacy of DNA\methylase inhibitors and to provide a means for the use of lower dosages of signaling Inhibitors to reduce the potential for adverse toxic side effects to the patient.

Preferences and Specific Embodiments:

In one embodiment, the DNA methylase inhibitor is temozolomide (3,4-dihydro-3-methyl-4-oxoimidazo[5,1-d]-as-tetrazine-8-carboxamide). Temozolomide is commercially available for example from Schering Corporation under the trade name Temodar, or may be prepared for example as described in German patent specification No. 3231255, or by processes analogous thereto.

Posology:

The DNA methylating agent (for example temozolomide) can be administered in a dosage such as 0.5 to 2.5 mg per square meter ($mg/m^2$) of body surface area, particularly about 1.3 $mg/m^2$. These dosages may be administered for example once, twice or more per course of treatment, which may be repeated for example every 7, 14, 21 or 28 days.

18. Proteasome Inhibitors

Definition:

The term "proteasome inhibitor" as used herein refers to compounds which directly or indirectly perturb, disrupt, block, modulate or inhibit the half-life of many short-lived biological processes, such as those involved in the cell cycle. The term therefore embraces compounds which block the action of proteasomes (large protein complexes that are involved in the turnover of other cellular proteins). The term also embraces the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological Activity:

The proteasome inhibitors working via one or more pharmacological actions as described herein have been identified as suitable anti-cancer agents.

Technical Background:

Another class of anticancer agents are the proteasome inhibitors. Proteasomes control the half-life of many short-lived biological processes, such as those involved in the cell cycle. Therefore, proteasome malfunction can lead to abnormal regulation of the cell cycle and uncontrolled cell growth.

The cell cycle is controlled by both positive and negative signals. In a normal cell, proteasomes break down proteins that inhibit the cell cycle, such as cyclin-dependent kinase inhibitors. Inhibition of proteasome function causes cell cycle arrest and cell death. Tumour cells are more susceptible to these effects than normal cells, in part because they divide more rapidly and in part because many of their normal regulatory pathways are disrupted. The mechanism for the differential response of normal and cancer cells to proteasome inhibition is not fully understood. Overall, cancer cells are more susceptible to proteasome inhibitors and, as a result, these inhibitors may be an effective treatment for certain cancers.

One such proteasome inhibitor is bortezimib, which has the chemical name [(1R)-3-methyl-1-[[(2S)-1-oxo-3-phenyl-2-[(pyrazinylcarbonyl)amino]propyl]amino]butyl]-boronic acid. Bortezimib specifically interacts with a key amino acid, namely threonine, within the catalytic site of the proteasome. Bortezimib is being used for the treatment of multiple myeloma and also for a number of other cancers, including leukemia and lymphoma, and prostate, pancreatic and colorectal carcinoma.

Problems:

The most common side effects with bortezimib are nausea, tiredness, diarrhea, constipation, decreased platelet blood count, fever, vomiting, and decreased appetite. Bortezimib can also cause peripheral neuropathy.

Thus, there is a need to provide a means for the use of lower dosages to reduce the potential of adverse toxic side effects to the patient.

Preferences and Specific Embodiments:

Preferred proteasome inhibitors for use in accordance with the invention include bortezimib. Bortezimib is commercially available for example from Millennium Pharmaceuticals Inc under the trade name Velcade, or may be prepared for example as described in PCT patent specification No. WO 96/13266, or by processes analogous thereto.

Posology:

The proteasome inhibitor (such as bortezimib) can be administered in a dosage such as 100 to 200 mg/m$^2$. These dosages may be administered for example once, twice or more per course of treatment, which may be repeated for example every 7, 14, 21 or 28 days.

The antibiotic bleomycin may also be used as a cytotoxic agent as an anti-cancer agent according to the invention.

Anti-Cancer Agent Combinations

The combinations of the Invention may comprise two or more ancillary compounds. In such embodiments, the ancillary compounds may be anti-cancer agents. In such embodiments, the two or more anticancer agents may be independently selected from carboplatin, cisplatin, taxol, taxotere, gemcitablne, and vinorelbine. Preferably the two or more further anti-cancer agents are carboplatin, taxol and vinorelbine, or carboplatin and taxol.

Combinations of compounds of Formula (I) with carboplatin, taxol and vinorelbine or combinations of compounds of Formula (I) with carboplatin and taxol, are particularly suitable for treating Non-Small cell lung cancer.

In one embodiment, the two or more anti-cancer agents are independently selected from 5-FU, leucovorin, oxaliplatin, CPT 11, and bevacizumab. Preferably, the two or more anti-cancer agents are 5-FU, leucovorin and CPT 11 or 5-FU, leucovorin and oxaliplatin.

Combinations of compounds of Formula (I) with 5-FU, leucovorin and CPT 11 or a combination of compounds of Formula (I) with 5-FU, leucovorin and oxaliplatin, are particularly suitable for treating colon cancer.

In one embodiment, the two or more anti-cancer agents are independently selected from methotrexate, taxanes, anthracyclines e.g. doxorubicin, herceptin, 5-FU, and cyclophosphamide. In one embodiment, the two or more anti-cancer agents are independently selected from taxanes, anthracyclines e.g. doxorubicin, herceptin, 5-FU, and cyclophosphamide. In one embodiment, the two or more anti-cancer agents are independently selected from 5-FU, methotrexate, cyclophosphamide and doxorubicin. Preferably the two or more anti-cancer agents are 5-FU, methotrexate and cyclophosphamide or 5-FU, doxorubicin and cyclophosphamide or doxorubicin and cyclophosphamide.

Combinations of compounds of Formula (I) with 5-FU, methotrexate and cyclophosphamide, or a combination of compounds of Formula (I) with 5-FU, doxorubicin and cyclophosphamide, or combinations of compounds of Formula (I) with doxorubicin and cyclophosphamide, are particularly suitable for treating breast cancer.

In one embodiment, the two or more anti-cancer agents are independently selected from cyclophosphamide, doxorubicin (hydroxydaunorubicin), vincristine, and prednisone. Preferably the two or more anti-cancer agents are cyclophosphamide, doxorubicin (hydroxydaunorubicin), vincristine and prednisone, or cyclophosphamide, vincristine and prednisone.

Combinations of compounds of Formula (I) with cyclophosphamide, doxorubicin (hydroxydaunorubicin), vincristine and prednisone are particularly suitable for treating non Hodgkin's lymphoma (and in particular high grade non Hodgkin's lymphoma). Combinations of compounds of Formula (I) with cyclophosphamide, vincristine and prednisone are particularly suitable for treating non Hodgkin's lymphoma (and in particular low grade non Hodgkin's lymphoma).

In one embodiment, the two or more anti-cancer agents are independently selected from vincristine, doxorubicin, and dexamethasone. Preferably the two or more anti-cancer agents are vincristine, doxorubicin and dexamethasone.

Combinations of compounds of Formula (I) with vincristine, doxorubicin and dexamethasone are particularly suitable for treating multiple myeloma.

In one embodiment, the two or more anti-cancer agents are independently selected from fludarabine and rituxamab. Preferably the two or more anti-cancer agents are fludarabine and rituxamab.

Combinations of compounds of Formula (I) with fludarabine and rituxamab are particularly suitable for treating chronic lymphocytic leukemia.

In one embodiment the combination of the invention optionally excludes combination of two or more of the following anti-cancer agents selected from a topoisomerase inhibitor, an alkylating agent, a antimetabolite, DNA binders, monoclonal antibodies, signal transduction inhibitors and microtubule inhibitors (tubulin targeting agents), such as cisplatin, cyclophosphamide, doxorubicin, irinotecan, fludarabine, 5FU, taxanes and mitomycin C.

In one embodiment the combination of the invention includes at least one anti-cancer agent selected from an antiandrogen, a histone deacetylase inhibitor (HDAC), cylcooxygenase-2 (COX-2) inhibitor, proteasome inhibitor, DNA methylation inhibitor and a CDK inhibitor.

Specific Combinations of the Invention

Particular combinations according to the invention Include compounds of Formula (I) and subgroups thereof as defined herein with the following two or more anti-cancer agents:

For cancer (and in particular acute myeloid leukemia) treatment, two or more anti-cancer agents independently selected from two or more of anthracycline, Ara C (a.k.a. Cytarabine), 6-mercaptopurine, methotrexate, mitoxantrone, daunorubicin, idarubicin, gemtuzumab ozogamicin and granulocyte colony stimulating factors. Alternatively, the two or more anti-cancer agents may be independently selected from two or more of anthracycline, Ara C (a.k.a. Cytarabine), daunorubicin, idarubicin, gemtuzumab ozogamicin and granulocyte colony stimulating factors.

For cancer (and in particular breast cancer) treatment, two or more anti-cancer agents independently selected from bevacizumab, taxanes, methotrexate, paclitaxel, docetaxel, gemcitabine, anastrozole, exemestane, letrozole, tamoxifen, doxorubicin, herceptin, 5-fluorouracil, cyclophosphamide, epirubicin and capecitabine, particularly 5-FU, methotrexate and cyclophosphamide; 5FU, doxorubicin and cyclophosphamide; or doxorubicin and cyclophosphamide. Preferably, for cancer (and in particular breast cancer) treatment, the two or more anti-cancer agents may also be independently selected from taxanes, methotrexate, paclitaxel, docetaxel, gemcitabine, anastrozole, exemestane, letrozole, tamoxifen, doxorubicin, herceptin, 5-fluorouracil, cyclophosphamide, epirubicin and capecitabine, particularly 5-FU, methotrexate and cyclophosphamide; 5FU, doxorubicin and cyclophosphamide; or doxorubicin and cyclophosphamide.

Typical dosing regimens include:
Cyclophosphamide at 100 mg/m$^2$ PO Daily×14 days, Doxorubicin at 30 mg/m$^2$ IV Day 1 & day 8 and fluorouracil at 500 mg/m$^2$ IV Day 1 & day 8, repeated every 28 days for up to 6 cycles
Cyclophosphamide at 600 mg/m$^2$ IV Day 1 and Doxorubicin at 60 mg/m$^2$ IV Day 1, repeated every 21 days for up to 4 cycles For cancer (and in particular chronic lymphocytic leukemia (CLL)) treatment, two or more anti-cancer agents independently selected from alemtuzumab, chlorambucil, cyclophosphamide, vincristine, predinisolone, fludarabine, mitoxantrone and rituximab/rituxamab, particularly fludarabine and rituxamab. Preferably, for cancer (and in particular chronic lymphocytic leukemia (CLL)) treatment, the two or more anti-cancer agents are independently selected from chlorambucil, cyclophosphamide, vincristine, predinisolone, fludarabine, mitoxantrone and rituximab/rituxamab, particularly fludarabine and rituxamab.

For cancer (and in particular chronic myeloid leukemia (CML)) treatment, two or more anti-cancer agents independently selected from hydroxyurea, cytarabine, and imatinib.

For cancer (and in particular Colon Cancer treatment), two or more anti-cancer agents independently selected from cetuximab, 5-Fluorouracil, leucovorin, irinotecan, oxaliplatin, raltirexed, capecitabine, bevacizumab, oxaliplatin, CPT 11, particularly 5-Fluorouracil, Leucovorin and CPT 11 or Fluorouracil, Leucovorin and Oxaliplatin.

Alternatively, for cancer (and in particular Colon Cancer treatment), two or more anti-cancer agents independently selected from 5-Fluorouracil, leucovorin, irinotecan, oxaliplatin, raltirexed, capecitabine, bevacizumab, oxaliplatin, CPT 11 and Avastin, particularly 5-Fluorouracil, Leucovorin and CPT 11 or Fluorouracil, Leucovorin and Oxaliplatin.

Typical dosing regimens include:
Fluorouracil at 400-425 mg/m$^2$ IV Days 1 to 5 and Leucovorin at 20 mg/m$^2$ IV Days 1 to 5, repeated every 28 days for 6 cycles
Irinotecan at 100-125 mg/m$^2$ IV over 90 minutes Days 1, 8, 15 & 22, Folinic acid at 20 mg/m2 IV Days 1, 8, 15 & 22, and Fluorouracil at 400-500 mg/m2 IV Days 1, 8, 15 & 22, repeated every 42 days until disease progression
Oxaliplatin at 85 mg/m2 IV in 500 mL of D5W over 120 minutes Day 1, Folinic acid at 200 mg/m2 IV over 120 minutes Days 1 & 2, Fluorouracil at 400 mg/m2 IV bolus, after Folinic Acid, Days 1 & 2, then Fluorouracil at 600 mg/m2 CIV over 22 hours Days 1 & 2, repeated every 12 days for up to 12 cycles For cancer (and in particular multiple myeloma treatment), two or more anti-cancer agents independently selected from vincristine, doxorubicin, dexamethasone, melphalan, prednisone, cyclophosphaimde, etoposide, pamidronate, zoledronate and bortezomib, particulary vincristine, doxorubicin and dexamethasone.

For cancer (and in particular Non-Hodgkin's lymphoma treatment), two or more anti-cancer agents independently selected from cyclophosphamide, doxorubicin/hydroxy-daunorubicin, vincristine/Onco-TCS (V/O), prednisolone, methotrexate, cytarabine, bleomycin, etoposide, rituximab/rituxamab, fludarabine, cisplatin, and ifosphamide, particularly cyclophosphamide, doxorubicin (hydroxydaunorubicin), vincristine and prednisone for high grade NHL or cyclophosphamide, vincristine and prednisone for low grade NHL.

For cancer (and in particular Non Small Cell Lung Cancer (NSCLC)) treatment, two or more anti-cancer agents may be independently selected from bevacizumab, gefitinib, erlotinib, cisplatin, carboplatin, etoposide, mitomycin, vinblastine, paclitaxel, docetaxel, gemcitabine and vinorelbine, especially taxol, vinorelbine and carboplatin or taxol and carboplatin. Particulalrly preferred for cancer (and in particular Non Small Cell Lung Cancer (NSCLC)) treatment, two or more anti-cancer agents are Independently selected from cisplatin, carboplatin, etoposide, mitomycin, vinblastine, paclitaxel, docetaxel, gemcitabine and vinorelbine, especially taxol, vinorelbine and carboplatin or taxol and carboplatin.

Typical dosing regimens include:
Gemcitabine at 1000 mg/m$^2$ IV Days 1, 8 & 15, and Cisplatin at 75-100 mg/m$^2$ IV Day 1, repeated every 28 days for 4-6 cycles
Paclitaxel at 135-225 mg/m$^2$ IV over 3 hrs Day 1 and Carboplatin at AUC 6.0 IV Day 1, repeated every 21 days for 4-6 cycles
Docetaxel at 75 mg/m$^2$ IV Day 1, and Carboplatin at AUC 5 or 6 IV Day 1, repeated every 21 days for 4-6 cycles
Docetaxel at 75 mg/m$^2$ IV Day 1, and Cisplatin at 75 mg/m$^2$ IV Day 1, repeated every 21 days for 4-6 cycles For cancer (and in particular ovarian cancer) treatment, two or more anti-cancer agents independently selected from platinum compounds (for example Cisplatin, Carboplatin), taxol, doxorubicin, liposomal doxorubicin, paclitaxel, docetaxel, gemcitabine, melphalan and mitoxantrone.

For cancer (and in in particular prostate cancer) treatment, two or more anti-cancer agents independently selected from mitoxantrone, prednisone, buserelin, goserelin, bicalutamide, nilutamide, flutamide, cyproterone acetate, megestrol/megestrel, diethylstilboestrol, docetaxel, paclitaxel, zoledronic acid and taxotere.

Pharmaceutical Formulations

While it is possible for the active compounds in the combinations of the invention to be administered alone, it is preferable to present them as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

Accordingly, in a further aspect, the invention provides compounds of the formula (I) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, Infusion or other means of delivery. The delivery can be by bolus Injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacterlostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alla, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (I) as defined herein, or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard Ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. A tablet can contain the solid solution blended with at least one disintegrant, a lubricant, a surfactant, and a glidant. The chewable tablet can contain the solid solution blended with a bulking agent, a lubricant, and if desired an additional sweetening agent (such as an artificial sweetener), and suitable flavours.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Protein Kinase Inhibitory Activity

The activity of the inhibitors of protein kinase A and protein kinase B can be measured using the assays set forth in the examples below and the level of activity exhibited by a given compound can be defined in terms of the IC50 value. Preferred compounds for use in the combinations of the present invention are compounds having an $IC_{50}$ value of less than 1 μM, more preferably less than 0.1 μM, against protein kinase B.

Therapeutic Uses

Prevention or Treatment of Proliferative Disorders

The combinations of the invention are expected to be useful in providing a means of preventing the growth of or inducing apoptosis of neoplasias. It is therefore anticipated that the combinations will prove useful in treating or preventing proliferative disorders such as cancers. In particular tumours with deletions or inactivating mutations in PTEN or loss of PTEN expression or rearrangements in the (T-cell lytmphocyte) TCL-1 gene may be particularly sensitive to PKB inhibitors. Tumours which have other abnormalities leading to an upregulated PKB pathway signal may also be particularly sensitive to inhibitors of PKB. Examples of such abnormalities include but are not limited to overexpression of one or more PI3K subunits, over-expression of one or more PKB Isoforms, or mutations in PI3K, PDK1, or PKB which lead to an increase in the basal activity of the enzyme in question, or upregulation or overexpression or mutational activation of a growth factor receptor such as a growth factor selected from the epidermal growth factor receptor (EGFR), fibroblast growth factor receptor (FGFR), platelet derived growth factor receptor (PDGFR), insulin-like growth factor 1 receptor (IGF-1R) and vascular endothelial growth factor receptor (VEGFR) families.

It is also envisaged that the combinations of the invention will be useful in treating other conditions which result from disorders in proliferation or survival such as viral infections, and neurodegenerative diseases for example. PKB plays an important role in maintaining the survival of immune cells during an immune response and therefore PKB inhibitors could be particularly beneficial in immune disorders including autoimmune conditions.

Therefore, the combinations could be useful in the treatment of diseases in which there is a disorder of proliferation, apoptosis or differentiation.

The combinations may also be useful in diseases resulting from insulin resistance and insensitivity, and the disruption of glucose, energy and fat storage such as metabolic disease and obesity.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoletic tumour of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukaemias, myelodysplastic syndrome, or promyelocytic leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include breast cancer, ovarian cancer, colon cancer, prostate cancer, oesophageal cancer, squamous cancer and non-small cell lung carcinomas.

A further subset of cancers includes breast cancer, ovarian cancer, prostate cancer, endometrial cancer and glioma.

Immune Disorders

Immune disorders for which the combinations may be beneficial include but are not limited to autoimmune conditions and chronic inflammatory diseases, for example systemic lupus erythematosus, autoimmune mediated glomerulonephritis, rheumatoid arthritis, psoriasis, inflammatory bowel disease, and autoimmune diabetes mellitus, Eczema hypersensitivity reactions, asthma, COPD, rhinitis, and upper respiratory tract disease.

Other Therapeutic Uses

PKB plays a role in apoptosis, proliferation, differentiation and therefore the combinations could also be useful in the treatment of the following diseases other than cancer and those associated with immune dysfunction; viral infections, for example herpes virus, pox virus, Epstein-Barr virus, Sindbis virus, adenovirus, HIV, HPV, HCV and HCMV; prevention of AIDS development in HIV-infected individuals; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, degenerative diseases of the musculoskeletal system, for example, osteoporosis and arthritis, aspirin-sensitive rhinosinusitis, cystic fibrosis, multiple sclerosis, kidney diseases.

Methods of Treatment and Posology

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The constituent compounds of the combinations of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compounds may be administered once or more than once each day. The compounds can be administered continuously (i.e. taken every day without a break for the duration of the treatment regimen). Alternatively, the compounds can be administered intermittently, i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week oft, or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The combinations of the invention as defined herein can be further combined and/or administered with one of more other compounds for treatment of a particular disease state, for example a neoplastic disease such as a cancer as hereinbefore defined. Examples of other therapeutic agents or treatments that may be administered together (whether concurrently or at different time intervals) with the combinations of the invention include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and,
Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromoembolic episodes.

For use in combination therapy with an ancillary compound, the compound of the formula (I) and one, two, three, four or more ancillary compounds can be, for example, formulated together in a dosage form containing two, three, four or more ancillary compounds. In an alternative, the constituent compounds of the combination of the invention may be formulated separately and presented together in the form of a kit, optionally with instructions for their use.

It is envisaged that the combinations of the Invention will useful in the prophylaxis or treatment of a range of disease states or conditions mediated by protein kinase A and/or protein kinase B. Examples of such disease states and conditions are set out above.

The combinations of the invention are generally administered to a subject in need of such administration, for example a human or animal patient, preferably a human.

The constituent compounds of the combination will typically be administered in amounts that are therapeutically or prophylactically useful and which generally are non-toxic. However, in certain situations (for example in the case of life threatening diseases), the benefits of administering the combination of the invention may outweigh the disadvantages of any toxic effects or side effects, in which case it may be considered desirable to administer the compound combination in amounts that are associated with a degree of toxicity.

The constituent compounds of the combinations of the invention may be administered over a prolonged term to maintain beneficial therapeutic effects or may be administered for a short period only. Alternatively they may be administered in a pulsatile or continuous manner.

The compounds of the combination can be administered simultaneously or sequentially. When administered sequentially, they can be administered at closely spaced intervals (for example over a period of 5-10 minutes) or at longer intervals (for example 1, 2, 3, 4 or more hours apart, or even longer periods, e.g. 1, 2, 3, 4, 5, 6, or 7 days, apart where required), the precise dosage regimen being commensurate with the properties of the therapeutic agent(s). With sequential administration, the delay in administering the second (or additional) active ingredient should not be such as to lose the advantageous benefit of the efficacious effect of the combination of the active ingredients. In addition, the delay in administering the second (or additional) active ingredient is typically timed so as to allow for any adverse side effects of the first compound to subside to an acceptable level before administration of the other compounds, whilst not losing the advantageous benefit of the efficacious effect of the combination of the active ingredients.

The two or more treatments may be given in individually varying dose schedules and via the same or different routes.

For example, one compound may be administered by the oral route and the other compound(s) administered by parenteral administration such as administration by injection (e.g. i.v.) or infusion. In an alternative, all compounds may be administered by injection or infusion. In a further alternative, all compounds may be given orally. In one particular embodiment, the compound of the formula (I) is administered by injection or infusion and one or more of the ancillary compound(s) are administered orally.

When administered at different times, the administration of at least one component of the combination may alternate with or interleaf with administration of one or more of the other components or the components of the combination may be administered in sequential blocks of therapy. As indicated above, the administration of the components of the combination may be spaced apart in time, for example by one or more hours, or days, or even weeks, provided that they form part of the same overall treatment.

In one embodiment of the invention, the compound of the formula (I) is administered sequentially or simultaneously with the ancillary compound(s).

In another embodiment of the invention, the compound of the formula (I) is administered sequentially with the ancillary compound(s) in either order.

In a further embodiment, one or more of the ancillary compound(s) are administered prior to the compound of the formula (I).

In another embodiment, one or more of the ancillary compound(s) are administered after the compound of the formula (I).

In another embodiment of the invention, the compound of the formula (I) and one or more of the ancillary compound(s) are administered simultaneously.

In another embodiment, the compound of the formula (I) and the ancillary compound(s) are each administered in a therapeutically effective amount with respect to the individual components; in other words, the compound of the formula (I) and the ancillary compound(s) are administered in amounts that would be therapeutically effective even if the components were administered other than in combination.

In another embodiment, the compound of the formula (I) and at least one of the ancillary compound(s) are each administered in a sub-therapeutic amount with respect to the individual components; in other words, the compound of the formula (I) and the ancillary compound are administered in amounts that would be therapeutically ineffective if the components were administered other than in combination.

Preferably, the compound of the formula (I) and one or more of the ancillary compound(s) interact in a synergistic or additive manner, and in particular an additive manner.

A typical daily dose of the compound of the formula (I) present in the combination of the invention can be in the range from 100 picograms to 100 milligrams per kilogram of body weight, typically 10 nanograms to 10 milligrams per kilogram of bodyweight, more typically 1 microgram to 10 milligrams although higher or lower doses may be administered where required. Each compound can be administered on a daily basis or on a repeat basis every 2, or 3, or 4, or 5, or 6, or 7, or 10 or 14, or 21, or 28 days for example.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

Accordingly, a person skilled in the art would know through their common general knowledge the dosing regimes and combination therapies to use. It will be appreciated that the preferred method and order of administration and the respective dosage amounts and regimes for each component of the combination will depend on the particular ancillary compound(s) and compound of Formula (I) being administered, their route of administration, the particular tumour being treated and the particular host being treated. The optimum method and order of administration and dosage amounts and regime can be readily determined by those skilled in the art using conventional methods and in view of the information set out herein.

As described infra, the compounds of the formula (I) are administered in combination therapy with an ancillary compound (e.g. one, two or more ancillary compounds), for example in the treatment of a particular disease state (for example a neoplastic disease such as a cancer as hereinbefore defined). Examples of suitable ancillary compounds that may be used in the combinations of the invention are described in detail above.

However, the combinations of the invention may also be further combined with other classes of therapeutic agents or treatments that may be administered together (whether concurrently or at different time intervals) with the combinations of the invention.

For example, the combinations within Group A (as set out above) may be further combined with other classes of therapeutic agents or treatments, including (but not limited to):

Topoisomerase I inhibitors
Antimetabolites
Tubulin targeting agents
DNA binder and topoisomerase II inhibitors
Alkylating Agents
Anti-Hormones
Cytokines and retinoids
Monoclonal antibodies
Other therapeutic or prophylactic agents, for example agents that reduce or alleviate some of the side effects associated with chemotherapy. These include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), leucovorin, granulocyte-colony stimulating factor (G-CSF). Also included are agents that inhibit bone resorption such as bisphosphonate agents e.g. zoledronate, pamidronate and ibandronate, as well as agents that suppress Inflammatory responses (such as dexamethazone).

In another embodiment, the combinations within Group B (as set out above) may be further combined with other classes of therapeutic agents or treatments, including (but not limited to):

Monoclonal Antibodies.
Anti-Hormones
Signal Transduction Inhibitors
Proteasome Inhibitors
DNA methyl transferases
Cytokines and retinoids
Other therapeutic or prophylactic agents, for example agents that reduce or alleviate some of the side effects associated with chemotherapy. These include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), leucovorin, granulocyte-colony stimulating factor (G-CSF). Also included are agents that Inhibit bone resorption such as bisphosphonate agents e.g. zoledronate, pamidronate and ibandronate, as well as agents that suppress inflammatory responses (such as dexamethazone).

In another embodiment, the combinations within Group C (as set out above) may be further combined with other classes of therapeutic agents or treatments, including (but not limited to):

Topoisomerase I inhibitors
Antimetabolites
Tubulin targeting agents
DNA binder and topoisomerase II inhibitors
Alkylating Agents
Anti-Hormones
Signal Transduction Inhibitors
Proteasome Inhibitors
DNA methyl transferases
Cytokines and retinoids
Other therapeutic or prophylactic agents, for example agents that reduce or alleviate some of the side effects associated with chemotherapy. These include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), leucovorin, granulocyte-colony stimulating factor (G-CSF). Also included are agents that inhibit bone resorption such as bisphosphonate agents e.g. zoledronate, pamidronate and ibandronate, as well as agents that suppress inflammatory responses (such as dexamethazone).

In another embodiment, the combinations within Group D (as set out above) may be further combined with other classes of therapeutic agents or treatments, including (but not limited to):
- Topoisomerase I inhibitors
- Antimetabolites
- Tubulin targeting agents
- DNA binder and topoisomerase II inhibitors
- Alkylating Agents
- Monoclonal Antibodies.
- Signal Transduction Inhibitors
- Proteasome Inhibitors
- DNA methyl transferases
- Other therapeutic or prophylactic agents, for example agents that reduce or alleviate some of the side effects associated with chemotherapy. These Include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), leucovorin, granulocyte-colony stimulating factor (G-CSF). Also included are agents that inhibit bone resorption such as bisphosphonate agents e.g. zoledronate, pamidronate and ibandronate, as well as agents that suppress inflammatory responses (such as dexamethazone).

In another embodiment, the combinations within Group E (as set out above) may be further combined with other classes of therapeutic agents or treatments, including (but not limited to):
- Topoisomerase I inhibitors
- Antimetabolites
- Tubulin targeting agents
- DNA binder and topoisomerase II inhibitors
- Alkylating Agents
- Monoclonal Antibodies.
- Anti-Hormones
- Signal Transduction Inhibitors
- Proteasome Inhibitors
- DNA methyl transferases
- Cytokines and retinoids Other therapeutic or prophylactic agents, for example agents that reduce or alleviate some of the side effects associated with chemotherapy. These include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), leucovorin, granulocyte-colony stimulating factor (G-CSF). Also included are agents that inhibit bone resorption such as bisphosphonate agents e.g. zoledronate, pamidronate and ibandronate, as well as agents that suppress inflammatory responses (such as dexamethazone).

Each of the compounds present in the combinations of the invention may be given in individually varying dose schedules and via different routes.

Thus, administration of the compound of the formula (I) in combination therapy with an ancillary compound (e.g. one, two or more ancillary compounds) may comprise simultaneous or sequential administration. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The combinations of the invention may also be administered in conjunction with non-chemotherapeutic treatments such as radiotherapy, photodynamic therapy, gene therapy, surgery and controlled diets.

The combination therapy may therefore involve the formulation of the compound of the formula (I) with two, three, four or more other therapeutic agents (including at least two ancillary compounds). Such formulations can be, for example, a dosage form containing two, three, four or more therapeutic agents. In an alternative, the individual therapeutic agents may be formulated separately and presented together in the form of a kit, optionally with instructions for their use.

A person skilled in the art would know through their common general knowledge the dosing regimes and combination therapies to use.

Methods of Diagnosis

Prior to administration of the combination of the invention, a patient may be screened to determine whether a disease or condition from which the patient is or may be suffering is one which would be susceptible to treatment with a compound of formula (I) and/or treatment with an ancillary compound (e.g. one, two or more ancillary compounds).

For example, a biological sample taken from a patient may be analysed to determine whether a condition or disease, such as cancer, that the patient is or may be suffering from is one which is characterised by a genetic abnormality or abnormal protein expression which leads to up-regulation of PKA and/or PKB or to sensitisation of a pathway to normal PKA and/or PKB activity, or to upregulation of a signal transduction component upstream of PKA and/or PKB such as, in the case of PKB, PI3K, GF receptor and PDK 1 & 2.

Alternatively, a biological sample taken from a patient may be analysed for loss of a negative regulator or suppressor of the PKB pathway such as PTEN. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of PKA and/or PKB. The term diagnosis includes screening. By marker we include genetic markers including, for example, the measurement of DNA composition to identify mutations of PKA and/or PKB. The term marker also includes markers which are characteristic of up regulation of PKA and/or PKB, including enzyme activity, enzyme levels, enzyme state (e.g. phosphorylated or not) and mRNA levels of the aforementioned proteins.

The above diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, or urine.

Identification of an individual carrying a mutation in PKA and/or PKB or a rearrangement of TCL-1 or loss of PTEN expression may mean that the patient would be particularly suitable for treatment with a PKA and/or PKB inhibitor. Tumours may preferentially be screened for presence of a PKA and/or PKB variant prior to treatment. The screening process will typically involve direct sequencing, oligonucleotide microarray analysis, or a mutant specific antibody.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence in Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of PKB, or detection of PKB variants could be applicable in the present case.

Therefore all of these techniques could also be used to identify tumours particularly suitable for treatment with PKA and/or PKB inhibitors.

For example, as stated above, PKB beta has been found to be upregulated in 10-40% of ovarian and pancreatic cancers (Bellacosa et at 1995, Int. J. Cancer 64, 280-285; Cheng et al 1996, PNAS 93, 3636-3641; Yuan et al 2000, Oncogene 19, 2324-2330). Therefore it is envisaged that PKB inhibitors, and in particular inhibitors of PKB beta, may be used to treat ovarian and pancreatic cancers.

PKB alpha is amplified in human gastric, prostate and breast cancer (Staal 1987, PNAS 84, 5034-5037; Sun et al 2001, Am. J. Pathol. 159, 431-437). Therefore it is envisaged that PKB inhibitors, and in particular inhibitors of PKB alpha, may be used to treat human gastric, prostate and breast cancer.

Increased PKB gamma activity has been observed in steroid independent breast and prostate cell lines (Nakatani et al 1999, J. Biol. Chem. 274, 21528-21532). Therefore it is envisaged that PKB Inhibitors, and in particular inhibitors of PKB gamma, may be used to treat steroid independent breast and prostate cancers.

EXPERIMENTAL

The invention will now be illustrated, but not limited, by reference to the specific embodiments described in the following procedures and examples.

The starting materials for each of the procedures described below are commercially available unless otherwise specified.

In the examples, the compounds prepared were characterised by liquid chromatography, mass spectroscopy and $^1$H nuclear magnetic resonance spectroscopy using the systems and operating conditions set out below.

Proton magnetic resonance ($^1$H NMR) spectra were recorded on a Bruker AV400 instrument operating at 400.13 MHz, in Me-d$_3$-OD at 27 C, unless otherwise stated and are reported as follows: chemical shift δ/ppm (number of protons, multiplicity where s=singlet, d=doublet, t=triplet, q=quartet, m=multiplet, br=broad). The residual protic solvent MeOH ($δ_H$=3.31 ppm) was used as the internal reference.

For the mass spectra, where chlorine is present, the mass quoted for the compound is for $^{35}$Cl.

In each of the examples, where the compounds are isolated or formed as the free base, they can be converted into a salt form such as an acetic acid or hydrochloric acid salt. Conversely, where the compounds are isolated or formed as a salt, the salt can be converted into the corresponding free base by methods well known to the skilled person, and then optionally converted to another salt.

A number of liquid chromatography systems were used and these are described below.

Platform System

| HPLC System: | Waters 2795 |
|---|---|
| Mass Spec Detector: | Micromass Platform LC |
| PDA Detector: | Waters 2996 PDA |

Acidic Analytical Conditions 1:

| Eluent A: | H$_2$O (0.1% Formic Acid) |
|---|---|
| Eluent B: | CH$_3$CN (0.1% Formic Acid) |
| Gradient: | 5-95% eluent B over 3.5 minutes |

-continued

| Flow:   | 1.5 ml/min                                      |
| ------- | ----------------------------------------------- |
| Column: | Phenomenex Synergi 4μ Max-RP 80A, 50 × 4.6 mm   |

Acidic Analytical Conditions 2:

| Eluent A:  | $H_2O$ (0.1% Formic Acid)                       |
| ---------- | ----------------------------------------------- |
| Eluent B:  | $CH_3CN$ (0.1% Formic Acid)                     |
| Gradient:  | 5-95% eluent B over 3.5 minutes                 |
| Flow:      | 0.8 ml/min                                      |
| Column:    | Phenomenex Synergi 4μ Max-RP 80A, 50 × 2.0 mm   |

Acidic Analytical Conditions 3:

| Eluent A:  | $H_2O$ (0.1% Formic Acid)                       |
| ---------- | ----------------------------------------------- |
| Eluent B:  | $CH_3CN$ (0.1% Formic Acid)                     |
| Gradient:  | 5-95% eluent B over 15 minutes                  |
| Flow:      | 0.4 ml/min                                      |
| Column:    | Phenomenex Synergi 4μ Max-RP 80A, 50 × 2.0 mm   |

Basic Analytical Conditions 1:

| Eluent A:  | $H_2O$ (10 mM $NH_4HCO_3$ buffer adjusted to pH = 9.5 with $NH_4OH$) |
| ---------- | ----------------------------------------------- |
| Eluent B:  | $CH_3CN$                                        |
| Gradient:  | 05-95% eluent B over 3.5 minutes                |
| Flow:      | 1.5 ml/min                                      |
| Column:    | Waters XTerra MS $C_{18}$ 5 μm 4.6 × 50 mm      |

Basic Analytical Conditions 2:

| Eluent A:  | $H_2O$ (10 mM $NH_4HCO_3$ buffer adjusted to pH = 9.5 with $NH_4OH$) |
| ---------- | ----------------------------------------------- |
| Eluent B:  | $CH_3CN$                                        |
| Gradient:  | 05-95% eluent B over 3.5 minutes                |
| Flow:      | 0.8 ml/min                                      |
| Column:    | Thermo Hypersil-Keystone BetaBasic-18 5 μm, 50 × 2.1 mm |

Basic Analytical Conditions 3:

| Eluent A:  | $H_2O$ (10 mM $NH_4HCO_3$ buffer adjusted to pH = 9.5 with $NH_4OH$) |
| ---------- | ----------------------------------------------- |
| Eluent B:  | $CH_3CN$                                        |
| Gradient:  | 05-95% eluent B over 3.5 minutes                |
| Flow:      | 0.8 ml/min                                      |
| Column:    | Phenomenex Luna C18(2) 5 μm, 50 × 2.0 mm        |

Basic Analytical Conditions 4:

| Eluent A:  | $H_2O$ (10 mM $NH_4HCO_3$ buffer adjusted to pH = 9.2 with $NH_4OH$) |
| ---------- | ----------------------------------------------- |
| Eluent B:  | $CH_3CN$                                        |
| Gradient:  | 05-95% eluent B over 15 minutes                 |
| Flow:      | 0.8 ml/min                                      |
| Column:    | Phenomenex Luna C18(2) 5 μm, 150 × 2.0 mm       |

Polar Analytical Conditions:

| Eluent A:  | $H_2O$ (0.1% Formic Acid)                       |
| ---------- | ----------------------------------------------- |
| Eluent B:  | $CH_3CN$ (0.1% Formic Acid)                     |
| Gradient:  | 00-50% eluent B over 3 minutes                  |
| Flow:      | 1.5 ml/min                                      |
| Column:    | Phenomenex Synergi 4μ Hydro 80A, 50 × 4.6 mm    |

MS Conditions:

| Capillary voltage:  | 3.5 kV or 3.6 kV                                |
| ------------------- | ----------------------------------------------- |
| Cone voltage:       | 30 V                                            |
| Source Temperature: | 120° C.                                         |
| Scan Range:         | 165-700 amu                                     |
| Ionisation Mode:    | ElectroSpray Negative, Positive or Positive & Negative |

FractionLynx System

| System:              | Waters FractionLynx (dual analytical/prep)     |
| -------------------- | ---------------------------------------------- |
| HPLC Pump:           | Waters 2525                                    |
| Injector-Autosampler:| Waters 2767                                    |
| Mass Spec Detector:  | Waters-Micromass ZQ                            |
| PDA Detector:        | Waters 2996 PDA                                |

Acidic Analytical Conditions:

| Eluent A:  | $H_2O$ (0.1% Formic Acid)                       |
| ---------- | ----------------------------------------------- |
| Eluent B:  | $CH_3CN$ (0.1% Formic Acid)                     |
| Gradient:  | 5-95% eluent B over 5 minutes                   |
| Flow:      | 2.0 ml/min                                      |
| Column:    | Phenomenex Synergi 4μ Max-RP 80A, 50 × 4.6 mm   |

Polar Analytical Conditions:

| Eluent A:  | $H_2O$ (0.1% Formic Acid)                       |
| ---------- | ----------------------------------------------- |
| Eluent B:  | $CH_3CN$ (0.1% Formic Acid)                     |
| Gradient:  | 00-50% eluent B over 5 minutes                  |
| Flow:      | 2.0 ml/min                                      |
| Column:    | Phenomenex Synergi 4μ Max-RP 80A, 50 × 4.6 mm   |

MS Parameters for Acidic and Polar Analytical Conditions:

| Capillary voltage:  | 3.5 kV                                          |
| ------------------- | ----------------------------------------------- |
| Cone voltage:       | 25 V                                            |
| Source Temperature: | 120° C.                                         |
| Scan Range:         | 125-800 amu                                     |
| Ionisation Mode:    | ElectroSpray Positive or ElectroSpray Positive & Negative |

Chiral Analytical Conditions:

| Eluent:        | MeOH + 0.1% NH4/TFA                             |
| -------------- | ----------------------------------------------- |
| Flow:          | 1.2 ml/min                                      |
| Total time:    | 16.00 min                                       |
| Inj. Volume:   | 10 μL                                           |
| Sample conc.:  | 2 mg/ml                                         |
| Column:        | Astec, Chirobiotic V; 250 × 4.6 mm              |

Mass spectrometer was taken off-line.
Agilent System

| HPLC System: | Agilent 1100 series |
|---|---|
| Mass Spec Detector: | Agilent LC/MSD VL |
| Multi Wavelength Detector: | Agilent 1100 series MWD |
| Software: | HP Chemstation |

Chiral Analytical Conditions:

| Eluent: | MeOH + 0.2% NH4/AcOH at room Temperature |
|---|---|
| Flow: | 2.0 ml/min |
| Total time: | 8.5 min |
| Inj. Volume: | 20 μL |
| Sample Conc: | 2 mg/ml |
| Column: | Astec, Chirobiotic V; 250 × 4.6 mm |

Chiral Preparative Conditions 1:

| Eluent: | MeOH + 0.1% NH4/TFA at room Temperature |
|---|---|
| Flow: | 6.0 ml/min |
| Total time: | 10 min |
| Inj. Volume: | 100 μL |
| Sample Conc: | 20 mg/ml |
| Column: | Astec, Chirobiotic V; 250 × 10 mm |

Chiral Preparative Conditions 2:

| Eluent: | MeOH + 0.2% NH4/AcOH at room Temperature |
|---|---|
| Flow: | 20.0 ml/min |
| Total time: | 19 min |
| Inj. Volume: | 950 μL |
| Sample Conc: | 25 mg/ml |
| Column: | Astec, Chirobiotic V2; 250 × 21.2 mm |

MS Conditions (Lust Analytical Method):

| Capillary voltage: | 3000 V |
|---|---|
| Fragmentor: | 150 |
| Gain: | 1.00 |
| Drying gas: | 12.0 L/min |
| Drying gas T: | 350° C. |
| Nebulizer pressure: | 35 (psig) |
| Scan Range: | 125-800 amu |
| Ionisation Mode: | ElectroSpray Positive |

In the examples below, the following key is used to identify the LCMS conditions used:

PS-A Platform System—acidic analytical conditions 1
PS-A2 Platform System—acidic analytical conditions 2
PS-A3 Platform System—acidic analytical conditions 3
PS-B Platform System—basic analytical conditions 1
PS-B2 Platform System—basic analytical conditions 2
PS-B3 Platform System—basic analytical conditions 3
PS-B4 Platform System—basic analytical conditions 4
PS-P Platform System—polar analytical conditions
FL-A FractionLynx System—acidic analytical conditions
FL-P FractionLynx System—polar analytical conditions
FL-C FractionLynx System—chiral analytical conditions
AG-CA Agilent System—chiral analytical conditions
AG-CP1 Agilent System—chiral preparative conditions 1
AG-CP2 Agilent System—chiral preparative conditions 2

Example 1

2-Phenyl-2-[4-(1H-pyrazol-4-yl)-phenyl]-ethylamine

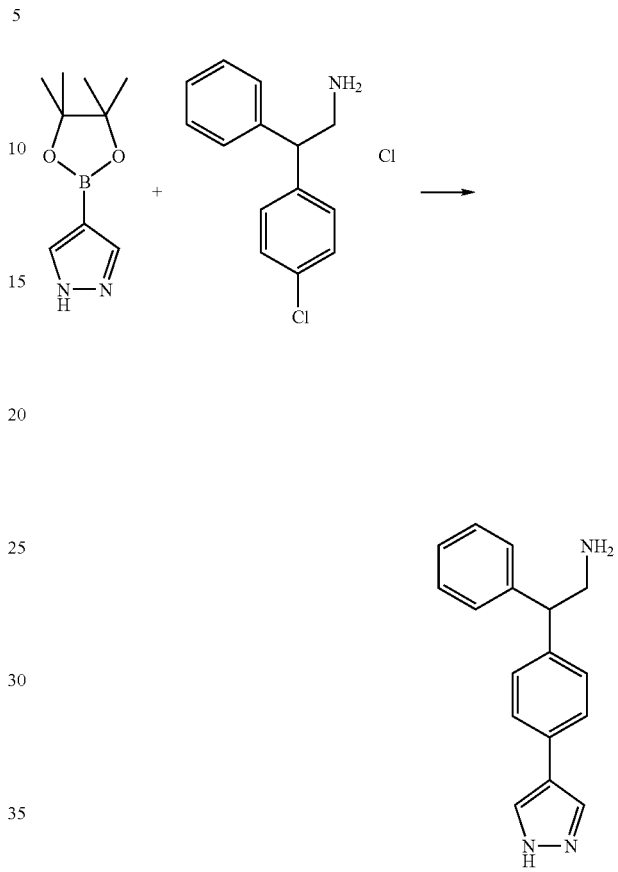

To a suspension of 2-(4-chlorophenyl)-2-phenylethylamine hydrochloride (134 mg, 0.5 mmol, 1.0 equiv.) (Array PPA-Q02-1) in toluene (0.8 ml) was added bis(tri-t-butylphosphine)palladium (0) (3 mg, 1 mol %) (Strem) and the mixture was purged with nitrogen. A suspension of 4-(4,4,5,5-tetramethyl-1,3,2-dioxaborolan-2-yl)-1H-pyrazole (107 mg, 0.55 mmol, 1.1 equiv.) (Aldrich 52,505-7) in ethanol (0.8 ml) was added followed by potassium carbonate (415 mg, 3.0 mmol, 6 equiv.) in water (2.5 ml). The mixture was purged with nitrogen and sealed. The reaction mixture was heated in a CEM Explorer™ microwave to 135° C. for 15 minutes using 50 watts power. The solvents were removed and the residue was partitioned between ethyl acetate and 2N NaOH. The aqueous layer was extracted with ethyl acetate and the combined organic layers were washed with brine, dried (MgSO$_4$) and concentrated under reduced pressure. The crude reaction mixture was purified by column chromatography (SiO$_2$), eluting with a mixture of dichloromethane (90 ml):methanol (18 ml):acetic acid (3 ml):H$_2$O (2 ml) to afford the title compound 14 mg (9%); LCMS (PS-A) R$_t$ 1.79 min; m/z [M+H]$^+$ 264.

Example 2

3-Phenyl-2-[3-(1H-pyrazol-4-yl)-phenyl]-propionitrile

2A. 2-(3-Bromo-phenyl)-3-phenyl-propionitrile

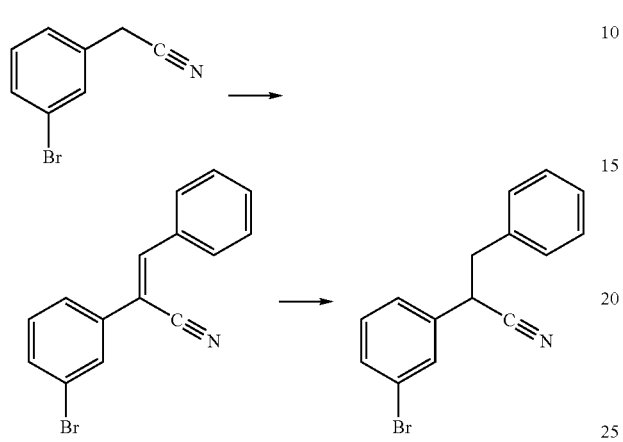

A solution of 40% KOH (2.83 g in 5.0 ml of $H_2O$) in ethanol (13 ml) was added to a solution of benzaldehyde (2.85 ml, 28.05 mmol) and 3-bromophenylacetonitrile (5 g, 25.50 mmol) in ethanol (9 ml). The reaction mixture was then stirred at room temperature for 2 hours and the precipitate was collected by suction filtration and washed with cold ethanol (6.68 g, 92%). The crude product (3.45 g, 12.14 mmol) was then dissolved in ethanol (35 ml) and heated to 65° C. Sodium borohydride (459 mg, 12.14 mmol) was added in portions and the reaction mixture was maintained at this temperature for a further 2 hours. Upon cooling, water (10 ml) was added and the solvent was removed under reduced pressure. The residue was partitioned between water (100 ml) and ethyl acetate (100 ml). The organic layer was separated, dried ($MgSO_4$), filtered and concentrated to afford the desired product (1.80 g, 52%), which was used without purification.

2B. 3-Phenyl-2-[3-(1H-pyrazol-4-yl)-phenyl]-propionitrile

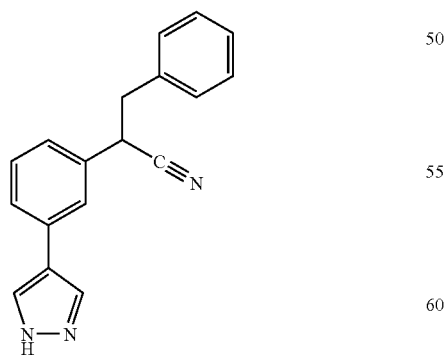

2-(3-Bromo-phenyl)-3-phenyl-propionitrile was reacted with 4-(4,4,5,5-tetramethyl-1,3,2-dioxaborolan-2-yl)-1H-pyrazole following the procedure set out in Example 1 to give the title compound. (LC/MS: (PS-A) $R_t$ 2.98 [M+H]$^+$ 274).

Example 3

2-[4-(3,5-Dimethyl-1H-pyrazol-4-yl)-phenyl]-2-phenyl-ethylamine

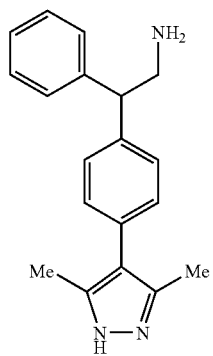 [SMILES: Cc1n[nH]c(C)c1-c1ccc(C(CN)c2ccccc2)cc1]

Following the procedure of Example 1 but using 3,5-dimethyl-4-(4,4,5,5-tetramethyl-[1,3,2]dioxaborolan-2-yl)-1H-pyrazole (Boron Molecular D03-BM152) instead of 4-(4,4,5,5-tetramethyl-1,3,2-dioxaborolan-2-yl)-1H-pyrazole gave the title compound. (LC/MS: (PS-A) $R_t$ 1.79 [M+H]$^+$ 292.

Example 4

2-(4-Chloro-phenyl)-2-[4-(1H-pyrazol-4-yl)-phenyl]-ethylamine

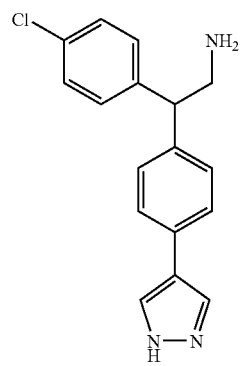 [SMILES: NCC(c1ccc(Cl)cc1)c1ccc(-c2cn[nH]c2)cc1]

Following the procedure of Example 1 but using 2,2-bis-(4-chloro-phenyl)-ethylamine in place of 2-(4-chlorophenyl)-2-phenylethylamine hydrochloride* gave the title compound. (LC/MS: (PS-A) $R_t$ 1.99 [M+H]$^+$ 298).

*This starting material can be made by the method described in *J. Amer. Chem. Soc.*, 1983, 105, 3183-3188.

Example 5

2-[3-(3,5-Dimethyl-1H-pyrazol-4-yl)-phenyl]-1-phenyl-ethylamine

5A. 2-(3-Bromo-phenyl)-1-phenyl-ethylamine

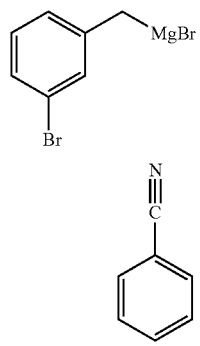

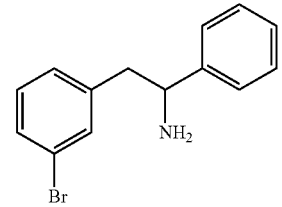

Benzonitrile (500 mg, 4.849 mmol) was added dropwise to a solution of 3-bromobenzylmagnesium bromide (0.275 M solution in diethyl ether, 21.1 ml, 5.818 mmol) under an atmosphere of nitrogen at room temperature. The reaction mixture was then heated to reflux for a period of 2 hours then allowed to cool. Lithium aluminium hydride (1.0 M in THF, 4.85 ml, 4.849 mmol) was then added cautiously and the reaction mixture was allowed to heat at reflux for a further 16 hours. Upon cooling, the reaction was quenched by cautious and dropwise addition of water (5 ml) and then partitioned between water (20 ml) and ethyl acetate (100 ml). The organic layer was separated, dried (MgSO$_4$), filtered and concentrated. Purification by ion exchange chromatography afforded the desired compound (420 mg, 31%).

5B. 2-[3-(3,5-Dimethyl-1H-pyrazol-4-yl)-phenyl]-1-phenyl-ethylamine

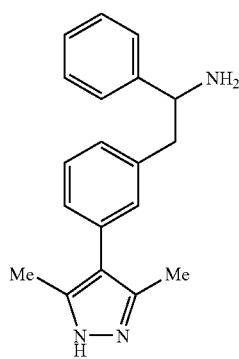 [SMILES: Cc1n[nH]c(C)c1-c1cccc(CC(N)c2ccccc2)c1]

The product of 5B was reacted with 3,5-dimethyl-4-(4,4,5,5-tetramethyl-[1,3,2]dioxaborolan-2-yl)-1H-pyrazole following the procedure set out in Example 1 to give the title compound. (LC/MS: (PS-B) R$_t$ 2.54 [M+H]$^+$ 292).

Example 6

3-Phenyl-2-[3-(1H-pyrazol-4-yl)-phenyl]-propylamine

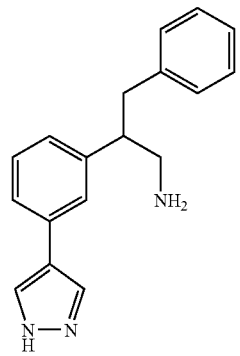 [SMILES: NCC(Cc1ccccc1)c1cccc(-c2cn[nH]c2)c1]

To a solution of the product of Example 2 (70 mg, 0.256 mmol, 1.0 equiv) in ethanol (25 ml) was added concentrated ammonia (0.5 ml) and Raney Nickel (approximately 0.5 ml of the water suspension) and the reaction mixture was subjected to a hydrogen atmosphere for 17 hours. The mixture was filtered through Celite® and the mother liquor was concentrated under reduced pressure to give the title compound which was purified by preparative liquid chromatography. (LC/MS: (PS-A) R$_t$ 1.89 [M+H]$^+$ 278.

Example 7

3-Phenyl-2-[4-(1H-pyrazol-4-yl)-phenyl]-propylamine

7A. 2-(4-Bromo-phenyl)-3-phenyl-propionitrile

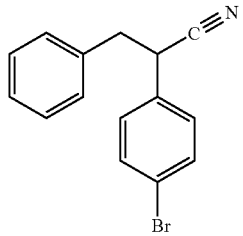 [SMILES: N#CC(Cc1ccccc1)c1ccc(Br)cc1]

Following the procedure described in Example 2A but substituting 4-bromophenylacetonitrile for 3-bromophenylacetonitrile gave the title compound was obtained which was used in the next step without further purification.

7B. 3-Phenyl-2-[4-(1H-pyrazol-4-yl)-phenyl]-propionitrile

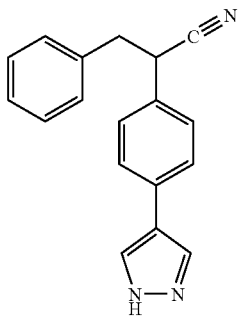 [SMILES: N#CC(Cc1ccccc1)c1ccc(-c2cn[nH]c2)cc1]

By following the procedure described in Example 1 but substituting 2-(4-Bromo-phenyl)-3-phenyl-propionitrile for 2-(4-chlorophenyl)-2-phenylethylamine, the title compound was obtained.

7C. 3-Phenyl-2-[4-(1H-pyrazol-4-yl)-phenyl]-propylamine

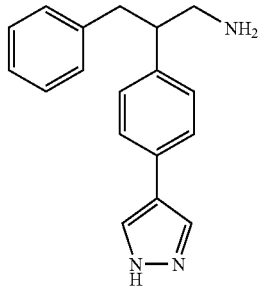 [SMILES: NCC(Cc1ccccc1)c1ccc(-c2cn[nH]c2)cc1]

The nitrile product of Example 7B was reduced using the conditions described in Example 6 to give the title compound. (LC/MS: (PS-B) $R_t$ 3.03 [M+H]$^+$ 278.

Example 8

{3-(4-Chloro-phenyl)-3-[4-(1H-pyrazol-4-yl)-phenyl]-propyl}-methyl-amine

8A. 3-(4-Bromo-phenyl)-2-cyano-acrylic acid ethyl ester (J. Med. Chem, 1983, 26, 935-947)

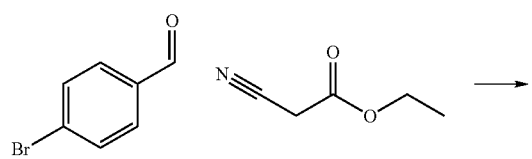

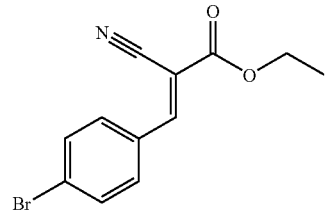

4-Bromobenzaldehyde (3 g, 16.21 mmol) and ethyl cyanoacetate (1.9 ml, 17.84 mmol) in toluene was added piperidine (27 μl) and the reaction mixture was refluxed for 1 hour with a Dean-Stark separator. The solvent was removed under reduced pressure, the residue triturated with warm ethyl acetate, filtered to yield the desired product as a yellow solid (4.03 g, 89% yield). LC/MS: (PS-A2) $R_t$ 3.44.

8B. 3-(4-Bromo-phenyl)-3-(4-chloro-phenyl)-2-cyano-propionic acid ethyl ester

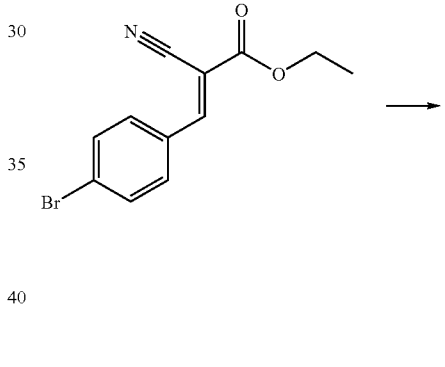

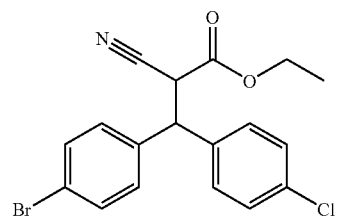

A solution of 3-(4-bromo-phenyl)-2-cyano-acrylic acid ethyl ester (1.5 g, 5.36 mmol) in dry toluene (12 ml) was added dropwise to 4-chlorophenylmagnesium bromide (0.5 M solution in tetrahydrofuran, 6.96 ml, 6.96 mmol) at 0° C. The reaction mixture was heated to 85° C. for 3 hours, poured onto ice, acidified with 1N HCl and extracted with ethyl acetate. The organic layer was separated, dried (MgSO$_4$), filtered and concentrated, the crude product was purified over flash silica chromatography eluting with petroleum ether to ethyl acetate/petroleum ether (5:95) to afford the desired product (1.91 g, 91% yield). LC/MS: (PS-A2) $R_t$ 3.78 [M+H]$^+$ 391.93.

8C. 3-(4-Bromo-phenyl)-3-(4-chloro-phenyl)-propionic acid

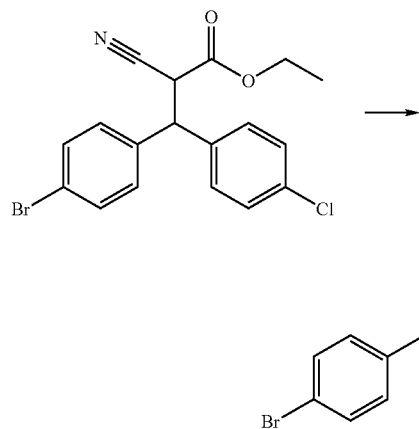

A mixture of 3-(4-bromo-phenyl)-3-(4-chloro-phenyl)-2-cyano-propionic acid ethyl ester (1.91, 4.87 mmol), acetic acid (10 ml), concentrated sulfuric acid (5 ml) and water (5 ml) were refluxed for 2 hours. Reaction mixture was poured into iced water and extracted with ethyl acetate. The organic layer was separated, dried (MgSO$_4$), filtered and concentrated, the crude product was purified over flash silica chromatography eluting with ethyl acetate/petroleum ether (1:1) to afford the desired product (0.82 g, 50% yield). LC/MS: (PS-A2) $R_t$ 3.39 [M+H]$^+$ 338.86.

8D. 3-(4-Bromo-phenyl)-3-(4-chloro-phenyl)-N-methyl-propionamide

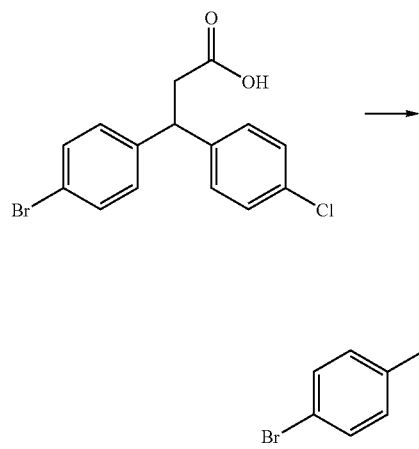

A mixture of 3-(4-bromo-phenyl)-3-(4-chloro-phenyl)-propionic acid (0.25 g, 0.74 mmol) and 1-hydroxybenatriazole (0.12 g, 0.88 mmol) in dichloromethane (3 ml) was stirred for 15 minutes before addition of methylamine (40% solution in water, 0.110, 1.47 mmol) and 1-(3-dimethylaminopropyl)-ethylcarbodiimide hydrochloride (0.17 g, 0.88 mmol). The reaction mixture was stirred for 16 hours, solvent removed under reduced pressure and the residue partitioned between ethyl acetate and 1N HCl. The organic layer was separated, washed with saturated sodium hydrogen carbonate, brine, dried (MgSO$_4$), filtered and concentrated to yield the title compound which was used in the next step without further purification. LC/MS: (PS-A2) $R_t$ 3.20 [M+H]$^+$ 353.95.

8E. [3-(4-Bromo-phenyl)-3-(4-chloro-phenyl)-propyl]-methyl-amine

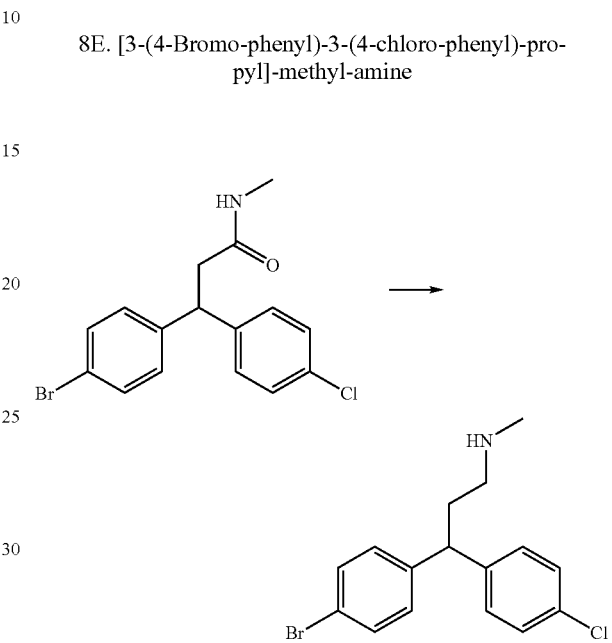

Under a nitrogen atmosphere, the crude 3-(4-bromo-phenyl)-3-(4-chloro-phenyl)-N-methyl-propionamide was cooled to 0° C., lithium aluminum hydride (0.075 g, 1.97 mmol) and diethyl ether (3 ml) were added. With cooling, aluminum chloride (0.23 g, 1.69 mmol) was dissolved in diethyl ether (2 ml) and added. The reaction mixture was stirred for 16 hours, quenched with addition of water, basified (2N NaOH) and extracted with ethyl acetate. The organic layer was separated, dried (MgSO$_4$), filtered and concentrated, the crude product was purified over Phenomenex_Strata_SCX column chromatography eluting with methanol followed by 2N ammonia in methanol to afford the desired product (0.254 g, 62% yield for steps 1D and 1E combined). LC/MS: (PS-B3) $R_t$ 3.20 [M+H]$^+$ 339.85.

8F. {3-(4-Chloro-phenyl)-3-[4-(1H-pyrazol-4-yl)-phenyl]-propyl}-methyl-amine

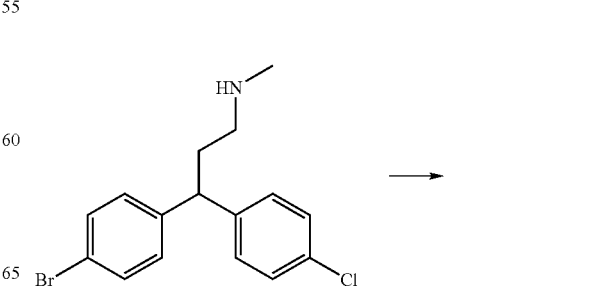

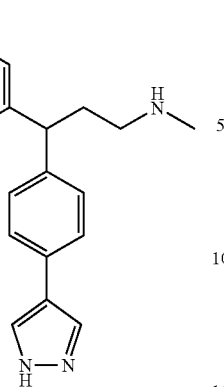

[3-(4-Bromo-phenyl)-3-(4-chloro-phenyl)-propyl]-methyl-amine was reacted with 4-(4,4,5,5-tetramethyl-1,3,2-dioxaborolan-2-yl)-1H-pyrazole following the procedure set out in Example 1 to give the title compound. LC/MS: (PS-B3) $R_t$ 2.63 [M+H]$^+$ 326.00. $^1$H NMR (Me-d$_3$-OD) δ 2.37-2.47 (2H, m), 2.66 (3H, s), 2.91 (2H, t), 4.05 (1H, t), 7.25-7.34 (6H, m), 7.54 (2H, d), 7.92 (2H, s), 8.51 (1H, br s—due to formic acid).

Example 9

{3-(3,4-Difluoro-phenyl)-3-[4-(1H-pyrazol-4-yl)-phenyl]-propyl}-methyl-amine

9A. 3-[4-Bromo-phenyl]-3-(3,4-difluoro-phenyl)-N-methyl-propionamide

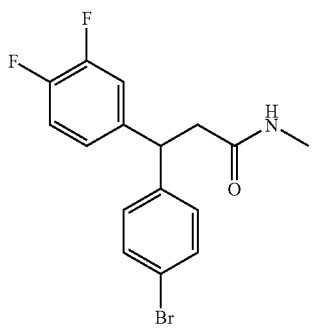 [SMILES: CNC(=O)CC(c1ccc(Br)cc1)c1ccc(F)c(F)c1]

By following the procedure described in Example 8A through to Example 8C but substituting 4-chlorophenylmagnesium bromide for 3,4-difluorophenylmagnesium bromide, the title compound was obtained. LC/MS: (PS-A2) $R_t$ 3.12 [M+H]$^+$ 355.84.

9B. 3-(3,4-Difluoro-phenyl)-N-methyl-3-[4-(1H-pyrazol-4-yl)-phenyl]-propionamide

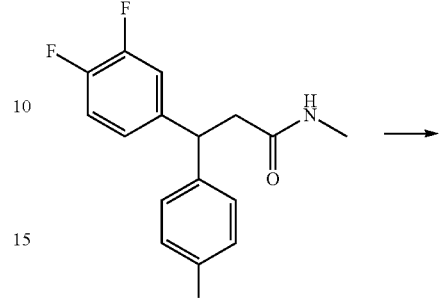

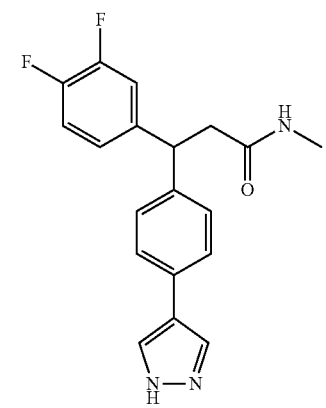

3-(4-Bromo-phenyl)-3-(3,4-difluoro-phenyl)-N-methyl-propionamide was reacted with 4-(4,4,5,5-tetramethyl-1,3,2-dioxaborolan-2-yl)-1H-pyrazole following the procedure set out in Example 1 to give the title compound. LC/MS: (PS-A2) $R_t$ 2.55 [M+H]$^+$ 341.93.

9C. {3-(3,4-Difluoro-phenyl)-3-[4-(1H-pyrazol-4-yl)-phenyl]-propyl}-methyl-amine

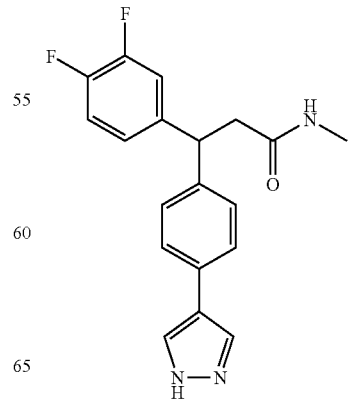

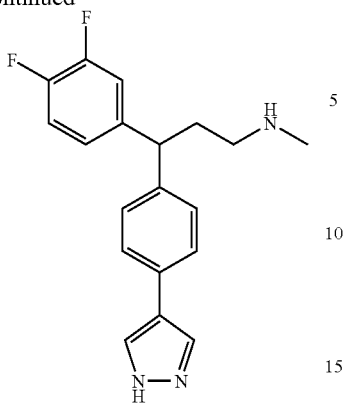

Lithium aluminium hydride was added to a suspension of 3-(3,4-Difluoro-phenyl)-N-methyl-3-[4-(1H-pyrazol-4-yl)-phenyl]-propionamide in diethyl ether, followed by a solution of aluminium chloride in diethyl ether at 0° C., under a nitrogen atmosphere. Toluene was added and the reaction mixture was heated at 70° C. for 18 hours. Upon cooling the reaction was quenched with addition of water, basified (2N NaOH) and extracted with ethyl acetate. The organic layer was separated, dried (MgSO$_4$), filtered and concentrated to afford the desired compound. LC/MS: (PS-A2) R$_t$ 2.15 [M+H]$^+$ 328.06. $^1$H NMR (Me-d$_3$-OD) δ 2.19-2.29 (2H, m), 2.35 (3H, s), 2.51 (2H, t), 4.00 (1H, t), 7.06-7.24 (3H, m), 7.27 (2H, d), 7.52 (2H, d), 7.92 (2H, s).

Example 10

{3-(3-Chloro-phenyl)-3-[4-(1H-pyrazol-4-yl)-phenyl]-propyl}-methyl-amine

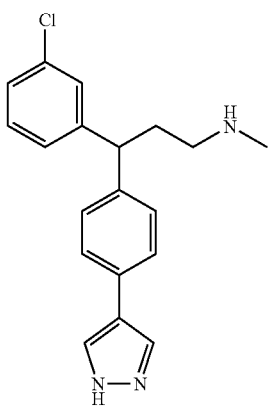 [SMILES: CNCCC(c1ccc(-c2cn[nH]c2)cc1)c1cccc(Cl)c1]

By following the procedure described in Example 8 but substituting 4-chlorophenylmagnesium bromide for 3-chlorophenylmagnesium bromide, the title compound was obtained. LC/MS: (PS-B3) R$_t$ 2.67 [M+H]$^+$ 326.00. $^1$H NMR (Me-d$_3$-OD) δ 2.43-2.50 (2H, m), 2.68 (3H, s), 2.94 (2H, m), 4.13 (1H, t), 7.24 (1H, m), 7.27-7.36 (3H, m), 7.41 (2H, d), 7.66 (2H, d), 8.50 (2H, s).

Example 11

3-(4-Chloro-phenyl)-3-[4-(1H-pyrazol-4-yl)-phenyl]-propionamide

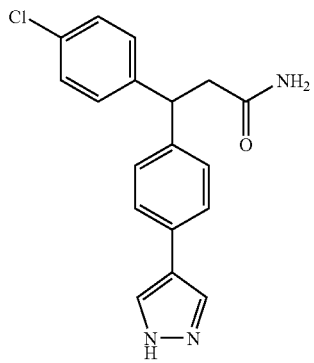 [SMILES: NC(=O)CC(c1ccc(Cl)cc1)c1ccc(-c2cn[nH]c2)cc1]

By following the procedure described in Example 9A and 9B but substituting 3,4-difluorophenylmagnesium bromide for 4-chlorophenylmagnesium bromide, the title compound was obtained. LC/MS: (PS-A2) R$_t$ 2.54 [M+H]$^+$ 326. $^1$H NMR (Me-d$_3$-OD) δ 2.95 (2H, d), 4.53 (1H, t), 7.27 (6H, m), 7.50 (2H, d), 7.91 (2H, s).

Example 12

3-(4-Chloro-phenyl)-3-[4-(1H-pyrazol-4-yl)-phenyl]-propylamine 12A. 3-(4-Bromo-phenyl)-3-(4-chloro-phenyl)-propionamide

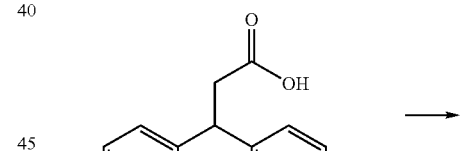

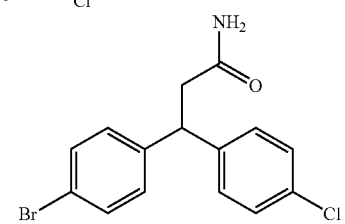

A solution of 3-(4-Bromo-phenyl)-3-(4-chloro-phenyl)-propionic acid* (0.25 g, 0.74 mmol) and 1,1'-carbonyldiimidazole (0.249, 1.47 mmol) in dichloromethane was stirred for 45 minutes before the addition of ammonia (2M solution in methanol, 3.68 ml, 7.36 mmol). The reaction mixture was stirred for 2 hours, solvent removed under reduced pressure and residue was purified over flash silica chromatography eluting with ethyl acetate/petroleum ether (1:4) to afford the title compound (0.091 g, 36% yield). LC/MS: (PS-A2) R$_t$ 3.08 [M+H]$^+$ 339.93.

*This starting material can be made by the method described in Example 8A through to 8C.

12B. 3-(4-Bromo-phenyl)-3-(4-chloro-phenyl)-propylamine

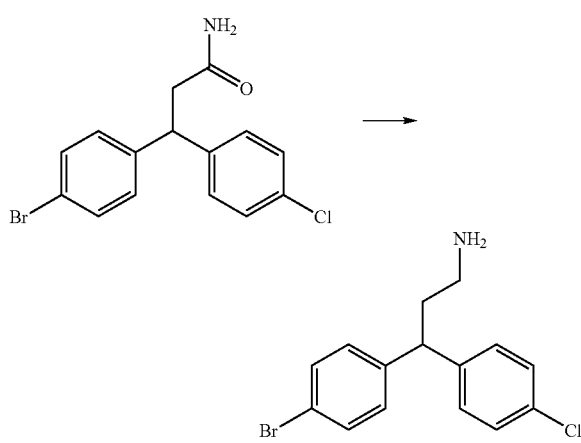

By following the procedure described in Example 8E but substituting 3-(4-Bromo-phenyl)-3-(4-chloro-phenyl)-propionamide for 3-(4-Bromo-phenyl)-3-(4-chloro-phenyl)-N-methyl-propionamide, the title compound was obtained. LC/MS: (PS-B2) $R_t$ 3.88 [M+H]$^+$ 359.87.

12C. 3-(4-Chloro-phenyl)-3-[4-(1H-pyrazol-4-yl)-phenyl]-propylamine

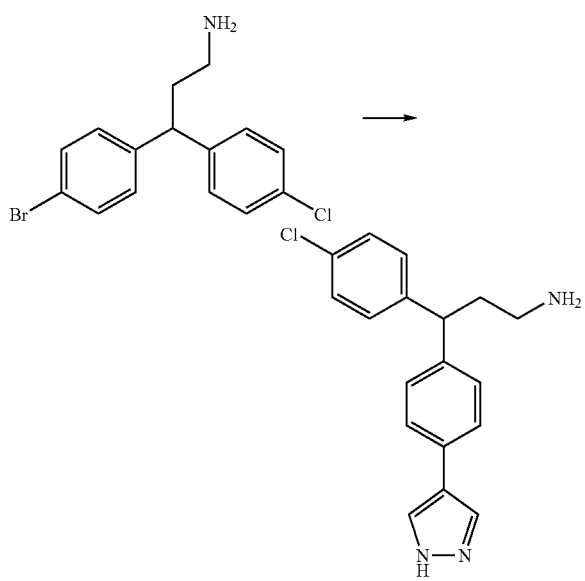

3-(4-Bromo-phenyl)-3-(4-chloro-phenyl)-propylamine was reacted with 4-(4,4,5,5-tetramethyl-1,3,2-dioxaborolan-2-yl)-1H-pyrazole following the procedure set out in Example 1 to give the title compound. LC/MS: (PS-B3) $R_t$ 2.54 [M+H]$^+$ 312.04. $^1$H NMR (Me-d$_3$-OD) δ 2.39 (2H, m), 2.84 (2H, t), 4.06 (1H, t), 7.27-7.33 (6H, m), 7.54 (2H, d), 7.91 (2H, s).

Example 13

3-(3,4-Dichloro-phenyl)-3-[4-(1H-pyrazol-4-yl)-phenyl]-propylamine

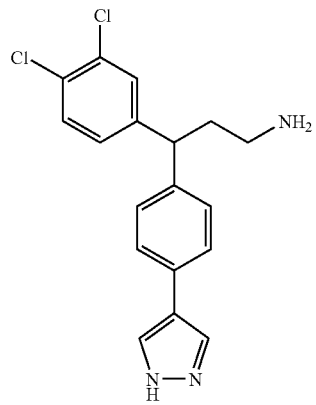 [SMILES: NCCC(c1ccc(-c2cn[nH]c2)cc1)c1ccc(Cl)c(Cl)c1]

By following the procedure described in Example 12 but substituting 4-chlorophenylmagnesium bromide for 3,4-dichlorophenylmagnesium bromide, the title compound was obtained. LC/MS: (PS-A2) $R_t$ 2.17 [M+H]$^+$ 345.95. $^1$H NMR (Me-d$_3$-OD) δ 2.39 (2H, m), 2.84 (2H, t), 4.07 (1H, t), 7.24-7.31 (4H, m), 7.45-7.49 (2H, m), 7.56 (2H, d), 7.93 (2H, s).

Example 14

4-(4-Chloro-phenyl)-4-[4-(1H-pyrazol-4-yl)-phenyl]-piperidine

14A. 4-(4-Bromo-phenyl)-4-(4-chloro-phenyl)-piperidine

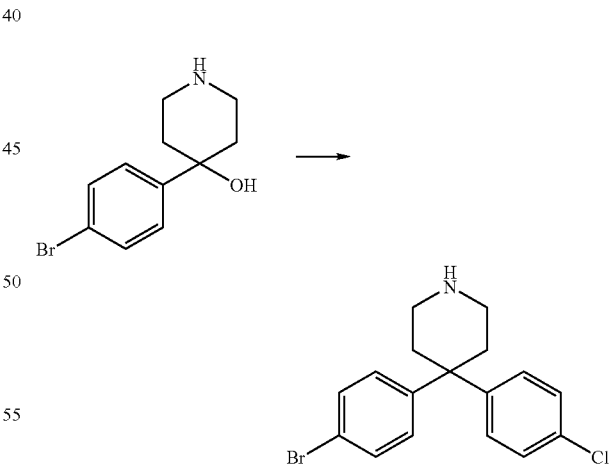

A suspension of 4-(4-Bromo-phenyl)-piperidin-4-ol (4.02 g, 15.7 mmol) in chlorobenzene (30 ml) was added dropwise to a suspension of aluminium chloride (7.32 g, 54.9 mmol) in chlorobenzene (10 ml) at 0° C. The reaction mixture was stirred at 0° C. for 2 hours, quenched by addition of ice then methyl t-butyl ether added. After stirring for 1 hour the precipitate was collected by filtration washed with water, methyl t-butyl ether and water to afford the title compound (5.59 g, 92% yield). LC/MS: (PS-B3) $R_t$ 3.57 [M+H]$^+$ 350, 352.

14B. 4-(4-Chloro-phenyl)-4-[4-(1H-pyrazol-4-yl)-phenyl]-piperidine

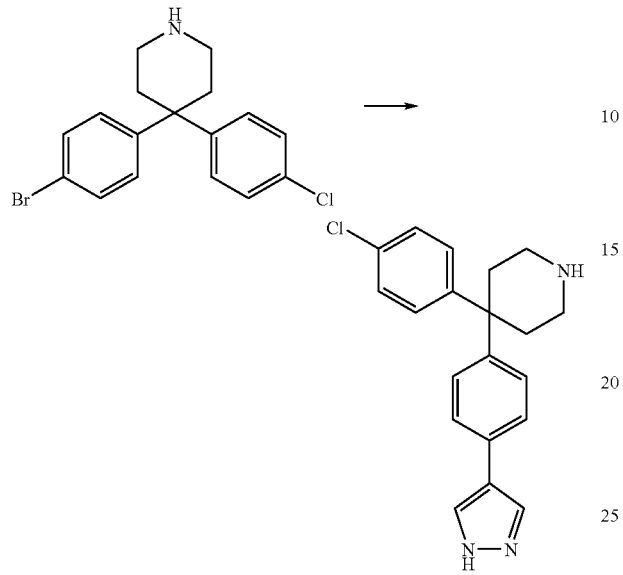

4-(4-Bromo-phenyl)-4-(4-chloro-phenyl)-piperidine was reacted with 4-(4,4,5,5-tetramethyl-1,3,2-dioxaborolan-2-yl)-1H-pyrazole following the procedure set out in Example 1 to give the title compound. LC/MS: (PS-A3) R$_t$ 7.22 [M+H]$^+$ 338.08. $^1$H NMR (Me-d$_3$-OD) δ 2.64-2.74 (4H, m), 3.22-3.25 (4H, m), 7.33-7.45 (6H, m), 7.65 (2H, d), 8.37 (2H, s).

Example 15

4-(4-Methoxy-phenyl)-4-[4-(1H-pyrazol-4-yl)-phenyl]-piperidine

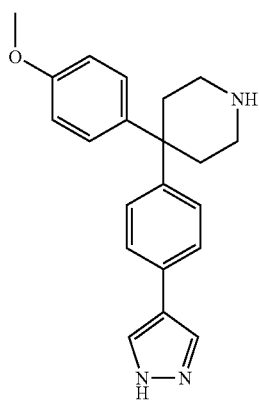 [SMILES: COc1ccc(C2(c3ccc(-c4cn[nH]c4)cc3)CCNCC2)cc1]

By following the procedure described in Example 14 but substituting chlorobenzene for anisole, the title compound was obtained. LC/MS: (PS-B3) R$_t$ 2.42 [M+H]$^+$ 334.00. $^1$H NMR (Me-d$_3$-OD) δ 2.69 (4H, m), 3.23 (4H, m), 3.76 (3H, s), 6.90 (2H, d), 7.28 (2H, d), 7.40 (2H, d), 7.65 (2H, d), 8.53 (2H, s).

Example 16

4-(4-Chloro-phenyl)-1-methyl-4-[4-(1H-pyrazol-4-yl)-phenyl]-piperidine

16A. 4-(4-Bromo-phenyl)-4-(4-chloro-phenyl)-piperidine-1-carboxylic acid ethyl ester

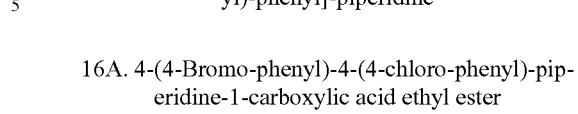

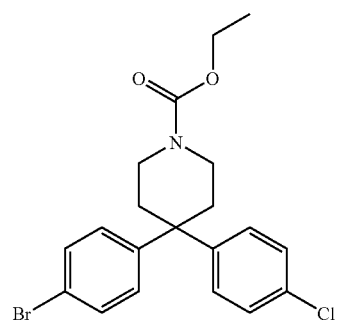

To a stirring suspension of 4-(4-Bromo-phenyl)-4-(4-chloro-phenyl)-piperidine* (0.28 g, 0.80 mmol) in dichloromethane (10 ml), were added triethylamine (0.45 ml, 3.2 mmol) and ethyl chloroformate (0.085 ml, 0.88 mmol). The reaction mixture was stirred for 3 hours, diluted with ethyl acetate and washed with 1N HCl, saturated sodium hydrogen carbonate and brine. The organic layer was separated, dried (MgSO$_4$), filtered and concentrated to afford the title compound (0.29 g, 94% yield). LCMS: (PS-A2), R$_t$ 4.02 [M+H]$^+$ 422, 424.

*This starting material can be made by the method described in Example 14A

16B. 4-(4-Bromo-phenyl)-4-(4-chloro-phenyl)-1-methyl-piperidine

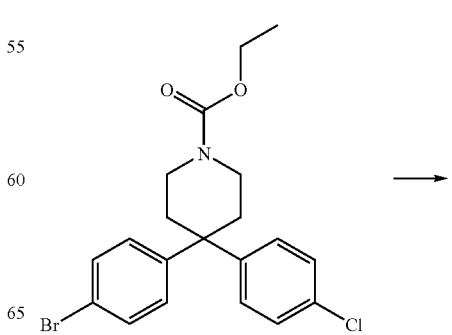

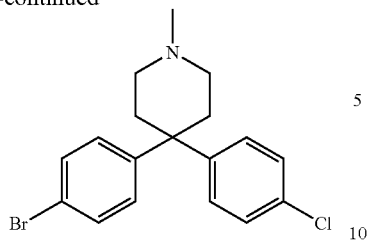

Under a nitrogen atmosphere 4-(4-Bromo-phenyl)-4-(4-chloro-phenyl)-piperidine-1-carboxylic acid ethyl ester (0.28 g, 0.66 mmol) and lithium aluminum hydride (0.051 g) were suspended in tetrahydrofuran (5 ml) and stirred for 2 hours. The reaction mixture was quenched with addition of water, solvent removed under reduced pressure, the residue was partitioned between ethyl acetate and 2N NaOH. The organic layer was washed with brine, dried (MgSO$_4$), filtered and concentrated to afford the desired product (0.241 g, 99% yield). LC/MS: (PS-B3) R$_t$ 3.78 [M+H]$^+$ 363.95, 365.73,

16C. 4-(4-Chloro-phenyl)-1-methyl-4-[4-(1H-pyrazol-4-yl)-phenyl]-piperidine

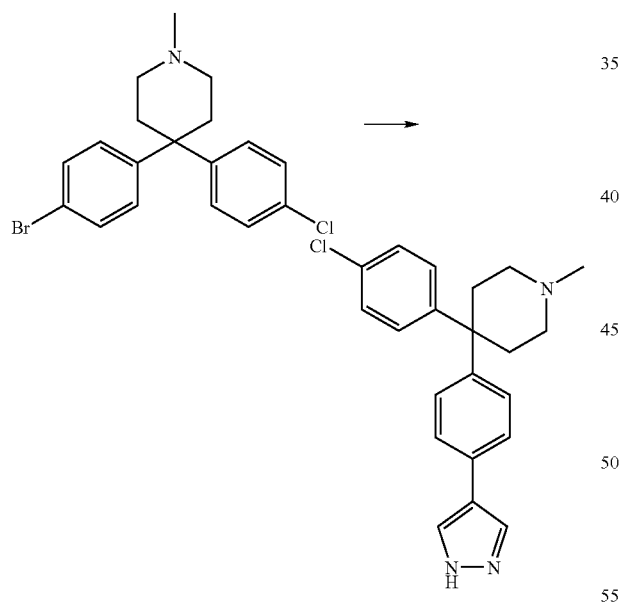

4-(4-Bromo-phenyl)-4-(4-chloro-phenyl)-1-methyl-piperidine was reacted with 4-(4,4,5,5-tetramethyl-1,3,2-dioxaborolan-2-yl)-1H-pyrazole following the procedure set out in Example 1 to give the title compound. LC/MS: (PS-B3) R$_t$ 2.90 [M+H]$^+$ 352. $^1$H NMR (Me-d$_3$-OD) δ 2.41-2.53 (2H, m), 2.82 (3H, d), 2.97-3.12 (4H, m), 3.56-3.59 (2H, m), 7.28 (2H, s), 7.34 (1H, m), 7.42 (1H, d), 7.49 (1H, d), 7.54 (1H, d), 7.61 (1H, d), 7.75 (1H, d), 8.52 (2H, d).

Example 17

4-Phenyl-4-[4-(1H-pyrazol-4-yl)-phenyl]-piperidine

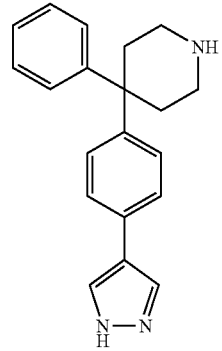 [SMILES: c1ccc(C2(c3ccc(-c4cn[nH]c4)cc3)CCNCC2)cc1]

By following the procedure described in Example 1 but substituting 2-(4-chlorophenyl)-2-phenylethylamine hydrochloride for 4-(4-Chloro-phenyl)-4-phenyl-piperidine, the title compound was obtained. LC/MS: (PS-A2) R$_t$ 1.88 [M+H]$^+$ 304. $^1$H NMR (Me-d$_3$-OD) δ 2.65-2.71 (4H, m), 3.21 (4H, t), 7.18-7.22 (1H, m), 7.32-7.38 (6H, m), 7.55 (2H, d), 7.93 (2H, s).

Example 18

4-[4-(3,5-Dimethyl-1H-pyrazol-4-yl)-phenyl]-4-phenyl-piperidine

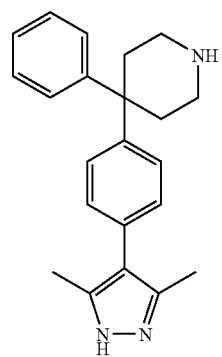 [SMILES: Cc1n[nH]c(C)c1-c1ccc(C2(c3ccccc3)CCNCC2)cc1]

By following the procedure described in Example 1 but substituting 2-(4-chlorophenyl)-2-phenylethylamine hydrochloride and 4-(4,4,5,5-tetramethyl-1,3,2-dioxaborolan-2-yl)-1H-pyrazole for 4-(4-chloro-phenyl)-4-phenyl-piperidine and 3,5-dimethyl-4-(4,4,5,6-tetramethyl-[1,3,2]dioxaborolan-2-yl)-1H-pyrazole, the title compound was obtained. LC/MS: (PS-A2) R$_t$ 2.95 [M+H]$^+$ 315. $^1$H NMR (Me-d$_3$-OD) δ 2.22 (6H, s), 2.66-2.76 (4H, m), 3.16-3.28 (4H, m), 7.19-7.44 (9H, m).

Example 19

Dimethyl-{3-[4-(1H-pyrazol-4-yl)-phenyl]-3-pyridin-2-yl-propyl}-amine

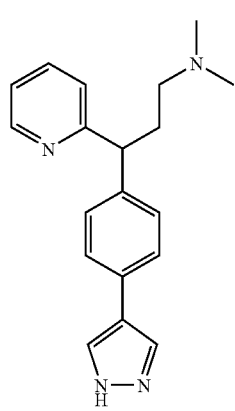 [SMILES: CN(C)CCC(c1ccc(-c2cn[nH]c2)cc1)c1ccccn1]

By following the procedure described in Example 1 but substituting 2-(4-chlorophenyl)-2-phenylethylamine hydrochloride for brompheniramine maleate, the title compound was obtained. LC/MS: (PS-B2) $R_t$ 2.29 [M+H]$^+$ 307. $^1$H NMR (Me-d$_3$-OD) δ 2.44-2.54 (1H, m), 2.59-2.70 (1H, m), 2.77 (6H, s), 2.93-3.01 (2H, m), 4.20 (1H, t), 7.25-7.28 (1H, m), 7.32-7.36 (3H, m), 7.54 (2H, d), 7.75 (1H, dt), 7.94 (2H, br s).

Example 20

{2-(4-Chloro-phenyl)-2-[4-(1H-pyrazol-4-yl)-phenyl]-ethyl}-dimethyl-amine

20A.
2,2-Bis-(4-chloro-phenyl)-N,N-dimethyl-acetamide

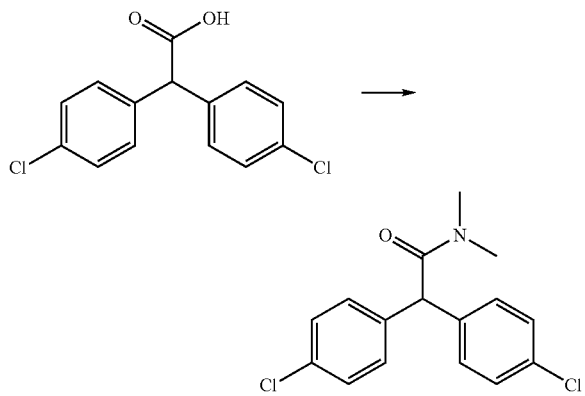

Bis-(4-chloro-phenyl)-acetic acid was reacted with dimethylamine following the procedure set out in Example 8D to give the title compound. LC/MS: (PS-A2) $R_t$ 3.40 [M+H]$^+$ 309.95.

20B.
[2,2-Bis-(4-chloro-phenyl)-ethyl]-dimethyl-amine

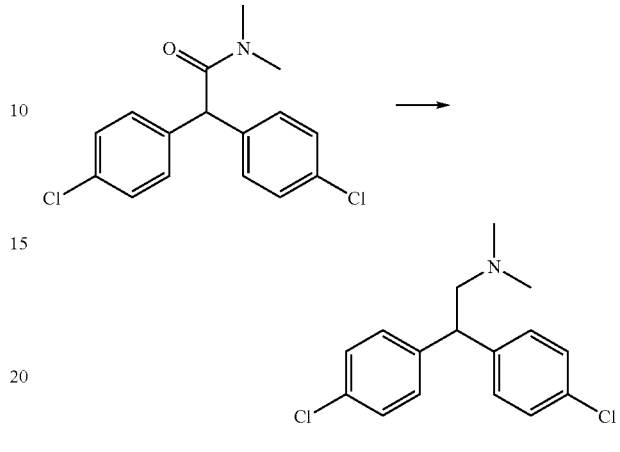

By following the procedure described in Example 8E but substituting 3-(4-Bromo-phenyl)-3-(4-chloro-phenyl)-N-methyl-propionamide for 2,2-Bis-(4-chloro-phenyl)-N,N-dimethyl-acetamide, the title compound was obtained. LC/MS: (PS-B2) $R_t$ 3.75 [M+H]$^+$ 295.99.

20C. {2-(4-Chloro-phenyl)-2-[4-(1H-pyrazol-4-yl)-phenyl]-ethyl}-dimethyl-amine

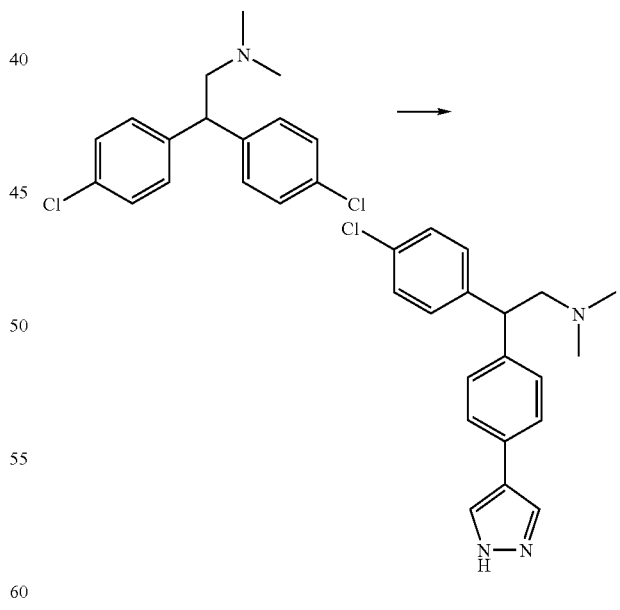

[2,2-Bis-(4-chloro-phenyl)-ethyl]-dimethyl-amine was reacted with 4-(4,4,5,5-tetramethyl-1,3,2-dioxaborolan-2-yl)-1H-pyrazole following the procedure set out in Example 1 to give the title compound. LC/MS: (PS-B2) $R_t$ 3.07 [M+H]$^+$ 325.99. $^1$H NMR (Me-d$_3$-OD) δ 2.5 (6H, s), 2.98 (2H, dd), 4.34 (1H, t), 7.31-7.36 (6H, m), 7.50 (2H, d), 7.92 (2H, s).

Example 21

{2-(4-Chloro-phenyl)-2-[4-(1H-pyrazol-4-yl)-phenyl]-ethyl}-methyl-amine

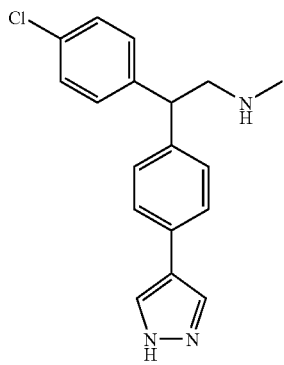 [SMILES: CNCC(c1ccc(Cl)cc1)c1ccc(-c2cn[nH]c2)cc1]

By following the procedure described in Example 20 but substituting dimethylamine for methylamine, the title compound was obtained. LC/MS: (PS-B2) $R_t$ 2.83 [M+H]$^+$ 312.07. $^1$H NMR (Me-d$_3$-OD) δ 2.42 (3H, s), 3.20-3.23 (2H, dd), 4.18 (1H, t), 7.27-7.33 (6H, m), 7.54 (2H, d), 7.92 (2H, br s).

Example 22

{2-(4-Chloro-phenyl)-2-[4-(1H-pyrazol-4-yl)-phenyl]-ethyl}-methyl-amine (R)

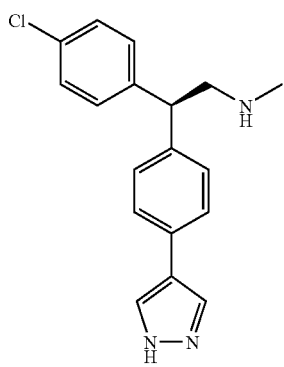 [SMILES: CNC[C@H](c1ccc(Cl)cc1)c1ccc(-c2cn[nH]c2)cc1]

Prepared using the same procedure as Example 21 but enantiomers separated by chiral preparative HPLC using method AG-CP2. LCMS: (AG-CA) $R_t$ 5.58 min, 97.4% ee. $^1$H NMR (Me-d$_3$-OD) δ 2.75 (3H, s), 3.78 (2H, d), 4.43 (1H, t), 7.39 (4H, s), 7.44 (2H, d), 7.69 (2H, d), 8.43 (2H, s).

Example 23

{2-(4-Chloro-phenyl)-2-[4-(1H-pyrazol-4-yl)-phenyl]-ethyl}-methyl-amine (S)

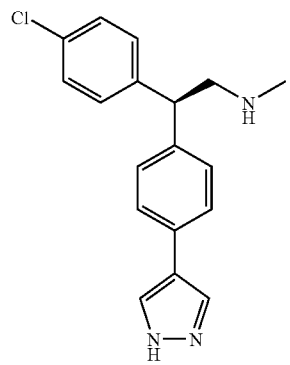 [SMILES: CNC[C@H](c1ccc(Cl)cc1)c1ccc(-c2cn[nH]c2)cc1]

Prepared using the same procedure as Example 21 but enantiomers separated by chiral preparative HPLC using method AG-CP2. LCMS: (AG-CA) $R_t$ 4.51 min, 98.0% ee. $^1$H NMR (Me-d$_3$-OD) δ 2.75 (3H, s), 3.79 (2H, d), 4.51 (1H, t), 7.37-7.43 (4H, m), 7.49 (2H, d), 7.73 (2H, d), 8.66 (2H, s).

Example 24

4-{2-(4-Chloro-phenyl)-2-[4-(1H-pyrazol-4-yl)-phenyl]-ethyl}-morpholine

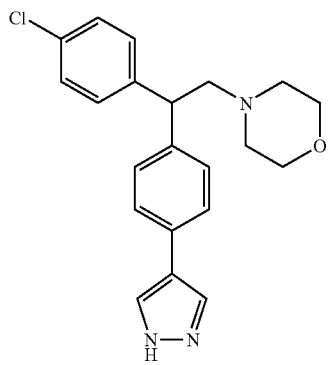 [SMILES: Clc1ccc(C(CN2CCOCC2)c2ccc(-c3cn[nH]c3)cc2)cc1]

By following the procedure described in Example 20 but substituting dimethylamine for morpholine, the title compound was obtained. LC/MS: (PS-B3) $R_t$ 3.07 [M+H]$^+$ 368.05. $^1$H NMR (Me-d$_3$-OD) δ 2.50 (4H, m), 2.97 (2H, m), 3.60 (4H, t), 4.26 (1H, t), 7.27 (6H, m). 7.49 (2H, d), 7.89 (2H, s).

Example 25

4-{4-[1-(4-Chloro-phenyl)-2-pyrrolidin-1-yl-ethyl]-phenyl}-1H-pyrazole

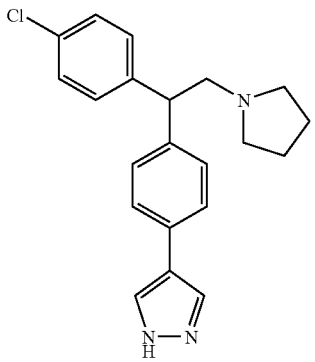 [SMILES: Clc1ccc(C(CN2CCCC2)c2ccc(-c3cn[nH]c3)cc2)cc1]

By following the procedure described in Example 20 but substituting dimethylamine for pyrrolidine, the title compound was obtained. LC/MS: (PS-A2) $R_t$ 2.06 [M+H]$^+$ 354.01. $^1$H NMR (Me-d$_3$-OD) δ 1.85 (4H, m), 2.87 (4H, m), 3.47 (2H, d), 4.31 (1H, t), 7.30-7.37 (6H, m), 7.54 (2H, d), 7.92 (2H, s).

Example 26

{2-(4-Chloro-phenyl)-2-[4-(1H-pyrazol-4-yl)-phenyl]-ethyl}-isopropyl-amine

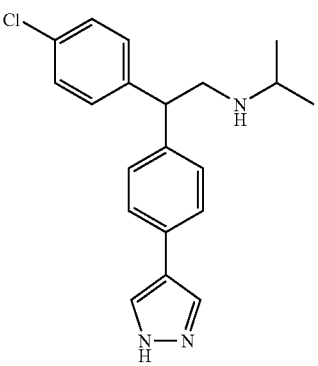 [SMILES: CC(C)NCC(c1ccc(Cl)cc1)c1ccc(-c2cn[nH]c2)cc1]

By following the procedure described in Example 20 but substituting dimethylamine for isopropylamine, the title compound was obtained. LC/MS: (PS-A2) $R_t$ 2.10 [M+H]$^+$ 340. $^1$H NMR (Me-d$_3$-OD) δ 1.31 (6H, d), 3.38-3.45 (1H, m), 3.65-3.74 (2H, m), 4.39 (1H, br t), 7.37 (6H, m), 7.59 (2H, d), 7.94 (2H, s).

Example 27

Dimethyl-{2-phenyl-2-[4-(1H-pyrazol-4-yl)-phenyl]-ethyl}-amine

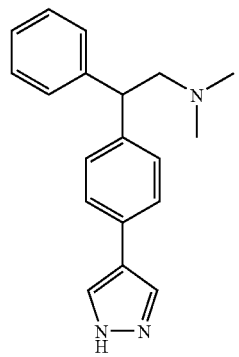 [SMILES: CN(C)CC(c1ccccc1)c1ccc(-c2cn[nH]c2)cc1]

By following the procedure described in Example 20, the title compound was obtained. LC/MS: (PS-B2) $R_t$ 2.82 [M+H]$^+$ 292.11. $^1$H NMR (Me-d$_3$-OD) δ 2.25 (6H, s), 2.95-3.04 (2H, m), 4.20 (1H, t), 7.16 (1H, t), 7.26-7.33 (6H, m), 7.49 (2H, d), 7.89 (2H, s).

Example 28

{2,2-Bis-[4-(1H-pyrazol-4-yl)-phenyl]-ethyl}-dimethyl-amine

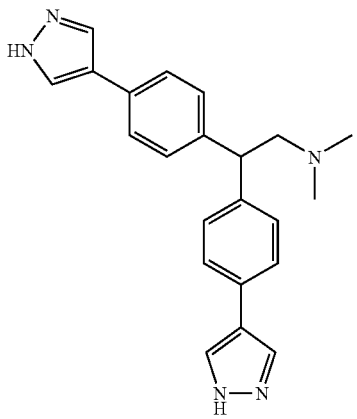 [SMILES: CN(C)CC(c1ccc(-c2cn[nH]c2)cc1)c1ccc(-c2cn[nH]c2)cc1]

By following the procedure described in Example 20, the title compound was obtained. LC/MS: (PS-B2) $R_t$ 2.45 [M+H]$^+$ 358.11. $^1$H NMR (Me-d$_3$-OD) δ 2.69 (6H, s), 3.59 (2H, d), 4.43 (1H, t), 7.39 (4H, d), 7.57 (4H, d), 7.93 (4H, s).

Example 29

{2,2-Bis-[4-(1H-pyrazol-4-yl)-phenyl]-ethyl}-methyl-amine

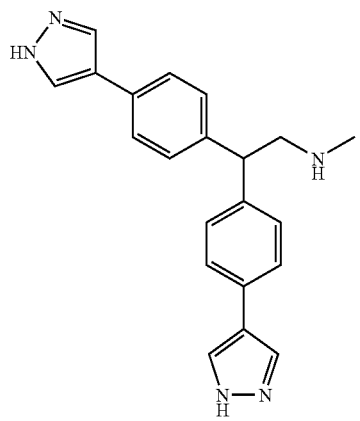 [SMILES: CNCC(c1ccc(-c2cn[nH]c2)cc1)c1ccc(-c2cn[nH]c2)cc1]

By following the procedure described in Example 21, the title compound was obtained. LC/MS: (PS-B2) $R_t$ 2.18 [M+H]$^+$ 344.11. $^1$H NMR (Me-d$_3$-OD) δ 2.65 (3H, s), 3.60 (2H, d), 4.34 (1H, t), 7.36 (4H, d), 7.59 (4H, d), 7.94 (4H, s).

Example 30

2-(4-Chloro-phenyl)-2-[4-(1H-pyrazol-4-yl)-phenyl]-ethylamine (R)

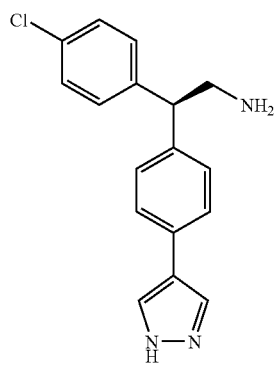 [SMILES: NC[C@H](c1ccc(Cl)cc1)c1ccc(-c2cn[nH]c2)cc1]

Prepared using the same procedure as Example 4 but enantiomers separated by chiral preparative HPLC using method AG-CP1. LCMS: (FL-C) $R_t$ 10.97 min, 95.7% ee. $^1$H NMR (Me-d$_3$-OD) δ 3.65 (2H, m), 4.30 (1H, t), 7.35-7.40 (6H, m), 7.64 (2H, d), 8.16 (2H, s).

Example 31

2-(4-Chloro-phenyl)-2-[4-(1H-pyrazol-4-yl)-phenyl]-ethylamine (S)

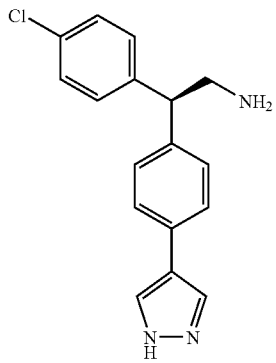 [SMILES: NC[C@H](c1ccc(Cl)cc1)c1ccc(-c2cn[nH]c2)cc1]

Prepared using the same procedure as Example 4 but enantiomers separated by chiral preparative HPLC using method AG-CP1. LCMS: (FL-C) $R_t$ 9.63 min, 100% ee. $^1$H NMR (Me-d$_3$-OD) δ 3.66 (2H, m), 4.30 (1H, t), 7.35-7.40 (6H, m), 7.64 (2H, d), 8.15 (2H, s).

Example 32

2-(4-Chloro-phenyl)-2-[4-(1H-pyrazol-4-yl)-phenyl]-acetamide

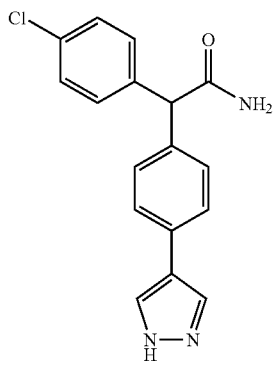 [SMILES: NC(=O)C(c1ccc(Cl)cc1)c1ccc(-c2cn[nH]c2)cc1]

By following the procedure described in Example 12A followed by 12C but substituting 3-(4-Bromo-phenyl)-3-(4-chloro-phenyl)-propionic acid for Bis-(4-chloro-phenyl)-acetic acid, the title compound was obtained. LC/MS: (PS-A2) $R_t$ 2.53 [M+H]$^+$ 312. $^1$H NMR (Me-d$_3$-OD) δ 4.99 (1H, s), 7.30-7.33 (6H, m), 7.55 (2H, d), 7.86-8.02 (2H, br s).

Example 33

1-{2-(4-Chloro-phenyl)-2-[4-(1H-pyrazol-4-yl)-phenyl]-ethyl}-piperazine

37A. Bis-(4-chloro-phenyl)-acetaldehyde

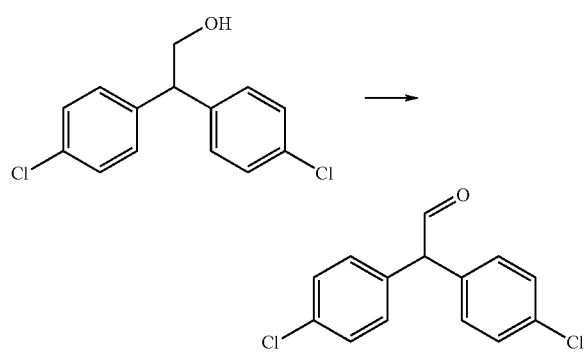

Dess-Martin periodinane (3.17 g, 7.49 mmol) was added to a solution of 2,2-Bis-(4-chloro-phenyl)-ethanol in dichloromethane (40 ml). The reaction mixture was stirred at room temperature for 17 hours under nitrogen, 2N NaOH added (15 ml) and the organic layer was separated, dried (MgSO4), filtered and concentrated to afford the title compounds which was used in the next step without further purification. LC/MS: (PS-B3) $R_t$ 3.62 [M+H]$^+$ 262.91.

33B. 4-[2,2-Bis-(4-chloro-phenyl)-ethyl]-piperazine-1-carboxylic acid tert-butyl ester

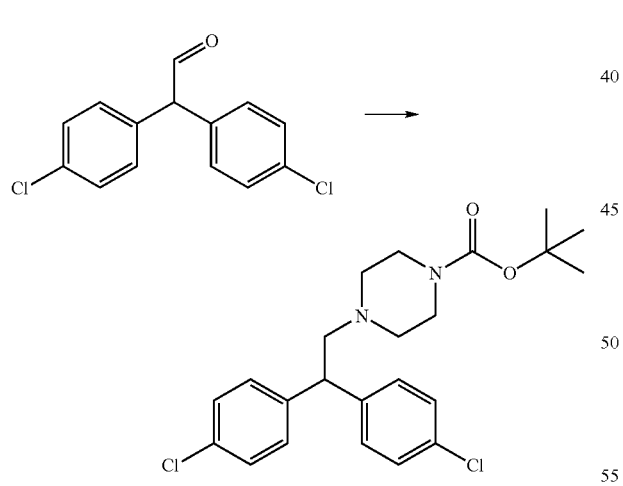

To a solution of bis-(4-chloro-phenyl)-acetaldehyde (3.74 mmol) in methanol under a nitrogen atmosphere, N—BOC-piperazine (1.05 g, 5.61 mmol) was added, the reaction mixture was stirred for 1 hour before addition of sodium cyanoborohydride (0.28 g, 4.49 mmol). The reaction mixture was stirred for 18 hours, water added (3 ml) and the solvent removed under reduced pressure. The residue was partitioned between dichloromethane and water, the organic layer was separated, dried (MgSO4), filtered and concentrated. Purified over flash silica chromatography eluting with ethyl acetate/petroleum ether (3:7) to yield the title compound (0.18 g, 11% yield for steps 30A and 30B combined). LC/MS: (PS-A2) $R_t$ 2.66 [M-BOC+H]$^+$ 335.02.

33C. 1-[2,2-Bis-(4-chloro-phenyl)-ethyl]-piperazine

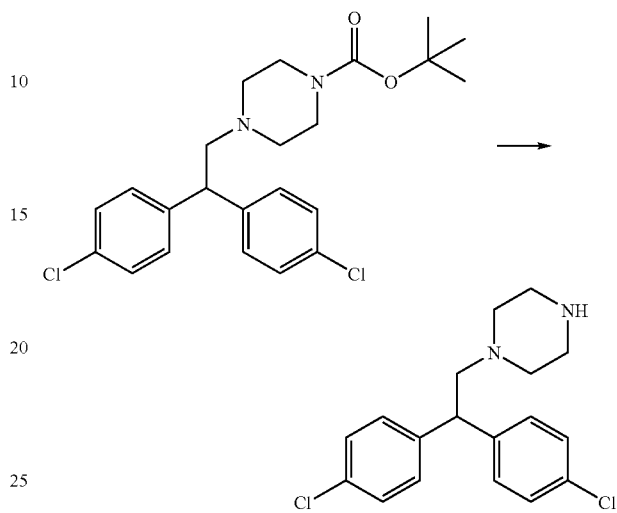

4-[2,2-Bis-(4-chloro-phenyl)-ethyl]-piperazine-1-carboxylic acid tert-butyl ester was treated with HCl in ethyl acetate (saturated, 5 ml) for 1 hour, solvent removed under reduced pressure to afford the title compound as the HCl salt

33D. 1-{2-(4-Chloro-phenyl)-2-[4-(1H-pyrazol-4-yl)-phenyl]-ethyl}-piperazine 1-[2,2-Bis-(4-chloro-phenyl)-ethyl]-piperazine was reacted with 4-(4,4,5,5-tetramethyl-1,3,2-dioxaborolan-2-yl)-1H-pyrazole following the procedure set out in Example 1 to give the title compound. LC/MS: (PS-B3) $R_t$ 2.63 [M+H]$^+$ 326.00. $^1$H NMR (Me-d$_3$-OD) δ 3.55-3.68 (8H, m), 3.74 (1H, t), 4.10-4.17 (2H, m), 7.39 (2H, d), 7.48 (2H, d), 7.54 (2H, d), 7.70 (2H, d), 8.57 (2H, br s).

Example 34

1-{2-(4-Chloro-phenyl)-2-[4-(1H-pyrazol-4-yl)-phenyl]-ethyl}-piperidine

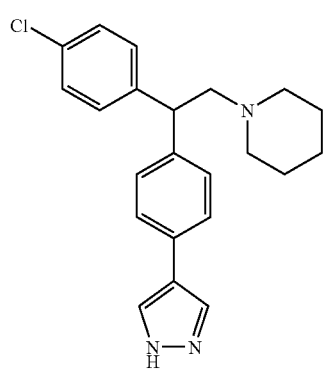 [SMILES: Clc1ccc(C(CN2CCCCC2)c2ccc(-c3cn[nH]c3)cc2)cc1]

By following the procedure described in Example 33A, 33B and 33D but substituting piperidine for N—BOC-piperazine, the title compound was obtained. LC/MS: (PS-A2) $R_t$ 2.21 [M+H]$^+$ 366.09. $^1$H NMR (Me-d$_3$-OD) δ 1.44 (2H, m), 1.53 (4H, m), 2.39-2.57 (4H, m), 2.94-3.09 (2H, m), 4.26 (1H, t), 7.22-7.35 (6H, m), 7.50 (2H, d), 7.91 (2H, s).

Example 35

4-{4-[2-Azetidin-1-yl-1-(4-chloro-phenyl)-ethyl]-phenyl}-1H-pyrazole

35A. 2-(4-Chloro-phenyl)-2-[4-(1H-pyrazol-4-yl)-phenyl]-ethanol

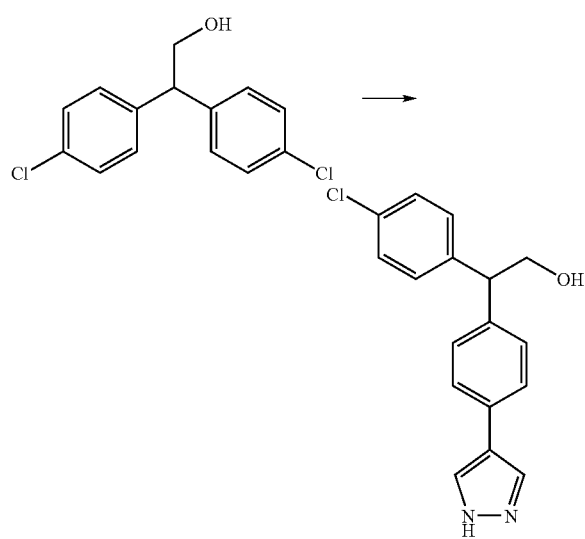

2,2-Bis-(4-chloro-phenyl)ethanol was reacted with 4-(4,4,5,5-tetramethyl-1,3,2-dioxaborolan-2-yl)-1H-pyrazole following the procedure set out in Example 1 to give the title compound. LC/MS: (PS-A2) $R_t$ 2.72 [M+H]$^+$ 299.00.

35B. (4-Chloro-phenyl)-[4-(1H-pyrazol-4-yl)-phenyl]-acetaldehyde

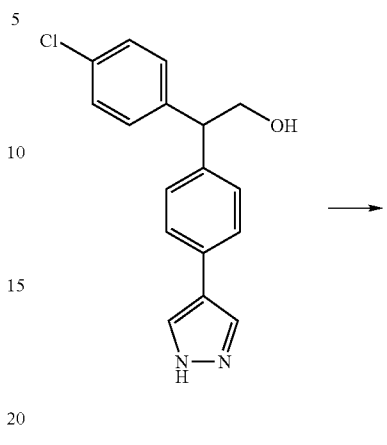

By following the procedure described in Example 33A but substituting 2,2-Bis-(4-chloro-phenyl)-ethanol for 2-(4-Chloro-phenyl)-2-[4-(1H-pyrazol-4-yl)-phenyl]ethanol, the title compound was obtained. LC/MS: (PS-B3) $R_t$ 2.97 [M+H]$^+$ 294.98.

35C. 4-{4-[2-Azetidin-1-yl-1-(4-chloro-phenyl)-ethyl]-phenyl}-1H-pyrazole

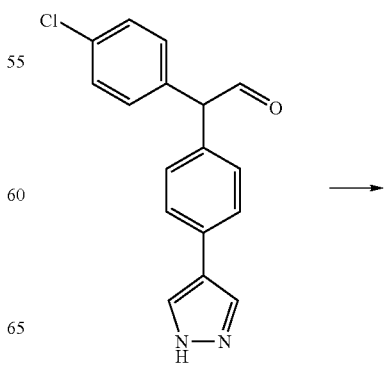

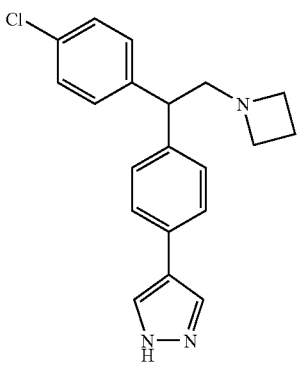

By following the procedure described in Example 33B but replacing bis-(4-chloro-phenyl)-acetaldehyde and N—BOC-piperazine with (4-Chloro-phenyl)-[4-(1H-pyrazol-4-yl)-phenyl]-acetaldehyde and azetidine, the title compound was obtained. LC/MS: (PS-B3) $R_t$ 2.99 [M+H]$^+$ 338.09. $^1$H NMR (Me-d$_3$-OD) δ 3.57-3.60 (1H, m), 3.63-3.70 (2H, m), 3.71-3.77 (1H, m), 4.01 (2H, m), 4.14 (2H, m), 4.40 (1H, t), 7.40 (4H, br s), 7.49 (2H, d), 7.73 (2H, d), 8.69 (2H, br s).

Example 36

1-Phenyl-2-[4-(1H-pyrazol-4-yl)-phenyl]-ethylamine

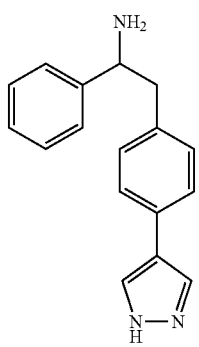 [SMILES: NC(Cc1ccc(-c2cn[nH]c2)cc1)c1ccccc1]

By following the procedure described in Example 5 but replacing 3-bromobenzylmagnesium bromide and 3,5-dimethyl-4-(4,4,5,5-tetramethyl-[1,3,2]dioxaborolan-2-yl)-1H-pyrazole with 4-bromobenzylmagnesium bromide and 4-(4,4,5,5-tetramethyl-1,3,2-dioxaborolan-2-yl)-1H-pyrazole, the title compound was obtained. LC/MS: (PS-B2) $R_t$ 2.44 [M+H]$^+$ 264.04. $^1$H NMR (Me-d$_3$-OD) δ 2.99 (2H, d), 4.13 (1H, t), 7.10 (2H, d), 7.20-7.38 (5H, m), 7.45 (2H, d), 7.91 (2H, s).

Example 37

[4-(5-Methyl-3-trifluoromethyl-1H-pyrazol-4-yl)-phenyl]-acetonitrile 37A. 4-Bromo-5-methyl-1-(tetrahydro-pyran-2-yl)-3-trifluoromethyl-1H-pyrazole

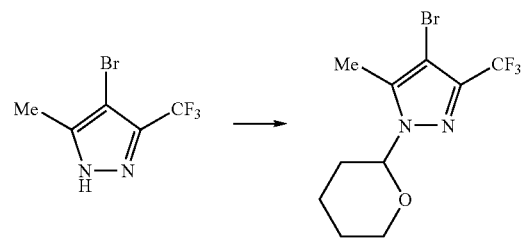 [SMILES: Cc1[nH]nc(C(F)(F)F)c1Br ; Cc1c(Br)c(C(F)(F)F)nn1C1CCCCO1]

To a solution of 4-bromo-5-methyl-3-trifluoromethyl-1H-pyrazole (1.4 g, 6.2 mmol, 1.0 equiv) in chloroform (31 ml) was added p-toluene sulphonic acid monohydrate (118 mg, 0.62 mmol, 0.1 equiv). The solution was cooled to 0° C. and 3,4-dihydro-2H-pyran (0.85 ml, 9.3 mmol, 1.5 equiv) was added drop-wise over 5 minutes. The mixture was allowed to warm to room temperature for 1 hour and the solvents were removed under reduced pressure. The crude mixture was purified by column chromatography (SiO$_2$), eluting with 0→25% EtOAc-petrol over a linear gradient to afford the title compound 1.4 g (59%), LCMS (PS-A) $R_t$ 3.72 min [M+H]$^+$ 314.

37B. {4-[5-Methyl-1-(tetrahydro-pyran-2-yl)-3-trifluoromethyl-1H-pyrazol-4-yl]-phenyl}-acetonitrile

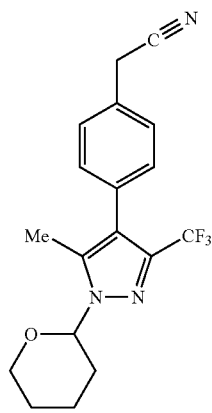 [SMILES: Cc1c(-c2ccc(CC#N)cc2)c(C(F)(F)F)nn1C1CCCCO1]

The product of Example 37A, 4-bromo-5-methyl-1-(tetrahydro-pyran-2-yl)-3-trifluoromethyl-1H-pyrazole, was reacted with 4-(cyanomethylphenyl)boronic acid (Combi-Blocks, San Diego, USA Cat. No. 2444-001) under the conditions described in Example 1, to give the title compound.

37C. [4-(5-Methyl-3-trifluoromethyl-1H-pyrazol-4-yl)-phenyl]-acetonitrile

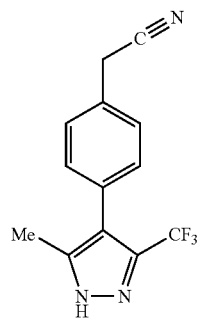 [SMILES: Cc1[nH]nc(C(F)(F)F)c1-c1ccc(CC#N)cc1]

To {4-[5-Methyl-1-(tetrahydro-pyran-2-yl)-3-trifluoromethyl-1H-pyrazol-4-yl]-phenyl}-acetonitrile (Example 8B) (35 mg, 0.1 mmol, 1.0 equiv) in ethyl acetate (1 ml) was added HCl in ethyl acetate (1 ml) and the mixture was stirred for 1 hour. The solvents were removed under reduced pressure and the title compound was purified by column chromatography ($SiO_2$) eluting with a linear gradient (0→30% ethyl acetate-petrol) 16 mg (60%); LCMS (PS-A) $R_t$ 2.85 min $[M+H]^+$ 266.

37D. Preparation of Compounds of the Formula (I) from [4-(5-Methyl-3-trifluoromethyl-1H-pyrazol-4-yl)-phenyl]-acetonitrile (i) The product of Example 37B can be reacted with benzaldehyde under the conditions described in Example 2 to give 2-[4-(5-methyl-1-(tetrahydro-pyran-2-yl)-3-trifluoromethyl-1H-pyrazol-4-yl)-phenyl]-3-phenyl-propionitrile which can be deprotected by removal of the 1-tetrahydropyranyl group under the conditions set out in Example 37C to give 2-[4-(5-methyl-3-trifluoromethyl-1H-pyrazol-4-yl)-phenyl]-3-phenyl-propionitrile.

2-[4-(5-Methyl-3-trifluoromethyl-1H-pyrazol-4-yl)-phenyl]-3-phenyl-propionitrile or its 1-tetrahydropyranyl derivative can be reduced according to the method of Example 6 (and thereafter where necessary deprotected according to the method of Example 41C) to give 2-[4-(5-methyl-3-trifluoromethyl-1H-pyrazol-4-yl)-phenyl]-3-phenyl-propylamine.

The product of Example 37B can also be reacted with benzyl magnesium bromide or phenyl magnesium bromide under the Grignard reaction conditions described in Example 5 to give (following deprotection by the method of Example 37C) 1-benzyl-2-[4-(5-methyl-3-trifluoromethyl-1H-pyrazol-4-yl)-phenyl]-ethylamine and 2-[4-(5-methyl-3-trifluoromethyl-1H-pyrazol-4-yl)-phenyl]-1-phenyl-ethylamine respectively.

Example 38

Construction of Pyrazole Ring System

38A. Synthesis of 4-(4-Bromo-phenyl)-3-methyl-1H-pyrazole

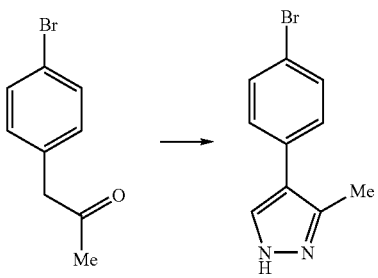 [SMILES: CC(=O)Cc1ccc(Br)cc1 ; Cc1n[nH]cc1-c1ccc(Br)cc1]

To 4-bromophenylacetone (5.0 g, 23.5 mmol, 1.0 equiv) (Acros Organics 34216) was added N,N-dimethylformamide dimethyl acetal (11.3 ml, 84.6 mmol, 3.6 equiv) and the mixture was heated to 90° C. for 6 hours. The solvents were removed and the resulting gum was dissolved in ethanol (235 ml) with additional heating. Hydrazine hydrate (1.37 ml, 28.2 mmol, 1.2 equiv) was added and the mixture was heated to reflux for 15 hours. The solvents were removed under reduced pressure and the solid was triturated with dichloromethane to afford the title compound, 2.24 g (40%); LCMS (PS-A) $R_t$ 2.87 min $[M+H]^+$ 238. Further material could be isolated from the mother liquor.

38B. Conversion of 4-(4-Bromo-phenyl)-3-methyl-1H-pyrazole to compounds of the Formula (I)

(i) 4-(4-Bromo-phenyl)-3-methyl-1H-pyrazole can be protected at the 1-position of the pyrazole ring by formation of the tetrahydropyranyl (THP) derivative by following the procedure set out in Example 38A. A Grignard reagent can then be prepared from the bromo-phenyl moiety by treating the protected derivative with magnesium in an ether solvent in standard fashion (see J. March, *Advanced Organic Chemistry*, 4$^{th}$ Edition, 1992, John Wiley, New York, pages 622-625). The Grignard reagent can be reacted with nitrostyrene (the nitrostyrene having been prepared by a standard method such as the method described in *Organic Syntheses*, Collective Volume 1, page 413) and the resulting nitroethyl compound reduced to give 2-{4-[3-methyl-1-(tetrahydro-pyran-2-yl)-1H-pyrazol-4-yl]-phenyl}-2-phenyl-ethylamine. Removal of the tetrahydropyranyl group using the method of Example 8C gives 2-{4-[3-methyl-1H-pyrazol-4-yl]-phenyl}-2-phenyl-ethylamine.

(ii) The bromo-compound of Example 38A can be converted into compounds of the formula (I) in which the group A contains a nitrogen atom which is attached to the group E. The introduction of a nitrogen containing entity can be accomplished by reaction of the compound of Example 38A with [3-(4-chloro-phenylamino)-propyl]-methyl-carbamic acid tert-butyl ester under palladium catalysed amination conditions of the type described in *Organic Letters*, 2002, vol. 4, No. 17, pp 2885-2888, followed by removal of the t-butyloxycarbonyl protecting group by standard methods.

Example 39

[3-(1H-Pyrazol-4-yl)-phenyl]-acetonitrile

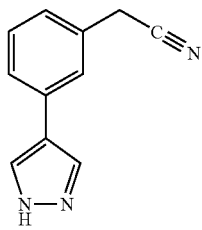 [SMILES: N#CCc1cccc(-c2cn[nH]c2)c1]

By following the procedure set out in Example 1 but using 3-bromophenyl-acetonitrile instead of 2-(4-chlorophenyl)-2-phenylethylamine, the title compound was obtained. LCMS (PS-A) 2.35 min [M+H]$^+$ 184.

3-(1H-Pyrazol-4-yl)-phenyl]-acetonitrile can be used as an intermediate in the preparation of compounds of the formula (I), for example by means of an aldehyde condensation reaction as described in Example 2 or a Grignard reaction as described in Example 5.

Example 40

2-(4-Chloro-phenyl)-N-methyl-2-[4-(1H-pyrazol-4-yl)-phenyl]-acetamide

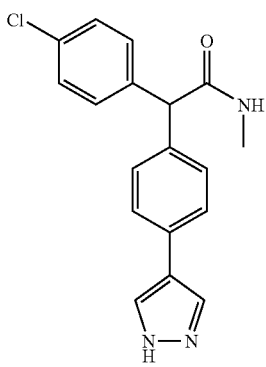 [SMILES: CNC(=O)C(c1ccc(Cl)cc1)c1ccc(-c2cn[nH]c2)cc1]

By following the procedure described in Example 12A followed by 12C but substituting 3-(4-Bromo-phenyl)-3-(4-chloro-phenyl)-propionic acid for Bis-(4-chloro-phenyl)-acetic acid and ammonia for methyl amine, the title compound was obtained. LC/MS (PS-A2): R$_t$ 2.64 [M+H]$^+$ 326. $^1$H NMR (Me-d$_3$-OD) δ 2.79 (3H, s), 4.94, (1H, br s), 7.26-7.35 (6H, m), 7.55-7.57 (2H, m), 7.96 (2H, br s)

Example 41

N-Methyl-2,2-bis-[4-(1H-pyrazol-4-yl)-phenyl]-acetamide

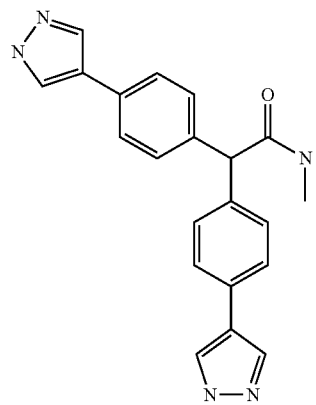 [SMILES: CNC(=O)C(c1ccc(-c2cn[nH]c2)cc1)c1ccc(-c2cn[nH]c2)cc1]

By following the procedure described in Example 40, the title compound was obtained. LC/MS (PS-A2): R$_t$ 2.19 [M+H]$^+$ 358. $^1$H NMR (Me-d$_3$-OD) δ 2.80 (3H, s), 4.95, (1H, br s), 7.32 (4H, d), 7.56 (4H, d), 7.98 (4H, br s)

Example 42

{2-(4-Chloro-phenyl)-2-[4-(1H-pyrazol-4-yl)-phenyl]-ethyl}-methyl-amine

42A. 1-(4-Bromo-phenyl)-2-methylamino-ethanol

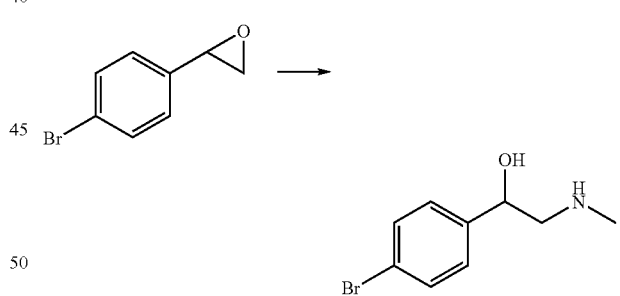

A solution of 2-(4-bromophenyl)-oxirane (0.5 g, 2.51 mmol) in methylamine (6.6 ml, 33% by volume in ethanol, 25.12 mmol) was stirred at room temperature under an atmosphere of nitrogen. After 18 hours the solvent was removed in vacuo and the residue was purified over flash silica eluting with dichloromethane:methanol:acetic acid:water (120:15:3:2) to afford the desired compound as the acetic acid salt. Further purification over a Phenomenex_Strata_SCX column eluting with methanol followed by 2N ammonia in methanol gave the desired product. LC/MS: (PS-B3) R$_t$ 2.52 [M+H]$^+$ 230.

42B. [2-(4-Bromo-phenyl)-2-(4-chloro-phenyl)-ethyl]-methyl-amine

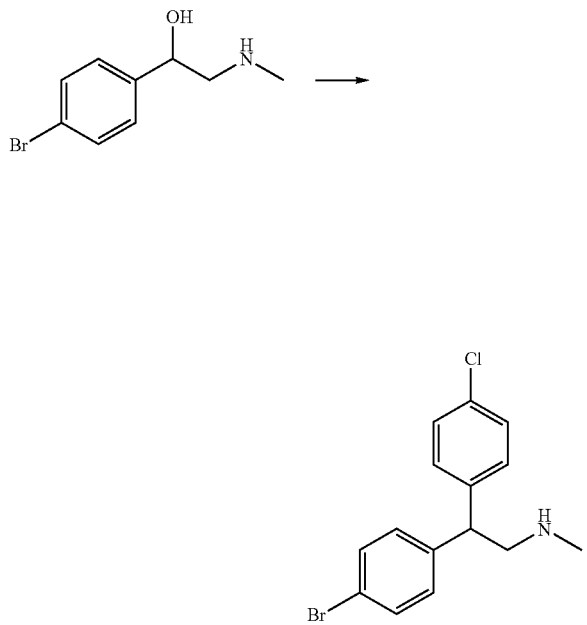

Aluminium chloride (278 mg, 2.087 mmol) was added portionwise to a stirred solution of 1-(4-Bromo-phenyl)-2-methylamino-ethanol (160 mg, 0.696 mmol) in chlorobenzene (3 ml) and the reaction mixture stirred at room temperature for 17 hours. Water (2 ml) was added dropwise and the reaction mixture was then partitioned between dichloromethane (100 ml) and saturated NaHCO$_3$ (30 ml). The organic layer was dried (MgSO$_4$), filtered and concentrated under reduced pressure. The crude product was then purified by Phenomenex_Strata_SCX column chromatography eluting with methanol followed by 2N ammonia in methanol to afford the desired product. LC/MS: (PS-B3) R$_t$ 3.58 [M+H]$^+$ 324.

42C. {2-(4-Chloro-phenyl)-2-[4-(1H-pyrazol-4-yl)-phenyl]-ethyl}-methyl-amine

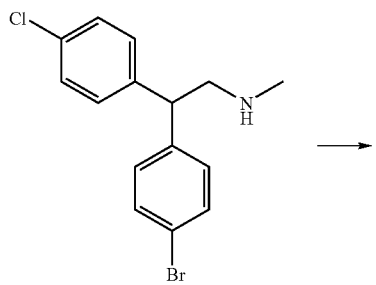

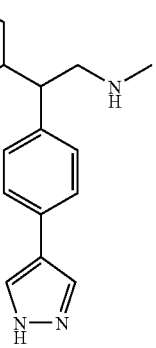

A solution of [2-(4-Bromo-phenyl)-2-(4-chloro-phenyl)ethyl]-methyl-amine (6.1 g, 13.716 mmol), 4-(4,4,5,5-tetramethyl-1,3,2-dioxaborolan-2-yl)-1H-pyrazole (5.3 g, 27.431 mmol) and K$_3$PO$_4$ (10.19 g, 48.00 mmol) in ethanol (7.5 ml), methanol (11.5 ml), toluene (7.5 ml) and water (11.5 ml) was purged with nitrogen for 2 minutes. Bis(tri-t-butylphosphine)palladium (0) (175 mg, 2.5 mol %) was then added and the reaction mixture purged with nitrogen for a further 2 minutes. The mixture was then heated to 80° C., under nitrogen for a period of 17 hours. The solvents were removed and the residue was partitioned between ethyl acetate and 2N NaOH. The aqueous layer was extracted with ethyl acetate and the combined organic layers were washed with brine, dried (MgSO$_4$) and concentrated under reduced pressure. The crude reaction mixture was purified by column chromatography (SiO$_2$), eluting with dichloromethane:methanol:acetic acid:water (90:18:3:2) to afford the title compound (3.6 g); LCMS (PS-A2) R$_t$ 2.08 min [M+H]$^+$ 312.

Example 43

{2-(4-Chloro-phenyl)-2-[4-(1H-pyrazol-4-yl)-phenyl]-ethyl}-ethyl-amine

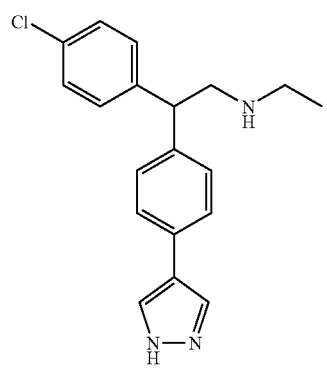 [SMILES: CCNCC(c1ccc(Cl)cc1)c1ccc(-c2cn[nH]c2)cc1]

By following the procedures described in Examples 42A through to 42C but substituting methylamine for ethylamine, the title compound was obtained. LC/MS: (PS-A2) R$_t$ 2.11 [M+H]$^+$ 326. $^1$H NMR (Me-d$_3$-OD) δ 1.15 (3H, t), 2.83 (2H, q), 3.35-3.43 (2H, m), 4.25 (1H, t), 7.30-7.48 (6H, m), 7.57 (2H, d), 7.95 (2H, s).

Example 44

4-{4-[1-(4-Chloro-phenyl)-2-imidazol-1-yl-ethyl]-phenyl}-1H-pyrazole

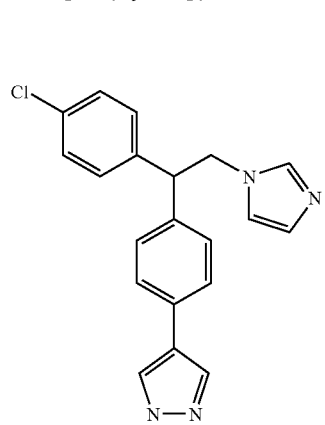

By following the procedures described in Examples 42A through to 42C but substituting methylamine for imidazole, the title compound was obtained. LC/MS: (PS-B3) $R_t$ 2.73 [M+H]$^+$ 349. $^1$H NMR (d$_6$-DMSO) δ 4.60 (1H, t), 4.95 (2H, d), 7.32 (2H, d), 7.42 (4H, s), 7.53-7.60 (3H, m), 7.70 (1H, s), 8.05 (2H, s), 9.0 (1H, s).

Example 45

Methyl-{2-(4-phenoxy-phenyl)-2-[4-(1H-pyrazol-4-yl)-phenyl]-ethyl}-amine

45A. [2-(4-Bromo-phenyl)-2-(4-phenoxy-phenyl)-ethyl]-methyl-amine

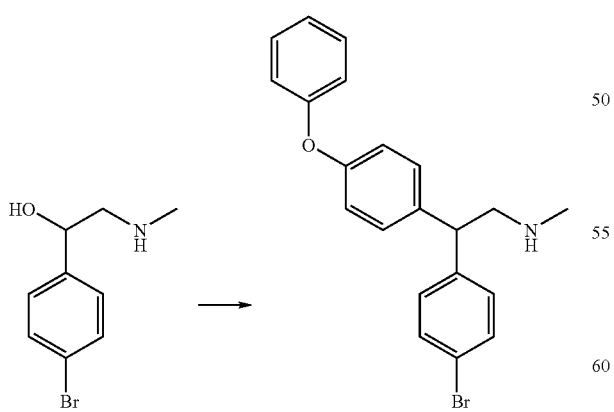

By following the procedure described in Example 42B but substituting chlorobenzene for diphenyl ether and employing nitrobenzene as solvent, the title compound was obtained. LC/MS: (PS-A2) $R_t$ 2.54 [M+H]$^+$ 382.

45B. Methyl-{2-(4-phenoxy-phenyl)-2-[4-(1H-pyrazol-4-yl)-phenyl]-ethyl}-amine

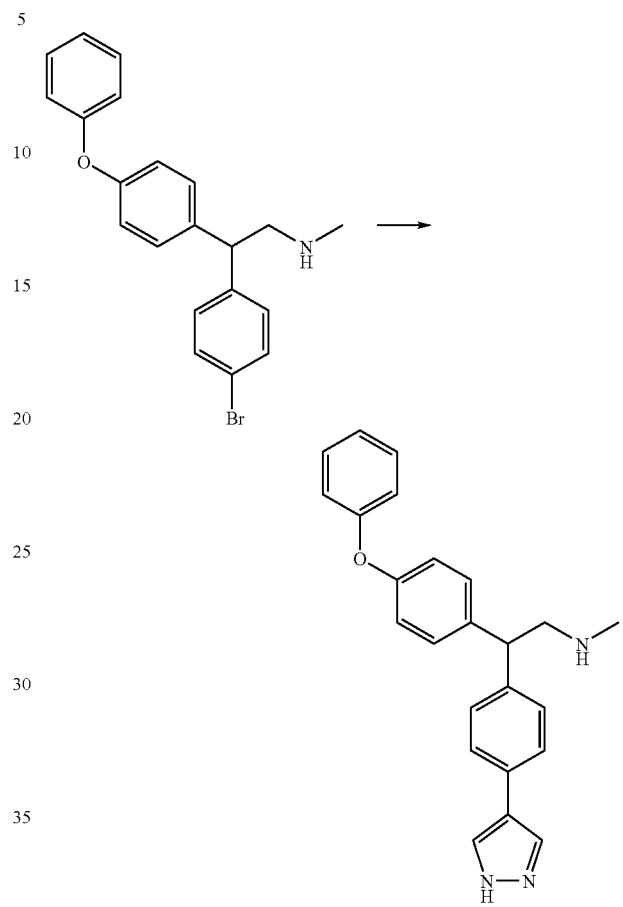

By following the procedure described in Example 42C but substituting [2-(4-Bromo-phenyl)-2-(4-chloro-phenyl)-ethyl]-methyl-amine for [2-(4-Bromo-phenyl)-2-(4-phenoxy-phenyl)-ethyl]-methyl-amine, the title compound was obtained. LC/MS: (PS-B3) $R_t$ 3.04 [M+H]$^+$ 370. $^1$H NMR (Me-d$_3$-OD) δ 2.75 (3H, s), 3.75 (2H, d), 4.38 (1H, t), 6.98 (4H, dd), 7.12 (1H, t), 7.33-7.40 (6H, m), 7.61 (2H, d), 7.95 (2H, s).

Example 46

{2-(4-Methoxy-phenyl)-2-[4-(1H-pyrazol-4-yl)-phenyl]-ethyl}-methyl-amine

46A. [2-(4-Bromo-phenyl)-2-(4-methoxy-phenyl)-ethyl]-methyl-amine

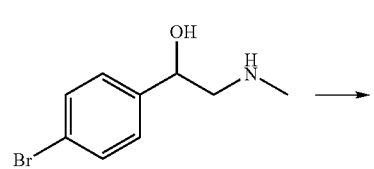

-continued

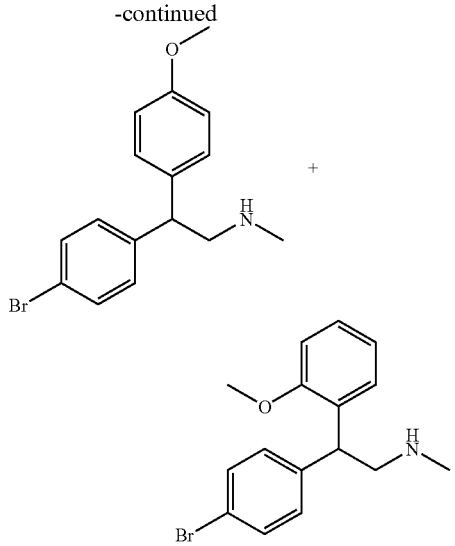

By following the procedure described in Example 42B but substituting chlorobenzene for anisole, the title compound was obtained as a mixture of regioisomers (ca 4:1) with the corresponding ortho-methoxy analogue. LC/MS: (PS-B3) $R_t$ 3.24 [M+H]$^+$ 320.

46B. [2-(4-Bromo-phenyl)-2-(4-methoxy-phenyl)-ethyl]-methyl-amine

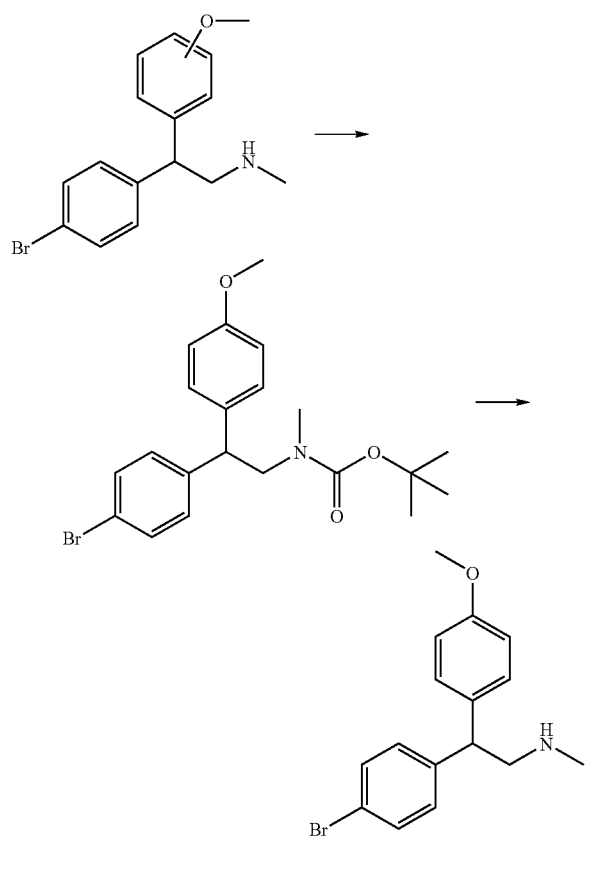

BOC$_2$O (941 mg, 4.309 mmol) was added to a solution of [2-(4-Bromo-phenyl)-2-(4-methoxy-phenyl)-ethyl]-methyl-amine (and its regioisomer) (1.38 g, 4.309 mmol) in dichloromethane (10 ml). After stirring at room temperature for 16 hours the solvent was removed under reduced pressure and the crude product was purified by flash chromatography eluting with ethyl acetate/petroleum ether (1:9) to yield the intermediate BOC protected compound as the desired single isomer (540 mg). The product was then stirred in a saturated solution of HCl in diethyl ether (30 ml) for 3 days. Removal of the solvent under reduced pressure afforded the title compound as the HCl salt. LC/MS: (PS-B3) $R_t$ 3.21 [M+H]$^+$ 320.

46C. {2-(4-Methoxy-phenyl)-2-[4-(1H-pyrazol-4-yl)-phenyl]-ethyl}-methyl-amine

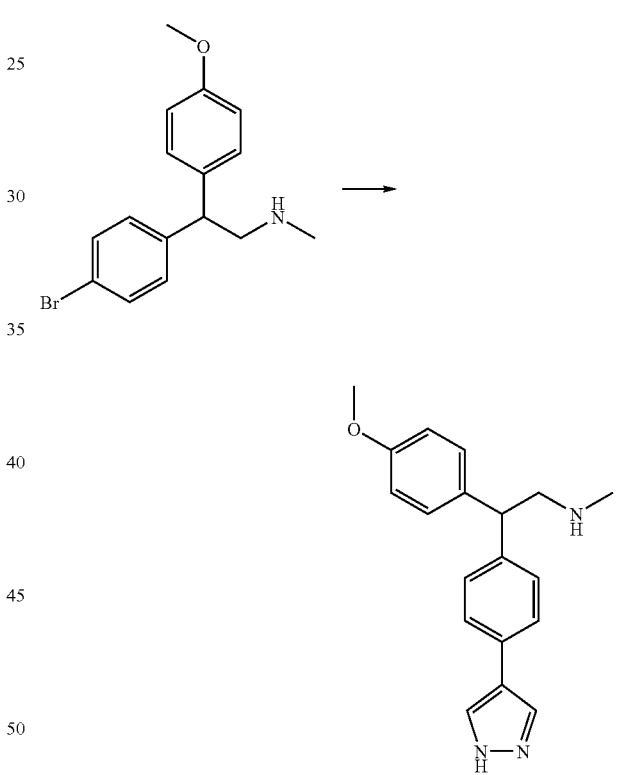

By following the procedure described in example 42C but substituting [2-(4-Bromo-phenyl)-2-(4-chloro-phenyl)-ethyl]-methyl-amine for [2-(4-Bromo-phenyl)-2-(4-methoxy-phenyl)-ethyl]-methyl-amine, the title compound was obtained. LC/MS: (PS-B3) $R_t$ 2.52 [M+H]$^+$ 308. $^1$H NMR (Me-d$_3$-OD) δ 2.75 (3H, s), 3.75 (2H, dd), 3.80 (3H, s), 4.38 (1H, t), 6.95 (2H, d), 7.32 (2H, d), 7.45 (2H, d), 7.70 (2H, d), 8.52 (2H, s).

Example 47

Methyl-{2-[4-(pyrazin-2-yloxy)-phenyl]-2-[4-(1H-pyrazol-4-yl)-phenyl]-ethyl}-amine

47A. 4-[1-(4-Bromo-phenyl)-2-methylamino-ethyl]-phenol

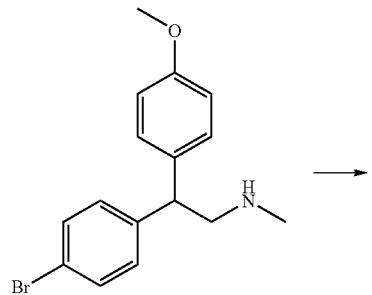

Boron tribromide (7.8 ml, 1.0M in dichloromethane) was added slowly to a solution of [2-(4-Bromo-phenyl)-2-(4-methoxy-phenyl)-ethyl]-methyl-amine (500 mg, 1.56 mmol) in dichloromethane (8 ml) at 0° C., under an atmosphere of nitrogen. The reaction mixture was allowed to warm to room temperature and then stirred for a further hour. The mixture was poured on to ice and then diluted with dichloromethane and saturated NaHCO$_3$ solution. The organic layer was dried (MgSO$_4$), filtered and concentrated to afford the desired product. LC/MS: (PS-B3) R$_t$ 2.76 [M+H]$^+$ 306.

47B. [2-(4-Bromo-phenyl)-2-(4-hydroxy-phenyl)-ethyl]-methyl-carbamic acid tert-butyl ester

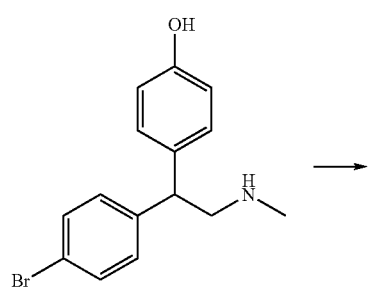

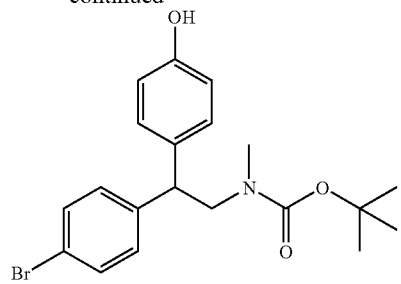

BOC$_2$O (269 mg, 1.23 mmol) was added to a solution of 4-[1-(4-Bromo-phenyl)-2-methylamino-ethyl]-phenol (360 mg, 1.18 mmol) in dichloromethane (20 ml). After stirring at room temperature for 16 hours the solvent was removed under reduced pressure and the crude product was purified by column chromatography (SiO$_2$), eluting with ethyl acetate/petroleum ether (1:4) to yield the title compound. LC/MS: (FL-A) R$_t$ 3.85 [M+H]$^+$ 406.

47C. {2-(4-Bromo-phenyl)-2-[4-(pyrazin-2-yloxy)-phenyl]-ethyl}-methyl-amine

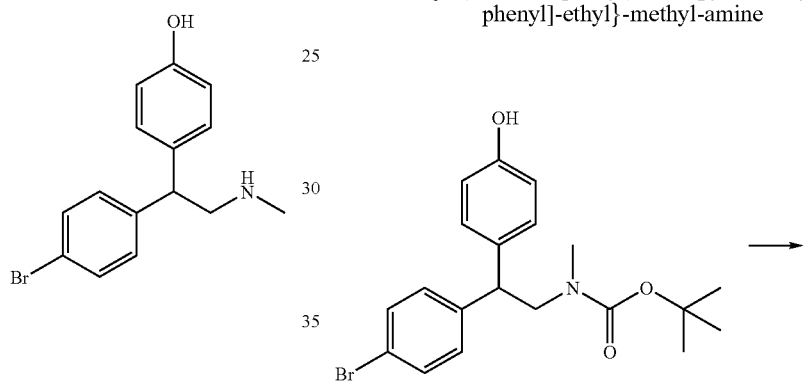

A solution of [2-(4-Bromo-phenyl)-2-(4-hydroxy-phenyl)-ethyl]-methyl-carbamic acid tert-butyl ester (125 mg, 0.31 mmol), 2-chloropyrazine (35.2 mg, 0.31 mmol) and K$_2$CO$_3$ (213 mg, 1.54 mmol) in dimethylformamide (8 ml) was heated to 100° C. for 17 hours. Upon cooling, the solvent was removed under reduced pressure and the residue was partitioned between ethyl acetate and saturated NaHCO$_3$ solution. The organic layer was dried (MgSO$_4$), filtered and concentrated. The crude product was then treated with saturated HCl in diethyl ether (15 ml) and stirred at room temperature for 72 hours. The solvent was then removed under reduced pressure and the crude product was purified by Phenomenex_Strata_SCX column chromatography eluting with methanol followed by 2N ammonia in methanol to afford the desired product (82 mg). LC/MS: (PS-B3) R$_t$ 3.17 [M+H]$^+$ 384.

47D. Methyl-{2-[4-(pyrazin-2-yloxy)-phenyl]-2-[4-(1H-pyrazol-4-yl)-phenyl]-ethyl}-amine

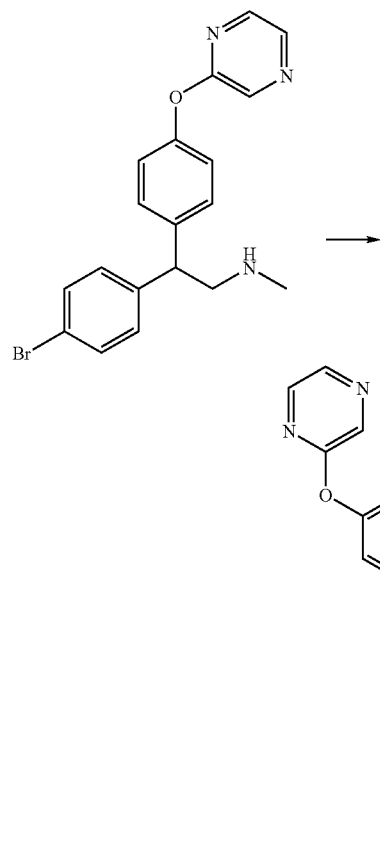

By following the procedure described in Example 42C, but substituting [2-(4-Bromo-phenyl)-2-(4-chloro-phenyl)-ethyl]-methyl-amine for {2-(4-Bromo-phenyl)-2-[4-(pyrazin-2-yloxy)-phenyl]-ethyl}-ethyl-amine, the title compound was obtained. LC/MS: (PS-B3) R$_t$ 2.48 [M+H]$^+$ 372.
$^1$H NMR (Me-d$_3$-OD) δ 2.80 (3H, s), 3.75-3.90 (2H, m), 4.50 (1H, t), 7.23 (2H, d), 7.50 (4H, t), 7.75 (2H, d), 8.12 (1H, d), 8.33 (1H, d), 8.42 (2H, s), 8.48 (1H, s).

Example 48

Methyl-{2-phenoxy-2-[4-(1H-pyrazol-4-yl)-phenyl]-ethyl}-amine

48A. [2-(4-Bromo-phenyl)-2-hydroxy-ethyl]-methyl-carbamic acid tert-butyl ester

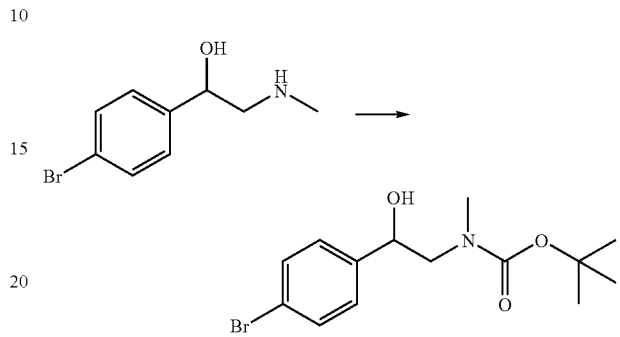

BOC$_2$O (1.90 g, 8.69 mmol) was added to a solution of 1-(4-Bromo-phenyl)-2-methylamino-ethanol (2.00 g, 8.69 mmol) in dichloromethane (20 ml). After stirring at room temperature for 16 hours the solvent was removed under reduced pressure and the crude product was purified by column chromatography (SiO$_2$), eluting with ethyl acetate/petroleum ether (1:4) to yield the desired product (2.1 g). LC/MS: (PS-B3) R$_t$ 3.16 [M+H]$^+$ 330.

48B. [2-(4-Bromo-phenyl)-2-phenoxy-ethyl]-methyl-amine

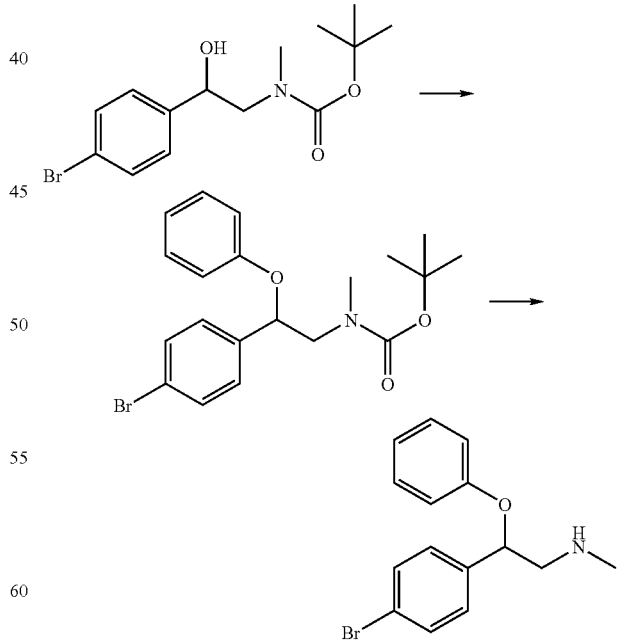

Diethyl azodicarboxylate (358 □l, 2.27 mmol) was added dropwise to a solution of [2-(4-Bromo-phenyl)-2-hydroxy-ethyl]-methyl-carbamic acid tert-butyl ester (500 mg, 1.51 mmol), triphenylphosphine (596 mg, 2.27 mmol) and phenol (285 mg, 3.03 mmol) in tetrahydrofuran (10 ml) and the reaction mixture stirred at room temperature, under an atmosphere of nitrogen, for 17 hours. The solvent was then removed under reduced pressure and the residue was partitioned between ethyl acetate and saturated NaHCO₃ solution. The organic layer was dried (MgSO₄), filtered and concentrated. The crude product was then purified by column chromatography (SiO₂), eluting with ethyl acetate/petroleum ether (1:9) to yield the intermediate BOC protected compound, which was then stirred in a saturated solution of HCl in diethyl ether (20 ml) for 24 hours. Removal of the solvent under reduced pressure afforded the title compound as the HCl salt. Further purification by Phenomenex_Strata_SCX column chromatography, eluting with methanol followed by 2N ammonia in methanol, afforded the desired product as the free base (94 mg). LC/MS: (PS-B3) $R_t$ 4.04 [M+H]⁺ 406.

48C. Methyl-(2-phenoxy-2-[4-(1H-pyrazol-4-yl)-phenyl]-ethyl)-amine

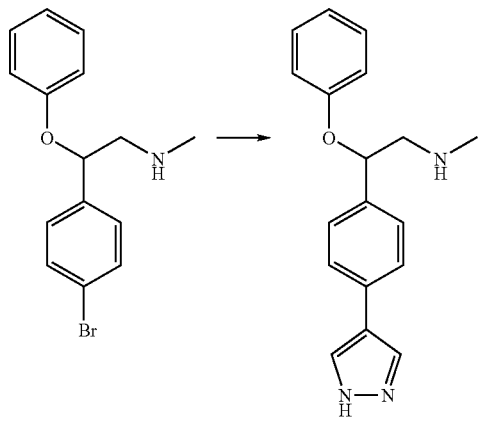 [SMILES: CNCC(Oc1ccccc1)c1ccc(Br)cc1 ; CNCC(Oc1ccccc1)c1ccc(-c2cn[nH]c2)cc1]

By following the procedure described in Example 42C, but substituting [2-(4-Bromo-phenyl)-2-(4-chloro-phenyl)-ethyl]-methyl-amine for [2-(4-Bromo-phenyl)-2-phenoxy-ethyl]-methyl-amine, the title compound was obtained. LC/MS: (PS-B3) $R_t$ 2.73 [M-PhO+H]⁺ 200. ¹H NMR (Me-d₃-OD) δ 2.50 (3H, s), 2.90 (1H, dd), 3.15 (1H, dd), 5.40 (1H, dd), 6.85 (1H, t), 6.90 (2H, d), 7.18 (2H, t), 7.40 (2H, d), 7.55 (2H, d), 7.93 (2H, s).

Example 49

2-{(4-Chloro-phenyl)-[4-(1H-pyrazol-4-yl)-phenyl]-methoxy}-ethylamine

49A. (4-Bromo-phenyl)-(4-chloro-phenyl)-methanol

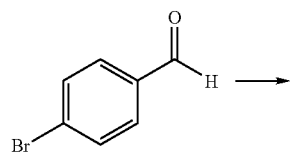

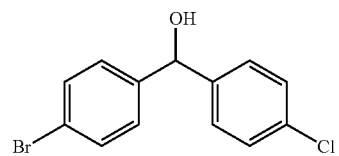

4-Chlorophenylmagnesium bromide (12.97 ml, 1M solution in diethyl ether) was added slowly to a solution of 4-bromobenzaldehyde (2.0 g, 10.81 mmol) in tetrahydrofuran (25 ml) at 0° C., under an atmosphere of nitrogen. The reaction mixture was allowed to warm to room temperature and was stirred for 17 hours. Water (3 ml) was then added and the solvent was removed under reduced pressure. The residue was then partitioned between ethyl acetate and 1N HCl solution. The organic layer was washed with brine, dried (MgSO₄), filtered and concentrated. The crude product was then purified by column chromatography (SiO₂), eluting with ethyl acetate/petroleum ether (1:9), to yield the title compound (2.30 g). LC/MS: (PS-B3) $R_t$ 3.49 [M-H]⁺ 297.

49B. 2-{2-[(4-Bromo-phenyl)-(4-chloro-phenyl)-methoxy]-ethyl}-isoindole-1,3-dione

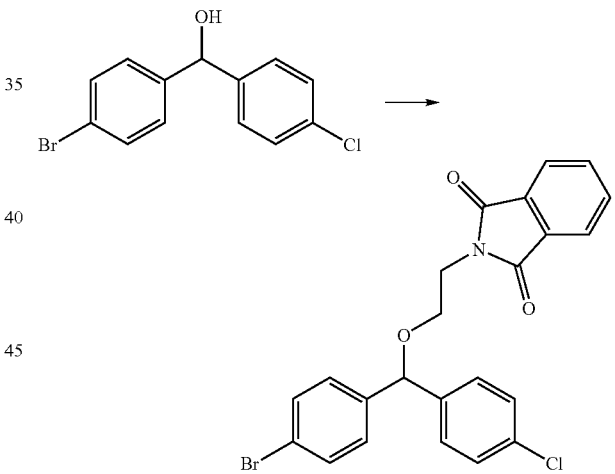

A mixture of (4-Bromo-phenyl)-(4-chloro-phenyl)-methanol (2.3 g, 7.73 mmol), N-(2-hydroxyethyl)phthalimide (1.4 g, 7.36 mmol) and para-toluenesulfonic acid monohydrate (560 mg, 2.94 mmol) in toluene (50 ml) was heated to reflux under Dean-Stark conditions for 17 hours. Upon cooling, the solvent was removed and the residue was partitioned between ethyl acetate and water. The organic layer was then dried (MgSO₄), filtered and concentrated. The crude product was purified by column chromatography (SiO₂), eluting with ethyl acetate/petroleum ether (1:4), to yield the title compound (1.95 g). LC/MS: (PS-B3) $R_t$ 4.07 no observable mass ion.

49C. N-(2-{(4-Chloro-phenyl)-[4-(1H-pyrazol-4-yl)-phenyl]-methoxy)-ethyl}-phthalamic acid

49D. 2-{(4-Chloro-phenyl)-[4-(1H-pyrazol-4-yl)-phenyl]-methoxy}-ethylamine

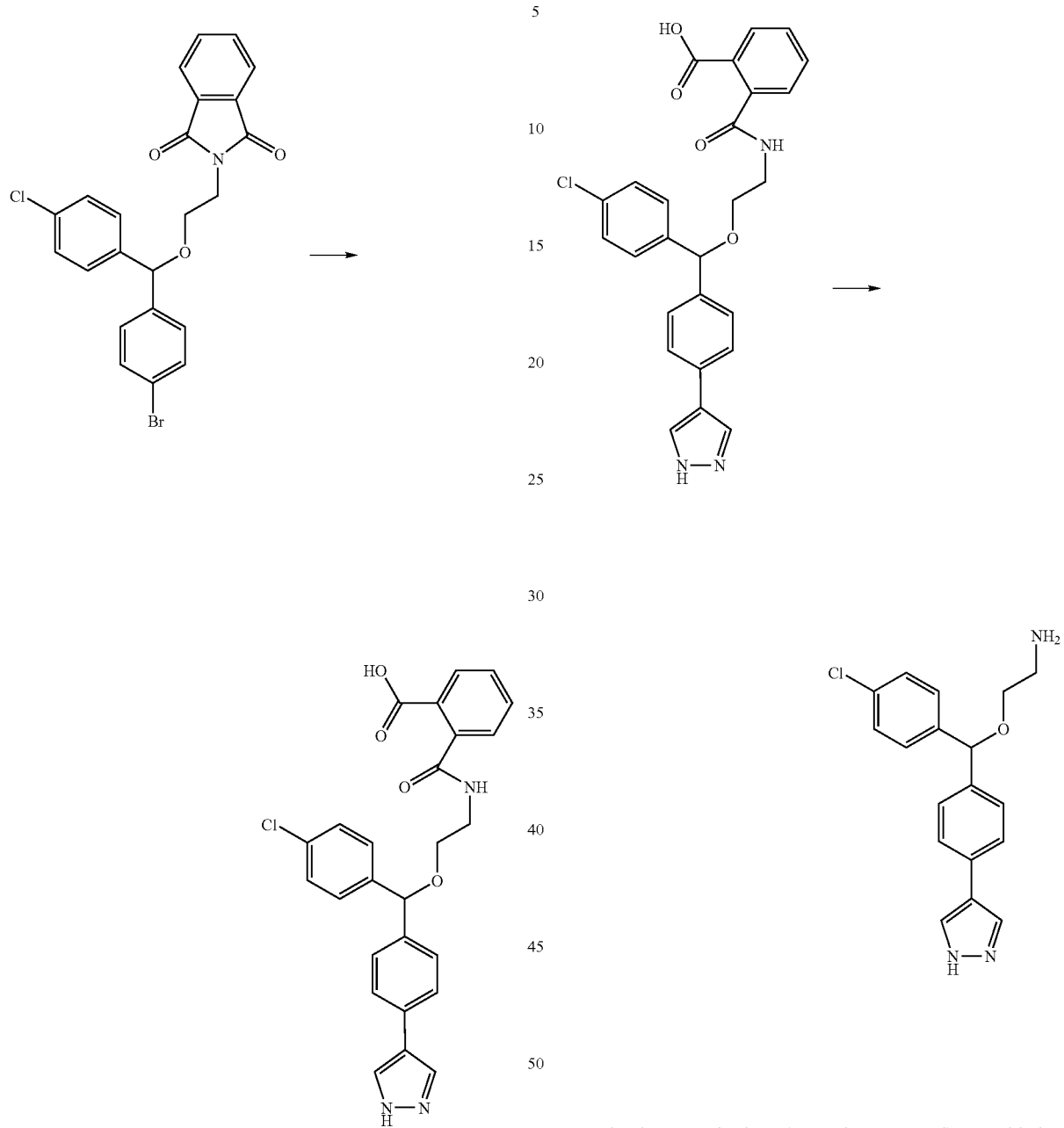

By following the procedure described in Example 42C, but substituting [2-(4-Bromo-phenyl)-2-(4-chloro-phenyl)-ethyl]-methyl-amine for 2-(2-[(4-Bromo-phenyl)-(4-chloro-phenyl)-methoxy]-ethyl)-isoindole-1,3-dione, the title compound was obtained. LC/MS: (FS-A) $R_t$ 2.85 [M–H]$^+$ 474.

Hydrazine monohydrate (159 □l, 3.28 mmol) was added to a solution of N-(2-{(4-Chloro-phenyl)-[4-(1H-pyrazol-4-yl)-phenyl]-methoxy}-ethyl)-phthalamic acid (260 mg, 0.55 mmol) in methanol (6 ml) and the reaction mixture stirred at 80° C. for 16 hours. Upon cooling, the solvent was removed under reduced pressure and the crude product was purified by column chromatography (SiO$_2$), eluting with dichloromethane:methanol:acetic acid:water (90:18:3:2). Further purification by Phenomenex_Strata_SCX column chromatography, eluting with methanol followed by 2N ammonia in methanol, afforded the desired product as the free base (120 mg). LC/MS: (FL-A) $R_t$ 2.07 [M-NH$_2$CH$_2$CH$_2$O+H]$^+$ 267. $^1$H NMR (Me-d$_3$-OD) δ 2.85 (2H, t), 3.55 (2H, t), 5.45 (1H, s), 7.35-7.40 (6H, m), 7.58 (2H, d), 7.95 (2H, s).

Example 50

4-{4-[1-(4-Chloro-phenyl)-3-pyrrolidin-1-yl-propyl]-phenyl}-1H-pyrazole

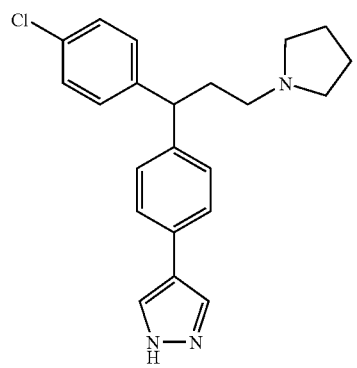 [SMILES: Clc1ccc(C(CCN2CCCC2)c2ccc(-c3cn[nH]c3)cc2)cc1]

By following the procedure described in Example 8 but substituting methylamine for pyrrolidine, the title compound was obtained. LC/MS: (PS-A2) $R_t$ 2.25 [M+H]$^+$ 366. $^1$H NMR (Me-d$_3$-OD) δ 1.83-1.95 (2H, m), 1.95-2.09 (2H, m), 2.4-2.5 (2H, m), 2.88-2.97 (2H, m), 3.02 (2H, dd), 3.52-3.61 (2H, m), 4.02 (1H, t), 7.25 (4H, q), 7.32 (2H, d), 7.55 (2H, d), 8.41 (2H, s).

Example 51

4-{4-[3-Azetidin-1-yl-1-(4-chloro-phenyl)-propyl]-phenyl}-1H-pyrazole

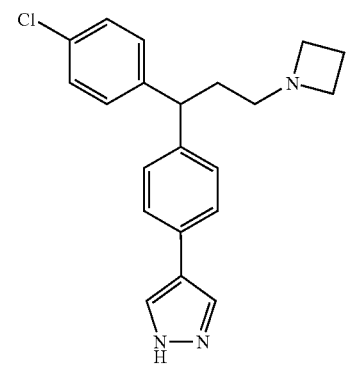 [SMILES: Clc1ccc(C(CCN2CCC2)c2ccc(-c3cn[nH]c3)cc2)cc1]

By following the procedure described in Example 8 but substituting methylamine for pyrrolidine, the title compound was obtained. LC/MS: (PS-A2) $R_t$ 2.18 [M+H]$^+$ 352. $^1$H NMR (Me-d$_3$-OD) δ 2.12-2.25 (2H, m), 3.00 (2H, t), 3.85-3.98 (5H, m), 4.05-4.17 (2H, m), 7.18 (2H, d), 7.19 (4H, s), 7.45 (2H, d), 7.83 (2H, s).

Example 52

Methyl-{3-naphthalen-2-yl-3-[4-(1H-pyrazol-4-yl)-phenyl]-propyl}-amine

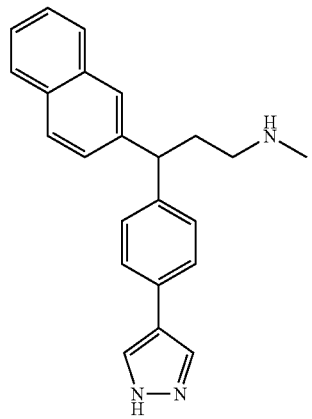 [SMILES: CNCCC(c1ccc(-c2cn[nH]c2)cc1)c1ccc2ccccc2c1]

By following the procedure described in Example 8 but substituting 4-chlorophenylmagnesium bromide for 2-naphthylmagnesium bromide, the title compound was obtained. LC/MS: (PS-A2) $R_t$ 2.26 [M+H]$^+$ 342. $^1$H NMR (Me-d$_3$-OD) δ 2.57-2.70 (2H, m), 2.70 (3H, s), 2.90-3.10 (2H, m), 4.32 (1H, t), 7.40-7.52 (5H, m), 7.70 (2H, m), 7.80-7.90 (4H, m), 8.70 (2H, s).

Example 53

Dimethyl-(4-{3-methylamino-1-[4-(1H-pyrazol-4-yl)-phenyl]-propyl}-phenyl)-amine

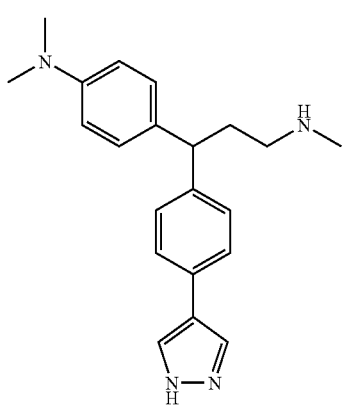

By following the procedure described in Example 8 but substituting 4-chlorophenylmagnesium bromide for 4-(N,N-dimethyl)anilinemagnesium bromide, the title compound was obtained. LC/MS: (PS-A2) $R_t$ 1.55 [M+H]$^+$ 335. $^1$H NMR (Me-d$_3$-OD) δ, 2.46-2.60 (2H, m), 2.69 (3H, s), 2.95 (2H, t), 3.27 (6H, s), 4.25 (1H, t), 7.45 (2H, d), 7.60-7.72 (6H, m), 8.50 (2H, s).

Example 54

{3-(4-Fluoro-phenyl)-3-[4-(1H-pyrazol-4-yl)-phenyl]-propyl}-methyl-amine

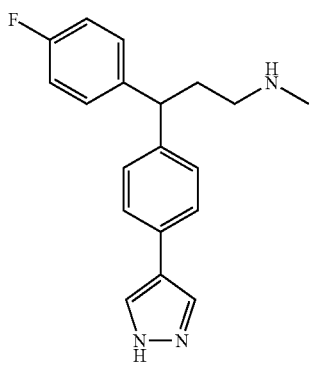 [SMILES: CNCCC(c1ccc(F)cc1)c1ccc(-c2cn[nH]c2)cc1]

By following the procedure described in Example 8 but substituting 4-chlorophenylmagnesium bromide for 4-fluorophenylmagnesium bromide, the title compound was obtained. LC/MS: (PS-A2) $R_t$ 2.05 [M+H]$^+$ 310. $^1$H NMR (Me-d$_3$-OD) δ 2.40-2.55 (2H, d), 2.70 (3H, s), 2.90-3.0 (2H, m), 4.12 (1H, t), 7.05 (2H, t), 7.32-7.40 (4H, m), 7.63 (2H, d), 8.33 (2H, s).

Example 55

4-{4-[4-(4-Chloro-phenyl)-piperidin-4-yl]-phenyl}-1H-pyrazole-3-carbonitrile

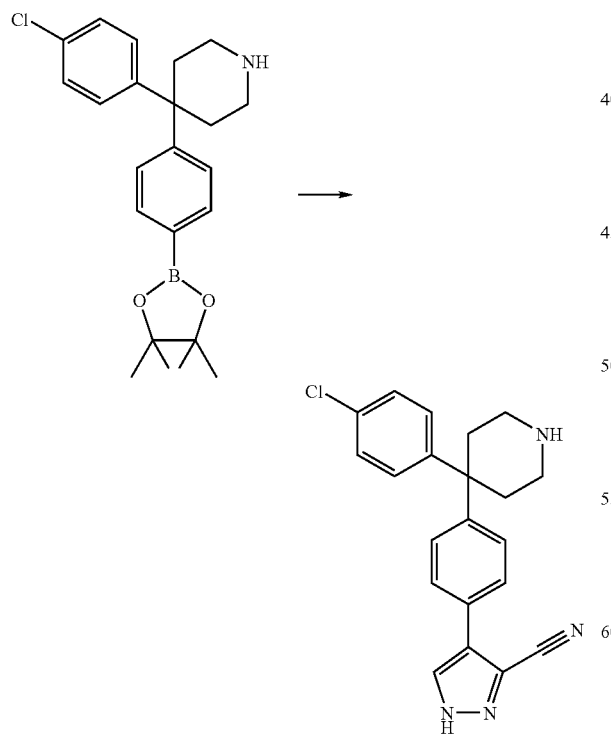

Following the procedure of Example 1 but using 4-(4-Chloro-phenyl)-4-[4-(4,4,5,5-tetramethyl-[1,3,2]dioxaborolan-2-yl)-phenyl]-piperidine instead of 4-(4,4,5,5-tetramethyl-1,3,2-dioxaborolan-2-yl)-1H-pyrazole and 4-bromo-1H-pyrazole-3-carbonitrile instead of 2-(4-chlorophenyl)-2-phenylethylamine hydrochloride gave the title compound. LC/MS: (PS-A2) $R_t$ 2.22 [M+H]$^+$ 363. $^1$H NMR (Me-d$_3$-OD) δ 2.52-2.70 (4H, m), 3.10-3.20 (4H, m), 7.25 (4H, s), 7.37 (2H, d), 7.58 (2H, d), 8.02 (1H, s).

Example 56

3-(4-Phenoxy-phenyl)-3-[4-(1H-pyrazol-4-yl)-phenyl]-propylamine

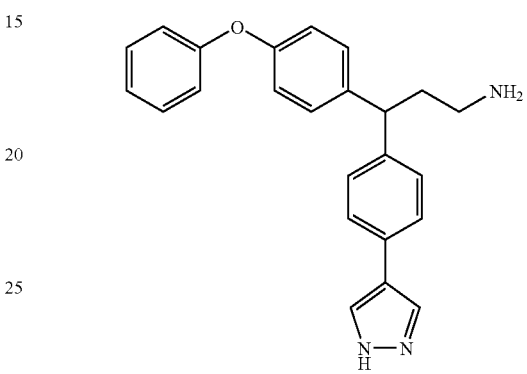

By following the procedure described in Example 8 but substituting 4-chlorophenylmagnesium bromide for 4-phenoxyphenylmagnesium bromide and methylamine for ammonia the title compound was obtained. LC/MS: (PS-A2) $R_t$ 2.28 [M+H]$^+$ 370.34. $^1$H NMR (Me-d$_3$-OD) δ 2.38-2.46 (2H, m), 2.85-2.92 (2H, t), 4.03-4.10 (1H, t), 6.94-7.0 (4H, d), 7.08-7.14 (1H, t), 7.30-7.39 (6H, m), 7.55-7.58 (2H, d), 7.90-7.97 (2H, br s), 8.54-8.60 (1H, br s).

Example 57

1-{(4-Chloro-phenyl)-[4-(1H-pyrazol-4-yl)-phenyl]-methyl}-piperazine

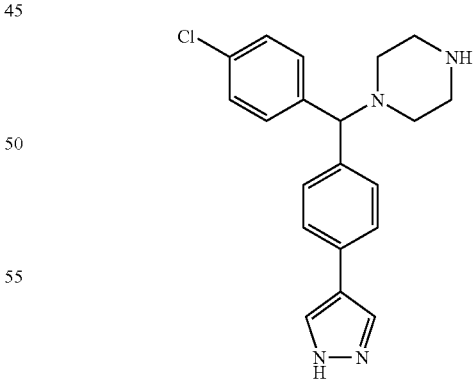

By following the procedure described in Example 1 but substituting 2-(4-chlorophenyl)-2-phenylethylamine hydrochloride for 1-(4,4'-dichloro-benzhydryl)-piperazine gave the title compound. LC/MS: (PS-B3) $R_t$ 2.82 [M−H]$^+$ 351.27. $^1$H NMR (Me-d$_3$-OD) δ 3.0-3.25 (4H, m), 3.45-3.65 (4H, m), 5.05-5.25 (1H, br s), 7.40-7.50 (2H, d), 7.65-7.83 (6H, m), 8.45 (2H, s).

Example 58

1-Methyl-4-{phenyl-[4-(1H-pyrazol-4-yl)-phenyl]-methyl}-[1,4]diazepane

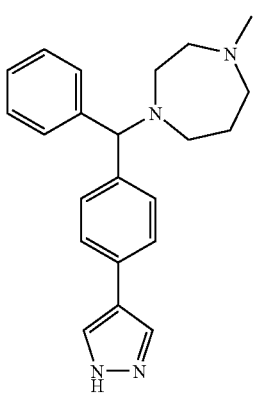 [SMILES: CN1CCCN(C(c2ccccc2)c2ccc(-c3cn[nH]c3)cc2)CC1]

By following the procedure described in Example 1 but substituting 2-(4-chlorophenyl)-2-phenylethylamine hydrochloride for 1-[p-chlorodiphenylmethyl]-4-methyl-1,4-diazacycloheptane dihydrochloride gave the title compound. LC/MS: (PS-B3) $R_t$ 2.85 [M+H]$^+$ 347.18. $^1$H NMR (Me-d$_3$-OD) δ 2.25-2.60 (2H, br m), 3.00 (3H, s), 3.40-4.18 (8H, br m), 5.78 (1H, s), 7.40-7.48 (1H, m), 7.49-7.55 (2H, t), 7.75-7.80 (2H, d), 7.82-7.98 (4H, m), 8.32 (2H, s).

Example 59

{3-(3-Chloro-phenoxy)-3-[4-(1H-pyrazol-4-yl)-phenyl]-propyl}-methyl-amine

59A. 1-(4-Bromo-phenyl)-3-chloro-propan-1-ol (J. Med. Chem, 2004, 47, 3924-3926)

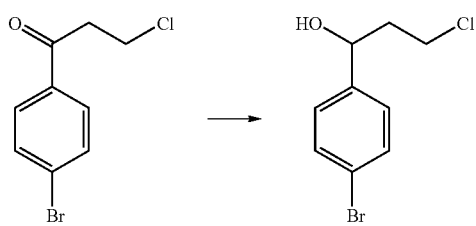 [SMILES: O=C(CCCl)c1ccc(Br)cc1 ; OC(CCCl)c1ccc(Br)cc1]

To a solution of 1-(4-Bromo-phenyl)-3-chloro-propan-1-one (1 g, 4.04 mmol) in tetrahydrofuran (9 ml) and water (0.58 ml) was added sodium borohydride (0.16 g, 4.28 mmol). The reaction mixture was stirred at room temperature for 2 hours, quenched with careful addition of water and extracted with ethyl acetate. The organic layers were separated, dried (MgSO$_4$), filtered and concentrated to afford the title compound, which was used in the next step without further purification. LC/MS: (PS-A2) $R_t$ 3.07 [M+H]$^+$ No ionization.

59B. [3-(4-Bromo-phenyl)-3-(3-chloro-phenoxy)-propyl]-chloride

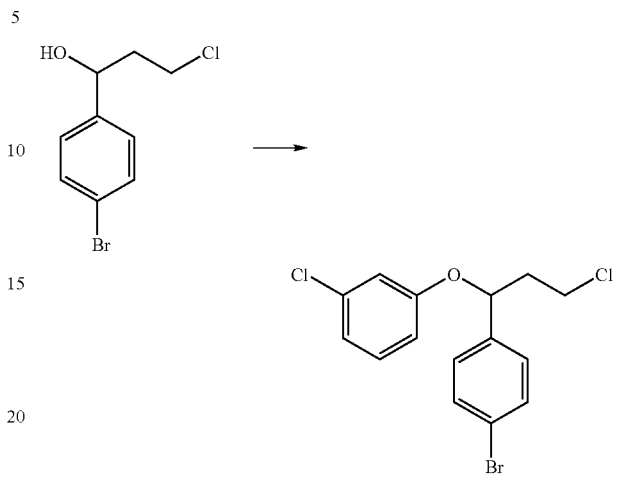

3-Chlorophenol was reacted with 1-(4-Bromo-phenyl)-3-chloro-propan-1-ol following the procedure set out in Example 48B to give the title compound, which was used in the next step without further purification.

59C. [3-(4-Bromo-phenyl)-3-(3-chloro-phenoxy)-propyl]-methyl-amine

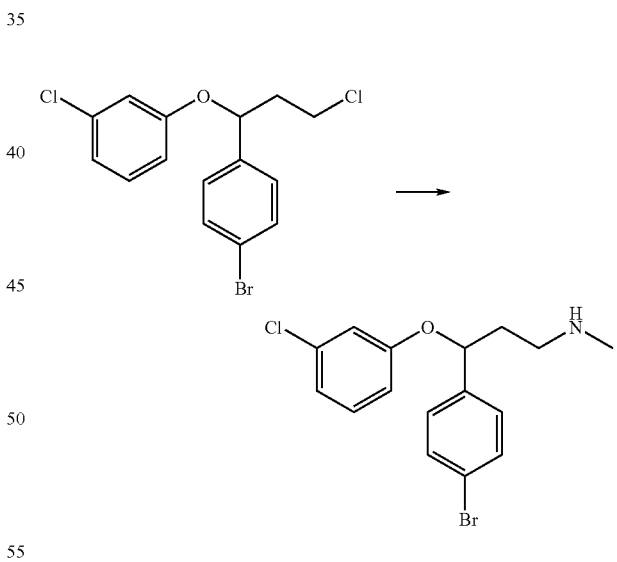

A solution of 3-(4-Bromo-phenyl)-3-(3-chloro-phenoxy)-propyl]-chloride in 33% methylamine in ethanol (4 ml) was heated in a CEM microwave at 100° C. for 30 minutes using 50 W power. Solvent was removed and the crude product was purified over Phenomenex_Strata_SCX ion exchange column eluting with methanol followed by 2N ammonia in methanol. The product was purified by column chromatography (SiO$_2$), eluting with dichloromethane to dichloromethane:methanol:acetic acid:water (90:18:3:2) using the SP4 biotage to afford the title compound. LC/MS: (PS-B3) $R_t$ 3.42 [M+H]$^+$ 356.19.

59D. {3-(3-Chloro-phenoxy)-3-[4-(1H-pyrazol-4-yl)-phenyl]-propyl}-methyl-amine

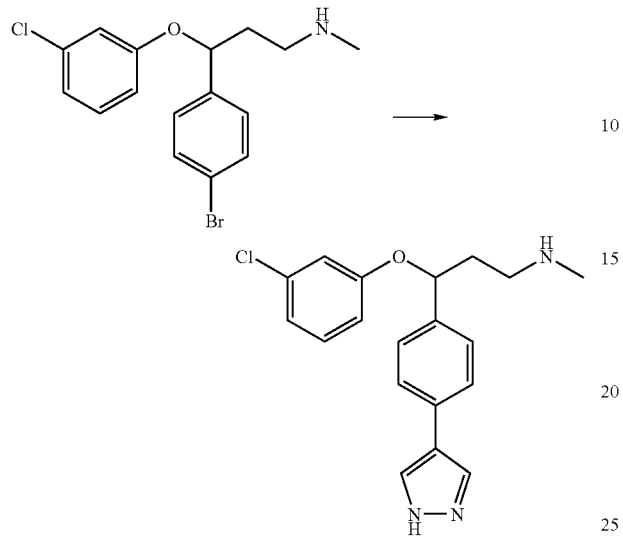

[3-(4-Bromo-phenyl)-3-(3-chloro-phenoxy)-propyl]-methyl-amine was reacted with 4-(4,4,5,5-tetramethyl-1,3,2-dioxaborolan-2-yl)-1H-pyrazole following the procedure set out in Example 1 to give the title compound. LC/MS: (PS-B3) $R_t$ 2.80 [M+H]$^+$ 342.26. $^1$H NMR (Me-d$_3$-OD) δ 2.19-2.30 (1H, m), 2.30-2.45 (1H, m), 2.72 (3H, s), 3.10-3.28 (2H, m), 5.40-5.47 (1H, m), 6.80-6.88 (1H, d), 6.88-6.94 (1H, d), 6.96 (1H, s), 7.15-7.20 (1H, t), 7.38-7.45 (2H, d), 7.57-7.65 (2H, d), 7.98 (2H, s).

Example 60

Methyl-{2-phenyl-2-[6-(1H-pyrazol-4-yl)-pyridin-3-yl]-ethyl}-amine

60A. 6-(3-Methyl-1-trityl-1H-pyrazol-4-yl)-nicotinonitrile

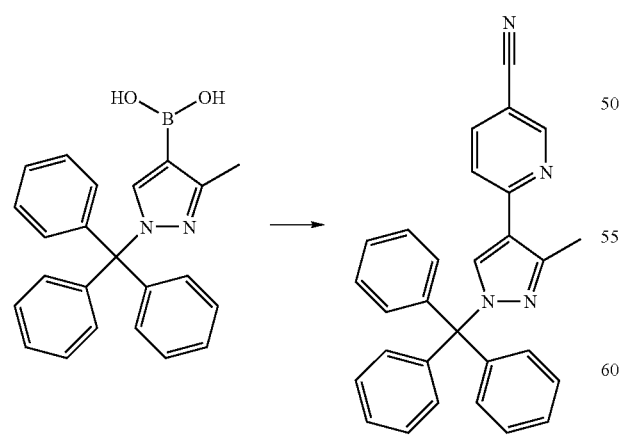

To a solution of 6-Chloro-nicotinonitrile (0.2 g, 1.49 mmol) and 3-methyl-1-trityl-1H-pyrazole-4-boronic acid* (0.5 g, 1.36 mmol) in ethylene glycol dimethyl ether (3 ml), was added sodium carbonate (0.36 g, 3.39 mmol) in water (1.5 ml). The reaction mixture was degassed with nitrogen before addition of tetrakis(triphenylphosphine)palladium (0) and then heated in a CEM microwave at 135° C. for 30 minutes (50 W power). Reaction partitioned between water and ethyl acetate, aqueous basified with 2N NaOH, organic extracts were combined, dried (MgSO$_4$) and solvent removed. Crude product suspended in small volume of methanol, white precipitate filtered to afford the title compound (0.32 g, 53% yield). LC/MS: (PS-A2) $R_t$ 4.52 [M+H]$^+$ 427.26.

* This starting material can be made by the method described in EP1382603A1

60B. (4-Chloro-phenyl)-[6-(3-methyl-1-trityl-1H-pyrazol-4-yl)-pyridin-3-yl]-methanone

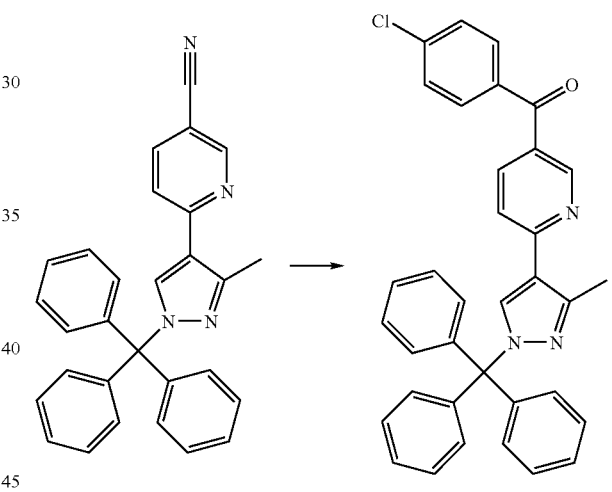

To a solution of 6-(3-Methyl-1-trityl-1H-pyrazol-4-yl)-nicotinonitrile (0.5 g, 1.17 mmol) in dry tetrahydrofuran (4 ml) was added 4-chlorobenzenemagnesium bromide (1.52 ml, 1.52 mmol, 1M in diethyl ether); the reaction mixture was stirred under nitrogen for 16 hours. The reaction was quenched to below pH 2 by the addition of 2N HCl and stirred for 1 hour. Then adjusted to pH 8 with saturated sodium bicarbonate and extracted with ethyl acetate. Organic extracts were combined, dried (MgSO$_4$), solvent removed and residue purified by column chromatography (SiO$_2$), eluting with petrol to ethyl acetate:petroleum ether (15:85) to yield the title compound (0.49 mg, 77% yield). LC/MS: (PS-A2) $R_t$ 4.45 [M+H]$^+$ 540.30, 542.28.

181

60C. {2-(4-Chloro-phenyl)-2-[6-(3-methyl-1-trityl-1H-pyrazol-4-yl)-pyridin-3-yl]-vinyl}-methyl-(1-phenyl-ethyl)-amine

182

60D. Methyl-{2-phenyl-2-[6-(1H-pyrazol-4-yl)-pyridin-3-yl]-ethyl}-amine

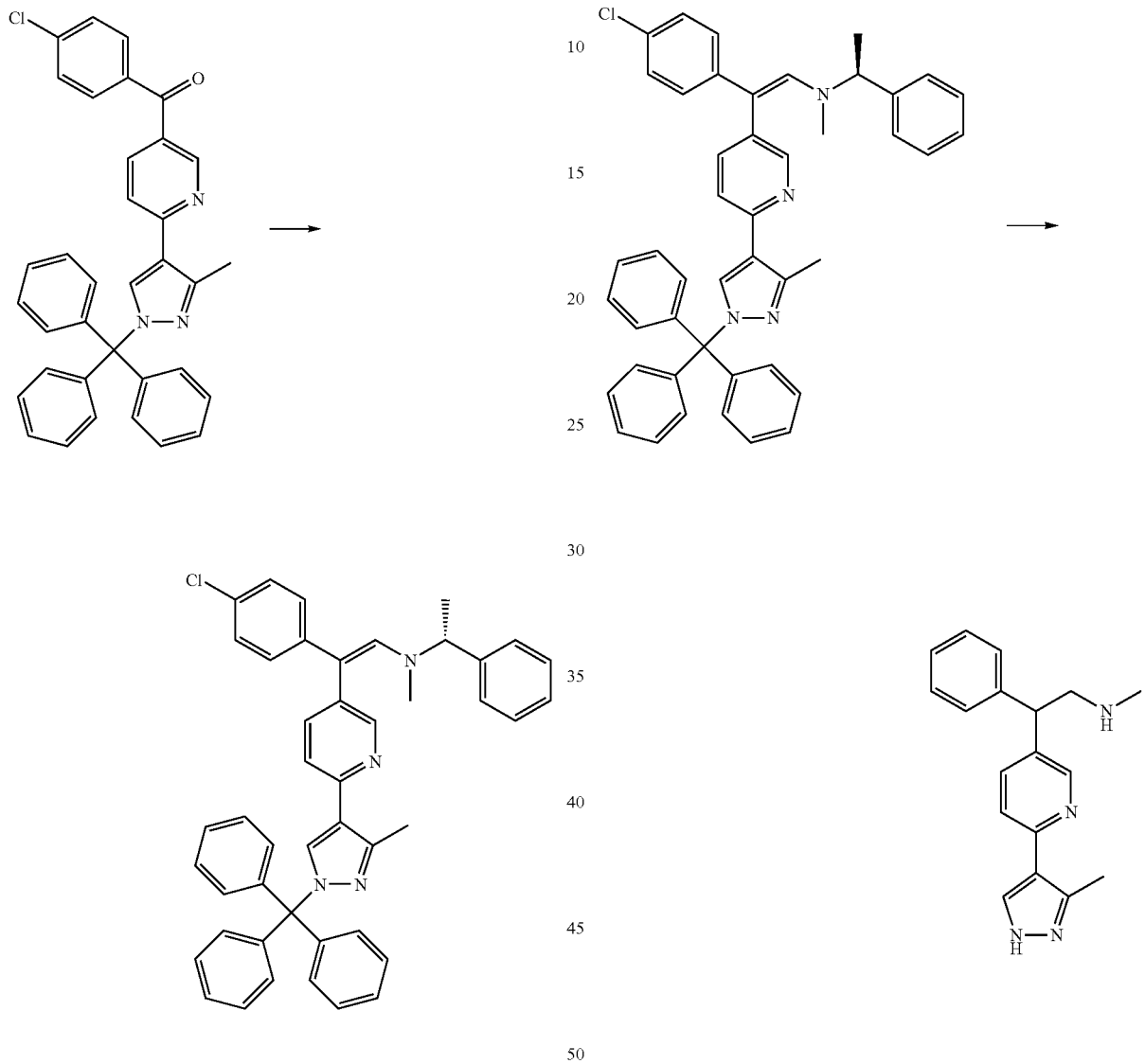

n-Butyllithium (0.47 ml, 0.76 mmol, 1.6M in Hexanes) was added dropwise to a solution of (R)(Diphenyl-phosphinoylmethyl)-methyl-(1-phenyl-ethyl)-amine* (0.18 g, 0.51 mmol) in dry tetrahydrofuran (9 ml) at −15° C. After 15 minutes a solution of (4-Chloro-phenyl)-[6-(3-methyl-1-trityl-1H-pyrazol-4-yl)-pyridin-3-yl]-methanone (0.14 g, 0.25 mmol) in tetrahydrofuran (0.9 ml) was added and the reaction mixture was stirred for a further 30 minutes at −15° C. before warming to room temperature over 1 hour. The reaction mixture was quenched with water, extracted with diethyl ether, organic extracts were combined, dried (MgSO$_4$) and concentrated to afford the title compound, which was used in the next step without further purification.

* This starting material can be made by the method described in Tetrahedron Asymmetry, 2003, 14, 1309-1316.

To a solution of {2-(4-Chloro-phenyl)-2-[6-(3-methyl-1-trityl-1H-pyrazol-4-yl)-pyridin-3-yl]-vinyl}-methyl-(1-phenyl-ethyl)-amine in ethanol was added palladium, 10 wt. % on activated carbon and the reaction mixture was subjected to a hydrogen atmosphere for 17 hours. The mixture was filtered through Celite®, the mother liquor was concentrated, the residue was purified by column chromatography (SiO$_2$), eluting with dichloromethane:methanol:acetic acid:water (240:20:3:2) to dichloromethane:methanol:acetic acid:water (90:18:3:2) to afford the title compound. LC/MS: (PS-A2) R$_t$ 1.59 [M+H]$^+$ 293.18. $^1$H NMR (Me-d$_3$-OD) δ 2.35 (3H, s), 2.40 (3H, s), 3.25 (2H, s), 4.15-4.20 (1H, t), 7.10-7.18 (1H, m), 7.25 (4H, m), 7.45 (1H, d), 7.67 (1H, dd), 7.80 (1H, s), 8.38 (1H, s).

Example 61

4-{4-[1-(4-Chloro-phenyl)-3-imidazol-1-yl-propyl]-phenyl}-1H-pyrazole

61A. 1-(4-Bromo-phenyl)-3-imidazol-1-yl-propan-1-ol

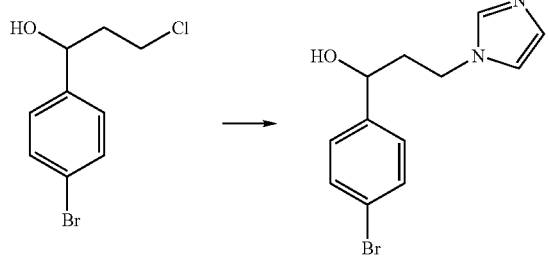

A solution of 1-(4-Bromo-phenyl)-3-chloro-propan-1-ol* (1.5 g, 6.01 mmol) and imidazole (1.23 g, 18.03 mmol) in dimethylformamide (18 ml) was heated at 100° C. for 18 hrs then partitioned between water and ethyl acetate. The organic extracts were combined, dried (MgSO$_4$), filtered, concentrated and purified by column chromatography (SiO$_2$), eluting with methanol:dichloromethane (2:98) to methanol:dichloromethane (6:94) to afford the title compound (0.75 g, 44% yield). LC/MS: (PS-B3) R$_t$ 2.48 [M+H]$^+$ 281.14, 283.11.

*This starting material can be made by the method described in Example 43A.

61B. 1-[3-(4-Bromo-phenyl)-3-(4-chloro-phenyl)-propyl]-1H-imidazole

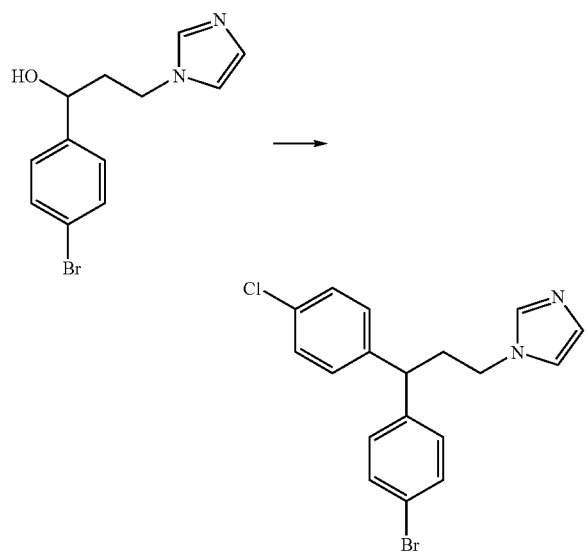

Chlorobenzene (5 ml) was reacted with 1-(4-Bromo-phenyl)-3-imidazol-1-yl-propan-1-ol (0.41 mg, 1.46 mmol) following the procedure set out in Example 42B to give the title compound (0.37 g, 67% yield). LC/MS: (PS-A2) R$_t$ 2.40 [M+H]$^+$ 375.16, 377.17.

61C. 4-{4-[1-(4-Chloro-phenyl)-3-imidazol-1-yl-propyl]-phenyl}-1H-pyrazole

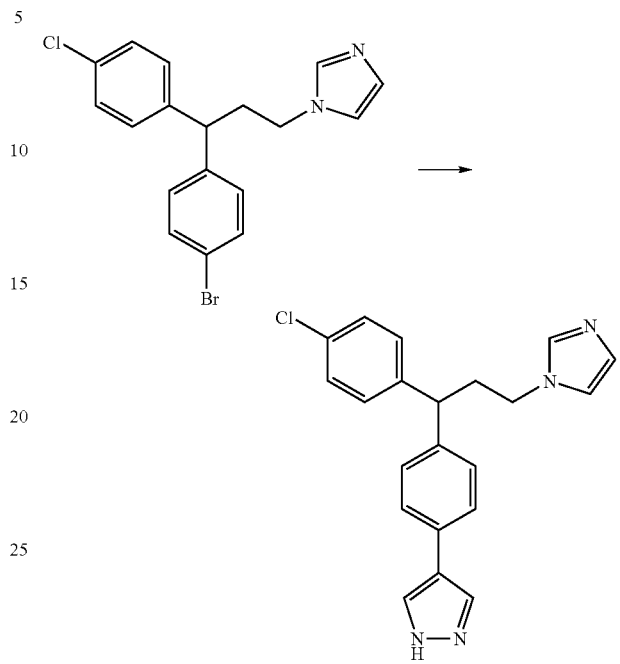

1-[3-(4-Bromo-phenyl)-3-(4-chloro-phenyl)-propyl]-1H-imidazole was reacted with 4-(4,4,5,5-tetramethyl-1,3,2-dioxaborolan-2-yl)-1H-pyrazole following the procedure set out in Example 1 to give the title compound. LC/MS: (PS-A2) R$_t$ 2.21 [M+H]$^+$ 363.28. $^1$H NMR (Me-d$_3$-OD) δ 2.55-2.70 (2H, m), 3.85-3.95 (1H, m), 3.95-4.10 (2H, m), 7.05 (1H, s), 7.10-7.60 (9H, m), 7.65 (1H, s), 7.90-8.00 (2H, d).

Example 62

4-[4-(3-Imidazol-1-yl-1-phenoxy-propyl)-phenyl]-1H-pyrazole

62A. 1-[3-(4-Bromo-phenyl)-3-phenoxy-propyl]-1H-imidazole

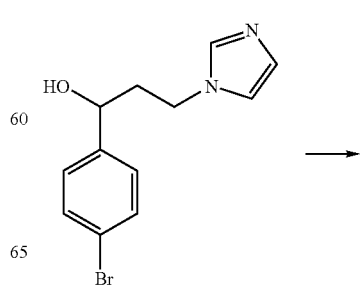

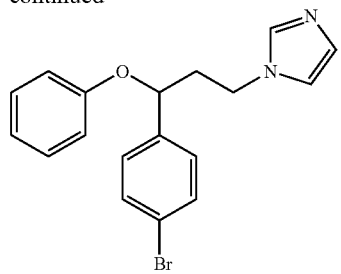

Phenol was reacted with 1-(4-Bromo-phenyl)-3-imidazol-1-yl-propan-1-ol* following the procedure set out in Example 48B to give the title compound. LC/MS: (PS-A2) $R_t$ 2.30 [M+H]$^+$ 357.26, 359.27.

*This starting material can be made by the method described in Example 47A.

62B. 4-[4-(3-Imidazol-1-yl-1-phenoxy-propyl)-phenyl]-1H-pyrazole

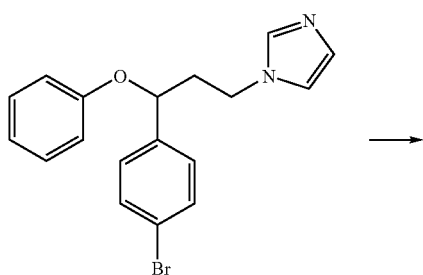

1-[3-(4-Bromo-phenyl)-3-phenoxy-propyl]-1H-imidazole was reacted with 4-(4,4,5,5-tetramethyl-1,3,2-dioxaborolan-2-yl)-1H-pyrazole following the procedure set out in Example 1 to give the title compound. LC/MS: (PS-A2) $R_t$ 2.05 [M+H]$^+$ 345.30. $^1$H NMR (Me-d$_3$-OD) δ 2.30-2.55 (2H, m), 4.25-4.45 (2H, m), 5.10-5.15 (1H, m), 6.80-6.90 (3H, m), 7.10 (1H, s), 7.15-7.20 (2H, t), 7.25 (1H, s), 7.35-7.40 (2H, d), 7.55-7.60 (2H, d), 7.85 (1H, s), 7.95 (2H, s).

Example 63

4-{4-[4-(1H-Pyrazol-4-yl)-phenyl]-piperidin-4-yl}-phenol

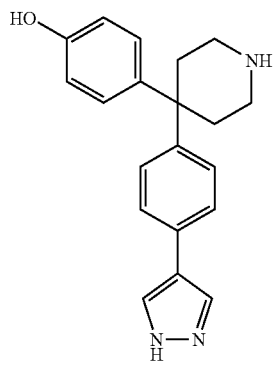 [SMILES: Oc1ccc(C2(c3ccc(-c4cn[nH]c4)cc3)CCNCC2)cc1]

By following the procedure described in Example 14 but substituting chlorobenzene for phenol using nitrobenzene as the solvent, the title compound was obtained. LC/MS: (PS-A3) $R_t$ 5.07 [M+H]$^+$ 320. $^1$H NMR (d$_6$-DMSO) δ 7.97 (2H, s), 7.49 (2H, d), 7.25 (2H, d), 7.10 (2H, d), 6.68 (2H, d), 2.840 (4H, bs), 2.376 (4H, bs).

Example 64

1-{(4-Chloro-phenyl)-[4-(1H-pyrazol-4-yl)-phenyl]-methyl}-piperazine

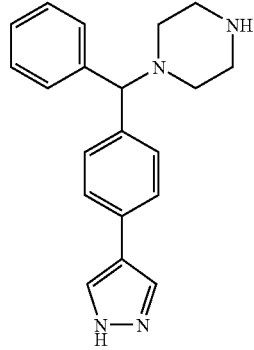 [SMILES: c1ccc(C(c2ccc(-c3cn[nH]c3)cc2)N2CCNCC2)cc1]

By following the procedure described in Example 57, the title compound was obtained. LCMS: (PS-A3) $R_t$ 6.38 [M+H]$^+$ 319. $^1$H NMR (Me-d$_3$-OD) δ 8.53 (2H, s), 7.90 (2H, d), 7.83 (2H, d), 7.71 (2H, d), 7.40-7.30 (3H, m), 5.70 (1H, s), 3.68 (4H, bs), 3.51-3.48 (4H, m).

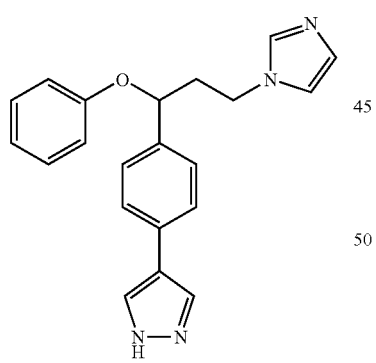

Example 65

{2-(4-Fluoro-phenyl)-2-[4-(1H-pyrazol-4-yl)-phenyl]-ethyl}-methyl-amine

65A. [2-(4-Bromo-phenyl)-2-(4-fluoro-phenyl)-ethyl]-carbamic acid benzyl ester

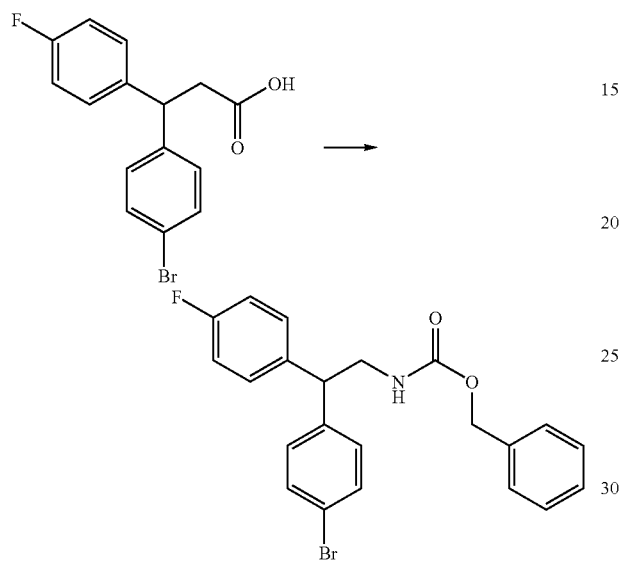

To a solution of 3-(4-fluorophenyl)-3-(4-bromophenyl) propionic acid* (1.0 g, 3.09 mmol) in acetone (4 ml) at 0° C. was sequentially added triethylamine (561 ul, 4.02 mmol) in acetone (1.6 ml) and ethyl chloroformate (443 ul, 4.64 mmol) in acetone (1.6 ml). The reaction was allowed to warm to room temperature, stirred for 30 minutes before cooling again to 0° C. and sodium azide (402 mg, 6.18 mmol) in water (1.6 ml) was added. The resultant brown solution was stirred for 45 minutes before addition of water (10 ml) and diethyl ether (10 ml). The aqueous layer was separated and extracted further with ethyl acetate (10 ml). The combined organic liquors were washed with saturated brine, dried (MgSO$_4$) and concentrating in vacuo. The residue was dissolved in anhydrous toluene (12 ml) before addition of benzyl alcohol (567 ul, 9.27 mmol) and heating to 80° C. for 40 minutes. The reaction was allowed to cool to room temperature before addition of ethyl acetate (50 ml) and saturated sodium bicarbonate (50 ml). The organic liquors were separated and washed with further bicarbonate solution (50 ml), hydrochloric acid (2N, 100 ml) and saturated brine (50 ml) before drying (MgSO$_4$) and concentrating in vacuo. The residue was purified by column chromatography (SiO$_2$), eluting with ethyl acetate/petrol (5:95) gradient to (15:85) to afford the title compound (594 mg, 45%). LC/MS: (PS-A2) R$_t$ 3.18 No ionisation.

* This starting material can be made by the method described in Example 8A to 8C, substituting 4-chlorophenylmagnesium bromide for 4-fluorophenylmagnesium bromide

65B. {2-(4-Fluoro-phenyl)-2-[4-(1H-pyrazol-4-yl)-phenyl]-ethyl}-carbamic acid benzyl ester

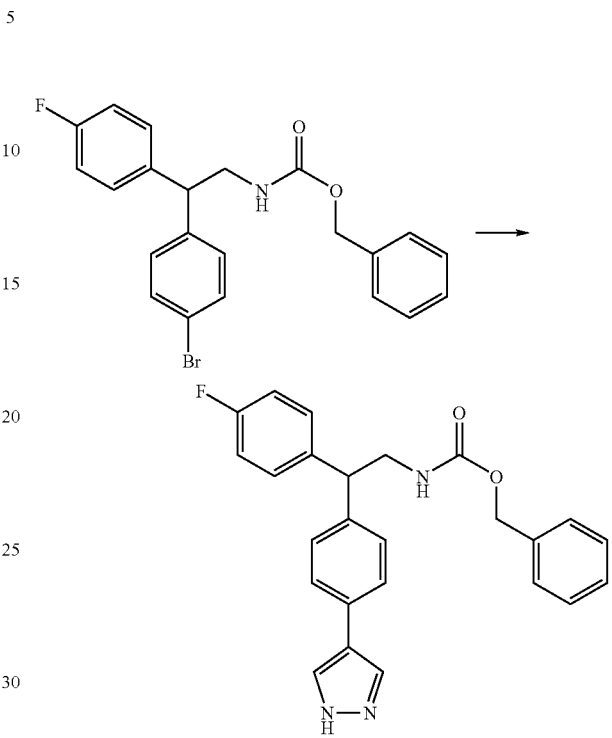

[2-(4-Bromo-phenyl)-2-(4-fluoro-phenyl)-ethyl]-carbamic acid benzyl ester was reacted with 4-(4,4,5,5-tetramethyl-1,3,2-dioxaborolan-2-yl)-1H-pyrazole following the procedure set out in Example 1 to give the title compound. LC/MS: (PS-A2) R$_t$ 3.20 [M+H]$^+$ 416.

65C. {2-(4-Fluoro-phenyl)-2-[4-(1H-pyrazol-4-yl)-phenyl]-ethyl}-methyl-amine

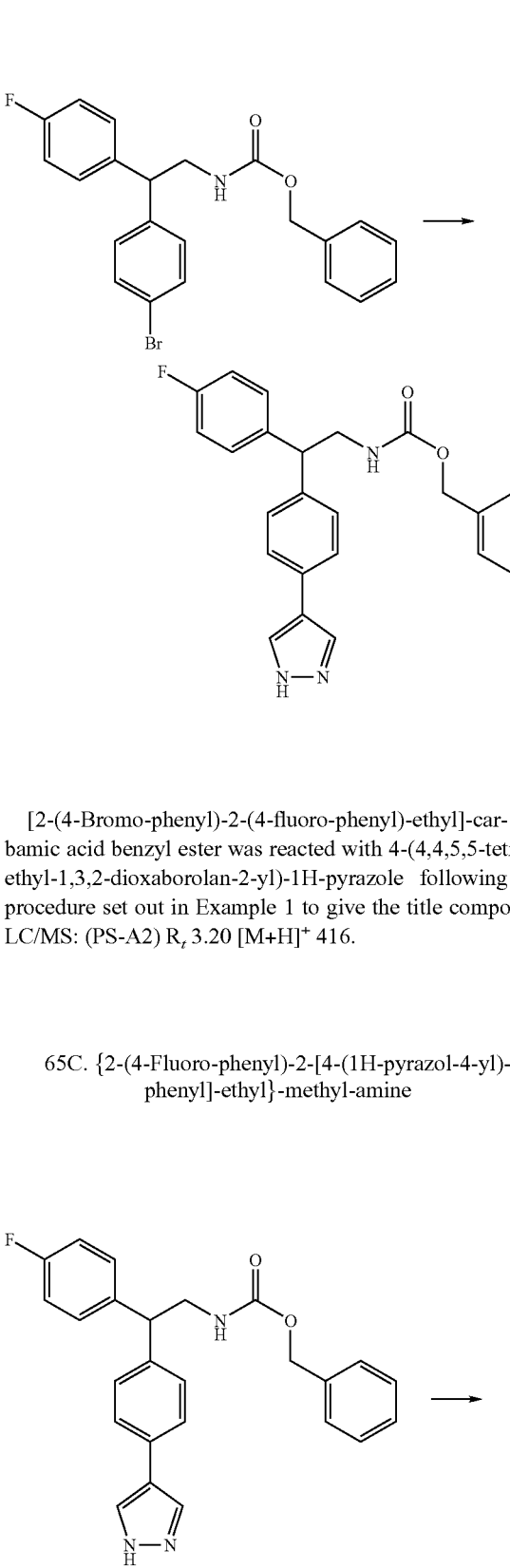

-continued

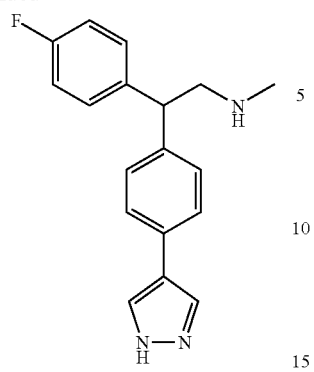

Lithium aluminium hydride (5.3 ml, 5.30 mmol, 1M in tetrahydrofuran) was slowly added to {2-(4-Fluoro-phenyl)-2-[4-(1-pyrazol-4-yl)-phenyl]-ethyl}-carbamic acid benzyl ester (439 mg, 1.06 mmol) in tetrahydrofuran (5 ml) at 0° C. under nitrogen. The reaction mixture was allowed to warm to room temperature, stirred for 51 hours and quenched with water (5 ml), aqueous sodium hydroxide (2N, 5 ml) and ethyl acetate (10 ml). The aqueous layer was separated, extracted with ethyl acetate (2×20 ml). The combined organic liquors were washed with saturated aqueous brine then dried (MgSO$_4$) and concentrated in vacuo. The residue was purified by column chromatography (SiO$_2$), eluting with dichloromethane:methanol:acetic acid:water (120:15:3:2) gradient to (90:18:3:2) to afford the title compound, which was subsequently converted to the hydrochloride salt (100 mg, 32%). LC/MS: (PS-A2) R$_t$ 1.87 [M+H]$^+$ 296. $^1$H NMR (Me-d$_3$-OD) δ 8.20 (2H, s), 7.57 (2H, d), 7.34-7.29 (4H, m), 7.02 (2H, t), 4.32 (1H, t), 3.67 (2H, d), 2.65 (3H, s).

Example 66

{2-(3-Chloro-phenyl)-2-[4-(1H-pyrazol-4-yl)-phenyl]-ethyl}-methyl-amine

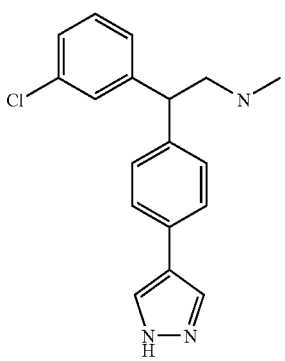 [SMILES: CNCC(c1ccc(-c2cn[nH]c2)cc1)c1cccc(Cl)c1]

By following the procedure described in Example 65 but substituting 4-fluorophenylmagnesium bromide for 3-chlorophenylmagnesium bromide the title compound was obtained. LC/MS: (PS-A3) R$_t$ 4.92 [M+H]$^+$ 312. $^1$H NMR (Me-d$_3$-OD) δ 8.50 (2H, s), 7.63 (2H, d), 7.39 (2H, d), 7.34 (1H, s), 7.30-7.20 (3H, m), 4.40 (1H, t), 3.70 (2H, d), 2.65 (3H, s).

Example 67

4-[4-(2-Methoxy-ethoxy)-phenyl]-4-[4-(1H-pyrazol-4-yl)-phenyl]-piperidine 67A. 4-(4-Bromo-phenyl)-4-(4-hydroxy-phenyl)-piperidine-1-carboxylic acid tert-butyl ester

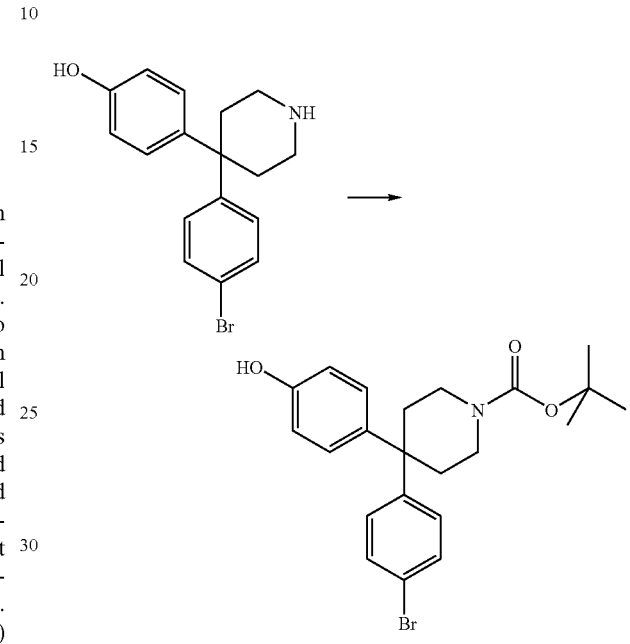

By following the procedure described in Example 47B but substituting 4-[1-(4-Bromo-phenyl)-2-methylamino-ethyl]-phenol for 4-[4-(4-Bromo-phenyl)-piperidin-4-yl]-phenol* the title compound was obtained. $^1$H NMR (d$_6$-DMSO) δ 7.45 (2H, d), 7.25 (2H, d), 7.11 (2H, d), 6.68 (2H, d), 3.35-3.18 (4H, m), 2.31-2.20 (4H, m), 1.38 (9H, s).

* This starting material can be made by the method described in Example 63

67B. 4-(4-Bromo-phenyl)-4-[4-(2-methoxy-ethoxy)-phenyl]-piperidine-1-carboxylic acid tert-butyl ester

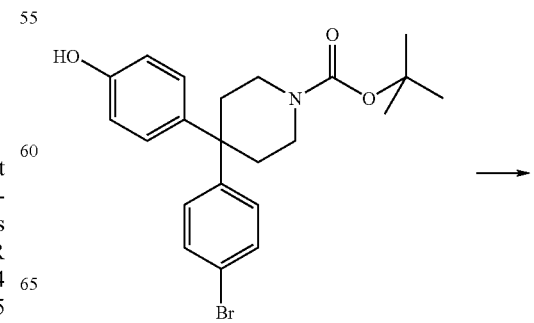

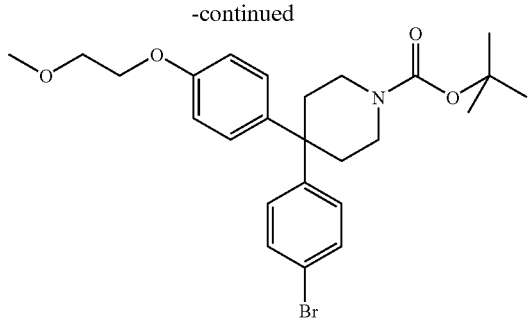

A solution of 4-(4-Bromo-phenyl)-4-(4-hydroxy-phenyl) piperidine-1-carboxylic acid tert-butyl ester (100 mg, 0.23 mmol), 2-bromoethyl methylether (200 ul) and potassium carbonate (64 mg, 0.46 mmol) in dimethylformamide (2 ml) was heated in a CEM Explorer™ microwave to 50° C. for 30 minutes using 50 watts power. The reaction was poured into sodium hydroxide (2N, 4 ml), stirred for 5 minutes then extracted into ethyl acetate (2×30 ml). The combined organic liquors were dried (MgSO$_4$), concentrated and the residue was purified by column chromatography (SiO$_2$), eluting with ethyl acetate/petrol (25:75) gradient to (50:50) to afford the title compound (82 mg). LCMS: (PS-A2) R$_t$ 4.00 [M+H]$^+$ 490.

67C. 4-[4-(2-Methoxy-ethoxy)-phenyl]-4-[4-(1H-pyrazol-4-yl)-phenyl]-piperidine

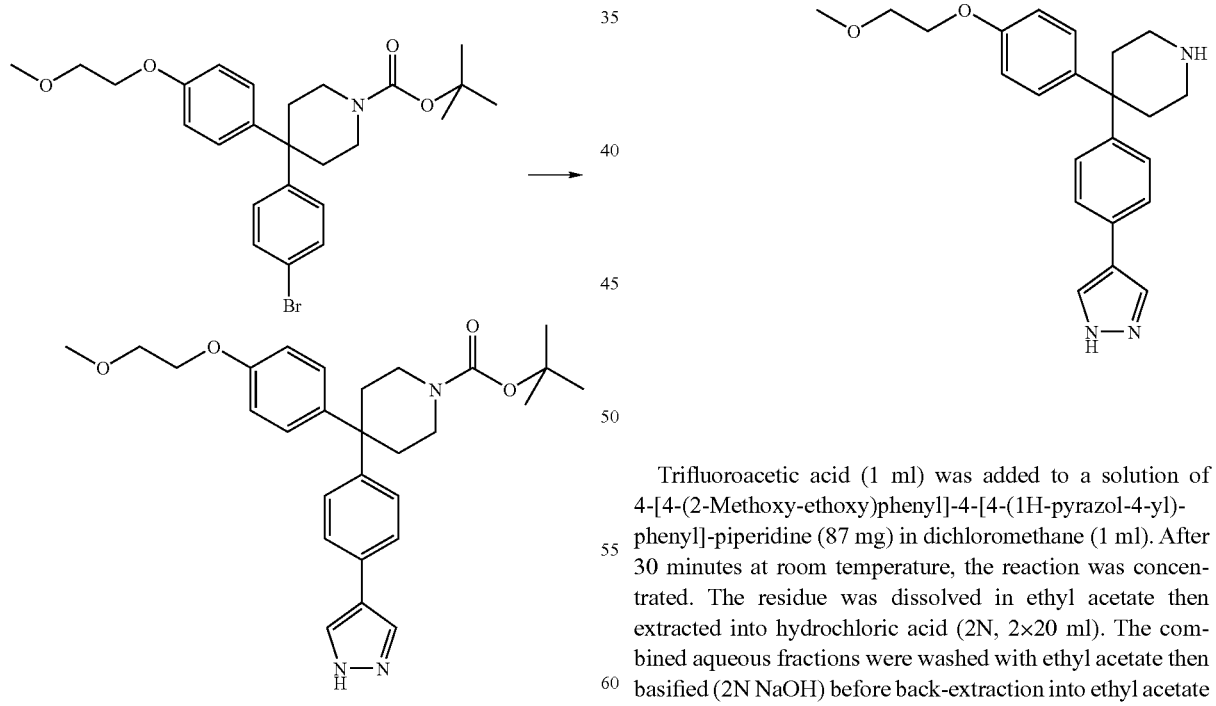

4-(4-Bromo-phenyl)-4-[4-(2-methoxy-ethoxy)-phenyl]-piperidine-1-carboxylic acid tert-butyl ester was reacted with 4-(4,4,5,5-tetramethyl-1,3,2-dioxaborolan-2-yl)1H-pyra-zole following the procedure set out in Example 1, substituting tetrakis triphenylphosphine palladium (0) as catalyst, the title compound was obtained. LC/MS: (PS-A2) R$_t$ 3.27 [M+H]$^+$ 478.

67D. 4-[4-(2-Methoxy-ethoxy)-phenyl]-4-[4-(1H-pyrazol-4-yl)-phenyl]-piperidine

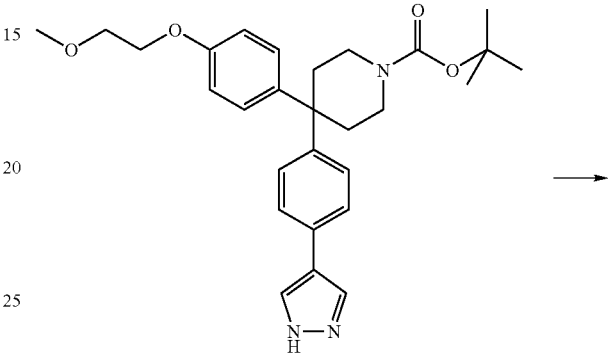

Trifluoroacetic acid (1 ml) was added to a solution of 4-[4-(2-Methoxy-ethoxy)phenyl]-4-[4-(1H-pyrazol-4-yl)-phenyl]-piperidine (87 mg) in dichloromethane (1 ml). After 30 minutes at room temperature, the reaction was concentrated. The residue was dissolved in ethyl acetate then extracted into hydrochloric acid (2N, 2×20 ml). The combined aqueous fractions were washed with ethyl acetate then basified (2N NaOH) before back-extraction into ethyl acetate (2×20 ml). The combined organic liquors were washed with saturated brine solution then dried (MgSO$_4$) and concentrated to yield the title compound (66 mg). LCMS: (PS-A3) R$_t$ 6.08 [M+H]$^+$ 378. $^1$H NMR (Me-d$_3$-OD) δ 7.92 (2H, s), 7.51 (2H, d), 7.31 (2H, d), 7.25 (2H, d), 6.89 (2H, d), 4.13 (2H, t), 3.73 (2H, t), 3.42 (3H, s), 2.94 (4H, bs), 2.44 (4H, bs).

Example 68

4-[4-(3-Methoxy-propoxy)-phenyl]-4-[4-(1H-pyrazol-4-yl)-phenyl]-piperidine

68A. 4-(4-Bromo-phenyl)-4-[4-(3-methoxy-propoxy)-phenyl]-piperidine-1-carboxylic acid tert-butyl ester

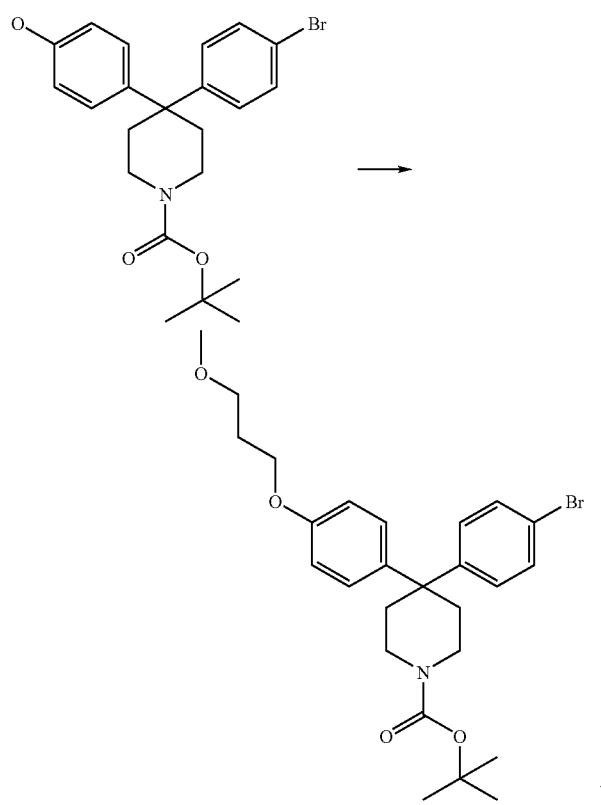

Tosyl chloride (572 mg, 3.0 mmol) was added to a solution of 3-methoxypropanol (191 ul, 2.0 mmol) in pyridine (1 ml). This was stirred at room temperature for 5.5 hours then diluted with ethyl acetate (20 ml) and washed with hydrochloric acid (2N, 3×10 ml) and saturated brine (10 ml). The liquors were dried (MgSO$_4$) and concentrated to furnish a colourless oil (600 mg). This oil was dissolved in dimethylformamide (2 ml) and to this solution was added potassium carbonate (64 mg, 0.46 mmol) and 4-(4-Bromo-phenyl)-4-(4-hydroxy-phenyl)-piperidine-1-carboxylic acid tert-butyl ester* (100 mg, 0.231 mmol). The resultant mixture was stirred at 100° C. for 4 hours. Once cooled, water (20 ml) was added and the mixture was extracted with ethyl acetate (3×10 ml). The combined organic liquors were washed with brine (10 ml) before drying (MgSO$_4$) and concentrating. The residue was purified by column chromatography (SiO$_2$), eluting with a gradient from 10-20% ethyl acetate/petrol to furnish the title compound as a colourless oil (131 mg). LCMS: R$_t$ 4.20 [M+H]$^+$ 504.

* This starting material can be made by the method described in Example 67A

68B. 4-[4-(3-Methoxy-propoxy)-phenyl]-4-[4-(1H-pyrazol-4-yl)-phenyl]-piperidine

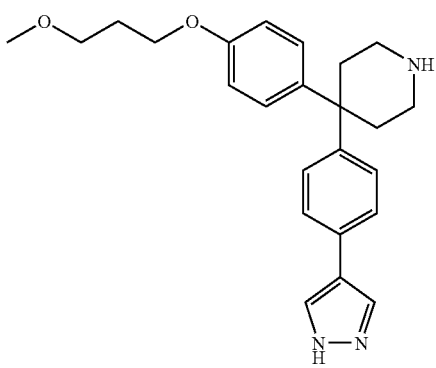 [SMILES: COCCCOc1ccc(C2(c3ccc(-c4cn[nH]c4)cc3)CCNCC2)cc1]

By following the procedure described in Example 67C and 67D but substituting 4-(4-Bromo-phenyl)-4-[4-(2-methoxy-ethoxy)-phenyl]-piperidine-1-carboxylic acid tert-butyl ester for 4-(4-Bromo-phenyl)-4-[4-(3-methoxy-propoxy)-phenyl]-piperidine-1-carboxylic acid tert-butyl ester the title compound was obtained. LCMS: R$_t$ 6.65 [M+H]$^+$ 392. $^1$H NMR (Me-d$_3$-OD) δ 7.94 (2H, s), 7.57 (2H, d), 7.34 (2H, d), 7.27 (2H, d), 6.91 (2H, d), 4.04 (2H, t), 3.56 (2H, t), 3.34-3.33 (5H, m), 3.24-3.22 (4H, m), 2.67-2.66 (4H, m)

Example 69

3-(3,4-Dichloro-phenyl)-3-[4-(1H-pyrazol-4-yl)-phenyl]-propionamide

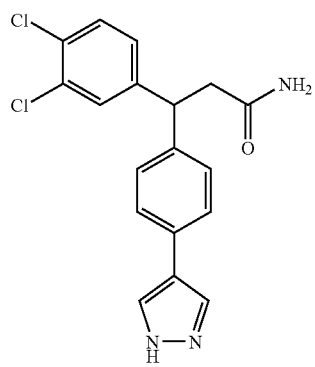 [SMILES: NC(=O)CC(c1ccc(-c2cn[nH]c2)cc1)c1ccc(Cl)c(Cl)c1]

By following the procedure described in Example 9A and 9B but substituting 3,4-difluorophenylmagnesium bromide for 3,4-dichlorophenylmagnesium bromide, the title compound was obtained. LC/MS: (PS-A3) R$_t$ 9.82 [M+H]$^+$ 360.14, 362.12. $^1$H NMR (Me-d$_3$-OD) δ 2.90-3.00 (2H, d), 4.50-4.60 (1H, t), 7.10-7.30 (3H, m), 7.40-7.45 (2H, d), 7.50-7.55 (2H, d), 7.85-8.05 (2H, br s).

Example 70

2-(4-{2-Methylamino-1-[4-(1H-pyrazol-4-yl)-phenyl]-ethyl}-phenoxy)-isonicotinamide

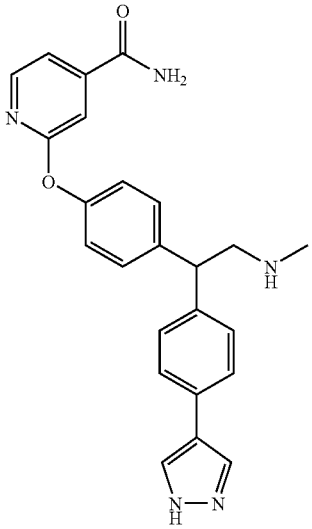 [SMILES: CNCC(c1ccc(Oc2cc(C(N)=O)ccn2)cc1)c1ccc(-c2cn[nH]c2)cc1]

By following the procedure described in Example 47, but substituting 2-chloropyrazine for 2-chloro-4-cyanopyridine, the title compound was obtained. LC/MS: (PS-B3) $R_t$ 2.27 [M+H]$^+$ 414. $^1$H NMR (Me-d$_3$-OD) δ 2.45 (3H, s), 3.55 (1H, dd), 3.65 (1H, dd), 4.25 (1H, t), 7.10 (2H, d), 7.30-7.38 (3H, m), 7.40 (2H, d), 7.48 (1H, d), 7.56 (2H, d), 7.95 (2H, s), 8.22 (1H, d).

Example 71

{2-(4-Chloro-phenoxy)-2-[4-(1H-pyrazol-4-yl)-phenyl]-ethyl}-methyl-amine

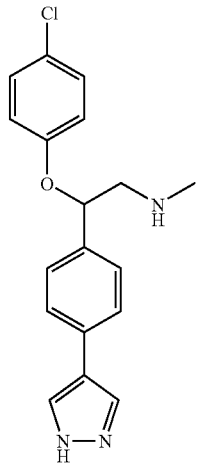 [SMILES: CNCC(Oc1ccc(Cl)cc1)c1ccc(-c2cn[nH]c2)cc1]

By following the procedure described in Example 48, but substituting phenol for 4-chlorophenol, the title compound was obtained. LC/MS: (PS-A3) $R_t$ 2.29 [M-ClPhO+H]$^+$ 200. $^1$H NMR (Me-d$_3$-OD) δ 2.50 (3H, s), 2.86 (1H, dd), 3.10 (1H, dd), 5.35 (1H, dd), 6.89 (2H, d), 7.17 (2H, d), 7.40 (2H, d), 7.57 (2H, d), 7.93 (2H, s).

Example 72

3-{2-(4-Chloro-phenyl)-2-[4-(1H-pyrazol-4-yl)-phenyl]-ethyl}-amino)-propan-1-ol

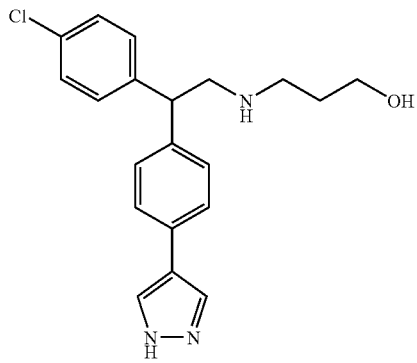 [SMILES: OCCCNCC(c1ccc(Cl)cc1)c1ccc(-c2cn[nH]c2)cc1]

By following the procedure described in Example 20 but substituting dimethylamine for 3-aminopropan-1-ol the title compound was obtained. LC/MS: (PS-A2) $R_t$ 2.05 [M+H]$^+$ 356. $^1$H NMR (Me-d$_3$-OD) δ 1.87 (2H, quintet), 1.98 (AcOH, s), 3.23 (2H, t), 3.68 (2H, t), 3.75 (2H, dd), 4.4 (1H, t), 7.36 (2H, d), 7.4 (4H, s), 7.62 (2H, d), 7.97 (2H, s).

Example 73

2-{2-(4-Chloro-phenyl)-2-[4-(1H-pyrazol-4-yl)-phenyl]-ethylamino}-ethanol

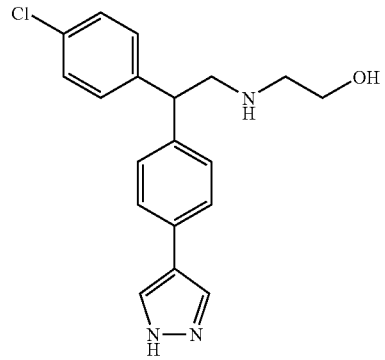 [SMILES: OCCNCC(c1ccc(Cl)cc1)c1ccc(-c2cn[nH]c2)cc1]

By following the procedure described in Example 20 but substituting dimethylamine for 2-aminoethan-1-ol the title compound was obtained. LC/MS: (PS-A2) $R_t$ 2.05 [M+H]$^+$ 342. $^1$H NMR (Me-d$_3$-OD) δ 1.98 (AcOH, s), 3.10 (2H, s), 3.69 (2H, dd), 3.78, (2H, t), 4.39 (1H, t), 7.36 (2H, d), 7.38 (4H, s), 7.61 (2H, d), 7.97 (2H, s).

Example 74

{2-(4-Chloro-phenyl)-2-[4-(1H-pyrazol-4-yl)-phenyl]-ethyl}-cyclopropylmethyl-amine

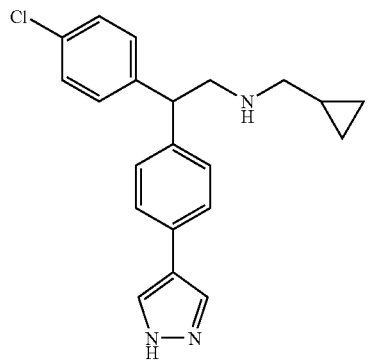 [SMILES: Clc1ccc(C(CNCC2CC2)c2ccc(-c3cn[nH]c3)cc2)cc1]

By following the procedure described in Example 20 but substituting dimethylamine for cyclopropylmethylamine the title compound was obtained. LC/MS: (PS-A2) $R_t$ 2.21 [M+H]$^+$ 352. $^1$H NMR (Me-d$_3$-OD) δ −0.4-0.3 (2H, m), 0.35-0.40 (2H, m), 0.78-0.87 (1H, m), 2.42 (2H, d), 3.15-3.25 (2H, m), 4.11 (1H, t), 7.16-7.27 (6H, m), 7.45 (2H, d), 7.82, (2H, s).

Example 75

Methyl-[2-[4-(1H-pyrazol-4-yl)-phenyl]-2-(4-pyridin-3-yl-phenyl)-ethyl]-amine

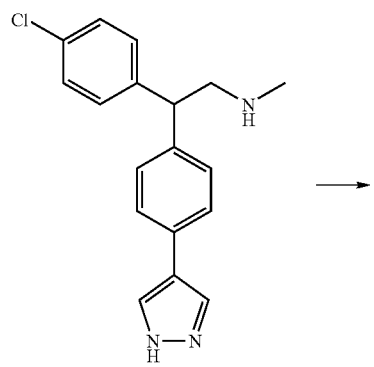

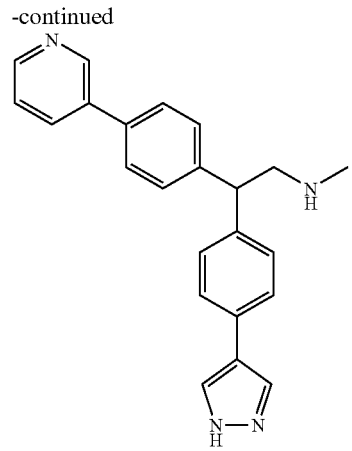

By following the procedure described in Example 1 but substituting 4-(4,4,5,5-tetramethyl-1,3,2-dioxaborolan-2-yl)-1H-pyrazole for 3-(4,4,5,5-Tetramethyl-[1,3,2]dioxaborolan-2-yl)-pyridine and coupling to {2-(4-Chloro-phenyl)-2-[4-(1H-pyrazol-4-yl)-phenyl]-ethyl}-methyl-amine*, the title compound was obtained. LC/MS: (PS-B3) $R_t$ 2.42 [M+H]$^+$ 355. $^1$H NMR (Me-d$_3$-OD) δ 1.94 (AcOH, s), 2.72 (3H, s), 3.73 (2H, d), 4.46 (1H, t), 7.41 (2H, d), 7.51-7.56 (3H, m), 7.63 (2H, d), 7.70 (2H, d), 7.96 (2H, s), 8.10 (1H, dt), 8.53 (1H, dd), 8.80 (1H, d).

* This starting material can be made by the method described in Example 21.

Example 76

4-{3-Methylamino-1-[4-(1H-pyrazol-4-yl)-phenyl]-propyl}-phenol

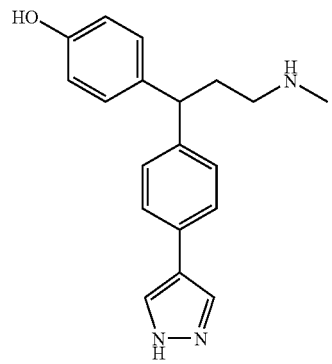 [SMILES: CNCCC(c1ccc(O)cc1)c1ccc(-c2cn[nH]c2)cc1]

By following the procedure described in Example 8 but substituting 4-chlorophenylmagnesium bromide for 4-anisylmagnesium bromide, the title compound can be obtained LC/MS: (PS-A2) $R_t$ 1.82 [M+H]$^+$ 308. $^1$H NMR (Me-d$_3$-OD) δ 1.92 (AcOH, s), 2.34-2.43 (2H, m), 2.64 (3H, s), 2.86-2.92 (2H, m), 3.96 (1H, t), 6.75 (2H, d), 7.13 (2H, d), 7.29 (2H, d), 7.52 (2H, d), 7.93 (2H, d).

Example 77

3-(4-Methoxy-phenyl)-3-[4-(1H-pyrazol-4-yl)-phenyl]-propylamine

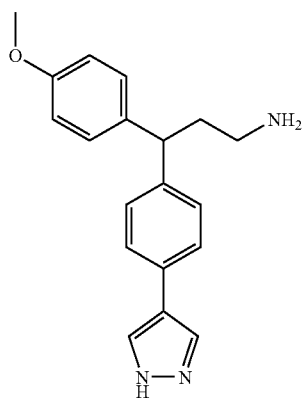 [SMILES: COc1ccc(C(CCN)c2ccc(-c3cn[nH]c3)cc2)cc1]

By following the procedure described in Example 8 but substituting 4-chlorophenylmagnesium bromide for 4-anisylmagnesium bromide and methylamine for ammonia (2M in methanol), the title compound was obtained. LC/MS: (PS-A2) $R_t$ 1.82 [M+H]$^+$ 308. $^1$H NMR (Me-d$_3$-OD) δ 2.23-2.32 (2H, m), 2.74 (2H, dd), 3.65 (3H, s), 3.89 (1H, t), 6.77 (2H, d), 7.11 (2H, s), 7.17 (2H, d), 7.41 (2H, d), 7.71 (2H, s), 8.41 (HCO$_2$H, br s).

Example 78

4-(4-Chloro-phenyl)-4-[4-(3-methyl-1H-pyrazol-4-yl)-phenyl]-piperidine

78A. 4-(4-Chloro-phenyl)-4-[4-(3-methyl-1-trityl-1H-pyrazol-4-yl)-phenyl]-pideridine

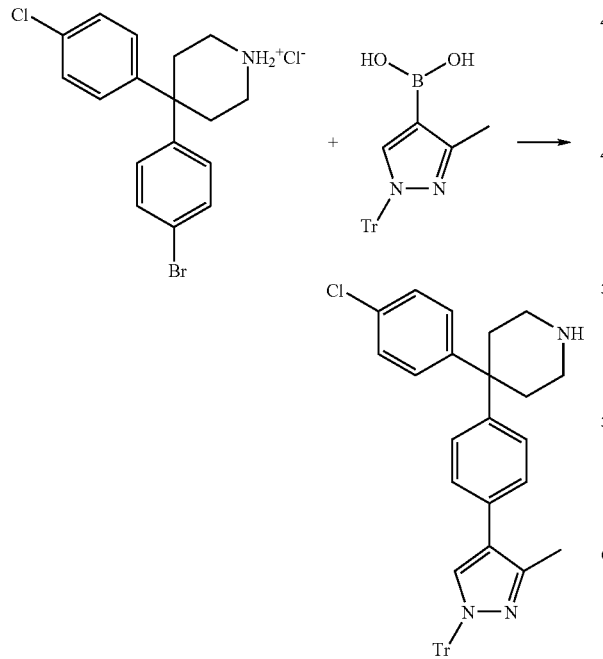

4-(4-bromo-phenyl)-4-(4-chloro-phenyl)-piperidine hydrochloride was reacted with 3-methyl-1-trityl-1H-pyrazole-4-boronic acid* following the procedure set out in Example 1, but using tetrakis(triphenylphosphine)palladium (0) as the catalyst to give the title compound. LC/MS: (PS-B3) $R_t$ 2.78 min [M+H]$^+$ 594.

\* This starting material can be made by the method described in EP1382603

78B. 4-(4-Chloro-phenyl)-4-[4-(3-methyl-1H-pyrazol-4-yl)-phenyl]-piperidine

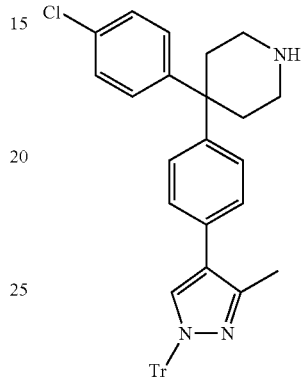

A suspension of 4-(4-chloro-phenyl)-4-[4-(3-methyl-1-trityl-1H-pyrazol-4-yl)-phenyl]-piperidine (178 mg, 0.30 mmol) in 5N hydrochloric acid (5 mL), THF (5 mL) and methanol (5 mL) was stirred for 140 minutes. The organic solvents were removed in vacuo then the resulting solution was diluted with 2N HCl and washed with ether. The aqueous phase was basified by addition of sodium hydroxide pellets then extracted with ethyl acetate. This organic extract was washed with brine, dried (MgSO$_4$), filtered and concentrated to give a residue which was purified by column chromatography (SiO$_2$), eluting with a gradient of 2M ammonia in methanol (5% to 7.5%) and dichloromethane. The product was further purified by preparative HPLC to give the title compound which was converted to its dihydrochloride salt (84 mg, 80%); LCMS (PS-A3) $R_t$ 6.86 min [M+H]$^+$ 352. $^1$H NMR (Me-d$_3$-OD) δ 2.55 (3H, s), 2.70-2.75 (4H, m), 3.22-3.27 (4H, m), 7.35-7.41 (4H, m), 7.47-7.54 (4H, m), 8.32 (2H, s).

Example 79

2-(4-Chloro-phenyl)-2-[4-(1H-pyrazol-4-yl)-phenyl]-morpholine 79A. 2-(4-Chloro-phenyl)-2-(4-iodo-phenyl)-oxirane

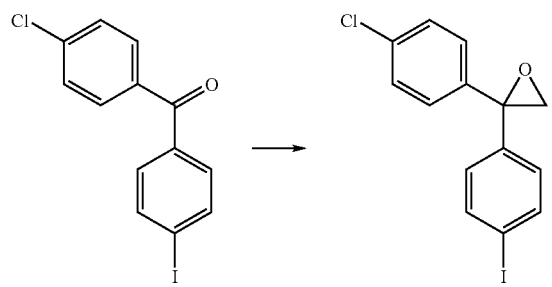 [SMILES: O=C(c1ccc(Cl)cc1)c1ccc(I)cc1 ; Clc1ccc(C2(c3ccc(I)cc3)CO2)cc1]

Sodium hydride (60% dispersion in oil, 128 mg, 3.2 mmol) was placed under N2 then DMSO (5 mL) was added. Trimethylsulfonium iodide (0.66 g, 3.2 mmol) was added as a solid after 15 min, followed after a further 30 min by (4-chloro-phenyl)-(4-iodo-phenyl)-methanone. The mixture was stirred at room temperature for 24 hours then diluted with ethyl acetate and washed with 1:2 water/brine, water and brine (×2). The organic phase was dried (MgSO$_4$), filtered and concentrated to give the title compound (1.01 g, 97%), which was used without further purification. LCMS (PS-A2) $R_t$ 4.07 min [M–H]$^+$ 355.

79B. 1-(4-Chloro-phenyl)-2-(2-hydroxy-ethylamino)-1-(4-iodo-phenyl)-ethanol

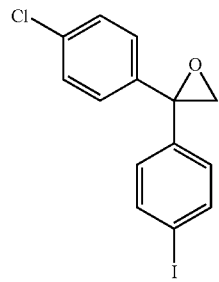

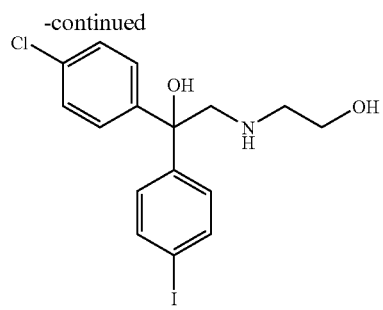

A solution of 2-(4-chloro-phenyl)-2-(4-iodo-phenyl)-oxirane (0.60 g, 1.68 mmol), ethanolamine (0.5 mL, 8.3 mmol) and triethylamine (0.5 mL, 3.6 mmol) in iso-propanol (5 mL) was maintained at 50° C. for 72 hours then concentrated in vacuo. The residue was taken up in ethyl acetate and washed with saturated potassium carbonate solution/water (1:9). The aqueous phase was extracted a second time with ethyl acetate, then the combined extracts were washed with brine, dried (MgSO$_4$), filtered and concentrated to give the title compound (701 mg, quantitative); LCMS (PS-A2) $R_t$ 2.29 min [M+H]$^+$ 418, [M–H$_2$O+H]$^+$ 400.

79C. 2-(4-Chloro-phenyl)-2-(4-iodo-phenyl)-morpholine

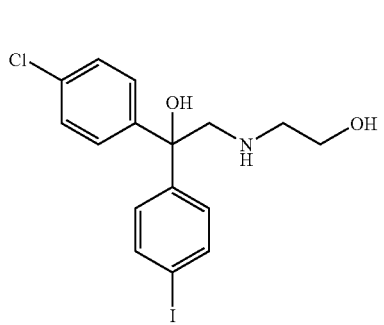

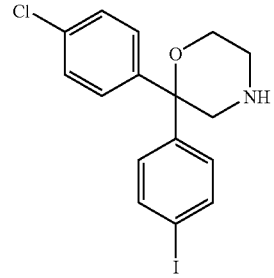

A solution of 1-(4-chloro-phenyl)-2-(2-hydroxy-ethylamino)-1-(4-iodo-phenyl)-ethanol (701 mg, 1.68 mmol) in DCM (10 mL) was treated with concentrated H$_2$SO$_4$ (0.1 mL, 1.9 mmol). After 20 hours, another portion of H$_2$SO$_4$ (1.0 mL, 19 mmol) was added and the mixture stirred for a further 2 hours. The mixture was diluted with ethyl acetate and washed with saturated potassium carbonate and brine then dried (MgSO$_4$), filtered and concentrated. The residue was purified by column chromatography (SiO$_2$), eluting with 0.5% triethylamine in ethyl acetate to afford the title compound (290 mg, 43%); LCMS (PS-A2) R$_t$ 2.40 min [M+H]$^+$ 400.

79D. 2-(4-Chloro-phenyl)-2-[4-(1H-pyrazol-4-yl)-phenyl]-morpholine

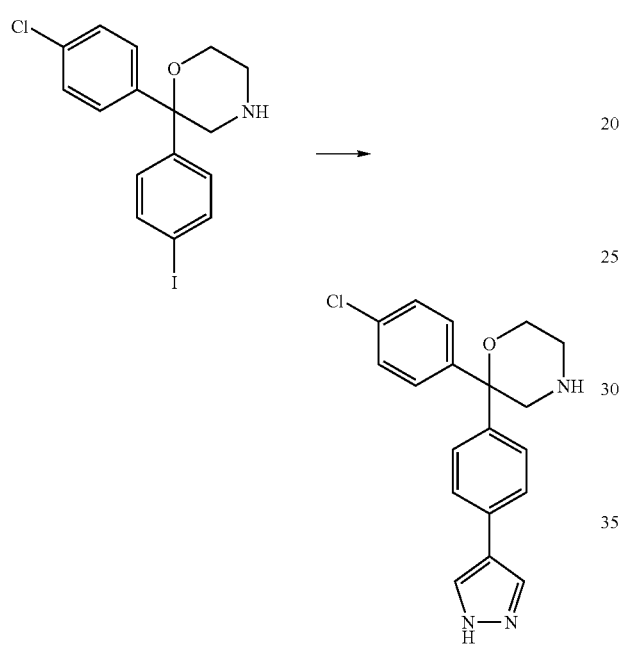

2-(4-chloro-phenyl)-2-(4-Iodo-phenyl)morpholine was reacted with 4-(4,4,5,5-tetramethyl-1,3,2-dioxaborolan-2-yl)-1H-pyrazole following the procedure set out in Example 1, but using tetrakis(triphenylphosphine)palladium (0) as the catalyst to give the title compound. LCMS (PS-A3) R$_t$ 6.88 min [M+H$^{+}$] 340. $^1$H NMR (Me-d$_3$-OD) δ 2.84-2.88 (2H, m), 3.32-3.36 (1H, m), 3.45-3.49 (1H, m), 3.69-3.72 (2H, m), 7.31 (2H, d), 7.40 (4H, apparent d), 7.56 (2H, d), 7.92 (2H, br.s).

Example 80

(4-{4-[4-(1H-Pyrazol-4-yl)-phenyl]-piperidin-4-yl}-phenoxy)-acetic acid and (4-{4-[4-(1H-Pyrazol-4-yl)-phenyl]-piperidin-4-yl}-phenoxy)-acetic acid, methyl ester

80A. {4-[4-(4-bromo-phenyl)-piperidin-4-yl]-phenoxy}-acetic acid ethyl ester

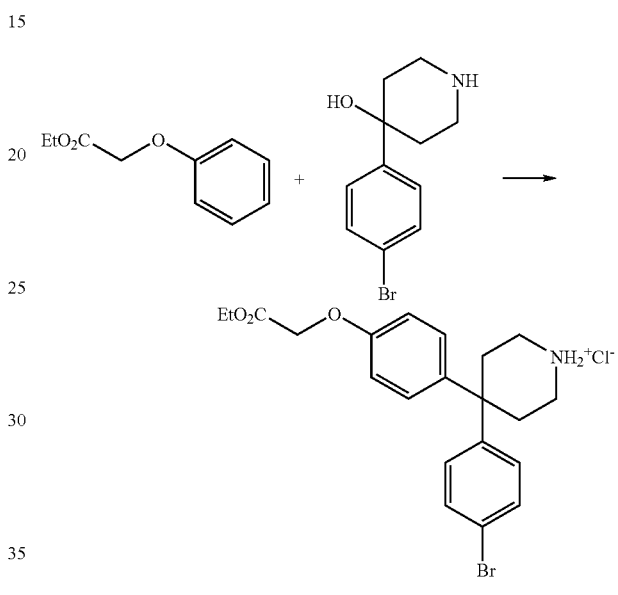

By following the procedure described in Example 42B but substituting chlorobenzene for ethyl phenoxyacetate and employing nitrobenzene as solvent, the title compound was obtained. LCMS (PS-A2) R$_t$ 2.37 min [M+H]$^+$ 418.

80B. (4-{4-[4-(1H-Pyrazol-4-yl)-phenyl]-piperidin-4-yl}-phenoxyl-acetic acid and (4-{4-[4-(1H-Pyrazol-4-yl)-phenyl]-piperidin-4-yl}-phenoxy)-acetic acid, methyl ester

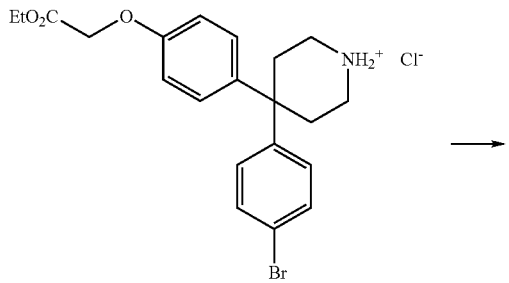

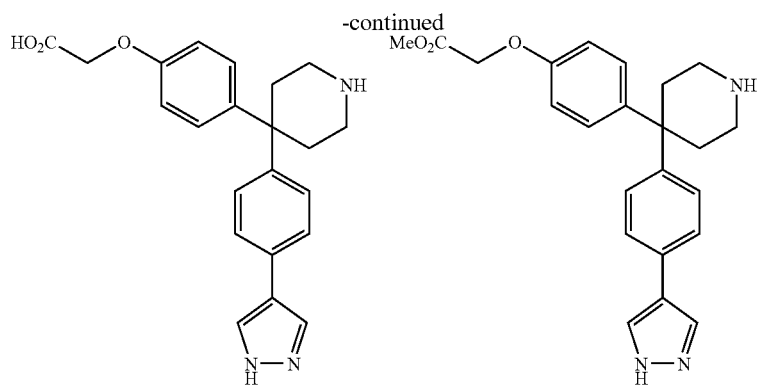

{4-[4-(4-bromo-phenyl)-piperidin-4-yl]-phenoxy}-acetic acid ethyl ester was reacted with 4-(4,4,5,5-tetramethyl-1,3,2-dioxaborolan-2-yl)-1H-pyrazole following the procedure set out in Example 1, but using tetrakis(triphenylphosphine) palladium (0) as the catalyst and heating at 80° C. for 30 minutes, to yield a mixture of the title compounds. On work up the basic aqueous extract was neutralised with hydrochloric acid and extracted with ethyl acetate (×2), then these organic extracts were combined and washed with brine, dried (MgSO$_4$), filtered and concentrated to give a crude product that was recrystallised from water to afford (4-{4-[4-(1H-pyrazol-4-yl)-phenyl]-piperidin-4-yl}-phenoxy)-acetic acid (12 mg, 5%); LCMS (PS-A3) R$_t$ 5.33 min [M+H]$^+$ 378. $^1$H NMR (DMSO-d$_6$) δ 2.22-2.26 (4H, m), 2.67-2.71 (4H, m), 4.65 (2H, s) 6.67 (2H, d), 7.11 (2H, d), 7.24 (2H, d), 7.46 (2H, d), 7.96 (2H, br.s).

The material which was not extracted into base was converted on standing in methanol to a single compound, {4-[4-(1H-pyrazol-4-yl)-phenyl]-piperidin-4-yl}-phenoxy)-acetic acid, methyl ester. This was purified by preparative HPLC to afford the title compound (18 mg, 7%); LCMS (PS-A3) R$_t$ 6.13 min [M+H]$^+$ 392. $^1$H NMR (Me-d$_3$-OD) δ 2.34-2.45 (4H, m), 2.87 (4H, apparent t), 3.75 (3H, s), 6.83 (2H, d), 7.21 (2H, d), 7.26 (2H, d), 7.47 (2H, d), 7.89 (2H, s).

Example 81

4-{4-[4-(1H-Pyrazol-4-yl)-phenyl]-piperidin-4-yl}-benzonitrile 81A. 4-(4-Chloro-phenyl)-4-(4-iodo-phenyl)-piperidine

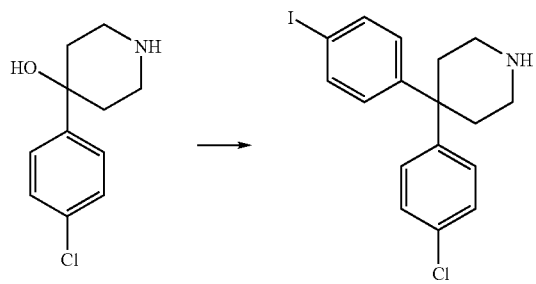 [SMILES: OC1(c2ccc(Cl)cc2)CCNCC1 ; Clc1ccc(C2(c3ccc(I)cc3)CCNCC2)cc1]

By following the procedure described in Example 42B but substituting chlorobenzene for iodobenzene, the title compound was obtained. LCMS (PS-A2) 2.68 min [M+H]$^+$ 398.

81B. 4-[4-(4-Chloro-phenyl)-piperidin-4-yl]-benzonitrile

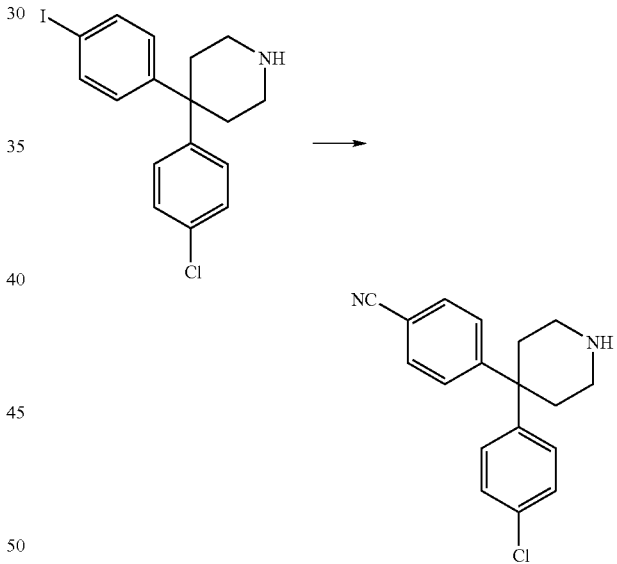

A mixture of 4-(4-chloro-phenyl)-4-(4-iodo-phenyl)-piperidine and copper (I) cyanide in DMF was heated at 140° C. under nitrogen for 6 hours then allowed to cool. The mixture was diluted with ethyl acetate, washed with a mixture of conc. ammonia and brine (×5), dried (MgSO$_4$), filtered and concentrated to give a residue which was partially purified by column chromatography (SiO$_2$), eluting with a gradient of 2M ammonia in methanol (5% to 10%) and dichloromethane to afford the title compound (46 mg, <16%). This was taken on to the next reaction without further purification. LCMS (PS-A2) R$_t$ 2.39 min [M+H]$^+$ 297.

81C. 4-{4-[4-(1H-Pyrazol-4-yl)-phenyl]-piperidin-4-yl}-benzonitrile

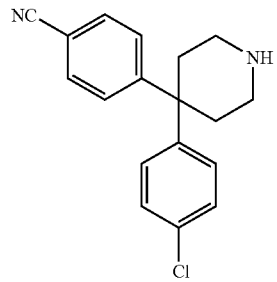

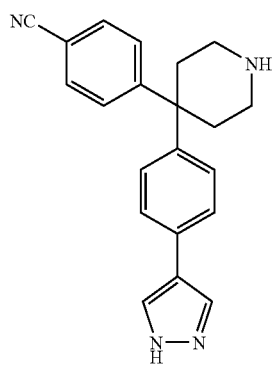

4-[4-(4-chloro-phenyl)-piperidin-4-yl]-benzonitrile was reacted with 4-(4,4,5,5-tetramethyl-1,3,2-dioxaborolan-2-yl)-1H-pyrazole following the procedure set out in Example 1, but using tetrakis(triphenylphosphine)palladium (0) as the catalyst and heating at 100° C. for 15 minutes, to obtain the title compound. LCMS (PS-A3) $R_t$ 6.68 min [M+H]$^+$ 329. $^1$H NMR (Me-d$_3$-OD) δ 2.65-2.73 (4H, m), 2.77-2.85 (4H, m), 3.75 (3H, s), 7.46 (2H, d), 7.59 (2H, d), 7.68 (2H, d), 7.71 (2H, d), 8.42 (2H, br.s).

Example 82

{2-(4-Chloro-phenyl)-2-[4-(1H-pyrazol-4-yl)-phenyl]-propyl}-methyl-amine

82A. Bis-(4-chloro-phenyl)-acetic acid methyl ester

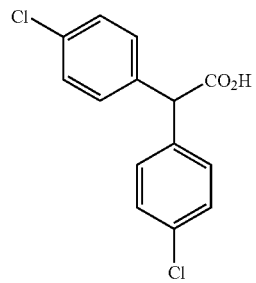

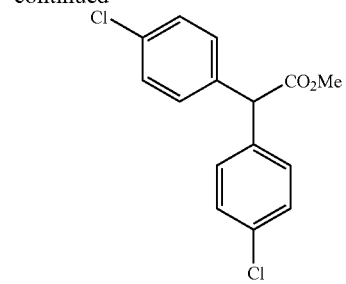

Bis-(4-chloro-phenyl)-acetic acid (4.33 g, 15.4 mmol) was suspended in anhydrous methanol (20 mL) and concentrated hydrochloric acid (5 drops) was added. After 1 day the reaction was quenched by the addition of saturated sodium bicarbonate solution, then the organic solvent was removed in vacuo. The residue was partitioned between ethyl acetate and 50% saturated potassium carbonate solution. The organic phase was washed with brine, dried (MgSO$_4$), filtered and concentrated to give a residue which was purified by column chromatography (SiO$_2$), eluting with 10% ethyl acetate/petrol, to afford the title compound as a colourless oil (3.57 g, 78%); LCMS (PS-B3) $R_t$ 3.79 min, No ionisation. $^1$H NMR (CDCl$_3$) δ 3.74 (3H, s), 4.96 (1H, s), 7.20-7.23 (4H, m), 7.28-7.32 (4H, m).

82B. 2,2-Bis-(4-chloro-phenyl)-propionic acid methyl ester

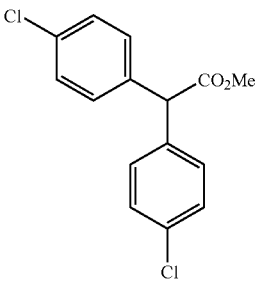

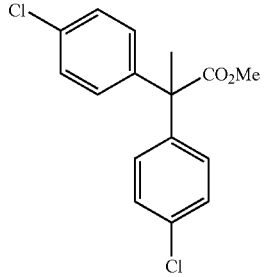

A solution of bis-(4-chloro-phenyl)-acetic acid methyl ester (1.19 g, 4.0 mmol) in THF (20 ml) was cooled to −78° C. under nitrogen. A solution of LDA (3.0 mL, 6.0 mmol, 2M in heptane/THF/ethylbenzene) was added over 5 minutes, then after a further 20 minutes, iodomethane (0.63 ml, 10.1 mmol) was added. After 4 hours the reaction was quenched by the addition of saturated ammonium chloride solution and allowed to warm to room temperature then concentrated in vacuo to remove organic solvents. The mixture was diluted with ethyl acetate/petrol 1:4 and washed with saturated ammonium chloride solution then brine, dried (MgSO₄), filtered and concentrated to give a residue which was purified by column chromatography (SiO₂), eluting with an ethyl acetate/petrol gradient (1% to 2%), to afford the title compound as a colourless oil (210 mg, 17%); LCMS (PS-B3) $R_t$ 4.01 min, No ionisation. ¹H NMR (CDCl₃) δ 1.88 (3H, s), 3.73 (3H, 5), 7.11-7.14 (4H, m), 7.26-7.30 (4H, m).

82C. 2,2-Bis-(4-chloro-phenyl)-propionic acid

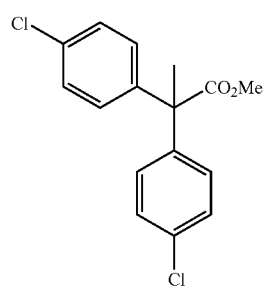

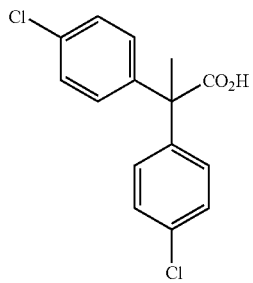

A solution of 2,2-bis-(4-chloro-phenyl)-propionic acid methyl ester (210 mg, 0.67 mmol) in THF/water/methanol (1:1:1, 18 mL) was stirred at room temperature for 5 days then concentrated in vacuo. The residue was partitioned between ethyl acetate and 2N hydrochloric acid, then the organic phase was washed with brine, dried (MgSO₄), filtered and concentrated to give the title compound (186 mg, 93%) as a yellow solid which was used without further purification. LCMS (PS-B3) $R_t$ 2.40 min [M-CO₂H]⁻ 249.

82D. 2,2-Bis-(4-chloro-phenyl)-N-methyl-propionamide

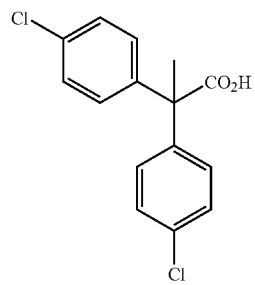

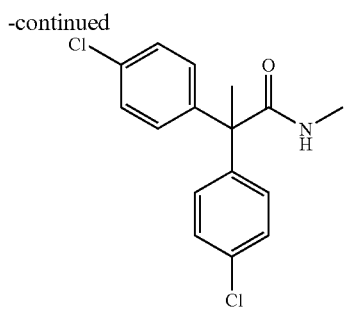

By following the procedure described in Example 8D but substituting 3-(4-bromo-phenyl)-3-(4-chloro-phenyl)-propionic acid for 2,2-bis-(4-chloro-phenyl)-propionic acid, the title compound was obtained. LCMS (PS-B3) $R_t$ 3.40 min [M+H]⁺ 308.

82E. [2,2-Bis-(4-chloro-phenyl)-propyl]-methyl-amine

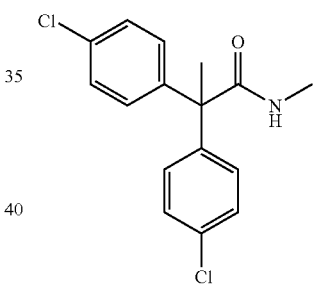

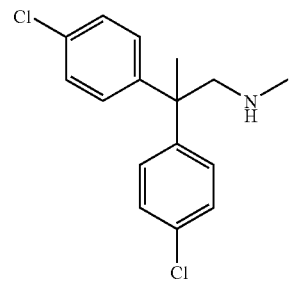

By following the procedure described in Example 8E but substituting 3-(4-Bromo-phenyl)-3-(4-chloro-phenyl)-N-methyl-propionamide for 2,2-Bis-(4-chloro-phenyl)-N-methyl-propionamide, the title compound was obtained. LCMS (FL-A) $R_t$ 2.35 min [M+H]⁺ 294

82F. {2-(4-Chloro-phenyl)-2-[4-(1H-pyrazol-4-yl)-phenyl]-propyl}-methyl-amine

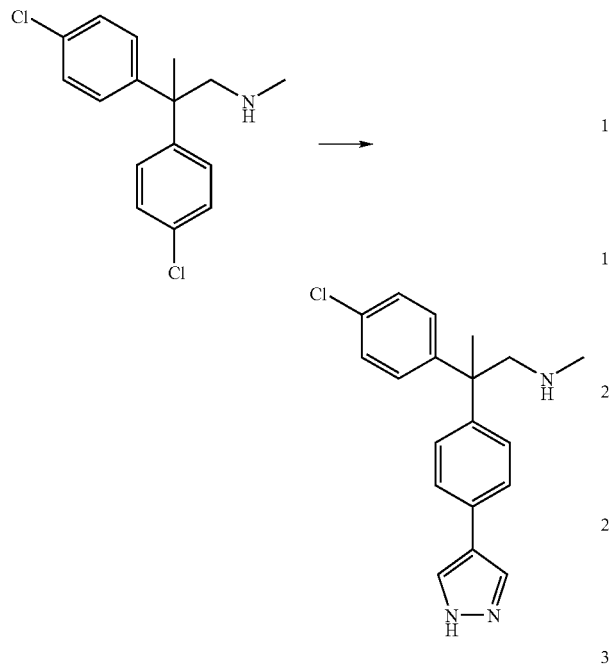

[2,2-Bis-(4-chloro-phenyl)-propyl]-methyl-amine was reacted with 4-(4,4,5,5-tetramethyl-1,3,2-dioxaborolan-2-yl)-1H-pyrazole following the procedure set out in Example 1 to give the title compound. LCMS (PS-A3) R$_t$ 6.94 min [M+H]$^+$ 326. $^1$H NMR (Me-d$_3$-OD) δ 1.86 (3H, s), 2.77 (3H, s), 3.89 (2H, s), 7.26-7.33 (4H, m), 7.37-7.40 (2H, m), 7.68 (2H, d), 8.35 (2H, s).

Example 83

1-(4-Chloro-phenyl)-2-methylamino-1-[4-(1H-pyrazol-4-yl)-phenyl]-ethanol

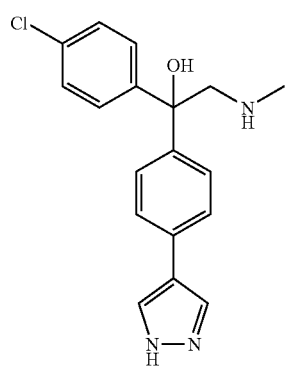 [SMILES: CNCC(O)(c1ccc(Cl)cc1)c1ccc(-c2cn[nH]c2)cc1]

By following the procedure described in Example 79A, 79B and 79D but substituting ethanolamine for methylamine, the title compound was obtained. LCMS (PS-A3) R$_t$ 5.28 min [M+H]$^+$ 328, [M−H$_2$O+H]$^+$ 310. $^1$H NMR (Me-d$_3$-OD) δ 2.38 (3H, s), 3.34 (2H, s), 7.28-7.31 (2H, m), 7.41-7.46 (4H, m), 7.51-7.54 (2H, m), 7.92 (2H, s).

Example 84

2-Amino-1-(4-chloro-phenyl)-1-[4-(1H-pyrazol-4-yl)-phenyl]-ethanol

84A. 2-[2-(4-Chloro-phenyl)-2-hydroxy-2-(4-iodo-phenyl)-ethyl]-isoindole-1,3-dione

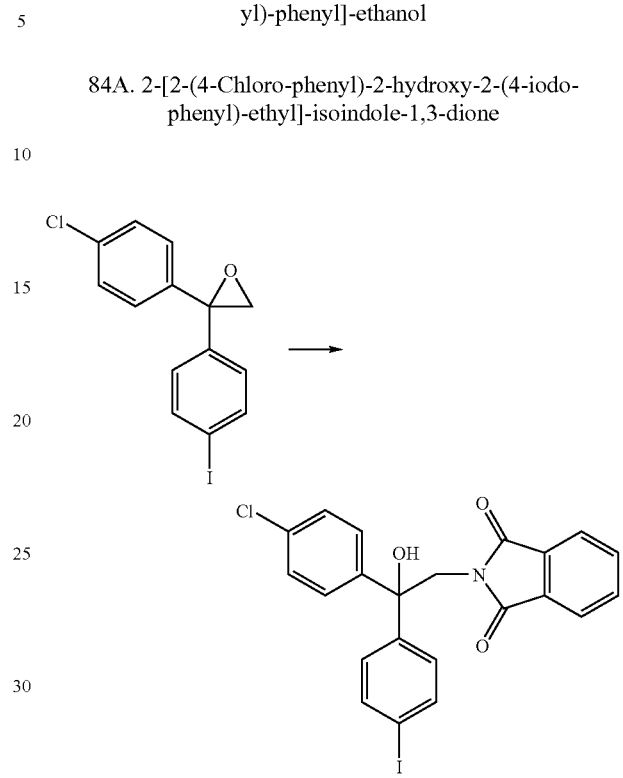

A mixture of 2-(4-chloro-phenyl)-2-(4-iodo-phenyl)-oxirane* (571 mg, 1.60 mmol) and potassium phthalimide (340 mg, 1.84 mmol) in THF (5 mL) and DMSO (2 mL) was heated at 100° C. for 20 hours. The mixture was concentrated in vacuo, diluted with ethyl acetate and washed with water and brine (×2), dried (MgSO$_4$), filtered and concentrated to give a crude product which was purified by column chromatography (SiO$_2$), eluting with a gradient of ethyl acetate/petrol (2.5% to 100%) then 10% methanol/dichloromethane to give the title compound (273 mg, 34%); LCMS (PS-A2) R$_t$ 3.22 min [M+H]$^+$ 504.

* This starting material can be made by the method described in Example 79A

84B. N-{2-(4-Chloro-phenyl)-2-hydroxy-2-[4-(1H-pyrazol-4-yl)-phenyl]-ethyl}-phthalamic acid

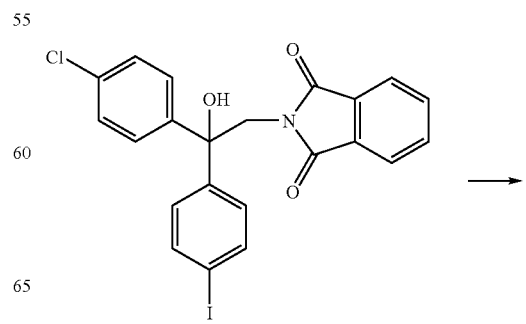

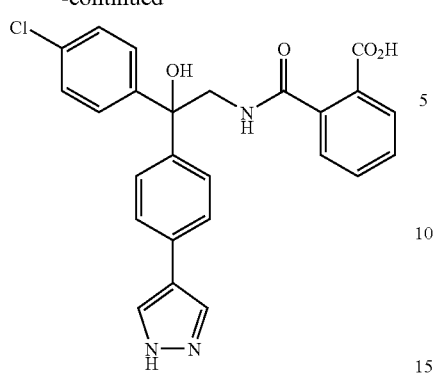

2-[2-(4-Chloro-phenyl)-2-hydroxy-2-(4-iodo-phenyl)-ethyl]-isoindole-1,3-dione was reacted with 4-(4,4,5,5-tetramethyl-1,3,2-dioxaborolan-2-yl)-1H-pyrazole following the procedure set out in Example 1, but using tetrakis(triphenylphosphine)palladium (0) as the catalyst, to obtain the title compound. LCMS (PS-A2) $R_t$ 2.62 min [M−H]⁻ 460.

84C. 2-Amino-1-(4-chloro-phenyl)-1-[4-(1H-pyrazol-4-yl)-phenyl]-ethanol

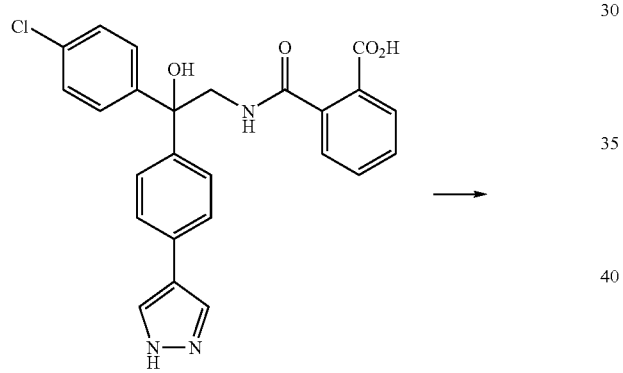

By following the procedure described in Example 49D but substituting N-(2-{(4-Chloro-phenyl)-[4-(1H-pyrazol-4-yl)-phenyl]-methoxy}-ethyl)-phthalamic acid for N-{2-(4-Chloro-phenyl)-2-hydroxy-2-[4-(1H-pyrazol-4-yl)-phenyl]-ethyl}-phthalamic acid, the title compound was obtained. LCMS (PS-A3) $R_t$ 6.29 min [M−H₂O+H]⁺ 296. ¹H NMR (Me-d₃-OD) δ 3.29-3.38 (2H, m), 7.32 (2H, d), 7.41-7.46 (4H, m), 7.55 (2H, d), 7.94 (2H, s).

Example 85

4-(3,4-Dichloro-phenyl)-4-[4-(1H-pyrazol-4-yl)-phenyl]-piperidine

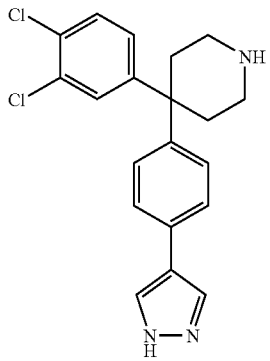 [SMILES: Clc1ccc(C2(c3ccc(-c4cn[nH]c4)cc3)CCNCC2)cc1Cl]

By following the procedure described in Example 14 but substituting chlorobenzene for 1,2-dichlorobenzene, the title compound was obtained. LCMS (PS-B4) $R_t$ 7.20 min [M+H]⁺ 372. ¹H NMR (Me-d₃-OD) δ 2.62-2.69 (2H, m), 2.73-2.81 (2H, m), 3.18-3.30 (4H, m), 7.34 (1H, dd), 7.46-7.52 (3H, m), 7.53 (1H, d), 7.72 (2H, d), 8.56 (2H, s).

Example 86

4-(3-Chloro-4-methoxy-phenyl)-4-[4-(1H-pyrazol-4-yl)-phenyl]-piperidine

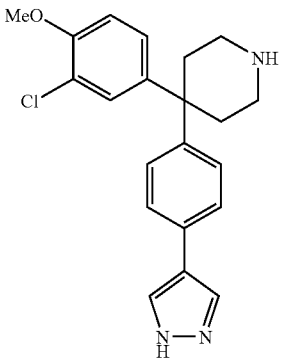 [SMILES: COc1ccc(C2(c3ccc(-c4cn[nH]c4)cc3)CCNCC2)cc1Cl]

By following the procedure described in Example 14 but substituting chlorobenzene for 2-chloroanisole, the title compound was obtained. LCMS (PS-B4) $R_t$ 6.24 min [M+H]⁺ 368. ¹H NMR (Me-d₃-OD) δ 2.62-2.75 (4H, m), 3.23 (4H, apparent t), 3.86 (3H, s), 7.06 (1H, d), 7.30 (1H, dd), 7.34 (1H, d), 7.45 (2H, d), 7.69 (2H, d), 8.57 (2H, s).

Example 87

4-(4-Chloro-3-fluoro-phenyl)-4-[4-(1H-pyrazol-4-yl)-phenyl]-piperidine

87A. 4-(4-Chloro-3-fluoro-phenyl)-4-hydroxy-piperidine-1-carboxylic acid tert-butyl ester

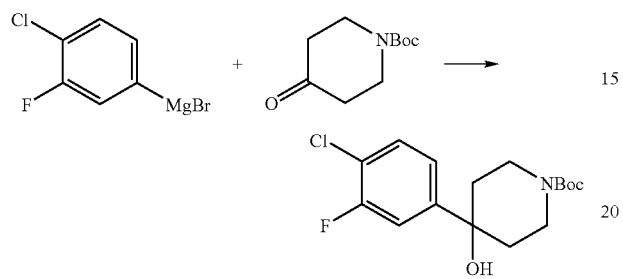

A solution of 4-chloro-3-fluorophenylmagnesium bromide (15 ml, 7.5 mmol, 0.5M in THF) was added, under nitrogen, to 4-oxo-piperidine-1-carboxylic acid tert-butyl ester (1.02 g, 5.1 mmol). After 24 hours, saturated ammonium chloride solution was added then the organic solvent was removed in vacuo. The mixture was extracted with ethyl acetate, then this extract was washed with brine, dried (MgSO$_4$), filtered and concentrated to afford a residue which was purified by column chromatography (SiO$_2$), eluting with gradient of ethyl acetate/petrol (0% to 20%) to afford the title compound (511 mg, 30%). $^1$H NMR (Me-d$_3$-OD) δ 1.48 (9H, s), 1.67 (2H, br.d), 1.92 (2H, td), 3.16-3.29 (2H, m), 3.99 (2H, br.d), 7.27 (1H, dd), 7.38 (1H, dd), 7.42 (1H, t).

87B. 4-(4-Bromo-phenyl)-4-(4-chloro-3-fluoro-phenyl)-piperidine

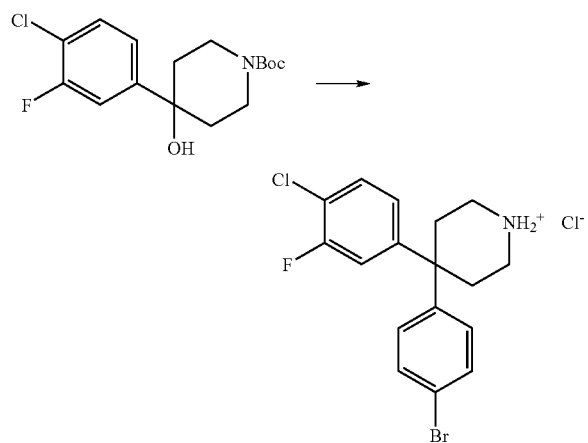

By following the procedure described in Example 42B but substituting chlorobenzene for bromobenzene, the title compound was obtained. LCMS (PS-A2) R$_t$ 2.43 min [M+H]$^+$ 368.

87C. 4-(4-Chloro-3-fluoro-phenyl)-4-[4-(1H-pyrazol-4-yl)-phenyl]-piperidine

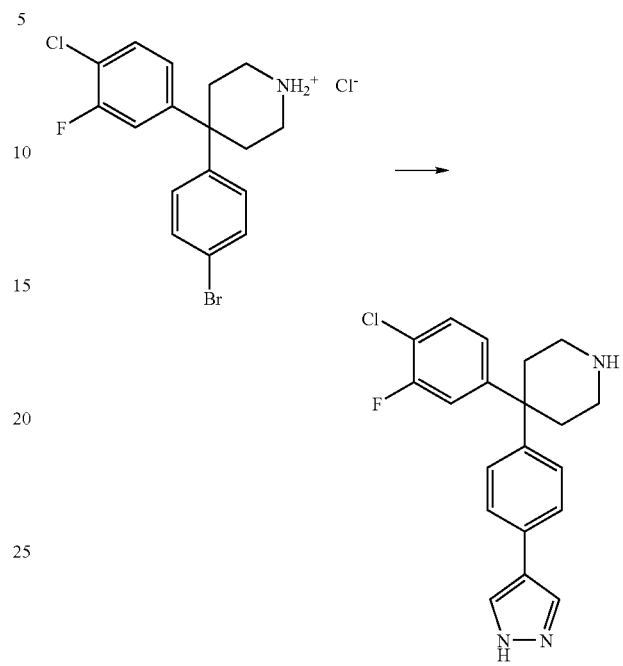

4-(4-Bromo-phenyl)-4-(4-chloro-3-fluoro-phenyl)-piperidine was reacted with 4-(4,4,5,5-tetramethyl-1,3,2-dioxaborolan-2-yl)-1H-pyrazole following the procedure set out in Example 1, but using tetrakis(triphenylphosphine)palladium (0) as the catalyst, to obtain the title compound. LCMS (PS-A3) R$_t$ 7.11 min [M+H]$^+$ 356. $^1$H NMR (Me-d$_3$-OD) δ 2.62-2.80 (4H, m), 3.18-3.30 (partially overlaps with solvent, 4H, m), 7.23 (1H, t), 7.34-7.39 (1H, m), 7.22 (1H, dd), 7.30 (1H, dd), 7.43-7.49 (3H, m), 7.71 (2H, d), 8.55 (2H, s).

Example 88

4-{4-[4-(1H-Pyrazol-4-yl)-phenyl]-piperidin-4-yl}-benzoic acid

88A. 4-(4-carboxy-phenyl)-4-(4-chloro-phenyl)-piperidine-1-carboxylic acid tert-butyl ester

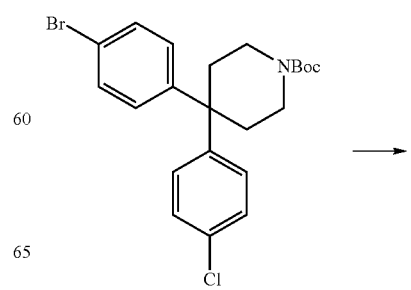

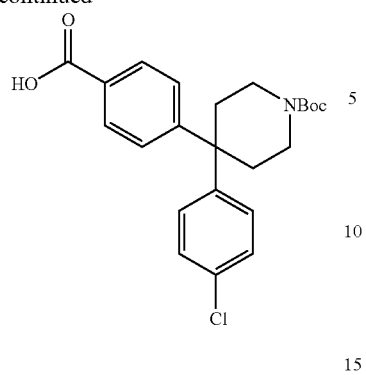

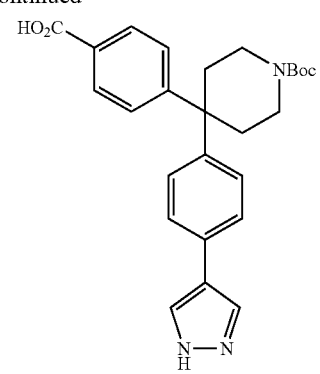

Under nitrogen, a solution of 4-(4-bromo-phenyl)-4-(4-chloro-phenyl)piperidine-1-carboxylic acid tert-butyl ester* (888 mg, 1.97 mmol) in THF (5 mL) was cooled to −78° C. A solution of n-butyllithium (1.5 mL, 1.6M in hexanes) was added dropwise and the mixture maintained at this temperature for 25 minutes. Carbon dioxide gas (generated from dry ice and dried by passage through a column of calcium chloride pellets) was bubbled through the anion solution for 80 minutes then the mixture was allowed to warm to room temperature. The solvents were removed in vacuo then the residue was partitioned between 1N hydrochloric acid and diethyl ether. The organic phase was separated, dried (MgSO$_4$), filtered and concentrated. The combined aqueous phases were further extracted with ethyl acetate, this extract also being dried (MgSO$_4$), filtered, combined with the ethereal extract and concentrated to afford 4-(4-carboxy-phenyl)-4-(4-chloro-phenyl)-piperidine-1-carboxylic acid tert-butyl ester (889 mg); LCMS (PS-A2) R$_t$ 3.52 min [M-$^t$Bu+H]$^+$ 360.

* This starting material can be made by the method described in Example 14A followed by Example 48A

88B. 4-(4-Carboxy-phenyl)-4-[4-(1H-pyrazol-4-yl)-phenyl]-piperidine-1-carboxylic acid tert-butyl ester

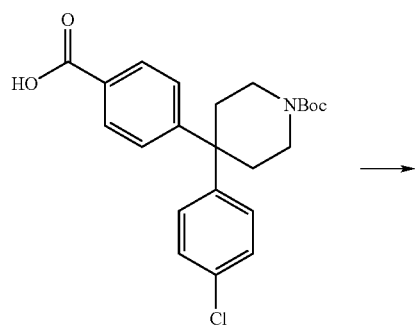

4-(4-Carboxy-phenyl)-4-(4-chloro-phenyl)-piperidine-1-carboxylic acid tert-butyl ester was reacted with 4-(4,4,5,5-tetramethyl-1,3,2-dioxaborolan-2-yl)-1H-pyrazole following the procedure set out in Example 1, to obtain the title compound. LCMS (PS-A2) R$_t$ 2.92 min [M+H]$^+$ 448.

88C. 4-{4-[4-(1H-Pyrazol-4-yl)-phenyl]-piperidin-4-yl}-benzoic acid

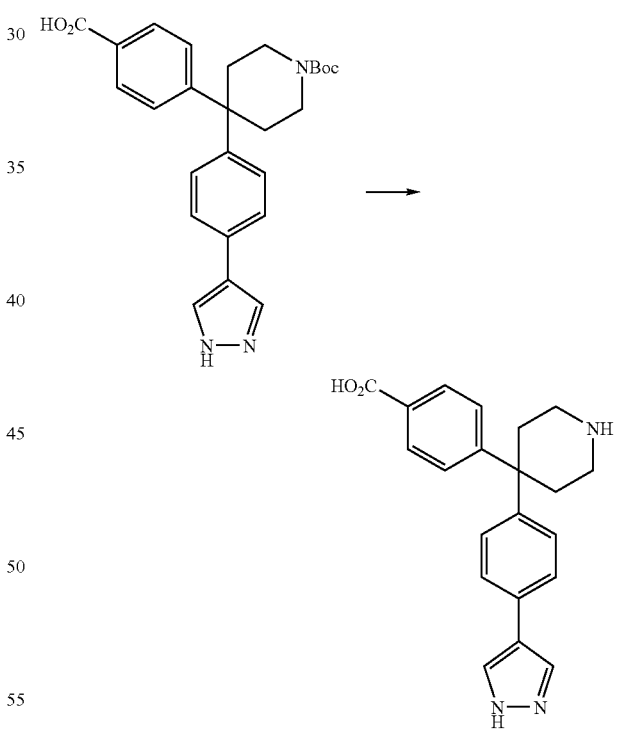

4-(4-Carboxy-phenyl)-4-[4-(1H-pyrazol-4-yl)-phenyl]-piperidine-1-carboxylic acid tert-butyl ester (26 mg, 0.06 mmol) was dissolved in dioxane (2 mL) and 1N hydrochloric acid (2 mL). After 24 hours the mixture was concentrated in vacuo and triturated with diethyl ether to afford the title compound as the dihydrochloride salt (22 mg, 90%); LCMS (PS-A3) R$_t$ 5.22 min [M+H]$^+$ 348. $^1$H NMR (Me-d$_3$-OD) δ 2.70-2.82 (4H, m), 3.26 (4H, apparent t), 7.46 (2H, d), 7.51 (2H, m), 7.68 (2H, d), 8.00 (2H, d), 8.47 (2H, s).

Example 89

4-[4-(1H-Pyrazol-4-yl)-phenyl]-1,2,3,4,5,6-hexahydro-[4,4']bipyridinyl 89A. 4-(4-Chloro-phenyl)-3,4,5,6-tetrahydro-2H-[4,4']bipyridinyl-1-carboxylic acid tert-butyl ester

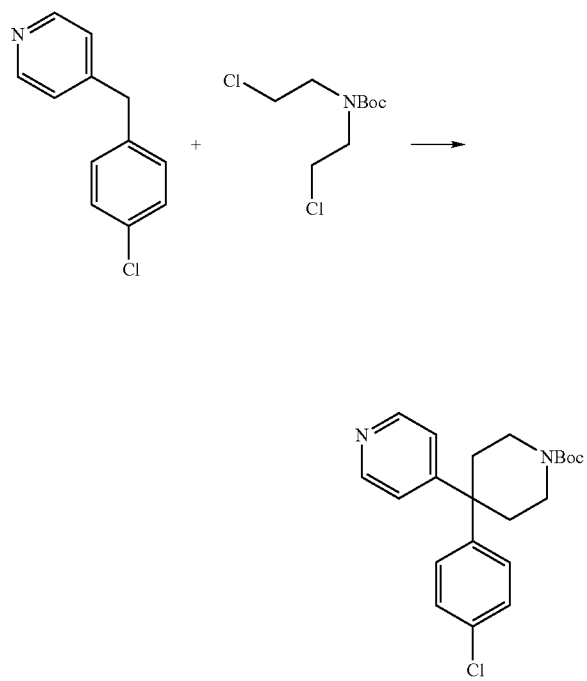

Under nitrogen, a solution of bis-(2-chloro-ethyl)-carbamic acid tert-butyl ester* (1.54 g, 6.36 mmol) in toluene (10 mL) was cooled in ice. 4-(4-Chloro-benzyl)-pyridine (1.30 g, 6.36 mmol) was added, followed over two minutes by sodium hexamethyldisilazide solution (10 mL, 20 mmol, 2M in THF). The mixture was stirred at 0° C. for 3.5 hours then allowed to warm to room temperature and stirred for a further 20 hours. Methanol was added then the mixture was concentrated in vacuo. The residue was taken up in ethyl acetate and washed with 1N hydrochloric acid (×3) and brine, dried (MgSO₄), filtered and concentrated to afford a residue which was purified by column chromatography (SiO₂), eluting with gradient of 2M methanolic ammonia in dichloromethane (1% to 5%). A second purification by column chromatography (SiO₂), eluting with 50% ethyl acetate/petrol gave the title compound (16 mg, 0.7%). LCMS (PS-A2) $R_t$ 2.65 min [M+H]⁺ 373.

* This starting material can be made by the method described in J. Chem. Soc., Perkin Trans 1, 2000, p 3444-3450

89B. 4-[4-(1H-Pyrazol-4-yl)-phenyl]-1,2,3,4,5,6-hexahydro-[4,4']bipyridinyl

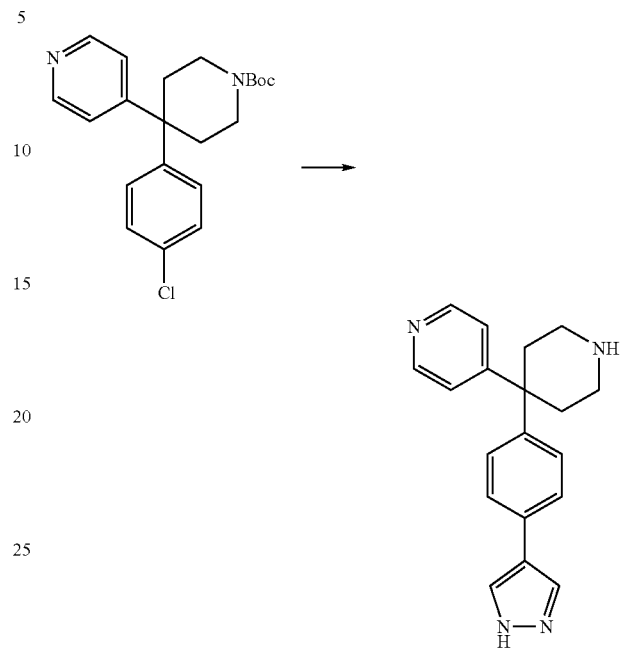

4-(4-Chloro-phenyl)-3,4,5,6-tetrahydro-2H-[4,4']bipyridinyl-1-carboxylic acid tert-butyl ester was reacted with 4-(4,4,5,5-tetramethyl-1,3,2-dioxaborolan-2-yl)-1H-pyrazole following the procedure set out in Example 1, followed by treatment with 4M HCl in dioxane, to obtain the title compound. LCMS (PS-B4) $R_t$ 4.28 min [M+H]⁺ 305. ¹H NMR (Me-d₃-OD) δ 2.76 (2H, br.t), 3.01 (2H, br.d), 3.24 (2H, br.t), 3.39 (2H, br.d), 7.58 (2H, d), 7.76 (2H, d), 8.17 (2H, d), 8.37 (2H, s), 8.82 (2H, d).

Example 90

3-(3-Chloro-phenyl)-3-[4-(1H-pyrazol-4-yl)-phenyl]-propylamine

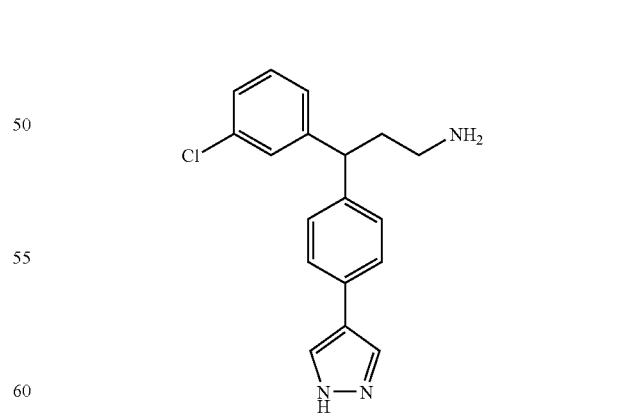

By following the procedure described in Example 8 but substituting 4-chlorophenylmagnesium bromide for 3-chlorophenylmagnesium bromide and methylamine for ammonia the title compound was obtained. LCMS (PS-B3) $R_t$ 2.60 min [M+H]⁺ 312. ¹H NMR (Me-d₃-OD) δ 2.44 (2H, apparent qd), 2.87 (2H, dd), 4.14 (1H, t), 7.24 (1H, dt), 7.27-7.33 (2H, m), 7.34 (1H, t), 7.42 (2H, d), 7.68 (2H, d), 8.58 (2H, s).

Example 91

2-Methylamino-1-(4-nitro-phenyl)-1-[4-(1H-pyrazol-4-yl)-phenyl]-ethanol

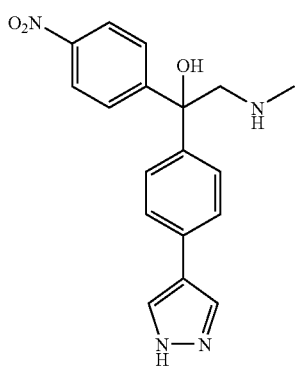 [SMILES: CNCC(O)(c1ccc(-c2cn[nH]c2)cc1)c1ccc([N+](=O)[O-])cc1]

By following the procedure described in Example 83 but substituting (4-chloro-phenyl)-(4-iodo-phenyl)-methanone for (4-Bromo-phenyl)-(4-nitro-phenyl)-methanone, the title compound was obtained. LCMS (PS-A) $R_t$ 1.79 [M+H]$^+$ 339. $^1$H NMR (Me-d$_3$-OD) δ 8.27 (2H, d), 7.98 (2H, s), 7.80 (2H, d), 7.65 (2H, d), 7.52 (2H, d), 4.00 (2H, dd), 2.73 (3H, s)—C$\underline{H}$(OH) signal presumed to be under water peak.

Example 92

2-(3-Chloro-4-methoxy-phenyl)-2-[4-(1H-pyrazol-4-yl)-phenyl]-ethylamine

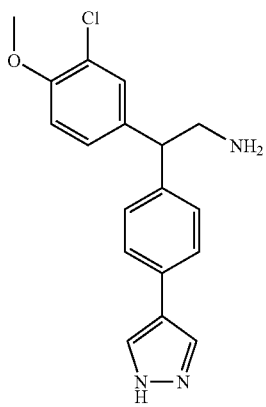 [SMILES: COc1ccc(C(CN)c2ccc(-c3cn[nH]c3)cc2)cc1Cl]

By following the procedure described in Example 87B and Example 42C but replacing 1-(4-bromo-phenyl)-2-methylamino-ethanol with 2-amino-1-(4-bromo-phenyl)-ethanol and chlorobenzene with 2-chloroanisole, the title compound was obtained. LCMS (PS-B3) $R_t$ 2.55 [M+H]$^+$ 328.20. $^1$H NMR (Me-d$_3$-OD) δ 3.65-3.70 (2H, d), 3.90 (3H, s), 4.30-4.35 (1H, t), 7.05-7.10 (1H, d), 7.30-7.35 (1H, d), 7.40 (1H, s), 7.45-7.50 (2H, d), 7.70-7.75 (2H, d), 8.60 (2H, s).

Example 93

2-(4-Chloro-phenyl)-2-fluoro-2-[4-(1H-pyrazol-4-yl)-phenyl]-ethylamine 93A. 2,2-Bis-(4-chloro-phenyl)-2-fluoro-ethylamine

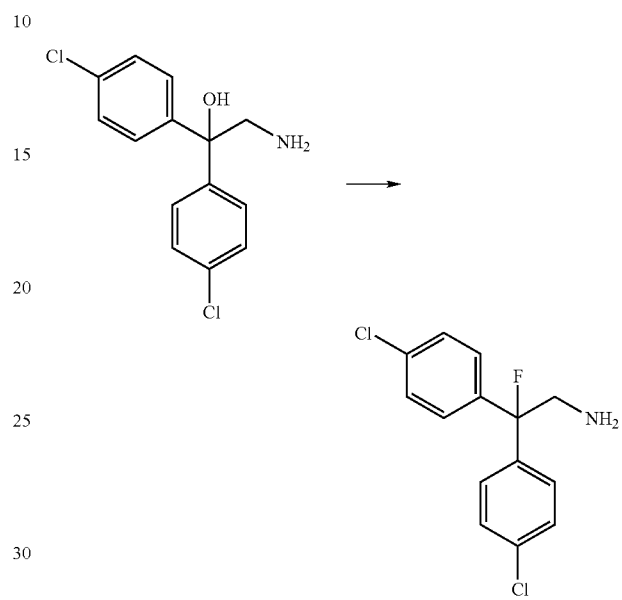

2-Amino-1,1-bis-(4-chloro-phenyl)-ethanol (293 mg, 1.04 mmol) was dissolved in pyridine-HF (2 ml) with cooling. After 24 hours the mixture was diluted into 1N sodium hydroxide solution and extracted with DCM (×3). Each extract was dried (MgSO$_4$) and filtered before being combined and concentrated to give a residue which was purified by column chromatography (SiO$_2$), eluting with 0.5% triethylamine in ethyl acetate to afford the title compound (192 mg, 65%); LCMS (PS-B3) $R_t$ 3.34 min [M-F$^-$]$^+$ 266. $^1$H NMR (DMSO-d$_6$) δ 3.41 (2H, d), 7.39-7.46 (8H, m).

93B. 2-(4-Chloro-phenyl)-2-fluoro-2-[4-(1H-pyrazol-4-yl)-phenyl]-ethylamine

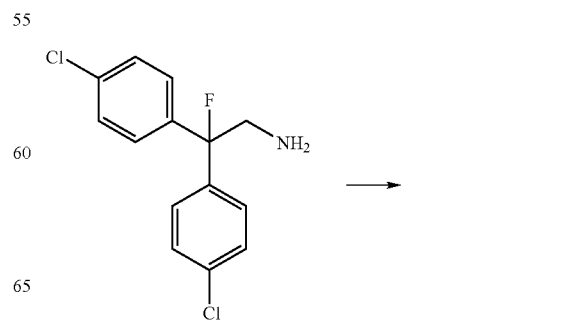

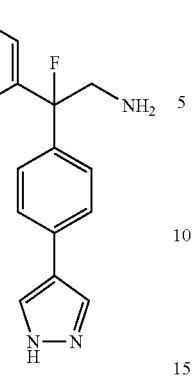

2,2-Bis-(4-chloro-phenyl)-2-fluoro-ethylamine was reacted with 4-(4,4,5,5-tetramethyl-1,3,2-dioxaborolan-2-yl)-1H-pyrazole following the procedure set out in Example 1 except that heating was carried out at 100° C. for 5 minutes using 300 W power in a CEM microwave, to obtain the title compound. LCMS (PS-B4) $R_t$ 6.69 min [M-F$^-$]$^+$ 296. $^1$H NMR (Me-d$_3$-OD) δ 4.04 (2H, d), 7.47-7.55 (6H, m), 7.77 (2H, d), 8.41 (2H, d).

Example 94

3-(3,4-Dichloro-phenyl)-3-[6-(1H-pyrazol-4-yl)-pyridin-3-yl]-propylamine

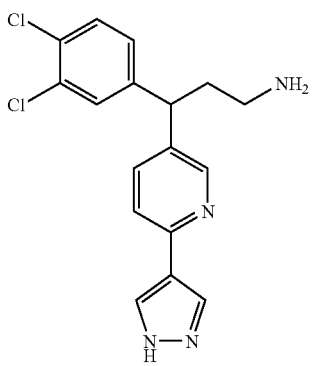 [SMILES: NCCC(c1ccc(-c2cn[nH]c2)nc1)c1ccc(Cl)c(Cl)c1]

By following the procedure described in Example 60 but replacing 6-chloro-nicotinonitrile with 6-chloro-pyridine-3-carbaldehyde and replacing 3-methyl-1-trityl-1H-pyrazole-4-boronic acid with 1-trityl-1H-pyrazole-4-boronic acid, and then following the procedure described in Example 8, the title compound could be obtained.

Example 95

2-(4-Chloro-3-fluoro-phenyl)-2-[4-(1H-pyrazol-4-yl)-phenyl]-ethylamine

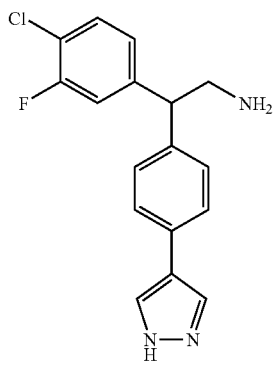 [SMILES: NCC(c1ccc(-c2cn[nH]c2)cc1)c1ccc(Cl)c(F)c1]

By following the procedure described in Example 87, but replacing 4-oxo-piperidine-1-carboxylic acid tert-butyl ester with (2-oxo-ethyl)-carbamic acid tert-butyl ester, the title compound could be obtained.

Example 96

4-(2-Chloro-3-fluoro-phenyl)-4-[4-(1H-pyrazol-4-yl)-phenyl]-piperidine

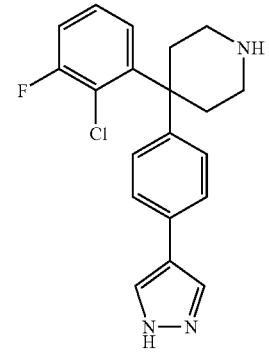 [SMILES: Fc1cccc(C2(c3ccc(-c4cn[nH]c4)cc3)CCNCC2)c1Cl]

By following the procedure described in Example 14, but replacing chlorobenzene with 1-chloro-2-fluorobenzene, the title compound can be obtained.

Example 97

1-{(3,4-Dichloro-phenyl)-[4-(1H-pyrazol-4-yl)-phenyl]-methyl}-piperazine

97A. (4-Chloro-phenyl)-(3,4-dichloro-phenyl)-methanol

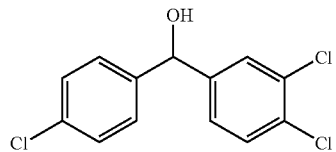

Commercially available chlorophenyl magnesium bromide and 3,4-dichlorobenzaldehyde can be reacted together according to the method described in *J. Medicinal Chem.*, (2000), 43(21), 3878-3894 to give the title compound.

97B. 1,2-Dichloro-4-[chloro-(4-chloro-phenyl)-methyl]-benzene

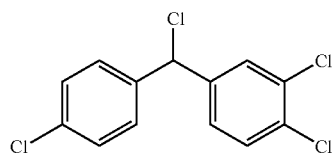 [SMILES: OC(c1ccc(Cl)cc1)c1ccc(Cl)c(Cl)c1]

The product of Example 97A can be reacted with $SO_2Cl_2$ according to the method described in *Organic Letters*, (2003), 5(8), 1167-1169 to give the title compound.

97C. 1-{(3,4-Dichloro-phenyl)-[4-(1H-pyrazol-4-yl)-phenyl]-methyl}-piperazine

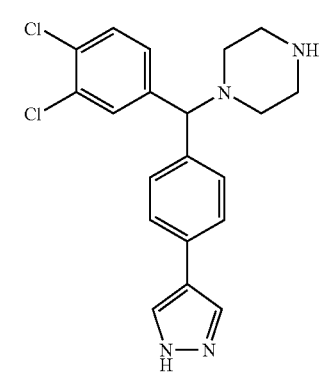 [SMILES: Clc1ccc(C(c2ccc(-c3cn[nH]c3)cc2)N2CCNCC2)cc1Cl]

The title compound may be prepared from the compound of Example 97C by using the method and conditions described in *Zhongguo Yaowu Huaxue Zazhi* (2002), 12(3), 125-129.

Example 98

2-(3,4-Dichloro-phenyl)-2-[4-(1H-pyrazol-4-yl)-phenyl]-ethylamine

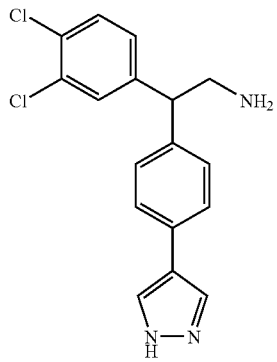 [SMILES: NCC(c1ccc(-c2cn[nH]c2)cc1)c1ccc(Cl)c(Cl)c1]

By following the procedure described in Example 42 but, in Example 42B, replacing chlorobenzene with 1,2-dichlorobenzene, the title compound can be obtained

Example 99

{2-(3-Chloro-4-methoxy-phenyl)-2-[4-(1H-pyrazol-4-yl)-phenyl]-ethyl}-methyl-amine

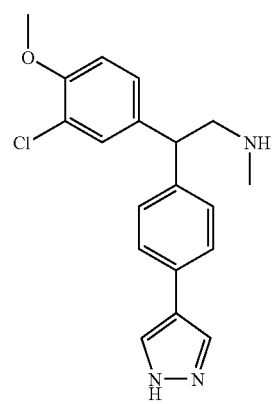 [SMILES: CNCC(c1ccc(-c2cn[nH]c2)cc1)c1ccc(OC)c(Cl)c1]

By following the procedure described in Example 42 but, in step 42B, substituting 2-chloroanisole for chlorobenzene, the title compound was obtained. LC/MS: (PS-A2) $R_t$ 2.03 [M+H]$^+$ 342. $^1$H NMR (Me-d$_3$-OD) 2.45 (3H, s), 3.22 (2H, d), 3.85 (3H, s), 4.15 (1H, t), 7.04 (1H, d), 7.33 (1H, d), 7.27-7.34 (3H, m), 7.55 (2H, d), 7.92 (2H, s).

Example 100

4-{4-[2-Azetidin-1-yl-1-(4-chloro-phenoxy)-ethyl]-phenyl}-1H-pyrazole

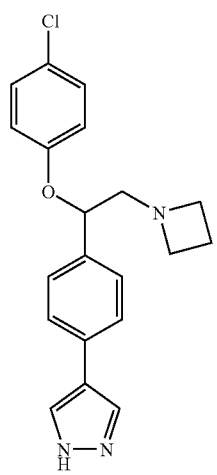 [SMILES: Clc1ccc(OC(CN2CCC2)c2ccc(-c3cn[nH]c3)cc2)cc1]

By following the procedure described in Example 42A, but replacing methylamine with azetidine and following the procedure in Example 45, the title compound could be obtained

Example 101

3-(3-Chloro-4-methoxy-phenyl)-3-[4-(1H-pyrazol-4-yl)-phenyl]-propylamine

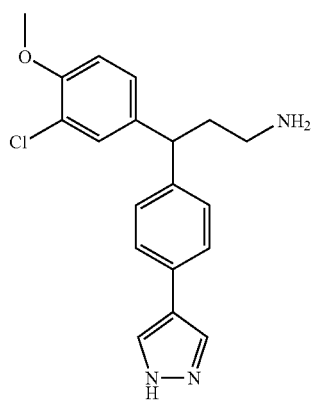 [SMILES: COc1ccc(C(CCN)c2ccc(-c3cn[nH]c3)cc2)cc1Cl]

By following the procedure described in Example 61, but replacing imidazole with potassium phthalimide in step 61A and replacing chlorobenzene with 1-chloro-2-methoxy-benzene in 61B, and then removing the phthaloyl protecting group under the conditions set out in Examples 84B and 84C, the title compound may be prepared.

Example 102

{3-(3-Chloro-4-methoxy-phenyl)-3-[4-(1H-pyrazol-4-yl)-phenyl]-propyl}-methyl-amine

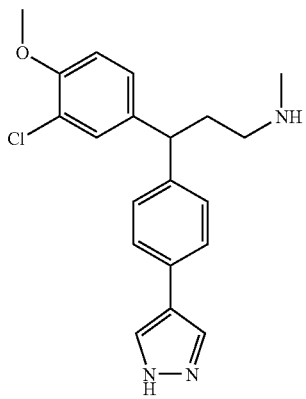 [SMILES: CNCCC(c1ccc(-c2cn[nH]c2)cc1)c1ccc(OC)c(Cl)c1]

By following the procedure described in Example 61, but substituting imidazole with methylamine in Example 61A and substituting chlorobenzene with 1-chloro-2-methoxy-benzene in Example 61B, the title compound may be obtained.

Example 103

1-[(3-Chloro-4-methoxy-phenyl)-(4-chloro-phenyl)-methyl]-piperazine 103A. (3-Chloro-4-methoxy-phenyl)-(4-chloro-phenyl)-methanol

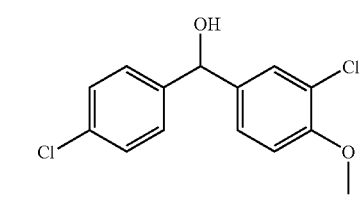 [SMILES: COc1ccc(C(O)c2ccc(Cl)cc2)cc1Cl]

The title compound can be prepared using the method of Example 97A but replacing 3,4-dichlorobenzaldehyde with 3-chloro-4-methoxybenzaldehyde.

103B. 2-Chloro-4-[chloro-(4-chloro-phenyl)-methyl]-1-methoxy-benzene

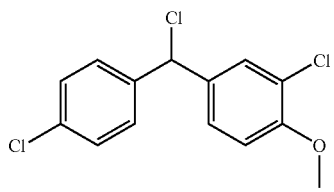 [SMILES: COc1ccc(C(Cl)c2ccc(Cl)cc2)cc1Cl]

The hydroxy compound of Example 103A can be converted into the title chloro compound by following the method of Example 97B.

103C. 1-[(3-Chloro-4-methoxy-phenyl)-(4-chloro-phenyl)-methyl]-piperazine

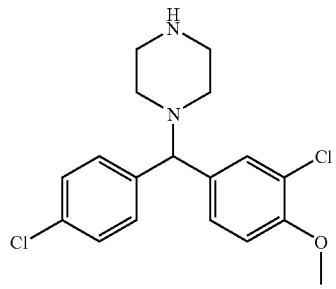 [SMILES: COc1ccc(C(c2ccc(Cl)cc2)N2CCNCC2)cc1Cl]

The title compound can be prepared from the product of Example 103B by following the method of Example 97C.

Example 104

C-(4-Chloro-phenyl)-C-[4-(1H-pyrazol-4-yl)-phenyl]-methylamine

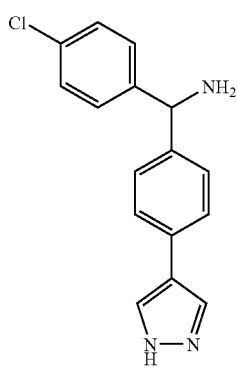 [SMILES: NC(c1ccc(Cl)cc1)c1ccc(-c2cn[nH]c2)cc1]

By following the procedure described in Example 1 but substituting 2-(4-chlorophenyl)-2-phenylethylamine hydrochloride with C,C-bis-(4-chloro-phenyl)-methylamine, the title compound could be obtained.

Example 105

{2-(4-Chloro-phenyl)-2-[4-(3-methyl-1H-pyrazol-4-yl)-phenyl]-ethyl}-methyl-amine 105A. 2-(4-Chloro-phenyl)-N-methyl-2-[4-(3-methyl-1-trityl-1H-pyrazol-4-yl)-phenyl]-acetamide

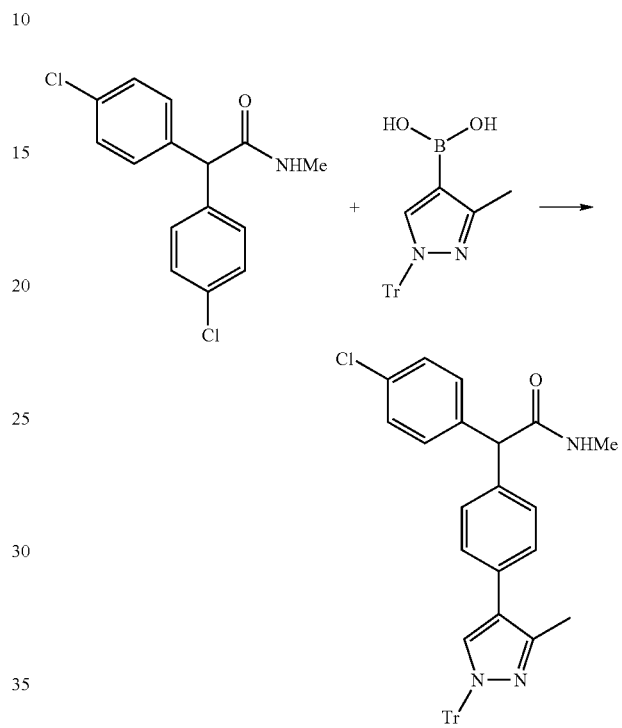

2,2-Bis-(4-chloro-phenyl)-N-methyl-acetamide was prepared by the reaction of the commercially available corresponding carboxylic acid with methylamine using the method of Example 21a. The N-methyl-acetamide compound was then converted to the title compound by the method described in Example 1.

LCMS (PS-B3) R$_t$ 4.21 min; m/z [M+H]$^+$ 582.

105B. 2-(4-Chloro-phenyl)-N-methyl-2-[4-(3-methyl-1H-pyrazol-4-yl)-phenyl]-acetamide

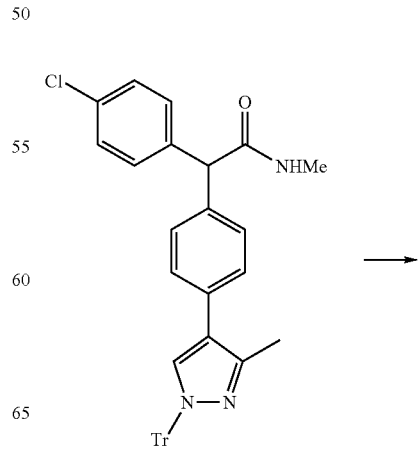

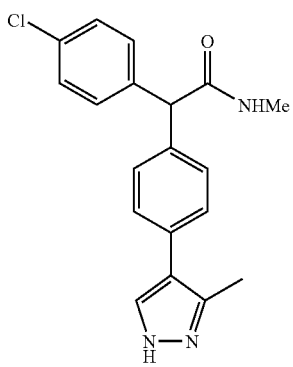

The trityl-protected compound of example 104A was deprotected by the method described in example 60D to give the title compound.

LCMS (PS-B3) $R_f$ 2.41 min; m/z [M+H]$^+$ 340. $^1$H NMR (methanol-d$_4$) δ 2.40 (3H, s), 2.78 (3H, s), 4.95 (1H, s), 7.29-7.34 (6H, m), 7.41 (2H, d), 7.69 (1H, s).

105C. {2-(4-Chloro-phenyl)-2-[4-(3-methyl-1H-pyrazol-4-yl)-phenyl]-ethyl}-methyl-amine

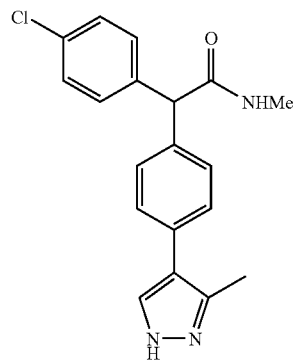
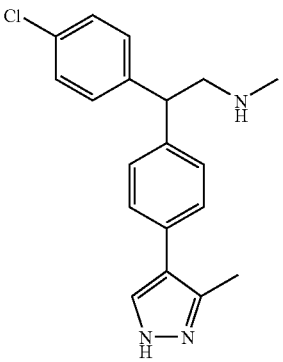

Following the procedure described in example 20B gave the title compound.

LCMS (PS-B3) $R_f$ 2.80 min; m/z [M+H]$^+$ 326. $^1$H NMR (methanol-d$_4$) δ 2.52 (3H, s), 2.75 (3H, s), 3.80 (2H, d), 4.46 (1H, t), 7.41 (4H, s), 7.49 (2H, d), 7.54 (2H, d), 8.24 (1H, s).

Biological Activity

Example 106

Measurement of PKA Kinase Inhibitory Activity (IC$_{50}$)

Compounds of the invention can be tested for PK inhibitory activity using the PKA catalytic domain from Upstate Biotechnology (#14-440) and the 9 residue PKA specific peptide (GRTGRRNSI), also from Upstate Biotechnology (#12-257), as the substrate. A final concentration of 1 nM enzyme is used in a buffer that includes 20 mM MOPS pH 7.2, 40 μM ATP/γ$^{33}$P-ATP and 5 μM substrate. Compounds are added in dimethylsulphoxide (DMSO) solution to a final DMSO concentration of 2.5%. The reaction is allowed to proceed for 20 minutes before addition of excess orthophosphoric acid to quench activity. Unincorporated γ$^{33}$P-ATP is then separated from phosphorylated proteins on a Millipore MAPH filter plate. The plates are washed, scintillant is added and the plates are then subjected to counting on a Packard Topcount.

The % inhibition of the PKA activity is calculated and plotted in order to determine the concentration of test compound required to inhibit 50% of the PKB activity (IC$_{50}$).

The compounds of Examples 1, 4, 43, 44, 45, 46, 47, 48, 49, 52, 54, 59, 63, 66, 67, 73, 78, 79, 81, 82, 83, 84, 85, 86 and 90 have IC$_{50}$ values of less than 1 μM whereas the compounds of Examples 5, 7 and 80 have IC$_{50}$ values of less than 15 μM.

Example 107

Measurement of PKB Kinase Inhibitory Activity (IC$_{50}$)

The inhibition of protein kinase B (PKB) activity by compounds can be determined determined essentially as described by Andjelkovic et al. (Mol. Cell. Biol. 19, 5061-5072 (1999)) but using a fusion protein described as PKB-PIF and described in full by Yang et al (Nature Structural Biology 9, 940-944 (2002)). The protein is purified and activated with PDK1 as described by Yang et al. The peptide AKTide-2T (H-A-R-K-R-E-R-T-Y-S-F-G-H-H-A-OH) obtained from Calbiochem (#123900) is used as a substrate. A final concentration of 0.6 nM enzyme is used in a buffer that includes 20 mM MOPS pH 7.2, 30 μM ATP/γ$^{33}$P-ATP and 25 μM substrate. Compounds are added in DMSO solution to a final DMSO concentration of 2.5%. The reaction is allowed to proceed for 20 minutes before addition of excess orthophosphoric acid to quench activity. The reaction mixture is transferred to a phosphocellulose filter plate where the peptide binds and the unused ATP is washed away. After washing, scintillant is added and the incorporated activity measured by scintillation counting.

The % inhibition of the PKB activity is calculated and plotted in order to determine the concentration of test compound required to inhibit 50% of the PKB activity (IC$_{50}$).

Following the protocol described above, the IC$_{50}$ values of the compounds of Examples 1, 4, 8-10, 12-17, 20-23, 25-31, 33-35, 43, 44, 46, 47, 49-52, 54, 56, 57, 59, 61, 63, 65, 66, 69, 71-73, 76-79, 81-87, 90, 91, 94 and 104 have been found to be less than 1 μM whilst the compounds of Examples 2, 3, 5, 6, 7, 11, 18, 19, 24, 32, 36, 45, 48, 53, 55, 58, 60, 64, 67, 68, 75, 80 and 89 each have IC$_{50}$ values of less than 5 μM, and the compounds of Examples 40, 41, 62 and 70 each have IC$_{50}$ values of less than 50 μM.

Example 108

Pharmaceutical Formulations (i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophillsation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

Example 109

Assay for Therapeutic Efficacy

The effect of a compound of formula I (Compound I) in combination with an ancillary compound (Compound II) was assessed using the following technique:

$IC_{50}$ Shift Assay

Cells from human cells lines (e.g. HCT116, MDA-MB-468, SKBr3 or colon carcinoma cell line HT29 (ECACC No. 91072201)) were seeded onto 96-well tissue culture plates at a concentration of $5 \times 10^3$ cells/well. Cells were allowed to recover overnight prior to addition of compound(s) or vehicle control (1% DMSO) as follows:

| Compound II | Conc | Compound I | | | | | | Compound I | | | | | |
|---|---|---|---|---|---|---|---|---|---|---|---|---|---|
| | | a | b | c | d | e | Control | a | b | c | d | e | Control |
| a | | | | | | | | | | | | | |
| b | | | | | | | | | | | | | |
| c | | | | | | | | | | | | | |
| d | | | | | | | | | | | | | |
| e | | | | | | | | | | | | | |
| f | | | | | | | | | | | | | |
| g | | | | | | | | | | | | | |
| Control | | | | | | | | | | | | | |

Compounds were added according to one of the following schedules;
 a) Concurrent for 72 hours.
 b) Compound I for 24 hours followed by Compound II for 48 hours.
 c) Compound II for 24 hours followed by Compound I for 48 hours.

For example, in the following case compounds were added concurrently for 72 hours. Following a total of 72 hours compound incubation, Alamar Blue™ was added to a final concentration of 10% (v/v) and incubated at 37° C. for 6 hours. Fluorescent product was quantified by reading at d535/25× (excitation) and d590/20m (emission) on a Fusion Reader (Perkin Elmer). The $IC_{50}$ for Compound II in the presence of varying doses of Compound I was determined. Synergy was determined when the $IC_{50}$ shifted down in the presence of sub-effective doses of Compound I. Additivity was determined when the response to Compound II and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

The above assay can be run with any ancillary compound (for example, with a cytotoxic compound or monoclonal antibody). For example, it was run using 4-(4-Chloro-phenyl)-4-[4-(1H-pyrazol-4-yl)-phenyl]-piperidine (see Example 14) as compound I and gefitinib (commercially available from AstraZeneca plc under the trade name Iressa) as compound II. The results are shown in FIG. 1.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A combination comprising an ancillary compound and a compound of the formula (I):

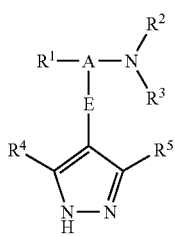
(I)

or a salt, solvate, tautomer or N-oxide thereof;
wherein A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$, wherein one of the carbon atoms in the linker group may optionally be replaced by an oxygen or nitrogen atom; and wherein the carbon atoms of the linker group A may optionally bear one or more substituents selected from oxo, fluorine and hydroxy, provided that the hydroxy group when present is not located at a carbon atom α with respect to the $NR^2R^3$ group and provided that the oxo group when present is located at a carbon atom α with respect to the $NR^2R^3$ group;
E is phenyl or pyridine wherein E is unsubstituted or has up to 4 substituents $R^8$ selected from hydroxy, chlorine, bromine, trifluoromethyl, cyano, $C_{1-4}$ hydrocarbyloxy optionally substituted by $C_{1-2}$ alkoxy or hydroxy, and $C_{1-4}$ hydrocarbyl optionally substituted by $C_{1-2}$ alkoxy or hydroxy;
$R^1$ is phenyl or pyridine which is unsubstituted or bears one or more substituents selected from hydroxy; $C_{1-4}$ acyloxy; fluorine; chlorine; bromine; trifluoromethyl; cyano; $CONH_2$; nitro; $C_{1-4}$ hydrocarbyloxy and $C_{1-4}$ hydrocarbyl each optionally substituted by $C_{1-2}$ alkoxy, carboxy or hydroxy; $C_{1-4}$ acylamino; benzoylamino; pyrrolidinocarbonyl; piperidinocarbonyl; morpholinocarbonyl; piperazinocarbonyl; five and six membered heteroaryl and heteroaryloxy groups containing one or two heteroatoms selected from N, O and S; phenyl; phenyl-$C_{1-4}$ alkyl; phenyl-$C_{1-4}$ alkoxy; heteroaryl-$C_{1-4}$ alkyl; heteroaryl-$C_{1-4}$ alkoxy and phenoxy, wherein the heteroaryl, heteroaryloxy, phenyl, phenyl-$C_{1-4}$ alkyl, phenyl-$C_{1-4}$ alkoxy, heteroaryl-$C_{1-4}$ alkyl, heteroaryl-$C_{1-4}$ alkoxy and phenoxy groups are each optionally substituted with 1, 2 or 3 substituents selected from $C_{1-2}$ acyloxy, fluorine, chlorine, bromine, trifluoromethyl, cyano, $CONH_2$, $C_{1-2}$ hydrocarbyloxy and $C_{1-2}$ hydrocarbyl each optionally substituted by methoxy or hydroxy;
$R^2$ and $R^3$ are independently selected from hydrogen, $C_{1-4}$ hydrocarbyl and $C_{1-4}$ acyl wherein the hydrocarbyl and acyl moieties are optionally substituted by one or more substituents selected from fluorine, hydroxy, amino, methylamino, dimethylamino and methoxy;
or $R^2$ and $R^3$ together with the nitrogen atom to which they are attached form a cyclic group selected from an imidazole group and a saturated monocyclic heterocyclic group having 4-7 ring members and optionally containing a second heteroatom ring member selected from O and N;
or one of $R^2$ and $R^3$ together with the nitrogen atom to which they are attached and one or more atoms from the linker group A form a saturated monocyclic heterocyclic group having 4-7 ring members and optionally containing a second heteroatom ring member selected from O and N;
or $NR^2R^3$ and the carbon atom of linker group A to which it is attached together form a cyano group;
$R^4$ is selected from hydrogen, halogen, $C_{1-5}$ saturated hydrocarbyl, $C_{1-5}$ saturated hydrocarbyloxy, cyano, and $CF_3$; and
$R^5$ is selected from hydrogen, halogen, $C_{1-5}$ saturated hydrocarbyl, $C_{1-5}$ saturated hydrocarbyloxy, cyano, $CONH_2$, $CONHR^9$, $CF_3$, $NH_2$, $NHCOR^9$ or $NHCONHR^9$;
$R^9$ is a group $R^{9a}$ or $(CH_2)R^{9a}$, wherein $R^{9a}$ is a monocyclic or bicyclic group which may be carbocyclic or heterocyclic;
the carbocyclic group or heterocyclic group $R^{9a}$ being optionally substituted by one or more substituents selected from halogen, hydroxy, trifluoromethyl, cyano, nitro, carboxy, amino, mono- or di-$C_{1-4}$ hydrocarbylamino; a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;
$R^c$ is selected from hydrogen and $C_{1-4}$ hydrocarbyl; and $X^1$ is O, S or $NR^c$ and $X^2$ is =O, =S or =$NR^c$;
and wherein
(I) the ancillary compound is selected from:
 (a) the group consisting of trastuzumab, cetuximab, erlotinib, gefitinib, bevacizumab, imatinib and sorafinib;
 (b) an ancillary PKB inhibitor;
 (c) a CDK inhibitor;
 (d) a COX-2 inhibitor;
 (e) a HDAC inhibitor;
 (f) temozolomide;
 (g) bortezimib; and
 (h) a combination of two or more of (a) to (g); or
(II) the ancillary compound is a cytotoxic compound selected from:
 (a) camptothecin compounds;
 (b) the group consisting of 5-fluorouracil, fludarabine, gemcitabine, capecitabine, cytarabine, ralitrexed, pemetrexed and methotrexate;
 (c) vinca alkaloids;
 (d) taxanes;
 (e) epothilones;
 (f) platinum compounds;
 (g) the group consisting of an anthracycline derivative, mitoxantrone and a podophyllotoxin derivative;
 (h) the group consisting of nitrogen mustard compound, a nitrosurea, cyclophosphamide, Busulfan and mitomycin C; and
 (i) a combination of two or more of (a) to (h); or
(III) the ancillary compound is selected from:
 (a) the group consisting of alemtuzumab, anti-CD20, CD22, CD33, or CD52, rituximab/rituxamab, tositumomab, gemtuzumab ozogamicin and bevacizumab; and
 (b) a combination of two or more of (a); or (IV) the ancillary compound is selected from:
(a) the group consisting of antiandrogens, antiestrogens, aromatase inhibitors, and GNRAs;
(b) the group consisting of interferons and interleukins;
(c) the group consisting of tretinoin, alitretinoin, and bexarotene; and
(d) a combination of two or more of (a) to (c).

2. A combination according to claim 1 comprising an ancillary compound and a compound of the formula (Ia):

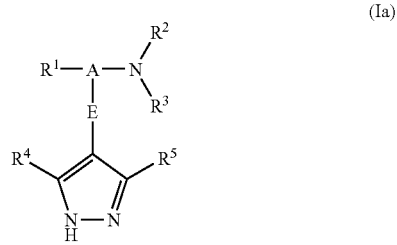

(Ia)

or a salt, solvate, tautomer or N-oxide thereof;
wherein
$R^2$ and $R^3$ are independently selected from hydrogen, $C_{1-4}$ hydrocarbyl and $C_{1-4}$ acyl;
or $R^2$ and $R^3$ together with the nitrogen atom to which they are attached form a saturated monocyclic heterocyclic group having 4-7 ring members and optionally containing a second heteroatom ring member selected from O and N;
or one of $R^2$ and $R^3$ together with the nitrogen atom to which they are attached and one or more atoms from the linker group A form a saturated monocyclic heterocyclic group having 4-7 ring members and optionally containing a second heteroatom ring member selected from O and N;
or $NR^2R^3$ and the carbon atom of linker group A to which it is attached together form a cyano group;
$R^4$ is selected from hydrogen, halogen, $C_{1-5}$ saturated hydrocarbyl, cyano and $CF_3$; and
$R^5$ is selected from hydrogen, halogen, $C_{1-5}$ saturated hydrocarbyl, cyano, $CONH_2$, $CONHR^9$, $CF_3$, $NH_2$, $NHCOR^9$ or $NHCONHR^9$; and
$R^9$ is phenyl or benzyl each optionally substituted by one or more substituents selected from halogen, hydroxy, trifluoromethyl, cyano, nitro, carboxy, amino, mono- or di-$C_{1-4}$ hydrocarbylamino; a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$.

3. A combination according to claim 1 wherein the portion $R^1$-A-$NR^2R^3$ is represented by the formula $R^1$-$(G)_k$-$(CH_2)_m$—W—$O_b$—$(CH_2)_n$—$(CR^6R^7)_p$—$NR^2R^3$ wherein G is NH, NMe or O; W is attached to the group E and is selected from $(CH_2)_j$—$CR^{20}$, $(CH_2)_j$—N and $(NH)_j$—CH; b is 0 or 1, j is 0 or 1, k is 0 or 1, m is 0 or 1, n is 0, 1, 2, or 3 and p is 0 or 1; the sum of b and k is 0 or 1; the sum of j, k, m, n and p does not exceed 4; $R^6$ and $R^7$ are the same or different and are selected from methyl and ethyl, or $CR^6R^7$ forms a cyclopropyl group; and $R^{20}$ is selected from hydrogen, methyl, hydroxy and fluorine.

4. A combination according to claim 3 wherein k is 0, m is 0 or 1, n is 0, 1, 2 or 3 and p is 0.

5. A combination according to claim 1 wherein E is selected from 1,4-phenylene, 1,3-phenylene, 2,5-pyridylene and 2,4-pyridylene, each of which is unsubstituted or substituted by up to 4 substituents $R^8$ as defined in claim 1.

6. A combination according to claim 1 wherein the compound of formula (I) is a compound of the formula (II):

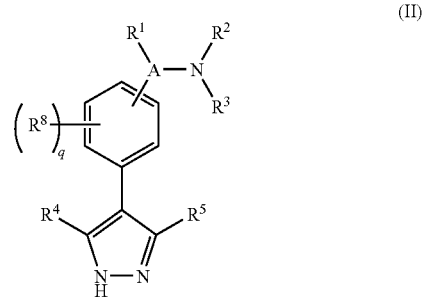

(II)

or a salt, solvate, tautomer or N-oxide thereof;
wherein the group A is attached to the meta or para position of the benzene ring and q is 0-4.

7. A combination according to claim 6 wherein the compound of formula (II) is a compound having the formula (III):

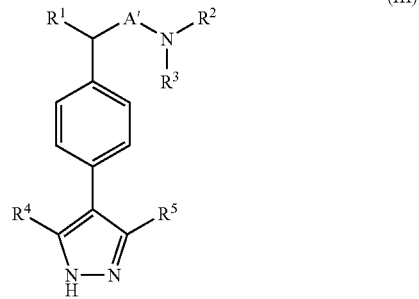

(III)

or a salt, solvate, tautomer or N-oxide thereof;
where A' is the residue of the group A.

8. A combination according to claim 1 wherein the compound of formula (I) is a compound having the formula (IV):

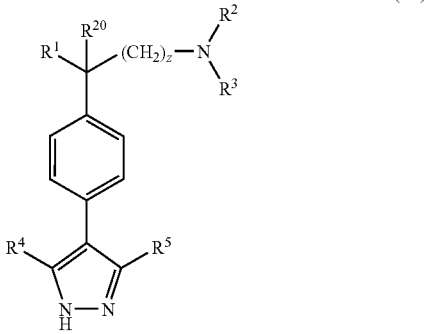

(IV)

or a salt, solvate, tautomer or N-oxide thereof;
wherein z is 0, 1 or 2, $R^{20}$ is selected from hydrogen, methyl, hydroxy and fluorine,
provided that when z is 0, $R^{20}$ is other than hydroxy.

9. A combination according to claim 1 wherein the compound of formula (I) is a compound having the formula (V):

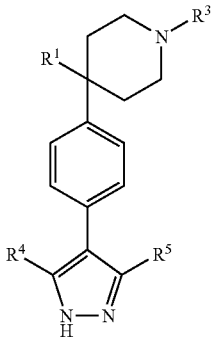

or a salt, solvate, tautomer or N-oxide thereof.

10. A combination according to claim 1 wherein $R^1$ is selected from phenyl, which is unsubstituted or bears one or more substituents selected from hydroxy; $C_{1-4}$ acyloxy; fluorine; chlorine; bromine; trifluoromethyl; cyano; $CONH_2$; nitro; $C_{1-4}$ hydrocarbyloxy and $C_{1-4}$ hydrocarbyl each optionally substituted by $C_{1-2}$ alkoxy, carboxy or hydroxy; $C_{1-4}$ acylamino; benzoylamino; pyrrolidinocarbonyl; piperidinocarbonyl; morpholinocarbonyl; piperazinocarbonyl; five and six membered heteroaryl and heteroaryloxy groups containing one or two heteroatoms selected from N, O and S; phenyl; phenyl-$C_{1-4}$ alkyl; phenyl-$C_{1-4}$ alkoxy; heteroaryl-$C_{1-4}$ alkyl; heteroaryl-$C_{1-4}$ alkoxy and phenoxy, wherein the heteroaryl, heteroaryloxy, phenyl, phenyl-$C_{1-4}$ alkyl, phenyl-$C_{1-4}$ alkoxy, heteroaryl-$C_{1-4}$ alkyl, heteroaryl-$C_{1-4}$ alkoxy and phenoxy groups are each optionally substituted with 1, 2 or 3 substituents selected from $C_{1-2}$ acyloxy, fluorine, chlorine, bromine, trifluoromethyl, cyano, $CONH_2$, $C_{1-2}$ hydrocarbyloxy and $C_{1-2}$ hydrocarbyl each optionally substituted by methoxy or hydroxy.

11. A combination according to claim 10 wherein $R^1$ is a mono-chlorophenyl or dichlorophenyl group.

12. A combination according to claim 1 wherein $R^4$ is selected from hydrogen and methyl and $R^5$ is selected from hydrogen, methyl and cyano.

13. A combination according to claim 1 wherein $R^2$ and $R^3$ are independently selected from hydrogen, $C_{1-4}$ hydrocarbyl and $C_{1-4}$ acyl.

14. A combination according to claim 13 wherein $R^2$ and $R^3$ are independently selected from hydrogen and methyl.

15. A combination according to claim 14 wherein $R^2$ and $R^3$ are both hydrogen.

16. A combination according to claim 1 wherein the compound of the formula (I) is selected from the group consisting of:
  2-phenyl-2-[4-(1H-pyrazol-4-yl)-phenyl]-ethylamine;
  3-phenyl-2-[3-(1H-pyrazol-4-yl)-phenyl]-propionitrile;
  2-[4-(3,5-dimethyl-1H-pyrazol-4-yl)-phenyl]-2-phenyl-ethylamine;
  2-(4-chloro-phenyl)-2-[4-(1H-pyrazol-4-yl)-phenyl]-ethylamine;
  2-[3-(3,5-dimethyl-1H-pyrazol-4-yl)-phenyl]-1-phenyl-ethylamine;
  3-phenyl-2-[3-(1H-pyrazol-4-yl)-phenyl]-propylamine;
  3-phenyl-2-[3-(1H-pyrazol-4-yl)-phenyl]-propylamine;
  {3-(4-chloro-phenyl)-3-[4-(1H-pyrazol-4-yl)-phenyl]-propyl}-methyl-amine;
  {3-(3,4-difluoro-phenyl)-3-[4-(1H-pyrazol-4-yl)-phenyl]-propyl}-methyl-amine;
  {3-(3-chloro-phenyl)-3-[4-(1H-pyrazol-4-yl)-phenyl]-propyl}-methyl-amine;
  3-(4-chloro-phenyl)-3-[4-(1H-pyrazol-4-yl)-phenyl]-propionamide;
  3-(4-chloro-phenyl)-3-[4-(1H-pyrazol-4-yl)-phenyl]-propylamine;
  3-(3,4-dichloro-phenyl)-3-[4-(1H-pyrazol-4-yl)-phenyl]-propylamine;
  4-(4-chloro-phenyl)-4-[4-(1H-pyrazol-4-yl)-phenyl]-piperidine;
  4-(4-methoxy-phenyl)-4-[4-(1H-pyrazol-4-yl)-phenyl]-piperidine;
  4-(4-chloro-phenyl)-1-methyl-4-[4-(1H-pyrazol-4-yl)-phenyl]-piperidine;
  4-phenyl-4-[4-(1H-pyrazol-4-yl)-phenyl]-piperidine;
  4-[4-(3,5-dimethyl-1H-pyrazol-4-yl)-phenyl]-4-phenyl-piperidine;
  dimethyl-{3-[4-(1H-pyrazol-4-yl)-phenyl]-3-pyridin-2-yl-propyl}-amine;
  {2-(4-chloro-phenyl)-2-[4-(1-pyrazol-4-yl)-phenyl]-ethyl}-dimethyl-amine;
  {2-(4-chloro-phenyl)-2-[4-(1-pyrazol-4-yl)-phenyl]-ethyl}-methyl-amine;
  {2-(4-chloro-phenyl)-2-[4-(1H-pyrazol-4-yl)-phenyl]-ethyl}-methyl-amine (R);
  {2-(4-chloro-phenyl)-2-[4-(1H-pyrazol-4-yl)-phenyl]-ethyl}-methyl-amine (S);
  4-{2-(4-chloro-phenyl)-2-[4-(1-pyrazol-4-yl)-phenyl]-ethyl}-morpholine;
  4-{4-[1-(4-chloro-phenyl)-2-pyrrolidin-1-yl-ethyl]-phenyl}-1H-pyrazole;
  {2-(4-chloro-phenyl)-2-[4-(1-pyrazol-4-yl)-phenyl]-ethyl}-isopropyl-amine;
  dimethyl-{2-phenyl-2-[4-(1-pyrazol-4-yl)-phenyl]-ethyl}-amine;
  {2,2-bis-[4-(1H-pyrazol-4-yl)-phenyl]-ethyl}-dimethyl-amine;
  {2,2-bis-[4-(1H-pyrazol-4-yl)-phenyl]-ethyl}-methyl-amine;
  2-(4-chloro-phenyl)-2-[4-(1H-pyrazol-4-yl)-phenyl]-ethylamine (R);
  2-(4-chloro-phenyl)-2-[4-(1H-pyrazol-4-yl)-phenyl]-ethylamine (S);
  2-(4-chloro-phenyl)-2-[4-(1H-pyrazol-4-yl)-phenyl]-acetamide;
  1-{2-(4-chloro-phenyl)-2-[4-(1-pyrazol-4-yl)-phenyl]-ethyl}-piperazine;
  1-{2-(4-chloro-phenyl)-2-[4-(1-pyrazol-4-yl)-phenyl]-ethyl}-piperidine;
  4-{4-[2-azetidin-1-yl-1-(4-chloro-phenyl)-ethyl]-phenyl}-1H-pyrazole;
  1-phenyl-2-[4-(1H-pyrazol-4-yl)-phenyl]-ethylamine;
  2-(4-chloro-phenyl)-N-methyl-2-[4-(1H-pyrazol-4-yl)-phenyl]-acetamide;
  N-methyl-2,2-bis-[4-(1H-pyrazol-4-yl)-phenyl]-acetamide;
  {2-(4-chloro-phenyl)-2-[4-(1-pyrazol-4-yl)-phenyl]-ethyl}-methyl-amine;
  {2-(4-chloro-phenyl)-2-[4-(1-pyrazol-4-yl)-phenyl]-ethyl}-ethyl-amine;
  4-{4-[1-(4-chloro-phenyl)-2-imidazol-1-yl-ethyl]-phenyl}-1H-pyrazole;
  methyl-{2-(4-phenoxy-phenyl)-2-[4-(1H-pyrazol-4-yl)-phenyl]-ethyl}-amine;

{2-(4-methoxy-phenyl)-2-[4-(1H-pyrazol-4-yl)-phenyl]-ethyl}-methyl-amine;
methyl-{2-[4-(pyrazin-2-yloxy)-phenyl]-2-[4-(1H-pyrazol-4-yl)-phenyl]-ethyl}-amine;
methyl-{2-phenoxy-2-[4-(1H-pyrazol-4-yl)-phenyl]-ethyl}-amine;
2-{(4-chloro-phenyl)-[4-(1H-pyrazol-4-yl)-phenyl]-methoxy}-ethylamine;
4-{4-[1-(4-chloro-phenyl)-3-pyrrolidin-1-yl-propyl]-phenyl}-1H-pyrazole;
4-{4-[3-azetidin-1-yl-1-(4-chloro-phenyl)-propyl]-phenyl}-1H-pyrazole;
methyl-{3-naphthalen-2-yl-3-[4-(1H-pyrazol-4-yl)-phenyl]-propyl}-amine;
{3-(4-fluoro-phenyl)-3-[4-(1H-pyrazol-4-yl)-phenyl]-propyl}-methyl-amine;
4-{4-[4-(4-chloro-phenyl)-piperidin-4-yl]-phenyl}-1H-pyrazole-3-carbonitrile;
3-(4-phenoxy-phenyl)-3-[4-(1H-pyrazol-4-yl)-phenyl]-propylamine;
1-{(4-chloro-phenyl)-[4-(1H-pyrazol-4-yl)-phenyl]-methyl}-piperazine;
1-methyl-4-{phenyl-[4-(1H-pyrazol-4-yl)-phenyl]-methyl}-[1,4]diazepane;
{3-(3-chloro-phenoxy)-3-[4-(1H-pyrazol-4-yl)-phenyl]-propyl}-methyl-amine;
methyl-{2-phenyl-2-[6-(1-pyrazol-4-yl)-pyridin-3-yl]-ethyl}-amine;
4-{4-[1-(4-chloro-phenyl)-3-imidazol-1-yl-propyl]-phenyl}-1H-pyrazole;
4-[4-(3-imidazol-1-yl-1-phenoxy-propyl)-phenyl]-1H-pyrazole;
4-{4-[4-(1H-pyrazol-4-yl)-phenyl]-piperidin-4-yl}-phenol;
1-{(4-chloro-phenyl)-[4-(1H-pyrazol-4-yl)-phenyl]-methyl}-piperazine;
{2-(4-fluoro-phenyl)-2-[4-(1H-pyrazol-4-yl)-phenyl]-ethyl}-methyl-amine;
{2-(3-chloro-phenyl)-2-[4-(1H-pyrazol-4-yl)-phenyl]-ethyl}-methyl-amine;
4-[4-(2-methoxy-ethoxy)-phenyl]-4-[4-(1H-pyrazol-4-yl)-phenyl]-piperidine;
4-[4-(3-methoxy-propoxy)-phenyl]-4-[4-(1H-pyrazol-4-yl)-phenyl]-piperidine;
3-(3,4-dichloro-phenyl)-3-[4-(1H-pyrazol-4-yl)-phenyl]-propionamide;
2-(4-{2-methylamino-1-[4-(1H-pyrazol-4-yl)-phenyl]-ethyl}-phenoxy)-isonicotinamide;
{2-(4-chloro-phenoxy)-2-[4-(1H-pyrazol-4-yl)-phenyl]-ethyl}-methyl-amine;
3-{2-(4-chloro-phenyl)-2-[4-(1-pyrazol-4-yl)-phenyl]-ethylamino}-propan-1-ol;
2-{2-(4-chloro-phenyl)-2-[4-(1-pyrazol-4-yl)-phenyl]-ethylamino}-ethanol;
3-{2-(4-chloro-phenyl)-2-[4-(1-pyrazol-4-yl)-phenyl]-ethylamino}-propan-1-ol;
{2-(4-chloro-phenyl)-2-[4-(1-pyrazol-4-yl)-phenyl]-ethyl}-cyclopropylmethyl-amine;
methyl-[2-[4-(1H-pyrazol-4-yl)-phenyl]-2-(4-pyridin-3-yl-phenyl)-ethyl]-amine;
4-{3-methylamino-1-[4-(1H-pyrazol-4-yl)-phenyl]-propyl}-phenol;
3-(4-methoxy-phenyl)-3-[4-(1H-pyrazol-4-yl)-phenyl]-propylamine;
4-(4-chloro-phenyl)-4-[4-(3-methyl-1H-pyrazol-4-yl)-phenyl]-piperidine;
2-(4-chloro-phenyl)-2-[4-(1H-pyrazol-4-yl)-phenyl]-morpholine;
(4-{4-[4-(1H-pyrazol-4-yl)-phenyl]-piperidin-4-yl}-phenoxy)-acetic acid;
4-{4-[4-(1H-pyrazol-4-yl)-phenyl]-piperidin-4-yl}-benzonitrile;
{2-(4-chloro-phenyl)-2-[4-(1-pyrazol-4-yl)-phenyl]-propyl}-methyl-amine;
1-(4-chloro-phenyl)-2-methylamino-1-[4-(1H-pyrazol-4-yl)-phenyl]-ethanol;
2-amino-1-(4-chloro-phenyl)-1-[4-(1H-pyrazol-4-yl)-phenyl]-ethanol;
4-(3,4-dichloro-phenyl)-4-[4-(1H-pyrazol-4-yl)-phenyl]-piperidine;
4-(3-chloro-4-methoxy-phenyl)-4-[4-(1H-pyrazol-4-yl)-phenyl]-piperidine;
4-(4-chloro-3-fluoro-phenyl)-4-[4-(1H-pyrazol-4-yl)-phenyl]-piperidine;
4-[4-(1H-pyrazol-4-yl)-phenyl]-1,2,3,4,5,6-hexahydro-[4,4']bipyridinyl;
3-(3-chloro-phenyl)-3-[4-(1H-pyrazol-4-yl)-phenyl]-propylamine;
2-methylamino-1-(4-nitro-phenyl)-1-[4-(1H-pyrazol-4-yl)-phenyl]-ethanol;
2-(3-chloro-4-methoxy-phenyl)-2-[4-(1H-pyrazol-4-yl)-phenyl]-ethylamine;
2-(4-chloro-phenyl)-2-fluoro-2-[4-(1H-pyrazol-4-yl)-phenyl]-ethylamine;
3-(3,4-dichloro-phenyl)-3-[6-(1H-pyrazol-4-yl)-pyridin-3-yl]-propylamine;
2-(4-chloro-3-fluoro-phenyl)-2-[4-(1H-pyrazol-4-yl)-phenyl]-ethylamine;
4-(2-chloro-3-fluoro-phenyl)-4-[4-(1H-pyrazol-4-yl)-phenyl]-piperidine;
1-{(3,4-dichloro-phenyl)-[4-(1H-pyrazol-4-yl)-phenyl]-methyl}-piperazine;
2-(3,4-dichloro-phenyl)-2-[4-(1H-pyrazol-4-yl)-phenyl]-ethylamine;
{2-(3-chloro-4-methoxy-phenyl)-2-[4-(1H-pyrazol-4-yl)-phenyl]-ethyl}-methyl-amine;
4-{4-[2-azetidin-1-yl-1-(4-chloro-phenoxy)-ethyl]-phenyl}-1H-pyrazole;
3-(3-chloro-4-methoxy-phenyl)-3-[4-(1H-pyrazol-4-yl)-phenyl]-propylamine;
{3-(3-chloro-4-methoxy-phenyl)-3-[4-(1H-pyrazol-4-yl)-phenyl]-propyl}-methyl-amine;
1-{(3,4-dichloro-phenyl)-[4-(1H-pyrazol-4-yl)-phenyl]-methyl}-piperazine; and
C-(4-chloro-phenyl)-C-[4-(1H-pyrazol-4-yl)-phenyl]-methylamine;
and salts, solvates, tautomers and N-oxides thereof.

17. A combination according to claim 1 in the form of a pharmaceutical pack, kit or patient pack.

18. A combination according to claim 1 wherein the ancillary compound comprises:
an antiandrogen, antiestrogen, aromatase inhibitor, or GNRA selected from tamoxifen, fulvestrant, raloxifene, toremifene, droloxifene, letrozole, anastrozole, exemestane, bicalutamide, luprolide, megestrol/megestrel acetate, vorozole, aminoglutethimide, bexarotene, goserelin, leuprolide/leuporelin, triptorelin, buserelin, abarelix, goserelin acetate and leuprolide acetate;
an ancillary PKB inhibitor selected from SF1126, rapamycin analogues, KRX-0401, API-2/TCN, RX-0201, enzastaurin HCl, SR-13668, PX-316, Perifosine, and NL-71-101;

a CDK inhibitor selected from seliciclib, alvocidib, 7-hydroxy-staurosporine, JNJ-7706621, BMS-387032, PHA533533, PD332991, ZK-304709, and AZD-5438;

COX-2 inhibitor celecoxib;

a HDAC inhibitor selected from TSA, SAHA, JNJ-16241199, LAQ-824, MGCD-0103, PXD-101, JNJ-16241199, LAQ-824, MGCD-0103, PXD-101, chlamydocin, and A-173;

a camptothecin compound selected from irinotecan and topotecan;

a vinca alkaloid selected from vinblastine, vincristine, vinorelbine, vindesine, and vinvesir;

a taxane selected from paclitaxel and docetaxel;

an epothilone selected from epothilone A, epothilone B, ixabepilone, patupilone, BMS-310705, BMS-247550, KOS-862 and ZK-EPO; or a platinum compound selected from chloro(diethylenediamino)-platinum (II) chloride, dichloro(ethylenediamino)-platinum (II), spiroplatin, iproplatin, diamino(2-ethylmalonato)platinum (II), (1,2-diaminocyclohexane)malonatoplatinum (II), (4-carboxyphthalo)-(1,2-diaminocyclohexane)platinum (II), (1,2-diaminocyclohexane)-(isocitrato)platinum (II), (1,2-diaminocyclohexane)-cis-(pyruvato)platinum (II), onnaplatin, tetraplatin, cisplatin, carboplatin and oxaliplatin.

19. A combination according to claim 1 containing two or more ancillary compounds.

20. A combination according to claim 19 wherein at least one of the two ancillary compounds and compound of formula (I), or a salt, solvate, tautomer or N-oxide thereof, are physically associated.

21. A combination according to claim 19 wherein at least one of the two ancillary compounds and compound of formula (I), or a salt, solvate, tautomer or N-oxide thereof, are non-physically associated.

22. A combination according to claim 1 wherein the compound of formula (I) is 2-amino-1-(4-chloro-phenyl)-1-[4-(1H-pyrazol-4-yl)-phenyl]-ethanol, or a salt, solvate, tautomer or N-oxide thereof.

23. A combination according to claim 22 wherein the compound of formula (I) is in the form of a salt.

24. A combination according to claim 22 wherein the compound of formula (I) is in the form of a di-hydrochloride salt.

25. A combination according to claim 1 wherein the ancillary compound and compound of formula (I), or a salt, solvate, tautomer or N-oxide thereof, are physically associated.

26. A combination according to claim 1 wherein the ancillary compound and compound of formula (I), or a salt, solvate, tautomer or N-oxide thereof, are non-physically associated.

* * * * *

UNITED STATES PATENT AND TRADEMARK OFFICE
CERTIFICATE OF CORRECTION

PATENT NO. : 8,541,461 B2  
APPLICATION NO. : 11/993823  
DATED : September 24, 2013  
INVENTOR(S) : Thompson et al.

Page 1 of 2

It is certified that error appears in the above-identified patent and that said Letters Patent is hereby corrected as shown below:

In the Claims:

Column 240, Line 35: Claim 16, Delete "-2-[4-(1-pyrazol-4-yl)-" and insert -- -2-[4-(1H-pyrazol-4-yl)- --

Column 240, Line 49: Claim 16, Delete "-2-[4-(1-pyrazol-4-yl)-" and insert -- -2-[4-(1H-pyrazol-4-yl)- --

Column 240, Line 51: Claim 16, Delete "-2-[4-(1-pyrazol-4-yl)-" and insert -- -2-[4-(1H-pyrazol-4-yl)- --

Column 240, Line 60: Claim 16, Delete "-2-[4-(1-pyrazol-4-yl)-" and insert -- -2-[4-(1H-pyrazol-4-yl)- --

Column 240, Line 62: Claim 16, Delete "-2-[4-(1-pyrazol-4-yl)-" and insert -- -2-[4-(1H-pyrazol-4-yl)- --

Column 241, Line 28: Claim 16, Delete "-2-[6-(1-pyrazol-4-yl)-" and insert -- -2-[6-(1H-pyrazol-4-yl)- --

Column 241, Line 52: Claim 16, Delete "-2-[4-(1-pyrazol-4-yl)-" and insert -- -2-[4-(1H-pyrazol-4-yl)- --

Column 241, Line 54: Claim 16, Delete "-2-[4-(1-pyrazol-4-yl)-" and insert -- -2-[4-(1H-pyrazol-4-yl)- --

Column 241, Line 56: Claim 16, Delete "-2-[4-(1-pyrazol-4-yl)-" and insert -- -2-[4-(1H-pyrazol-4-yl)- --

Signed and Sealed this  
Twenty-sixth Day of November, 2013

Margaret A. Focarino  
*Commissioner for Patents of the United States Patent and Trademark Office*

CERTIFICATE OF CORRECTION (continued)
U.S. Pat. No. 8,541,461 B2

Column 241, Line 58: Claim 16, Delete "-2-[4-(1-pyrazol-4-yl)-" and insert
-- -2-[4-(1H-pyrazol-4-yl)- --

Column 242, Line 7: Claim 16, Delete "-2-[4-(1-pyrazol-4-yl)-" and insert
-- -2-[4-(1H-pyrazol-4-yl)- --